(12) United States Patent
Egawa et al.

(10) Patent No.: US 8,110,980 B2
(45) Date of Patent: Feb. 7, 2012

(54) ANTHRACENE DERIVATIVE, AND LIGHT EMITTING ELEMENT, LIGHT EMITTING DEVICE, ELECTRONIC DEVICE USING ANTHRACENE DERIVATIVE

(75) Inventors: Masakazu Egawa, Oyama (JP); Sachiko Kawakami, Kanagawa (JP); Harue Osaka, Kanagawa (JP); Tsunenori Suzuki, Kanagawa (JP); Ryoji Nomura, Kanagawa (JP)

(73) Assignee: Semiconductor Energy laboratory Co., Ltd. (JP)

( * ) Notice: Subject to any disclaimer, the term of this patent is extended or adjusted under 35 U.S.C. 154(b) by 140 days.

(21) Appl. No.: 12/717,218

(22) Filed: Mar. 4, 2010

(65) Prior Publication Data
US 2010/0164376 A1    Jul. 1, 2010

Related U.S. Application Data

(62) Division of application No. 11/874,525, filed on Oct. 18, 2007, now Pat. No. 7,674,914.

(30) Foreign Application Priority Data

Oct. 24, 2006 (JP) .................. 2006-288924

(51) Int. Cl.
*H01J 1/00* (2006.01)
*C07D 209/56* (2006.01)
(52) U.S. Cl. ........................ 313/503; 548/442
(58) Field of Classification Search .................. 313/503; 548/442
See application file for complete search history.

(56) References Cited

U.S. PATENT DOCUMENTS

| 2005/0260442 A1 | 11/2005 | Yu et al. |
| 2006/0043859 A1 | 3/2006 | Fukuoka et al. |
| 2006/0158102 A1 | 7/2006 | Kawamura et al. |

FOREIGN PATENT DOCUMENTS

| JP | 2000-68057 | 3/2000 |
| JP | 2003-146951 | 5/2003 |
| JP | 2003-313156 | 11/2003 |
| JP | 2004-91334 | 3/2004 |
| JP | 2004-95850 | 3/2004 |
| JP | 2004-273163 | 9/2004 |

OTHER PUBLICATIONS

International Search Report re application No. PCT/JP2007/058896, dated Aug. 14, 2007.

Written Opinion re application No. PCT/JP2007/058896, dated Aug. 14, 2007.

*Primary Examiner* — Rebecca Anderson
*Assistant Examiner* — Samantha Shterengarts
(74) *Attorney, Agent, or Firm* — Husch Blackwell LLP

(57) ABSTRACT

A novel anthracene derivative represented by General Formula (1) is provided, which enables the production of a light-emitting element with high luminous efficiency and a long lifetime. A high-performance light-emitting device and electronic device in which the anthracene derivative is employed are also disclosed. The anthracene derivative of the present invention is represented by General Formula (1), in which the unit A represents any one of substituents represented by General Formulae (1-1) to (1-3). The variables shown in Formulae (1) and (1-1) to (1-3) are defined in the specification.

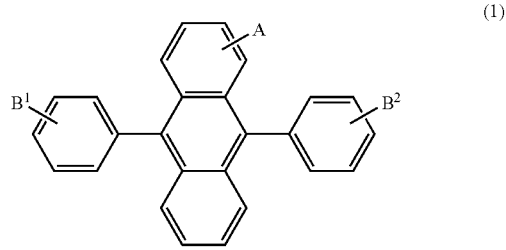

(1)

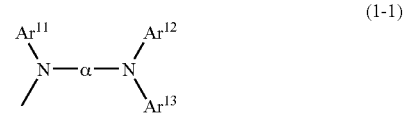

(1-1)

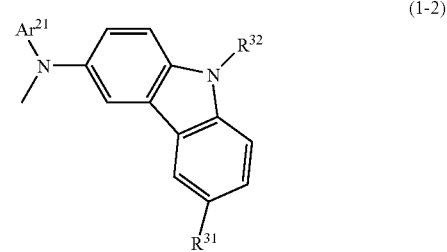

(1-2)

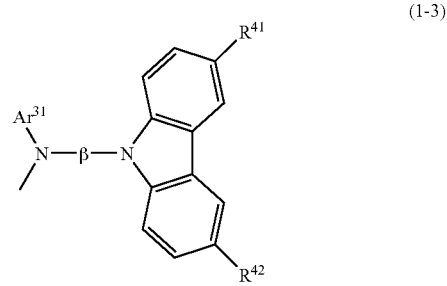

(1-3)

28 Claims, 28 Drawing Sheets

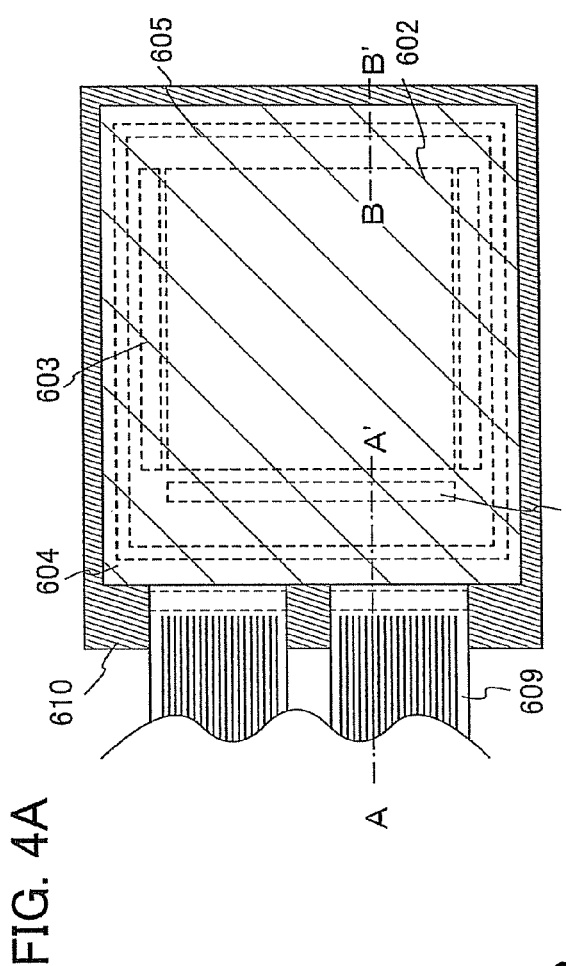
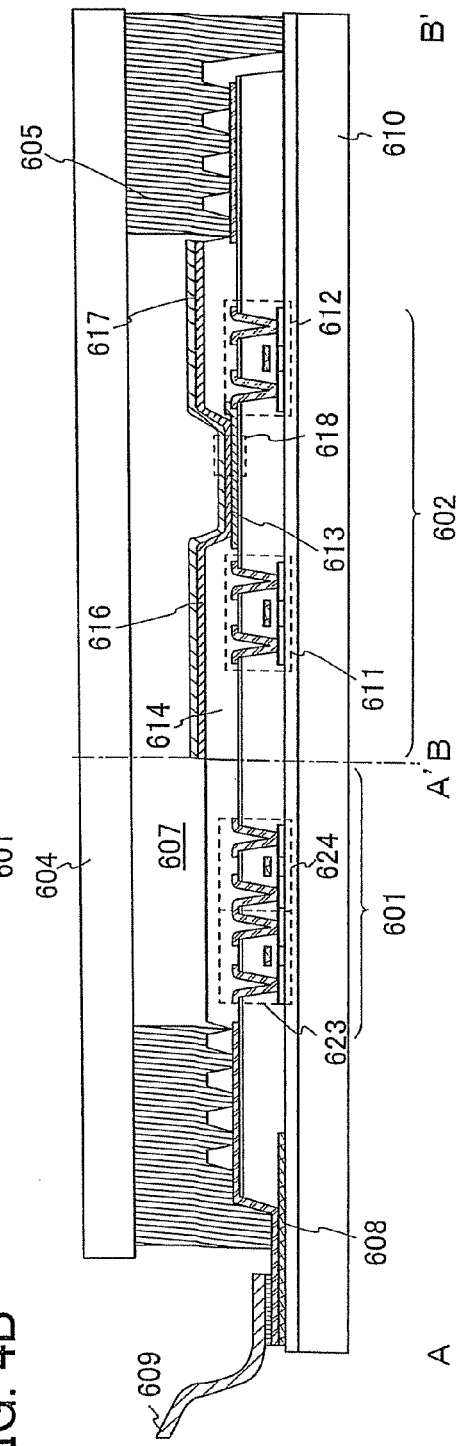
FIG. 4A
FIG. 4B

ANTHRACENE DERIVATIVE, AND LIGHT EMITTING ELEMENT, LIGHT EMITTING DEVICE, ELECTRONIC DEVICE USING ANTHRACENE DERIVATIVE

This application is a divisional of application Ser. No. 11/874,525 filed on Oct. 18, 2007 now U.S. Pat. No. 7,674,914.

BACKGROUND OF THE INVENTION

1. Field of the Invention

The present invention relates to an anthracene derivative, and a light-emitting element, a light-emitting device, and an electronic device each using the anthracene derivative.

2. Description of the Related Art

In comparison with inorganic compounds, organic compounds can have various structures. By appropriate molecular design of organic compounds, materials having various functions can be synthesized. Owing to these advantages, photo electronics and electronics, which employ functional organic materials, have been attracting attention in recent years.

A solar cell, a light-emitting element, an organic transistor, and the like can be given as typical examples of an electronic device using an organic compound as a functional material. Such devices take advantage of electrical properties and optical properties of the organic compound. Among them, in particular, a light-emitting element has been making remarkable progress.

It is considered that a light emission mechanism of a light-emitting element is as follows: when a voltage is applied between a pair of electrodes which interpose a light-emitting layer, electrons injected from a cathode and holes injected from an anode are recombined in the light-emitting layer to form a molecular exciton, and when the molecular exciton relaxes to the ground state, energy is released and light is generated. As excited states, a singlet excited state and a triplet excited state are known, and light emission is considered to be possible through either of these excited states.

In improving the performance of such a light-emitting element, there are many problems which depend on the material, and in order to solve such problems, improvement of the element structure and development of materials have been carried out.

For example, in Reference 1 (United States Patent Application Laid-Open No. 2005/0260442), an anthracene derivative exhibiting green light emission is disclosed. However, in Reference 1, only the PL spectrum of the anthracene derivative is described, and the device performance when the anthracene derivative is applied to a light-emitting element is not disclosed.

Also, in Reference 2 (Japanese Published Patent Application No. 2004-91334), a light-emitting element using an anthracene derivative as a charge transporting layer is mentioned. However, in Reference 2, there is no description on the lifetime of the light-emitting element.

If commercialization of light-emitting elements is considered, extending the lifetime is an important issue. Further, the development of light-emitting elements with much higher performances is desired.

SUMMARY OF THE INVENTION

In view of the foregoing problems, it is an object of the present invention to provide a novel anthracene derivative.

In addition, it is another object of the present invention to provide a light-emitting element with high luminous efficiency as well as a long lifetime. It is still another object of the present invention to provide a light-emitting device and an electronic device each having low power consumption and a long lifetime by using such a light-emitting element.

One feature of the present invention is an anthracene derivative represented by General Formula (1).

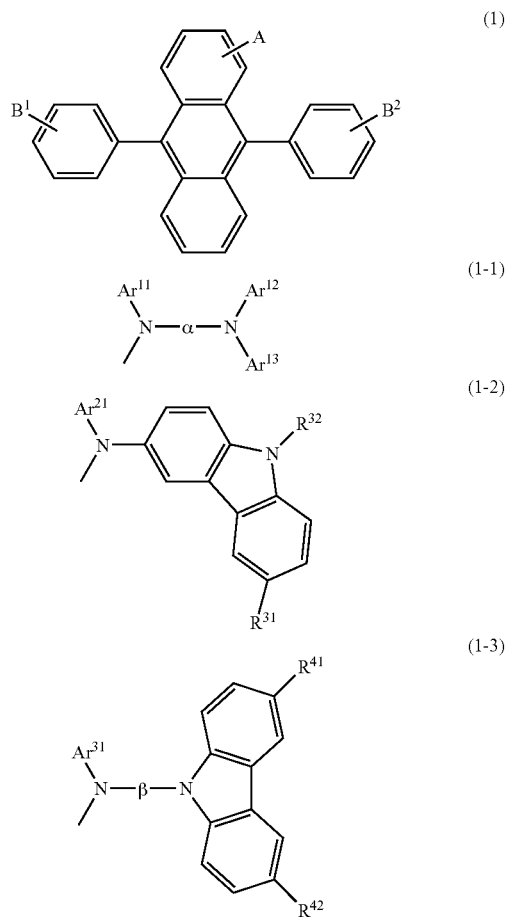

(In the formula, each of $B^1$ and $B^2$ represents any one of halogen, a haloalkyl group, a cyano group, an acyl group, a carboxyl group, an acyloxy group, an alkoxy group, a pyridyl group, a quinolyl group, an isoquinolyl group, and an oxazolyl group, while A represents a substituent given by any one of General Formulae (1-1) to (1-3). In General Formulae (1-1) to (1-3), each of $Ar^{11}$ to $Ar^{13}$ represents an aryl group having 6 to 25 carbon atoms; a represents an arylene group having 6 to 25 carbon atoms; $Ar^{21}$ represents an aryl group having 6 to 25 carbon atoms; $R^{31}$ represents any one of a hydrogen atom, an alkyl group having 1 to 4 carbon atoms, and an aryl group having 6 to 25 carbon atoms; $R^{32}$ represents an alkyl group having 1 to 4 carbon atoms or an aryl group having 6 to 25 carbon atoms; $Ar^{31}$ represents an aryl group having 6 to 25 carbon atoms; β represents an arylene group having 6 to 25 carbon atoms; and each of $R^{41}$ and $R^{42}$ represents any one of a hydrogen atom, an alkyl group having 1 to 4 carbon atoms, and an aryl group having 6 to 25 carbon atoms.)

Another feature of the present invention is an anthracene derivative represented by General Formula (2).

(2)

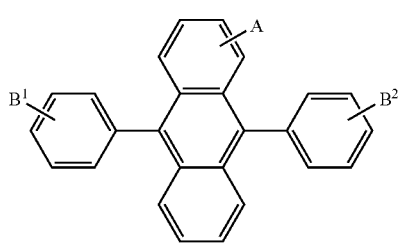

(2-1)

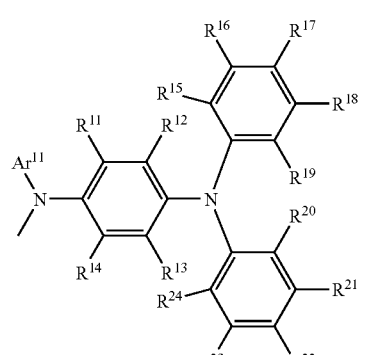

(2-2)

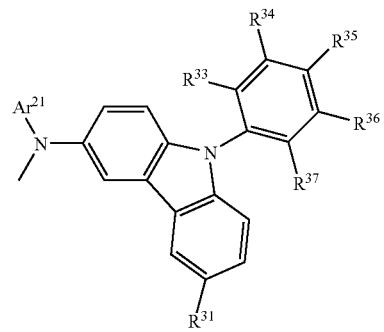

(2-3)

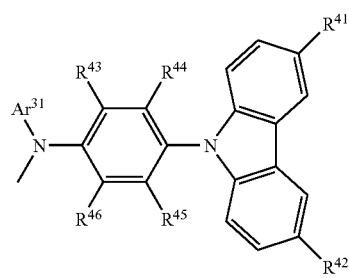

(In the formula, each of $B^1$ and $B^2$ represents any one of halogen, a haloalkyl group, a cyano group, an acyl group, a carboxyl group, an acyloxy group, an alkoxy group, a pyridyl group, a quinolyl group, an isoquinolyl group, and an oxazolyl group, while A represents a substituent given by any one of General Formulae (2-1) to (2-3). In General Formulae (2-1) to (2-3), $Ar^{11}$ represents an aryl group having 6 to 25 carbon atoms; each of $R^{11}$ to $R^{24}$ represents any one of a hydrogen atom, an alkyl group having 1 to 4 carbon atoms, and an aryl group having 6 to 15 carbon atoms; $Ar^{21}$ represents an aryl group having 6 to 25 carbon atoms; $R^{31}$ represents any one of a hydrogen atom, an alkyl group having 1 to 4 carbon atoms, and an aryl group having 6 to 25 carbon atoms; each of $R^{33}$ to $R^{37}$ represents any one of a hydrogen atom, an alkyl group having 1 to 4 carbon atoms, and an aryl group having 6 to 15 carbon atoms; $Ar^{31}$ represents an aryl group having 6 to 25 carbon atoms; each of $R^{41}$ and $R^{42}$ represents any one of a hydrogen atom, an alkyl group having 1 to 4 carbon atoms, and an aryl group having 6 to 25 carbon atoms; and each of $R^{43}$ to $R^{46}$ represents any one of a hydrogen atom, an alkyl group having 1 to 4 carbon atoms, and an aryl group having 6 to 15 carbon atoms.)

Yet another feature of the present invention is an anthracene derivative represented by General Formula (3).

(3)

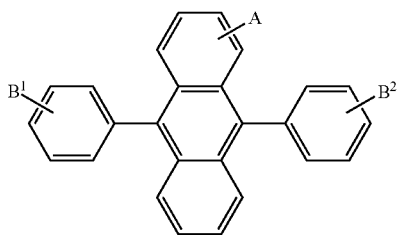

(3-1)

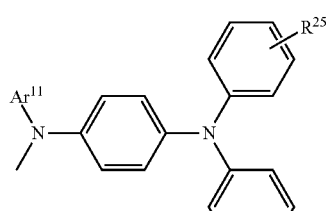

(3-2)

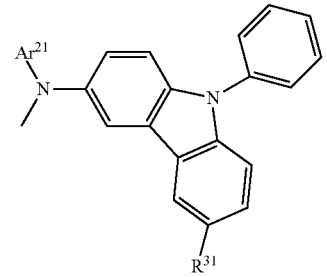

(3-3)

(In the formula, each of $B^1$ and $B^2$ represents any one of halogen, a haloalkyl group, a cyano group, an acyl group, a carboxyl group, an acyloxy group, an alkoxy group, a pyridyl group, a quinolyl group, an isoquinolyl group, and an oxazolyl group, while A represents a substituent given by any one of General Formulae (3-1) to (3-3). In General Formulae (3-1) to (3-3), $Ar^{11}$ represents an aryl group having 6 to 25 carbon atoms; each of $R^{25}$ and $R^{26}$ represents any one of a hydrogen atom, an alkyl group having 1 to 4 carbon atoms, and an aryl group having 6 to 15 carbon atoms; $Ar^{21}$ represents an aryl group having 6 to 25 carbon atoms; $R^{31}$ represents any one of a hydrogen atom, an alkyl group having 1 to 4 carbon atoms, and an aryl group having 6 to 25 carbon atoms; $Ar^{31}$ represents an aryl group having 6 to 25 carbon atoms; and each of $R^{41}$ and $R^{42}$ represents any one of a hydrogen atom, an alkyl group having 1 to 4 carbon atoms, and an aryl group having 6 to 25 carbon atoms.)

Still another feature of the present invention is an anthracene derivative represented by General Formula (4).

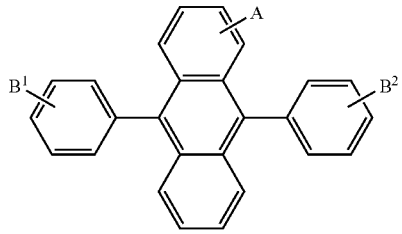
(4)

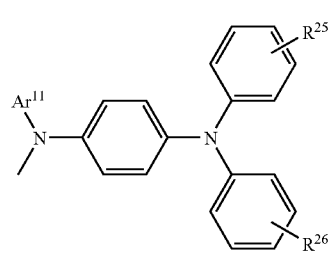
(4-1)

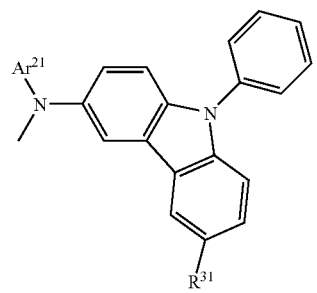
(4-2)

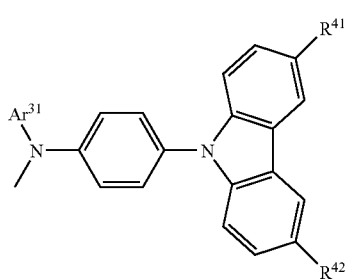
(4-3)

(In the formula, each of $B^1$ and $B^2$ represents any one of halogen, a haloalkyl group, a cyano group, an acyl group, a carboxyl group, an acyloxy group, an alkoxy group, a pyridyl group, a quinolyl group, an isoquinolyl group, and an oxazolyl group, while A represents a substituent given by any one of General Formulae (4-1) to (4-3). In General Formulae (4-1) to (4-3), $Ar^{11}$ represents any one of a phenyl group, a 1-naphthyl group, and a 2-naphthyl group; each of $R^{25}$ and $R^{26}$ represents any one of a hydrogen atom, an alkyl group having 1 to 4 carbon atoms, and an aryl group having 6 to 15 carbon atoms; $Ar^{21}$ represents any one of a phenyl group, a 1-naphthyl group, and a 2-naphthyl group; $R^{31}$ represents any one of a hydrogen atom, an alkyl group having 1 to 4 carbon atoms, and an aryl group having 6 to 25 carbon atoms; $Ar^{31}$ represents any one of a phenyl group, a 1-naphthyl group, and a 2-naphthyl group; and each of $R^{41}$ and $R^{42}$ represents any one of a hydrogen atom, an alkyl group having 1 to 4 carbon atoms, and an aryl group having 6 to 25 carbon atoms.)

Another feature of the present invention is an anthracene derivative represented by General Formula (5).

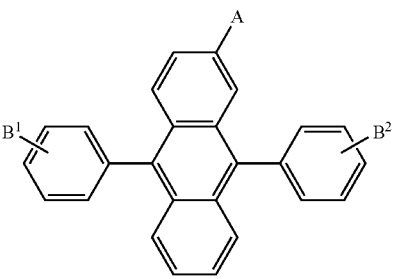
(5)

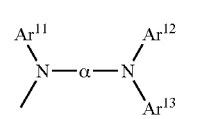
(5-1)

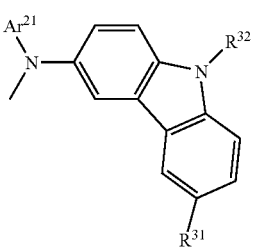
(5-2)

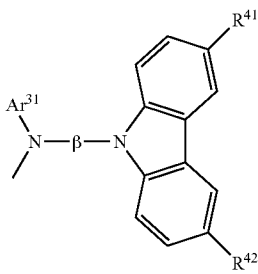
(5-3)

(In the formula, each of $B^1$ and $B^2$ represents any one of halogen, a haloalkyl group, a cyano group, an acyl group, a carboxyl group, an acyloxy group, an alkoxy group, a pyridyl group, a quinolyl group, an isoquinolyl group, and an oxazolyl group, while A represents a substituent given by any one of General Formulae (5-1) to (5-3). In General Formulae (5-1) to (5-3), each of $Ar^{11}$ to $Ar^{13}$ represents an aryl group having 6 to 25 carbon atoms; a represents an arylene group having 6 to 25 carbon atoms; $Ar^{21}$ represents an aryl group having 6 to 25 carbon atoms; $R^{31}$ represents any one of a hydrogen atom, an alkyl group having 1 to 4 carbon atoms, and an aryl group having 6 to 25 carbon atoms; $R^{32}$ represents an alkyl group having 1 to 4 carbon atoms or an aryl group having 6 to 25 carbon atoms; $Ar^{31}$ represents an aryl group having 6 to 25 carbon atoms; β represents an arylene group having 6 to 25 carbon atoms; and each of $R^{41}$ and $R^{42}$ represents any one of a hydrogen atom, an alkyl group having 1 to 4 carbon atoms, and an aryl group having 6 to 25 carbon atoms.)

Further, one feature of the present invention is an anthracene derivative represented by General Formula (6).

(6)

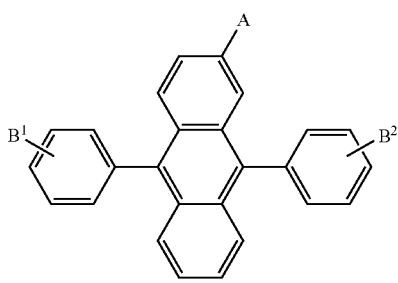

(6-1)

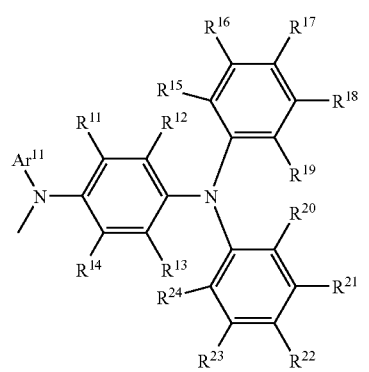

(6-2)

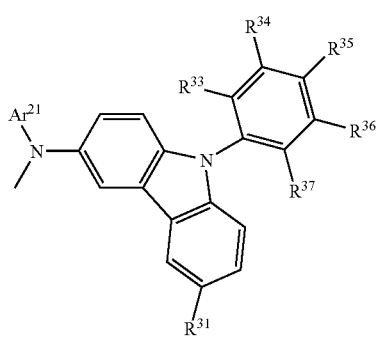

(6-3)

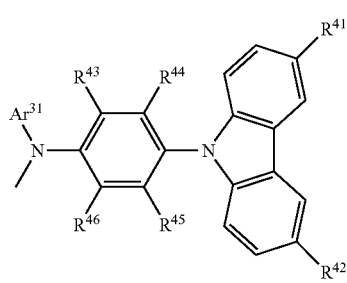

(In the formula, each of $B^1$ and $B^2$ represents any one of halogen, a haloalkyl group, a cyano group, an acyl group, a carboxyl group, an acyloxy group, an alkoxy group, a pyridyl group, a quinolyl group, an isoquinolyl group, and an oxazolyl group, while A represents a substituent given by any one of General Formulae (64) to (6-3). In General Formulae (6-1) to (6-3), $Ar^{11}$ represents an aryl group having 6 to 25 carbon atoms; each of $R^{11}$ to $R^{24}$ represents any one of a hydrogen atom, an alkyl group having 1 to 4 carbon atoms, and an aryl group having 6 to 15 carbon atoms; $A^{21}$ represents an aryl group having 6 to 25 carbon atoms; $R^{31}$ represents any one of a hydrogen atom, an alkyl group having 1 to 4 carbon atoms, and an aryl group having 6 to 25 carbon atoms; each of $R^{33}$ to $R^{37}$ represents any one of a hydrogen atom, an alkyl group having 1 to 4 carbon atoms, and an aryl group having 6 to 15 carbon atoms; $Ar^{31}$ represents an aryl group having 6 to 25 carbon atoms; each of $R^{41}$ and $R^{42}$ represents any one of a hydrogen atom, an alkyl group having 1 to 4 carbon atoms, and an aryl group having 6 to 25 carbon atoms; and each of $R^{43}$ to $R^{46}$ represents any one of a hydrogen atom, an alkyl group having 1 to 4 carbon atoms, and an aryl group having 6 to 15 carbon atoms.)

Also, one feature of the present invention is an anthracene derivative represented by General Formula (7).

(7)

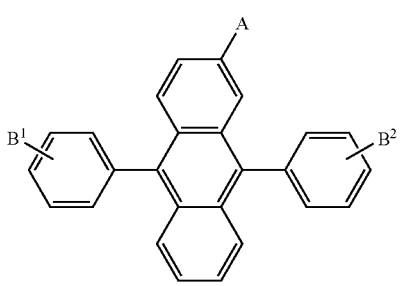

(7-1)

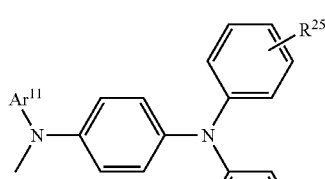

(7-2)

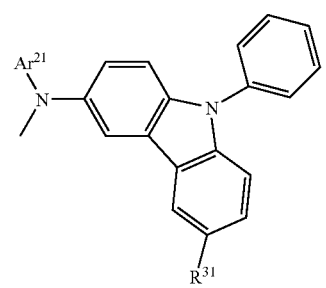

(7-3)

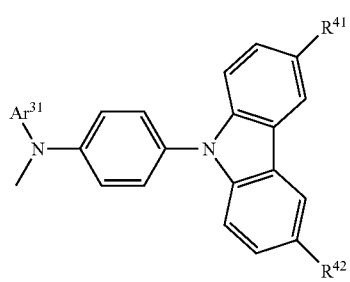

(In the formula, each of $B^1$ and $B^2$ represents any one of halogen, a haloalkyl group, a cyano group, an acyl group, a carboxyl group, an acyloxy group, an alkoxy group, a pyridyl group, a quinolyl group, an isoquinolyl group, and an oxazolyl group, while A represents a substituent given by any one of General Formulae (7-1) to (7-3). In General Formulae (7-1) to (7-3), $Ar^{11}$ represents an aryl group having 6 to 25 carbon atoms; each of $R^{25}$ and $R^{26}$ represents any one of a hydrogen atom, an alkyl group having 1 to 4 carbon atoms, and an aryl group having 6 to 15 carbon atoms; $Ar^{21}$ represents an aryl group having 6 to 25 carbon atoms; $R^{31}$ represents any one of a hydrogen atom, an alkyl group having 1 to 4 carbon atoms, and an aryl group having 6 to 25 carbon atoms; $Ar^{31}$ represents an aryl group having 6 to 25 carbon atoms; and each of $R^{41}$ and $R^{42}$ represents any one of a hydrogen atom, an alkyl group having 1 to 4 carbon atoms, and an aryl group having 6 to 25 carbon atoms.)

Yet another feature of the present invention is an anthracene derivative represented by General Formula (8).

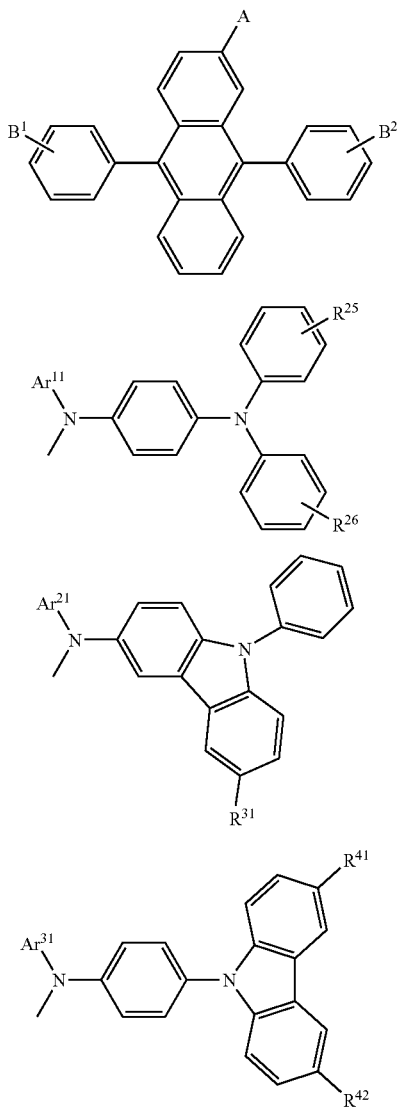

(In the formula, each of $B^1$ and $B^2$ represents any one of halogen, a haloalkyl group, a cyano group, an acyl group, a carboxyl group, an acyloxy group, an alkoxy group, a pyridyl group, a quinolyl group, an isoquinolyl group, and an oxazolyl group, while A represents a substituent given by any one of General Formulae (8-1) to (8-3). In General Formulae (8-1) to (8-3), $Ar^{11}$ represents any one of a phenyl group, a 1-naphthyl group, and a 2-naphthyl group; each of $R^{25}$ and $R^{26}$ represents any one of a hydrogen atom, an alkyl group having 1 to 4 carbon atoms, and an aryl group having 6 to 15 carbon atoms; $Ar^{21}$ represents any one of a phenyl group, a 1-naphthyl group, and a 2-naphthyl group; $R^{31}$ represents any one of a hydrogen atom, an alkyl group having 1 to 4 carbon atoms, and an aryl group having 6 to 25 carbon atoms; $Ar^{31}$ represents any one of a phenyl group, a 1-naphthyl group, and a 2-naphthyl group; and each of $R^{41}$ and $R^{42}$ represents any one of a hydrogen atom, an alkyl group having 1 to 4 carbon atoms, and an aryl group having 6 to 25 carbon atoms.)

In the abovementioned structure, each of $B^1$ and $B^2$ is preferably halogen or a haloalkyl group. In particular, each of $B^1$ and $B^2$ is preferably a fluoro group or a trifluoromethyl group.

Also, in the abovementioned structure, $B^1$ and $B^2$ are preferably substituents having the same structure.

Further, one feature of the present invention is a light-emitting element using the foregoing anthracene derivative. Specifically, the feature of the present invention is a light-emitting element having the anthracene derivative between a pair of electrodes.

Another feature of the present invention is a light-emitting element having a light-emitting layer between a pair of electrodes, in which the light-emitting layer includes the abovementioned anthracene derivative. It is particularly preferable to use the abovementioned anthracene derivative as a light-emitting substance. That is, it is preferable to have a structure in which the anthracene derivative emits light.

When light-emitting elements using an organic compound are operated by applying voltage between the electrodes, the quantity of holes is generally excessive relative to that of electrons (hole-excessive state) in the light-emitting layer. This is because, in general, holes are readily injected into and transported in a layer comprising an organic compound. If the light-emitting layer has such a hole-excessive state, high luminous efficiency cannot be attained because carrier balance is lost in the light-emitting layer, resulting in decrease in recombination probability of electrons and holes. However, the anthracene derivative of the present invention has a low lowest unoccupied molecular orbital (LUMO) level, and thus, exhibits an electron trapping property, which prevents the light-emitting layer from existing in the hole-excessive state. Therefore, by using the anthracene derivative of the present invention as a light-emitting substance, recombination probability of electrons and holes in the light-emitting substance can be increased, whereby a light-emitting element with high luminous efficiency can be obtained.

One feature of the present invention is a light-emitting element having an electron transporting layer and a hole transporting layer between a first electrode and a second electrode, and a first layer and a second layer between the electron transporting layer and the hole transporting layer. The first layer includes a first organic compound and a second organic compound; the second layer includes a third organic compound and a fourth organic compound; the first layer is provided on the first-electrode side of the second layer, the second organic compound has an electron transporting property; the third organic compound is the abovementioned anthracene derivative, the fourth organic compound has an electron transporting property; the light-emission colors of the first organic compound and the third organic compound are similar; and light emission from the first organic compound is obtained by applying a voltage between the first electrode and the second electrode such that the first electrode has a higher potential than the second electrode.

The abovementioned anthracene derivative has an electron withdrawing group and has a low lowest unoccupied molecular orbital (LUMO) level. Therefore, the anthracene derivative has an electron trapping property with respect to other organic compounds, and readily traps electrons injected from the second electrode. Thus, carrier balance can be improved and luminous efficiency of the light-emitting element can be increased. The improved carrier balance allows the fabrication of a light-emitting element with a long lifetime.

Another feature of the present invention is a light-emitting element having an electron transporting layer and a hole transporting layer between a first electrode and a second electrode, and a first layer and a second layer between the electron transporting layer and the hole transporting layer. The first layer includes a first organic compound and a second organic compound; the second layer includes a third organic compound and a fourth organic compound; the first layer is provided on the first-electrode side of the second layer, the first organic compound is the abovementioned anthracene derivative; the second organic compound has an electron transporting property; the third organic compound has an electron trapping property; the fourth organic compound has an electron transporting property; the light-emission colors of the first organic compound and the third organic compound are similar; and light emission from the first organic compound is obtained by applying a voltage between the first electrode and the second electrode such that the first electrode has a higher potential than the second electrode.

In the abovementioned structure, the lowest unoccupied molecular orbital level of the third organic compound is preferably lower than the lowest unoccupied molecular orbital level of the fourth organic compound by 0.3 eV or more.

Still another feature of the present invention is a light-emitting element having an electron transporting layer and a hole transporting layer between a first electrode and a second electrode, and a first layer and a second layer between the electron transporting layer and the hole transporting layer. The first layer includes a first organic compound and a second organic compound; the second layer includes a third organic compound and a fourth organic compound; the first layer is provided on the first-electrode side of the second layer; the first organic compound is the above mentioned anthracene derivative; the second organic compound has an electron transporting property; the third organic compound has a hole transporting property; the fourth organic compound has an electron transporting property; the weight percent of the fourth organic compound is higher than the weight percent of the third organic compound in the second layer; the light-emission colors of the first organic compound and the third organic compound are similar; and light emission from the first organic compound is obtained by applying a voltage between the first electrode and the second electrode such that the first electrode has a higher potential than the second electrode.

In the abovementioned structure, a difference between the lowest unoccupied molecular orbital levels of the third organic compound and the fourth organic compound is preferably less than 0.3 eV.

Also, in the abovementioned structure, a difference between the peak value of the emission spectrum of the first organic compound and the peak value of the emission spectrum of the third organic compound is preferably less than or equal to 30 nm.

Yet another feature of the present invention is a light-emitting element having an electron transporting layer and a hole transporting layer between a first electrode and a second electrode, and a first layer and a second layer between the electron transporting layer and the hole transporting layer. The first layer includes a first organic compound and a second organic compound; the second layer includes a third organic compound and a fourth organic compound; the first layer is provided on the first-electrode side of the second layer; the first organic compound is the abovementioned anthracene derivative; the second organic compound has an electron transporting property; the third organic compound is the abovementioned anthracene derivative; the fourth organic compound has an electron transporting property; and light emission from the first organic compound is obtained by applying a voltage between the first electrode and the second electrode such that the first electrode has a higher potential than the second electrode.

In the abovementioned structure, the first layer and the second layer are preferably provided to be in contact with each other.

A light-emitting device of the present invention has the abovementioned light-emitting element. The light-emitting element has a layer including a light-emitting substance between a pair of electrodes, and the layer including the light-emitting substance includes the foregoing anthracene derivative. The light-emitting device of the present invention also possesses a controller for controlling light emission of the light-emitting element. The light-emitting device in this specification includes an image display device, a light-emitting device, and a light source (including a lighting device). Further, the light-emitting device also includes a module in which a connector such as an FPC (Flexible Printed Circuit), a TAB (Tape Automated Bonding) tape, or a TCP (Tape Carrier Package) is attached to a panel, a module in which a printed wiring board is provided at an end of a TAB tape or a TCP, and a module in which an IC (Integrated Circuit) is directly mounted on the light-emitting device by a COG (Chip On Glass) method.

Further, an electronic device using the light-emitting element of the present invention in its display portion is also included in the category of the present invention. Therefore, the electronic device of the present invention has a display portion, and the display portion is equipped with the abovementioned light-emitting element and controller for controlling light emission of the light-emitting element.

The anthracene derivative of the present invention has high luminous efficiency. Therefore, by using the anthracene derivative of the present invention in a light-emitting element, a light-emitting element with high luminous efficiency can be obtained. Also, by using the anthracene derivative of the present invention in a light-emitting element, a light-emitting element with a long lifetime can be obtained.

Further, by using the anthracene derivative of the present invention, a light-emitting device and an electronic device each with low power consumption can be obtained. Also, by using the anthracene derivative of the present invention, a light-emitting device and an electronic device each with a long lifetime can be obtained.

BRIEF DESCRIPTION OF THE DRAWINGS

In the accompanying drawings:

FIGS. 4A and 4B illustrate a light-emitting device of the present invention;

DETAILED DESCRIPTION OF THE INVENTION

Figure 1A:
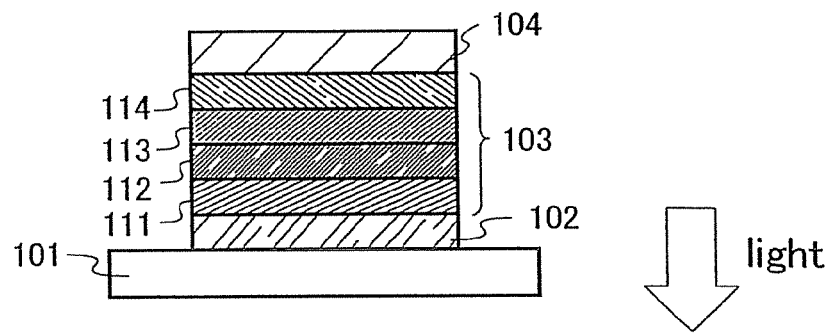
FIGS. 1A to 1C each illustrate a light-emitting element of the present invention.

Hereinafter, embodiment modes of the present invention will be described with reference to the accompanied drawings. However, the present invention is not limited to the following description, and it is easily understood by those skilled in the art that the modes and details thereof can be changed in various ways without departing from the spirit and scope of the present invention. Therefore, the present invention should not be interpreted limited to the following description of embodiment modes.

Embodiment Mode 1

In this embodiment mode, an anthracene derivative of the present invention will be described.

The anthracene derivative of the present invention is an anthracene derivative having a phenyl group with an electron withdrawing group or a heteroaromatic group. Specifically, the anthracene derivative is represented by General Formula (1).

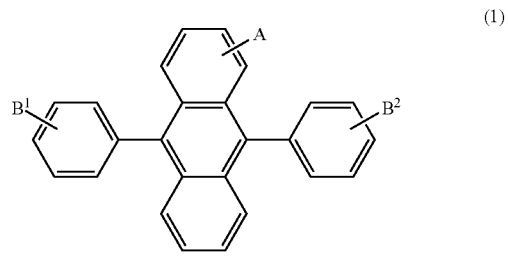

(1)

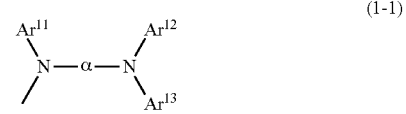

(1-1)

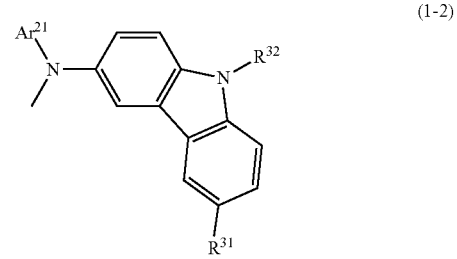

(1-2)

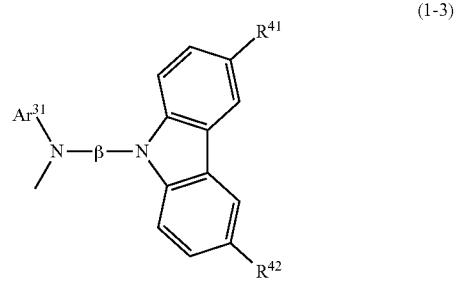

(1-3)

(In the formula, each of $B^1$ and $B^2$ represents any one of halogen, a haloalkyl group, a cyano group, an acyl group, a carboxyl group, an acyloxy group, an alkoxy group, a pyridyl group, a quinolyl group, an isoquinolyl group, and an oxazolyl group, while A represents a substituent given by any one of General Formulae (1-1) to (1-3). In General Formulae (1-1) to (1-3), each of $Ar^{11}$ to $Ar^{13}$ represents an aryl group having 6 to 25 carbon atoms; α represents an arylene group having 6 to 25 carbon atoms; $Ar^{21}$ represents an aryl group having 6 to 25 carbon atoms; $R^{31}$ represents any one of a hydrogen atom, an alkyl group having 1 to 4 carbon atoms, and an aryl group having 6 to 25 carbon atoms; $R^{32}$ represents an alkyl group having 1 to 4 carbon atoms or an aryl group having 6 to 25 carbon atoms; $Ar^{31}$ represents an aryl group having 6 to 25 carbon atoms; β represents an arylene group having 6 to 25 carbon atoms; and each of $R^{41}$ and $R^{42}$ represents any one of a hydrogen atom, an alkyl group having 1 to 4 carbon atoms, and an aryl group having 6 to 25 carbon atoms.)

In General Formula (1), the substituent represented by $B^1$ and $B^2$ can be, for example, halogen such as fluorine, a haloalkyl group such as a trifluoromethyl group, a cyano group, an acyl group such as an acetyl group, a carboxyl group, an acyloxy group such as an acetoxy group, an alkoxy group such as a methoxy group, a pyridyl group, a quinolyl group, an isoquinolyl group, or an oxazolyl group. For example, substituents represented by Structural Formulae (20-1) to (20-12) can be given.

It is to be noted that the substitution position of the pyridyl group, the quinolyl group, the isoquinolyl group, or the oxazolyl group is not specifically limited.

In General Formula (1-1), a substituent represented by Structural Formulae (21-1) to (21-10) can be given as a substituent represented by each of $Ar^{11}$ to $Ar^{13}$, for example.

(21-6)
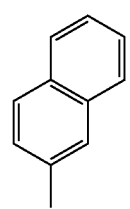
(21-7)
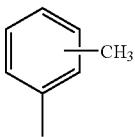
(21-8)
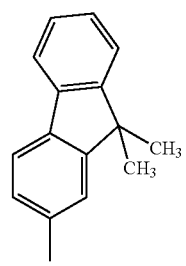
(21-9)
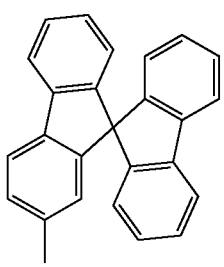
(21-10)
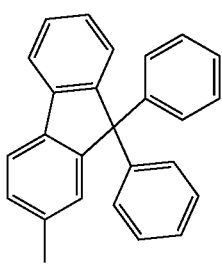
Also, in General Formula (1-1), a substituent represented by Structural Formulae (22-1) to (22-9) can be given as a substituent represented by α, for example.
(22-1)
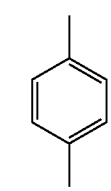
(22-2)
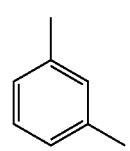
(22-3)
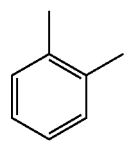
(22-4)
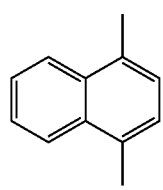
(22-5)
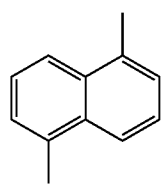
(22-6)
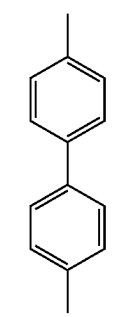
(22-7)
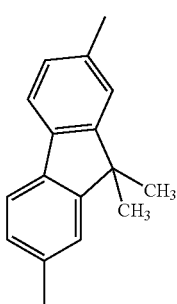
(22-8)
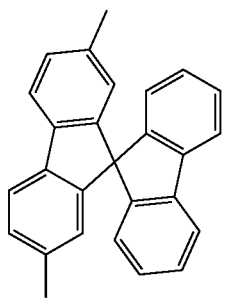

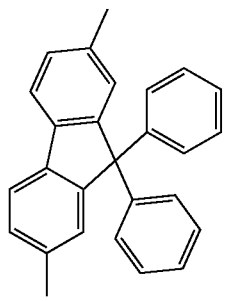
(22-9)
Consequently, a substituent represented by Structural Formulae (31-1) to (31-27) can be given as a substituent represented by General Formula (1-1), for example.
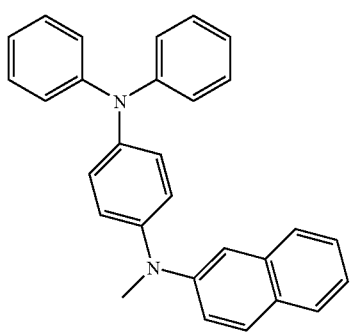
(31-1)
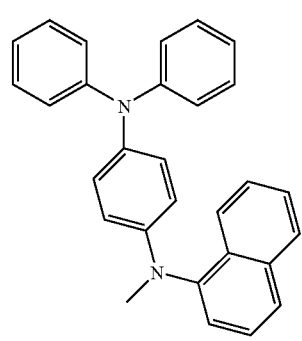
(31-2)
(31-3)
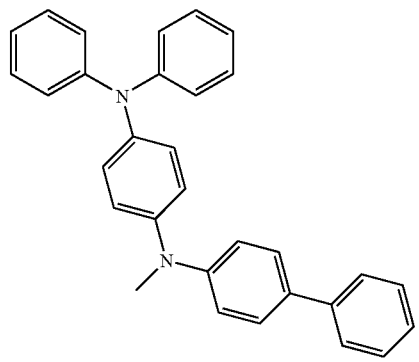
(31-4)
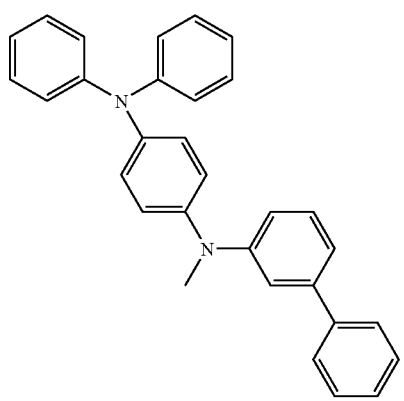
(31-5)
(31-6)
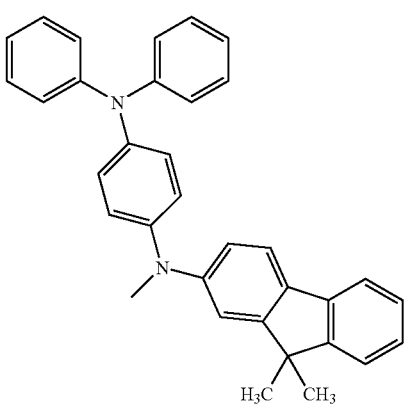
(31-7)

(31-8) 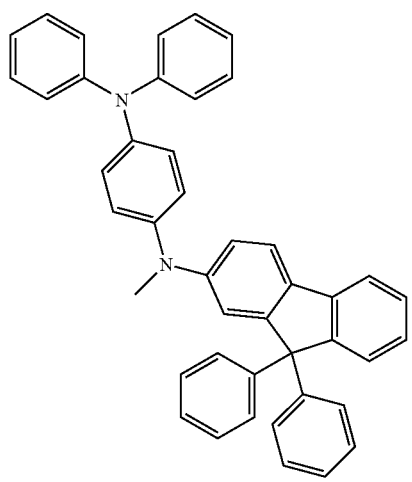
(31-9) 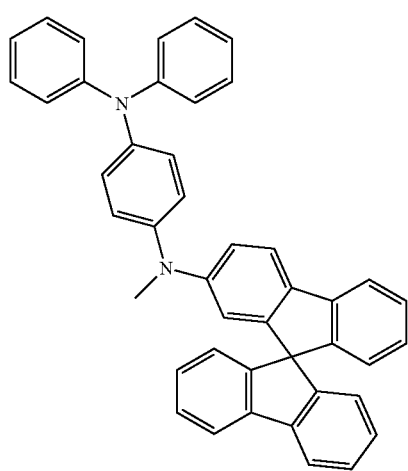
(31-10) 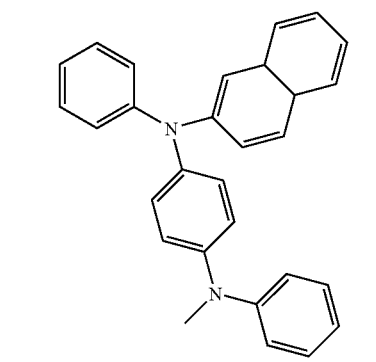
(31-11) 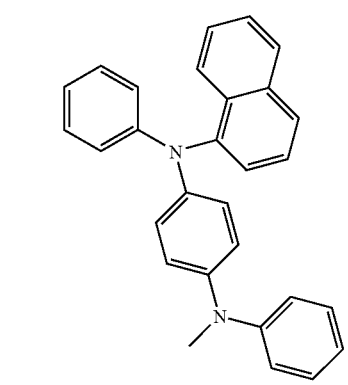
(31-12) 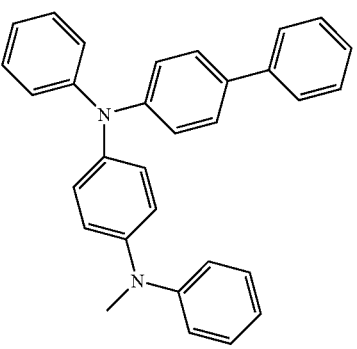
(31-13) 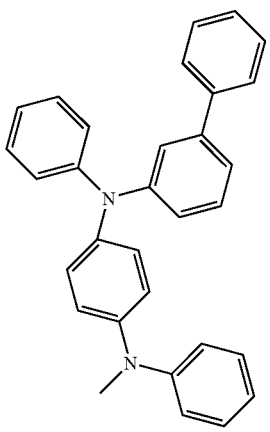
(31-14) 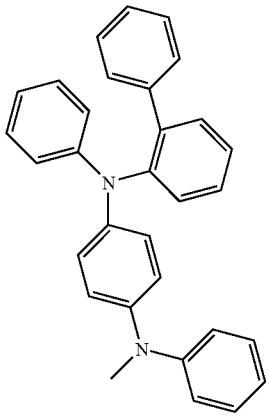
(31-15) 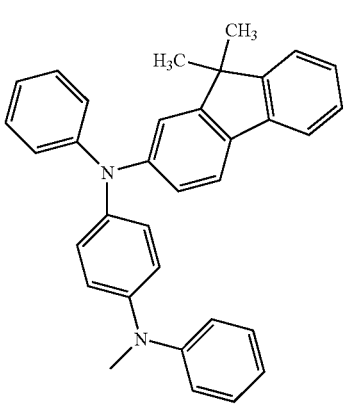

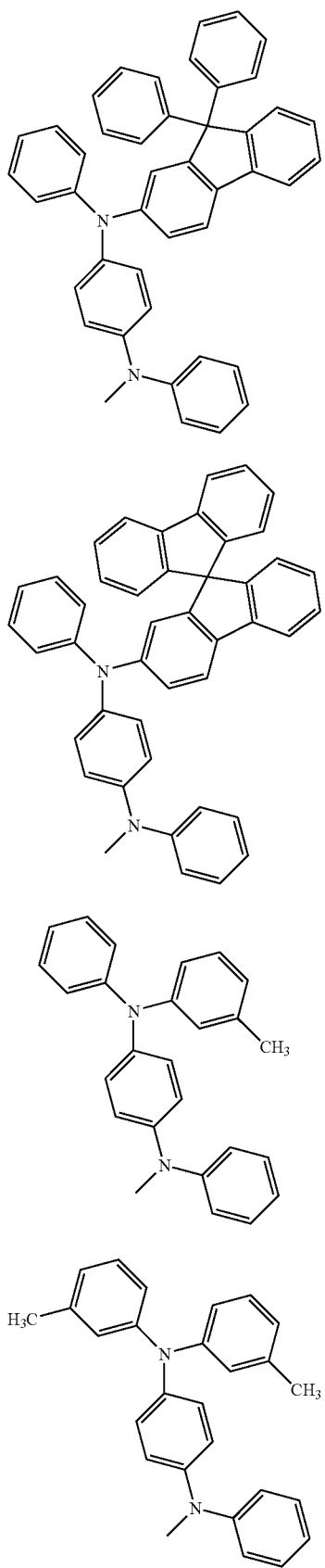
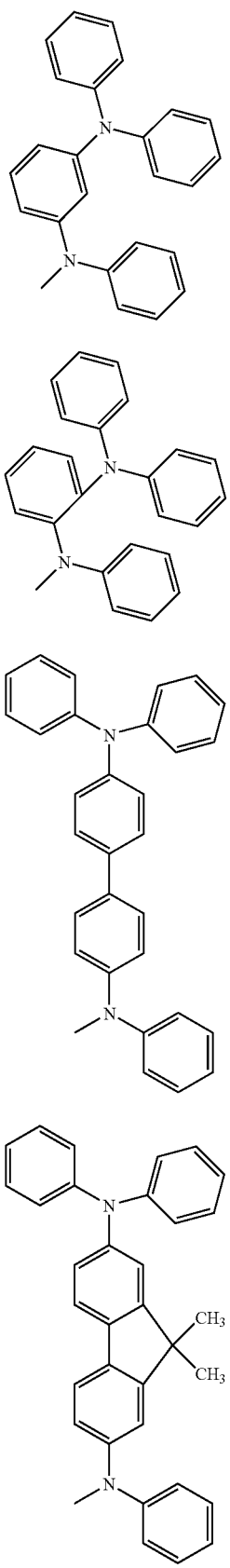

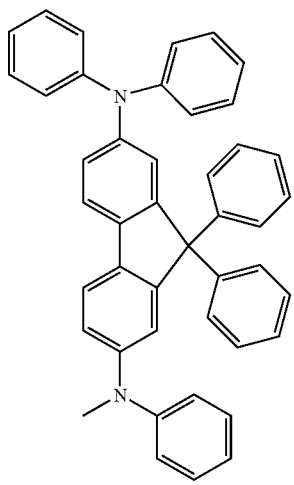
(31-24)
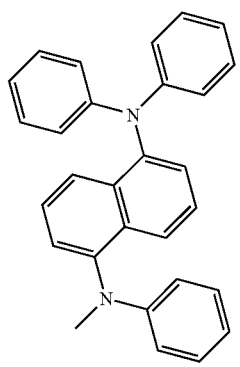
(31-27)
Further, in General Formula (1-2), a substituent represented by Structural Formulae (23-1) to (23-9) can be given as a substituent represented by $Ar^{21}$, for example.
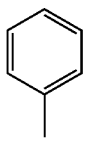
(23-1)
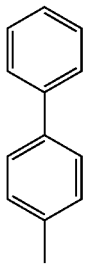
(23-2)
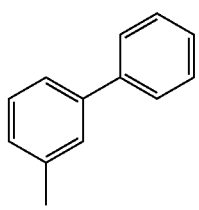
(23-3)
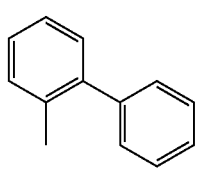
(23-4)
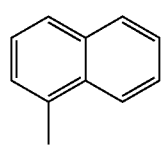
(23-5)
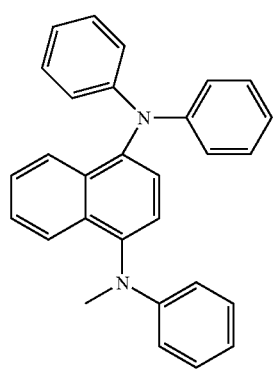
(31-25)
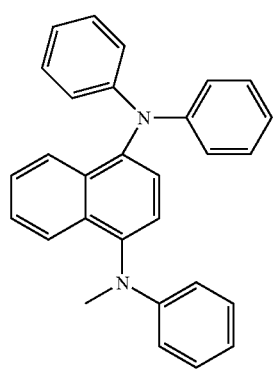
(31-26)

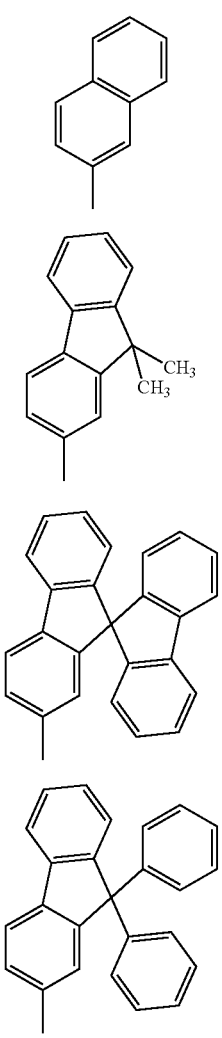
(23-6)
(23-7)
(23-8)
(23-9)
Furthermore, in General Formula (1-2), Structural Formulae (24-1) to (24-18) can be given as specific examples a substituent represented by $R^{31}$, for example.
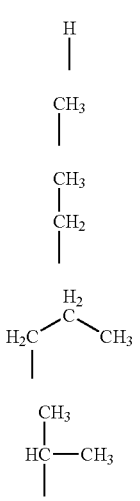
(24-1)
(24-2)
(24-3)
(24-4)
(24-5)
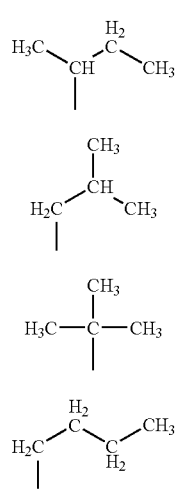
(24-6)
(24-7)
(24-8)
(24-9)
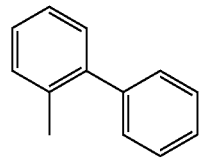
(24-10)
(24-11)
(24-12)
(24-13)
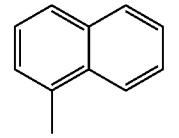
(24-14)
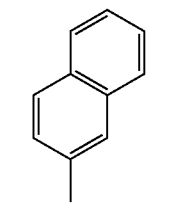
(24-15)

(24-16)
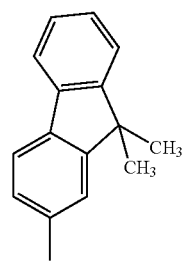
(24-17)
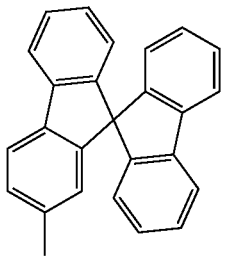
(24-18)
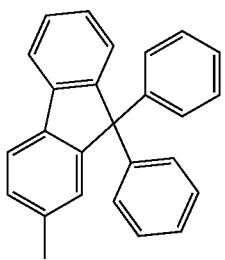
Also, in General Formula (1-2), Structural Formulae (25-1) to (25-17) can be given as specific examples of a substituent represented by $R^{32}$, for example.
(25-1)
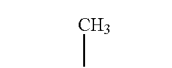
(25-2)
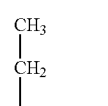
(25-3)
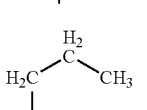
(25-4)
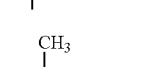
(25-5)
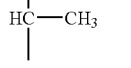
(25-6)
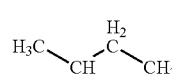
(25-7)
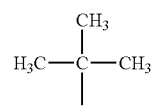
(25-8)
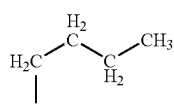
(25-9)
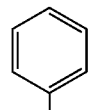
(25-10)
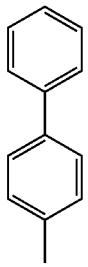
(25-11)
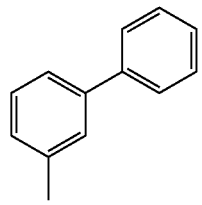
(25-12)
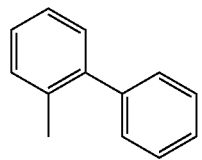
(25-13)
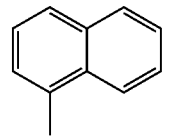
(25-14)
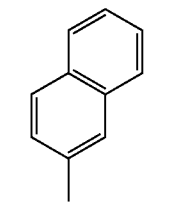
(25-15)
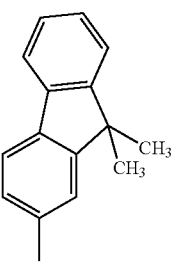

(25-16)
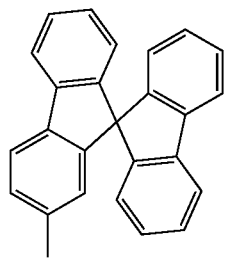
(25-17)
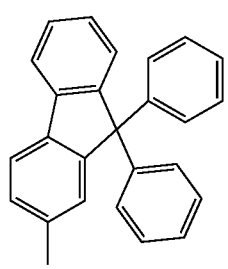
Consequently, Structural Formulae (32-1) to (32-42) can be given as specific examples of a substituent represented by General Formula (1-2), for example.
(32-1)
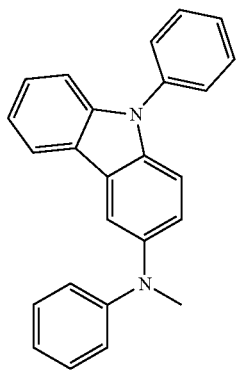
(32-2)
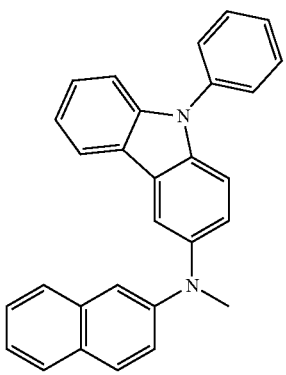
(32-3)
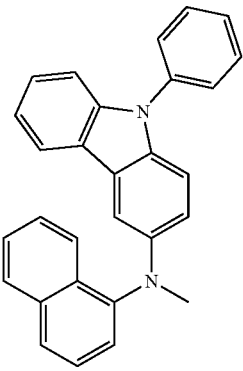
(32-4)
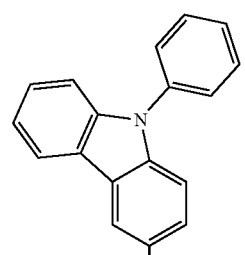
(32-5)
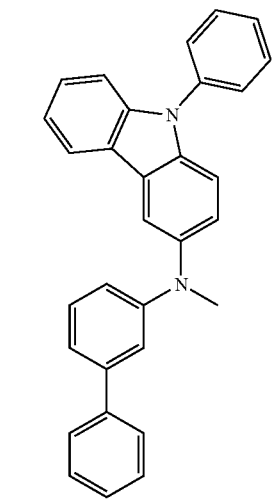

(32-6)
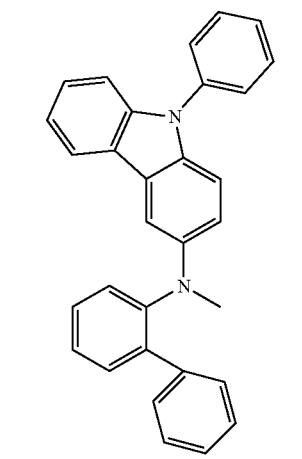
(32-7)
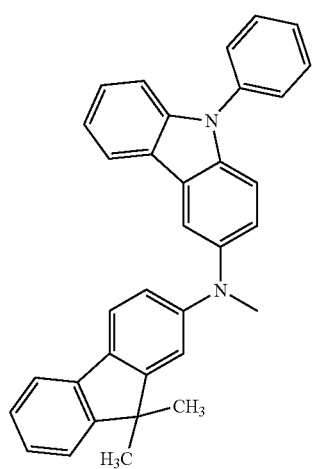
(32-8)
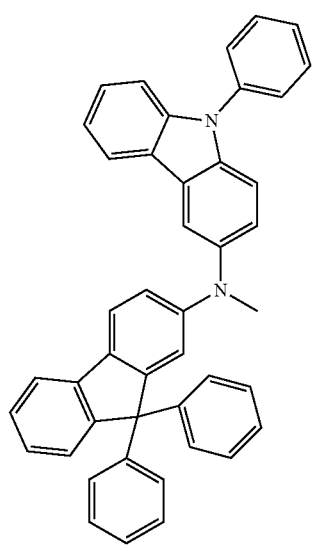
(32-9)
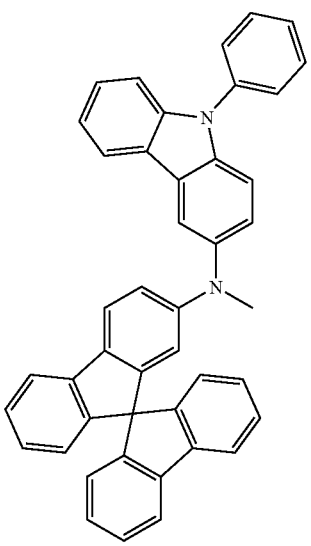
(32-10)
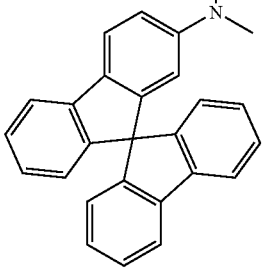
(32-11)
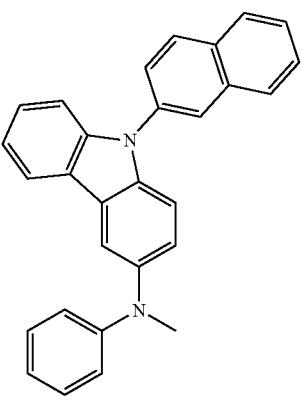

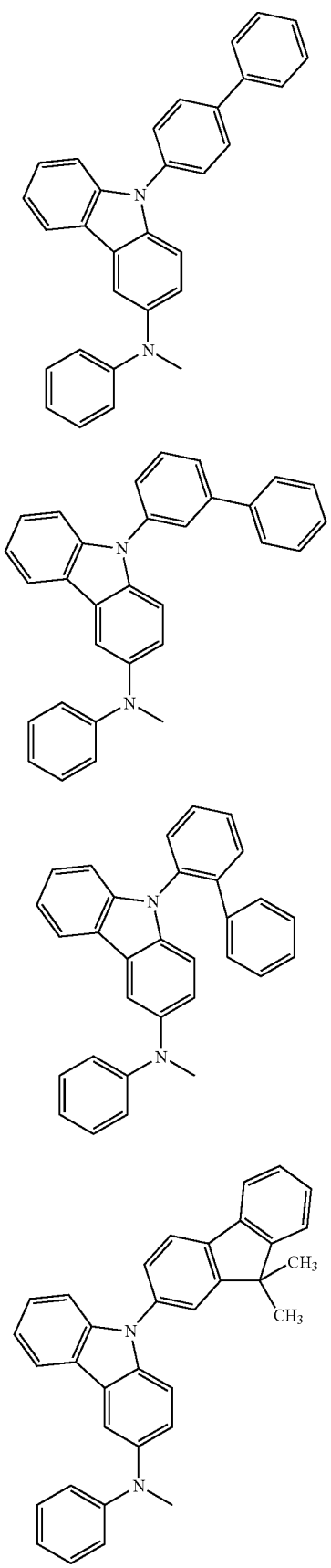
(32-12)
(32-13)
(32-14)
(32-15)
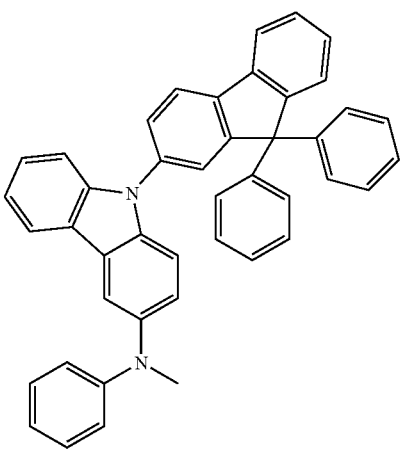
(32-16)
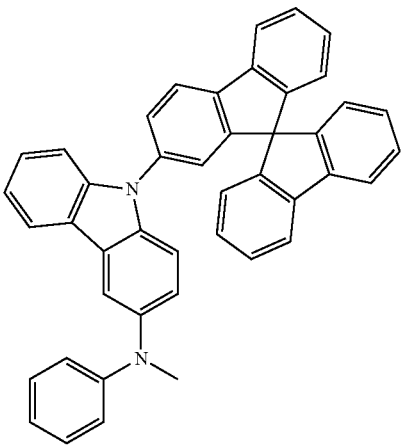
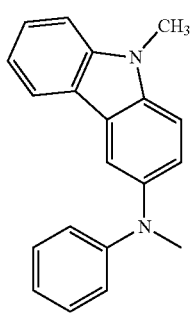
(32-18)
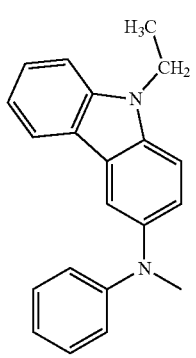
(32-19)

(32-20)
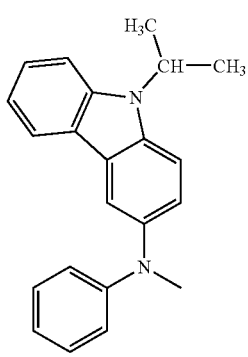
(32-21)
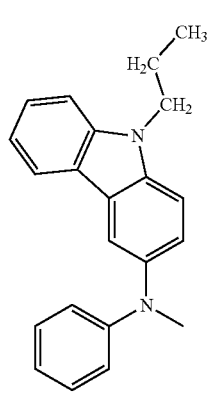
(32-22)
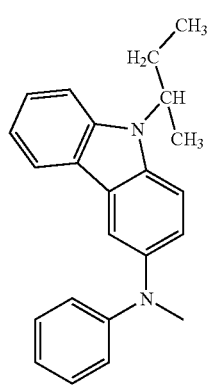
(32-23)
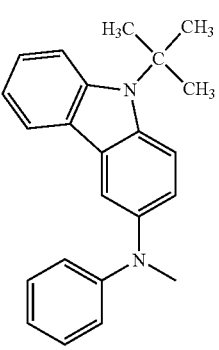
(32-24)
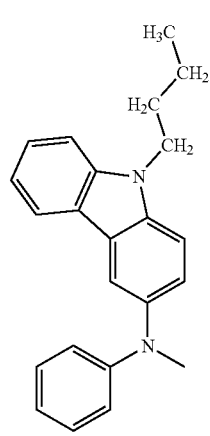
(32-25)
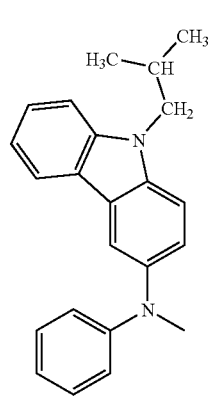
(32-26)
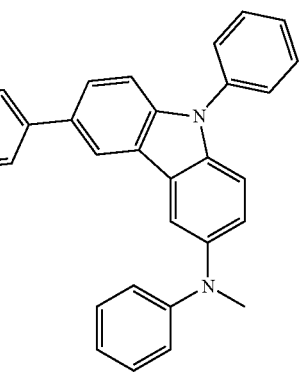
(32-27)
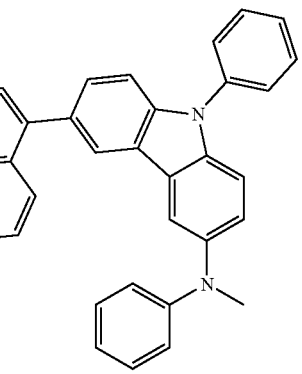

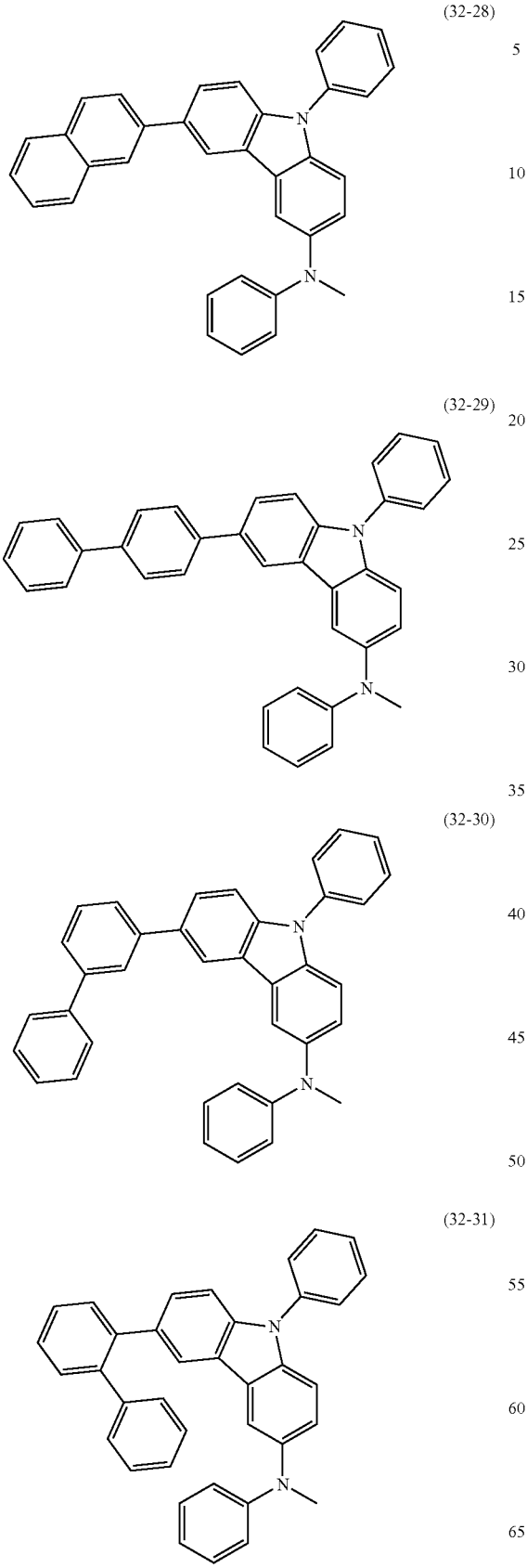
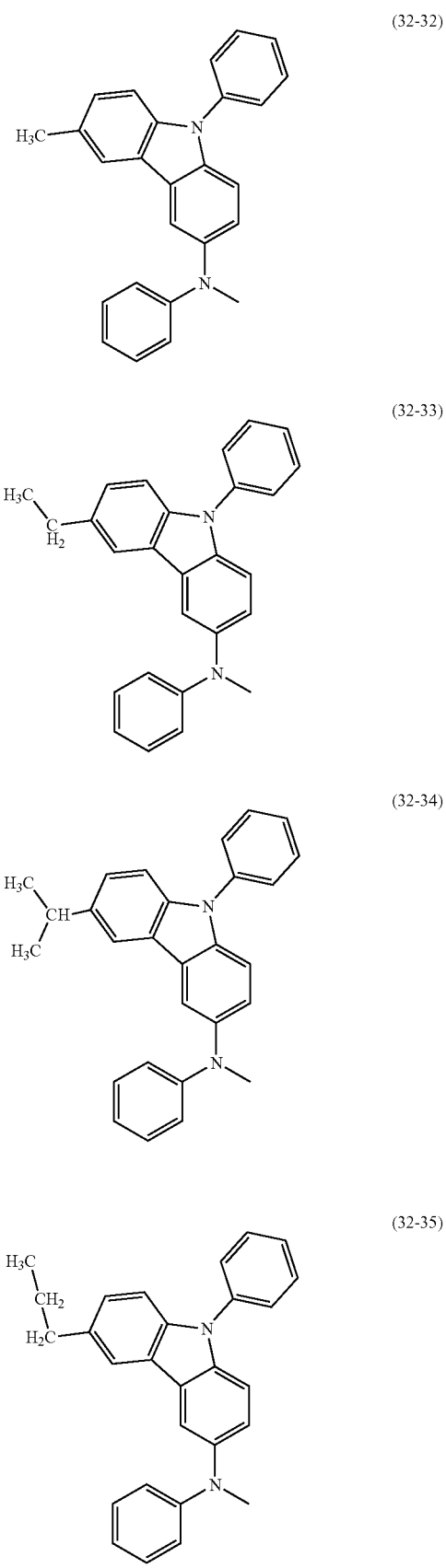

(32-36)
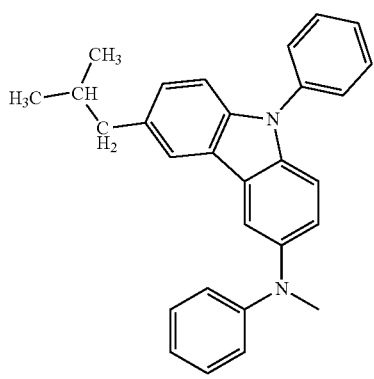
(32-37)
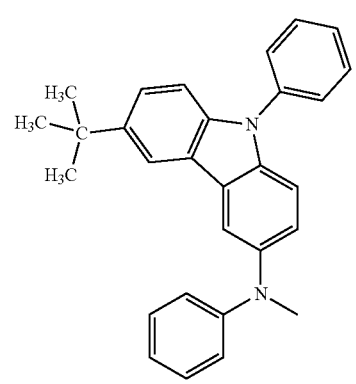
(32-38)
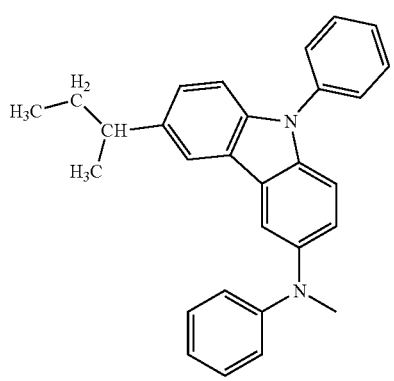
(32-39)
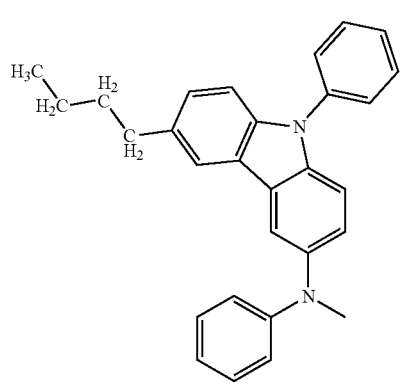
(32-40)
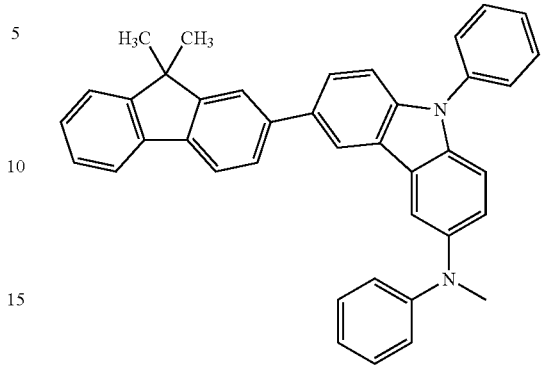
(32-41)
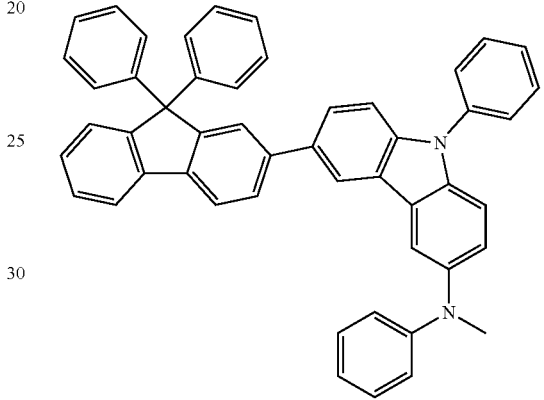
(32-42)
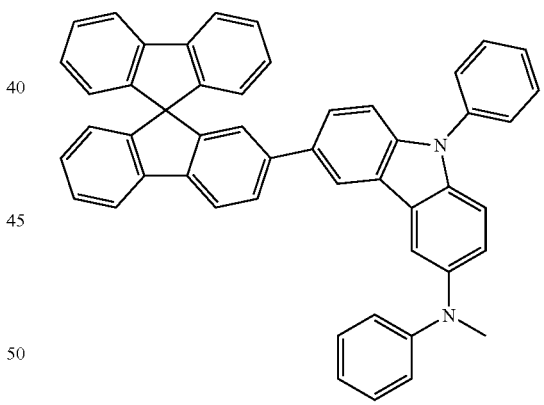
Also, in General Formula (1-3), Structural Formulae (26-1) to (26-9) can be given as specific examples of a substituent represented by $Ar^{31}$, for example.
(26-1)
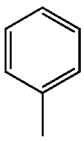

(26-2) 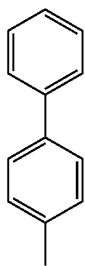
(26-3) 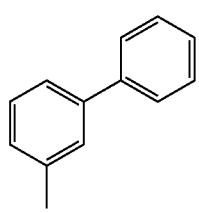
(26-4) 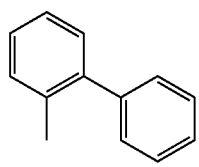
(26-5) 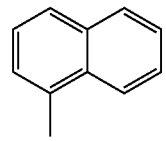
(26-6) 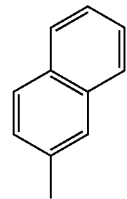
(26-7) 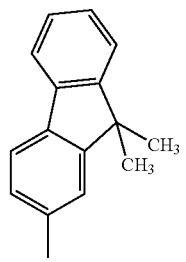
(26-8) 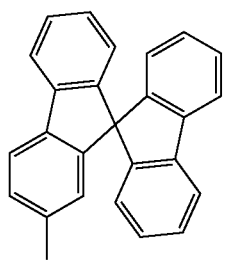
(26-9) 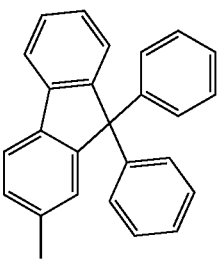
Also, in General Formula (1-3), Structural Formulae (27-1) to (27-10) can be given as specific examples of a substituent represented by β, for example.
(27-1) 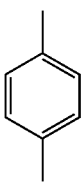
(27-2) 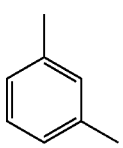
(27-3) 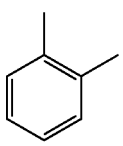
(27-4) 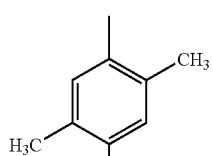
(27-5) 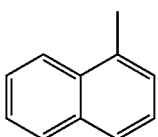
(27-6) 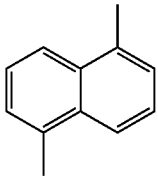

-continued
(27-7) 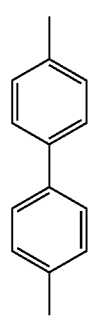
(27-8) 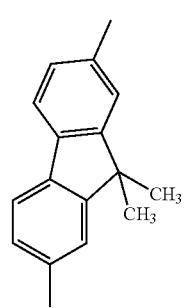
(27-9) 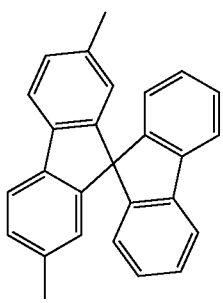
(27-10) 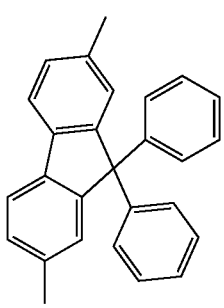
Further, in General Formula (1-3), Structural Formulae (28-1) to (28-18) can be given as specific examples of substituents represented by $R^{41}$ and $R^{42}$, for example.
(28-1) H
(28-2) CH₃
(28-3) CH₃—CH₂
-continued
(28-4) 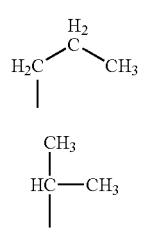
(28-5) 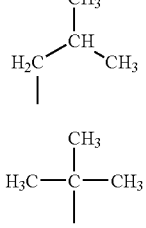
(28-6) 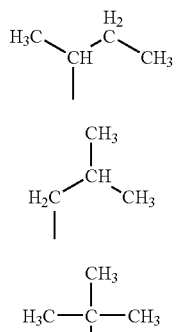
(28-7) 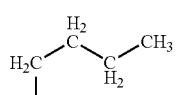
(28-8) 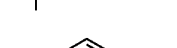
(28-9) 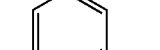
(28-10) 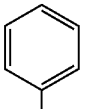
(28-11) 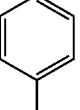
(28-12) 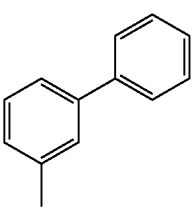
(28-13) 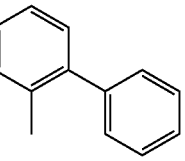
(28-14) 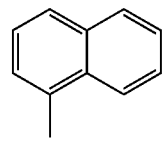

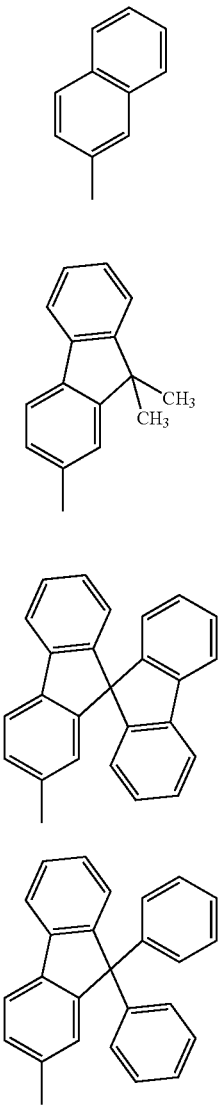
(28-15)
(28-16)
(28-17)
(28-18)
Consequently, Structural Formulae (33-1) to (33-34) can be given as specific examples of a substituent represented by General Formula (1-3), for example.
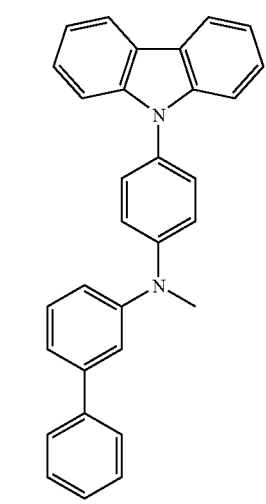
(33-1)
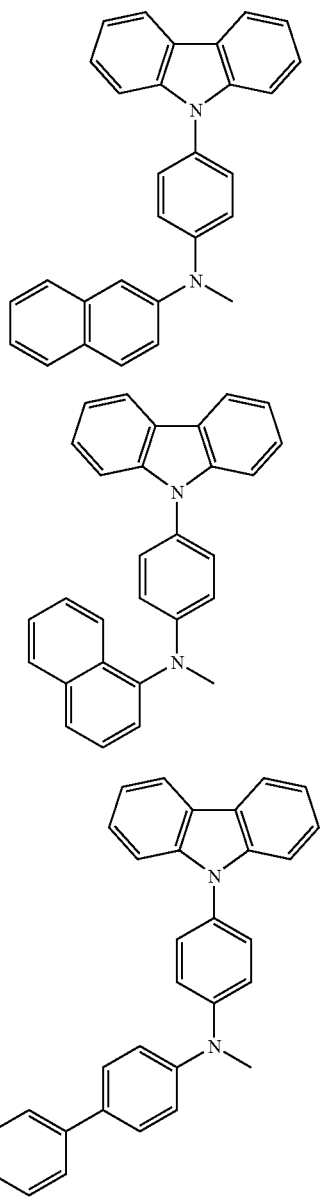
(33-2)
(33-3)
(33-4)
(33-5)

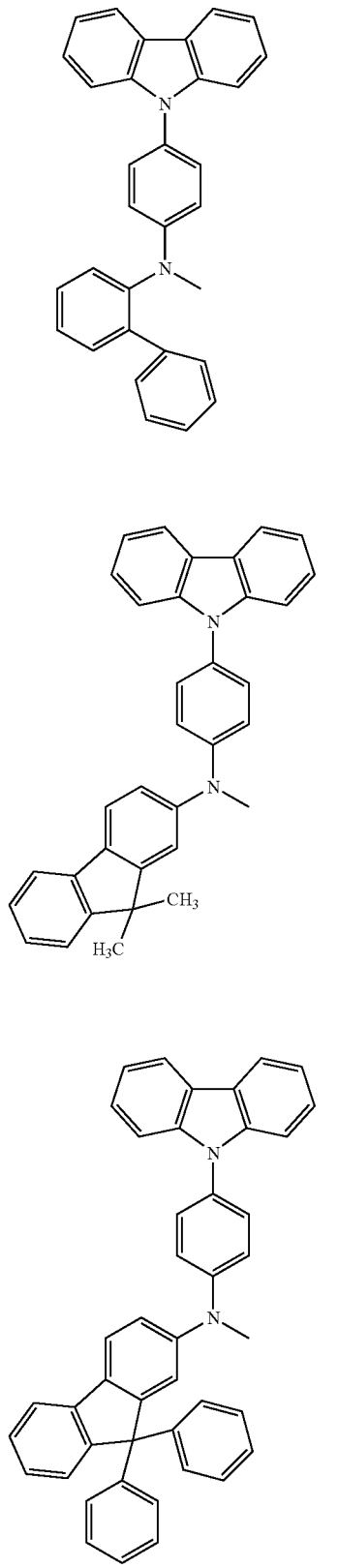
(33-6)
(33-7)
(33-8)
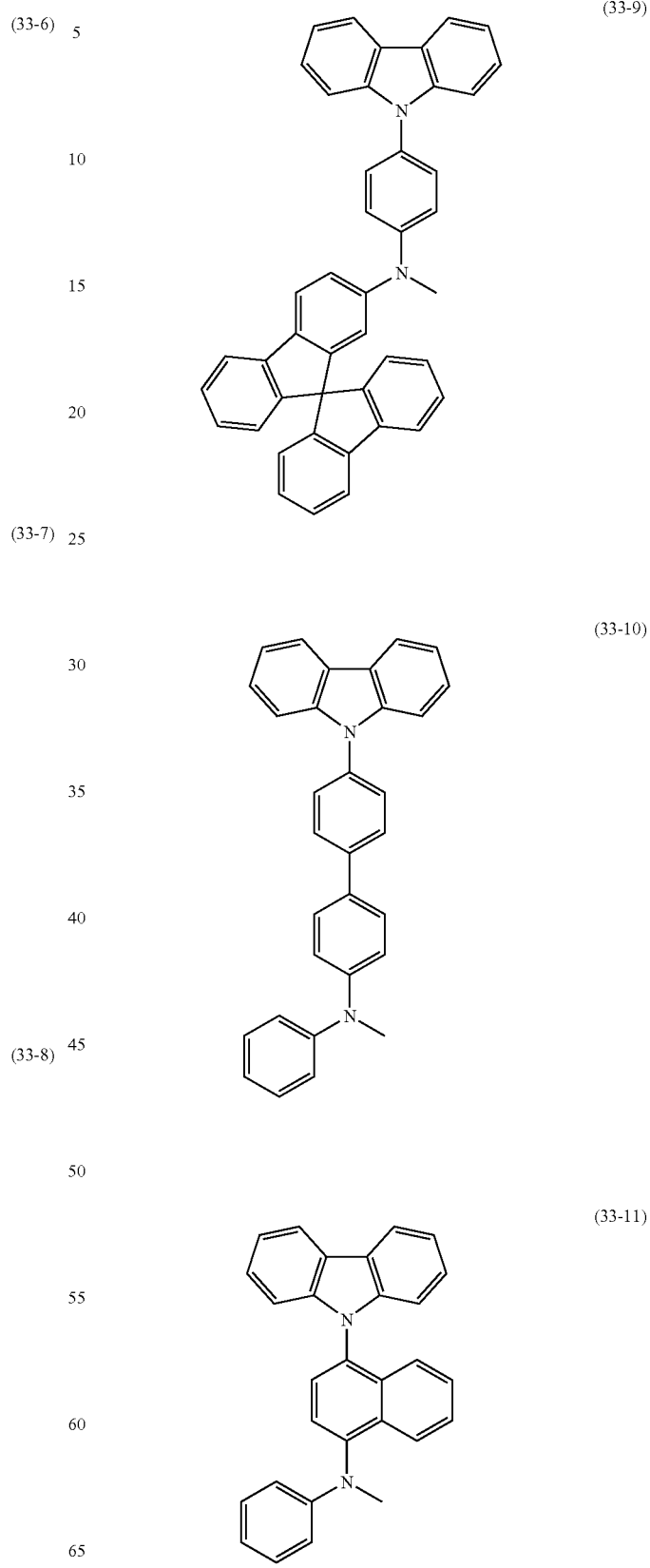
(33-9)
(33-10)
(33-11)

(33-12)
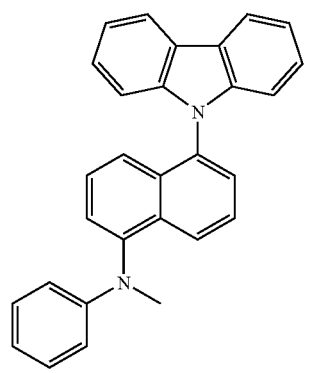
(33-13)
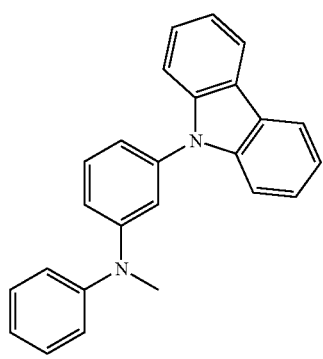
(33-14)
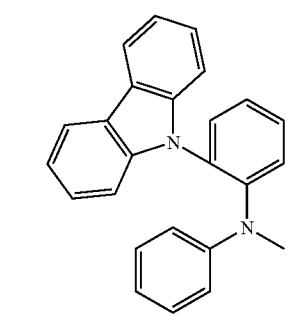
(33-15)
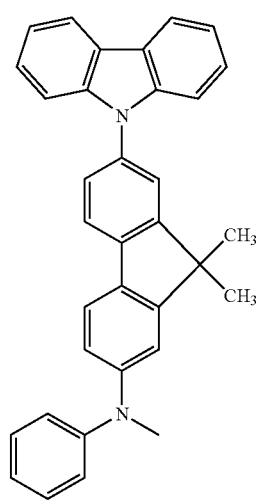
(33-16)
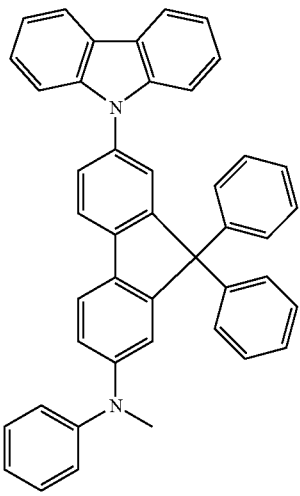
(33-17)
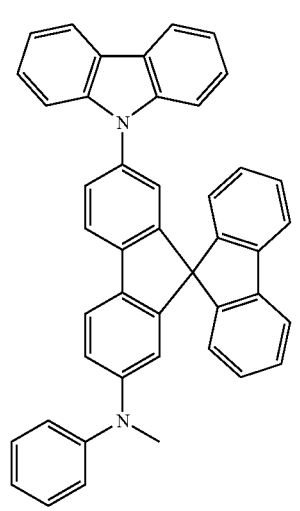
(33-18)
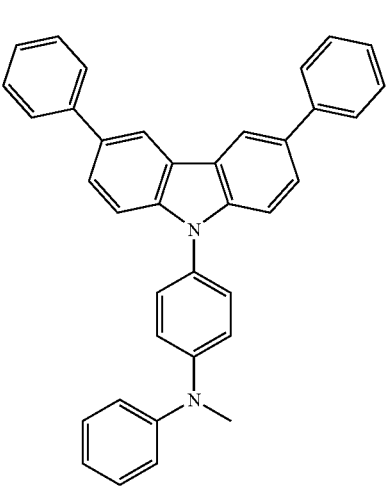

(33-19)
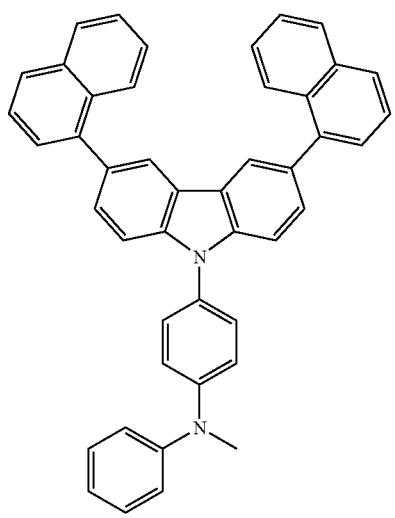
(33-22)
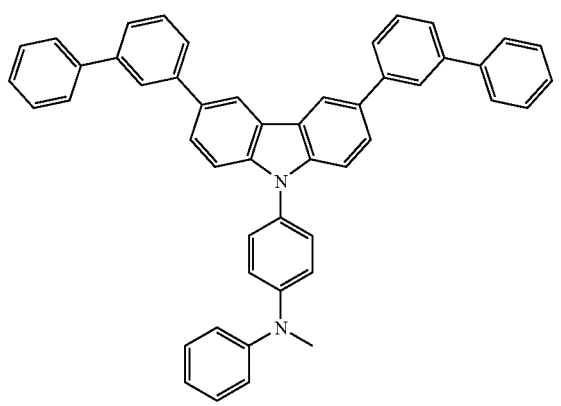
(33-20)
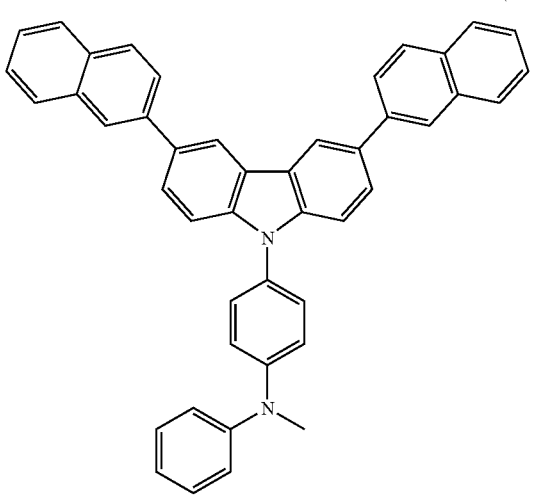
(33-23)
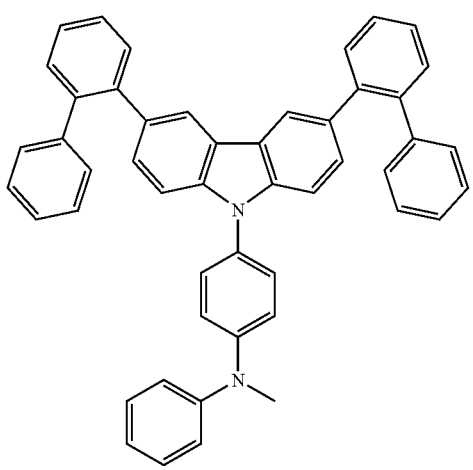
(33-21)
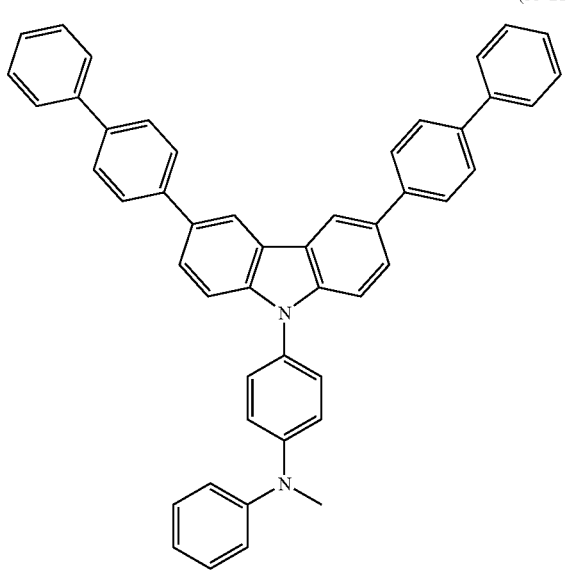
(33-24)
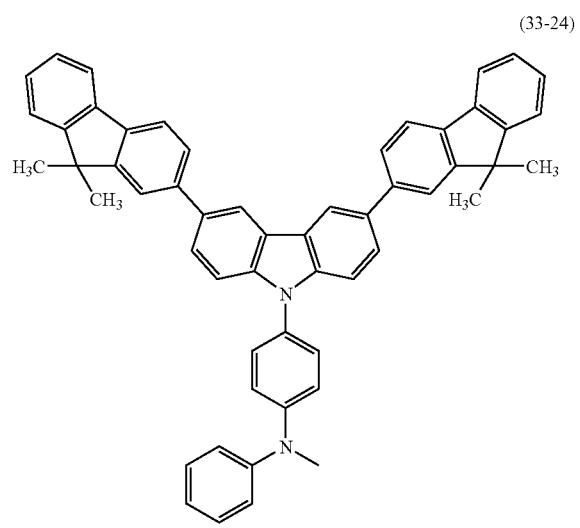

(33-25)
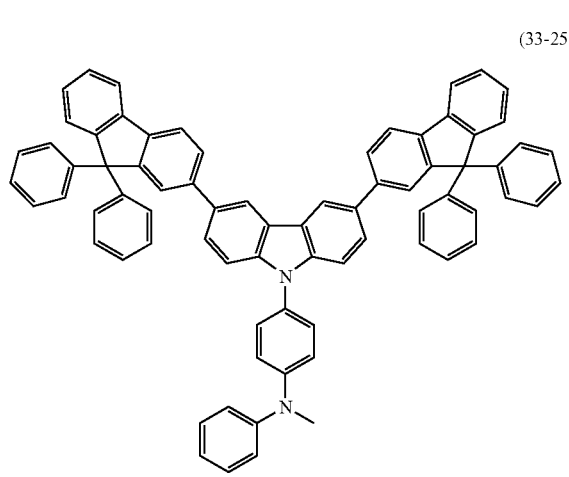
(33-28)
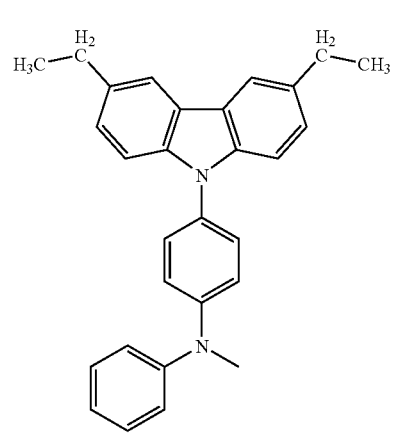
(33-26)
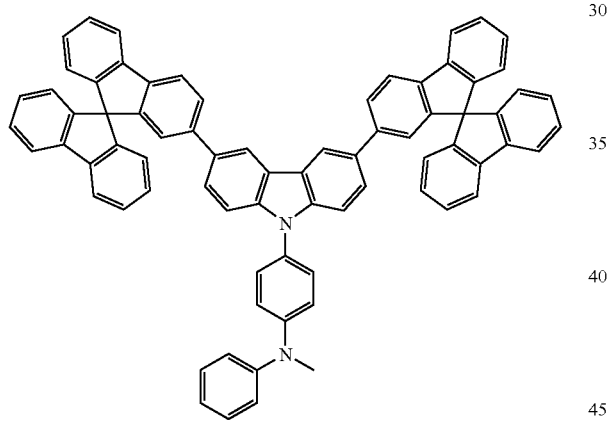
(33-29)
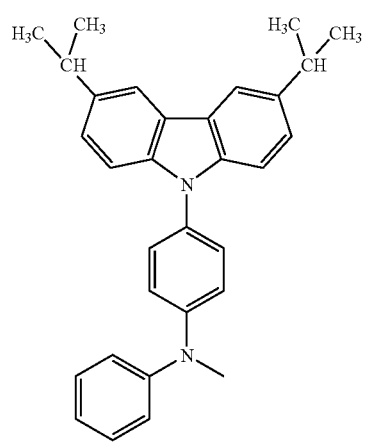
(33-27)
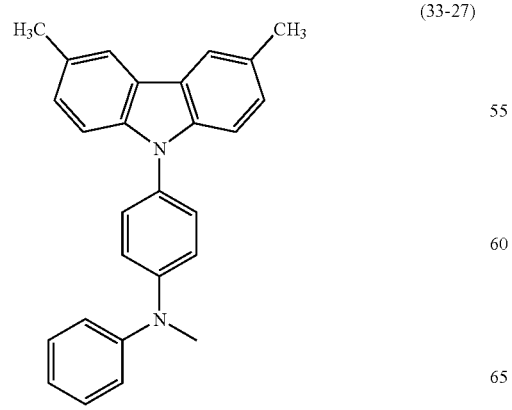
(33-30)
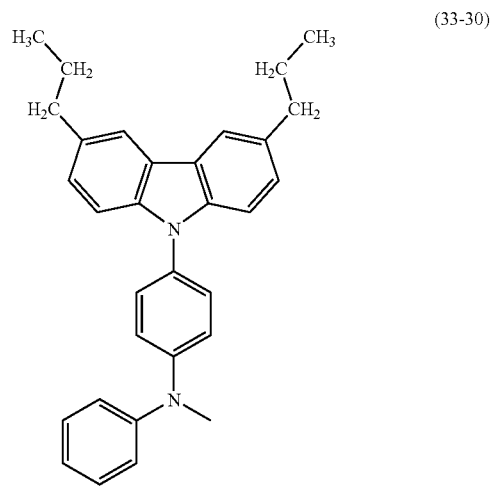

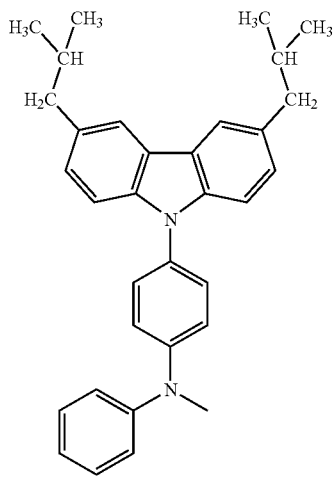
(33-31)
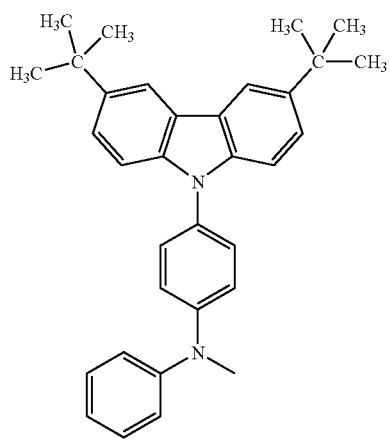
(33-32)
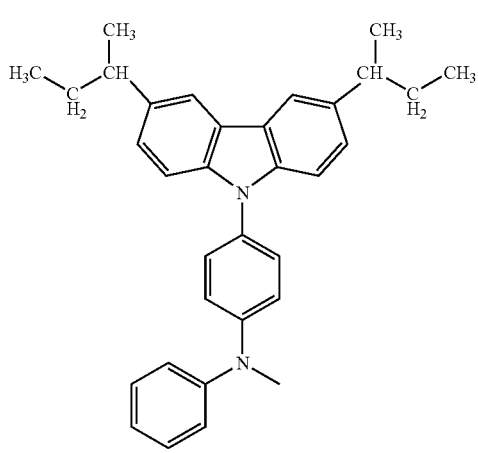
(33-33)
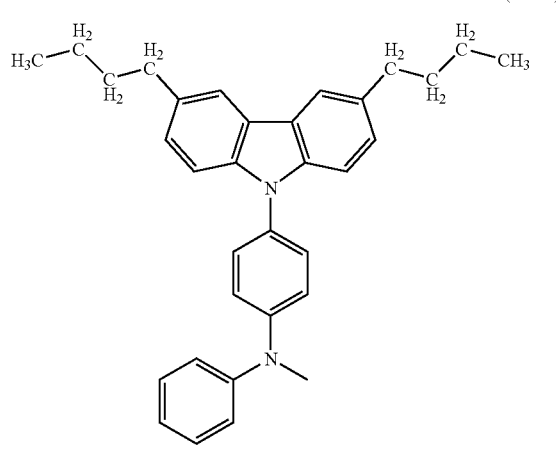
(33-34)
Also, among anthracene derivatives represented by General Formula (1), the anthracene derivative represented by General Formula (2) is preferable.
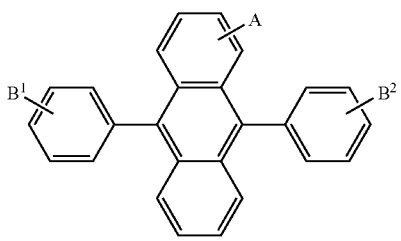
(2)
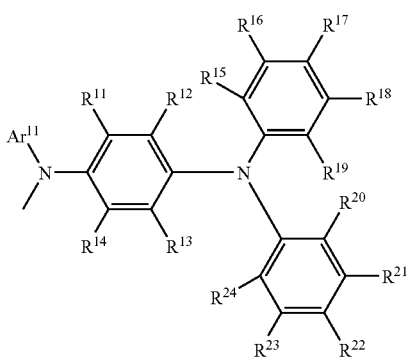
(2-1)
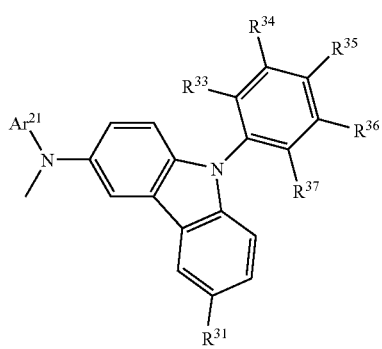
(2-2)

-continued

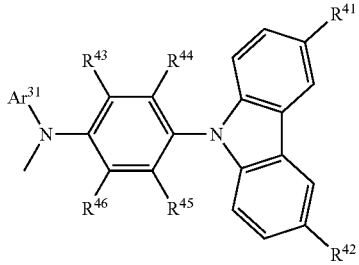
(2-3)

(In the formula, each of $B^1$ and $B^2$ represents any one of halogen, a haloalkyl group, a cyano group, an acyl group, a carboxyl group, an acyloxy group, an alkoxy group, a pyridyl group, a quinolyl group, an isoquinolyl group, and an oxazolyl group, while A represents a substituent given by any one of General Formulae (2-1) to (2-3). In General Formulae (2-1) to (2-3), $Ar^{11}$ represents an aryl group having 6 to 25 carbon atoms; each of $R^{11}$ to $R^{24}$ represents any one of a hydrogen atom, an alkyl group having 1 to 4 carbon atoms, and an aryl group having 6 to 15 carbon atoms; $Ar^{21}$ represents an aryl group having 6 to 25 carbon atoms; $R^{31}$ represents any one of a hydrogen atom, an alkyl group having 1 to 4 carbon atoms, and an aryl group having 6 to 25 carbon atoms; each of $R^{33}$ to $R^{37}$ represents any one of a hydrogen atom, an alkyl group having 1 to 4 carbon atoms, and an aryl group having 6 to 15 carbon atoms; $Ar^{31}$ represents an aryl group having 6 to 25 carbon atoms; each of $R^{41}$ and $R^{42}$ represents any one of a hydrogen atom, an alkyl group having 1 to 4 carbon atoms, and an aryl group having 6 to 25 carbon atoms; and each of $R^{43}$ to $R^{46}$ represents any one of a hydrogen atom, an alkyl group having 1 to 4 carbon atoms, and an aryl group having 6 to 15 carbon atoms.)

Also, among anthracene derivatives represented by General Formula (1), the anthracene derivative represented by General Formula (3) is preferable.

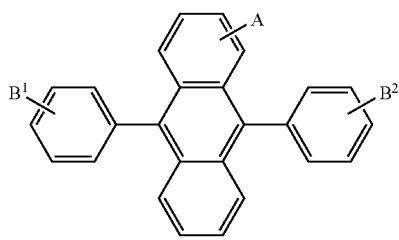
(3)

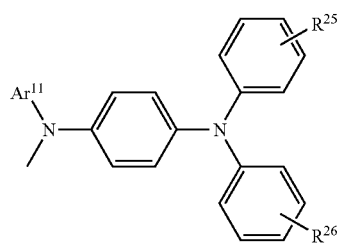
(3-1)

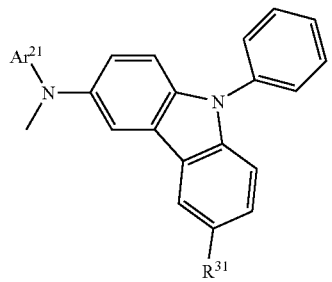
(3-2)

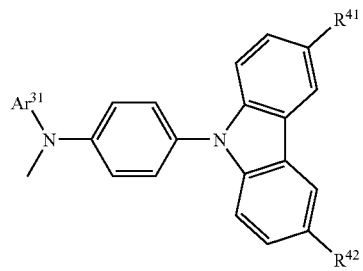
(3-3)

(In the formula, each of $B^1$ and $B^2$ represents any one of halogen, a haloalkyl group, a cyano group, an acyl group, a carboxyl group, an acyloxy group, an alkoxy group, a pyridyl group, a quinolyl group, an isoquinolyl group, and an oxazolyl group, while A represents a substituent given by any one of General Formulae (3-1) to (3-3). In General Formulae (3-1) to (3-3), $Ar^{11}$ represents an aryl group having 6 to 25 carbon atoms; each of $R^{25}$ and $R^{26}$ represents any one of a hydrogen atom, an alkyl group having 1 to 4 carbon atoms, and an aryl group having 6 to 15 carbon atoms; $Ar^{21}$ represents an aryl group having 6 to 25 carbon atoms; $R^{31}$ represents any one of a hydrogen atom, an alkyl group having 1 to 4 carbon atoms, and an aryl group having 6 to 25 carbon atoms; $Ar^{31}$ represents an aryl group having 6 to 25 carbon atoms; and each of $R^{41}$ and $R^{42}$ represents any one of a hydrogen atom, an alkyl group having 1 to 4 carbon atoms, and an aryl group having 6 to 25 carbon atoms.)

Also, among anthracene derivatives represented by General Formula (1), the anthracene derivative represented by General Formula (4) is preferable.

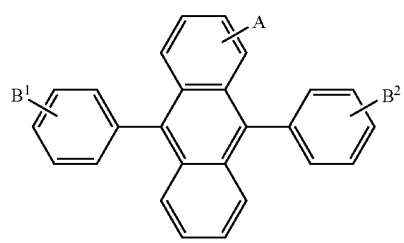
(4)

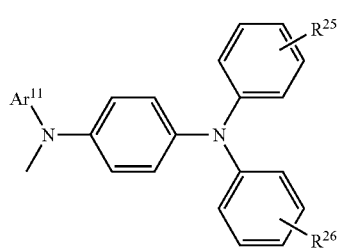
(4-1)

-continued (4-2)

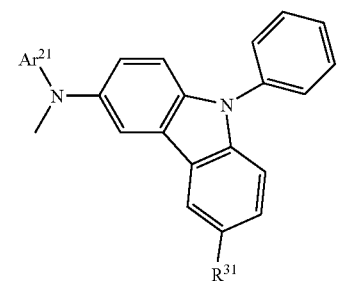

(4-3)

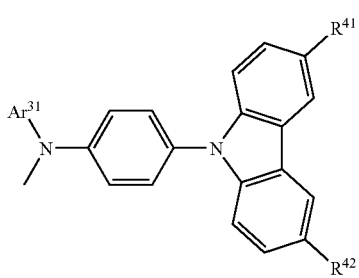

(In the formula, each of $B^1$ and $B^2$ represents any one of halogen, a haloalkyl group, a cyano group, an acyl group, a carboxyl group, an acyloxy group, an alkoxy group, a pyridyl group, a quinolyl group, an isoquinolyl group, and an oxazolyl group, while A represents a substituent given by any one of General Formulae (4-1) to (4-3). In General Formulae (4-1) to (4-3), $Ar^{11}$ represents any one of a phenyl group, a 1-naphthyl group, and a 2-naphthyl group; each of $R^{25}$ and $R^{26}$ represents any one of a hydrogen atom, an alkyl group having 1 to 4 carbon atoms, and an aryl group having 6 to 15 carbon atoms; $Ar^{21}$ represents any one of a phenyl group, a 1-naphthyl group, and a 2-naphthyl group; $R^{31}$ represents any one of a hydrogen atom, an alkyl group having 1 to 4 carbon atoms, and an aryl group having 6 to 25 carbon atoms; $Ar^{31}$ represents any one of a phenyl group, a 1-naphthyl group, and a 2-naphthyl group; and each of $R^{41}$ and $R^{42}$ represents any one of a hydrogen atom, an alkyl group having 1 to 4 carbon atoms, and an aryl group having 6 to 25 carbon atoms.)

Further, in foregoing General Formulae (1) to (4), $B^1$ and $B^2$ are preferably substituents having the same structure. Using the substituents having the same structure can facilitate synthesis thereof.

Furthermore, in foregoing General Formulae (1) to (4), A preferably bonds at the 2-position of the anthracene skeleton. By bonding at the 2-position, steric hindrance between A and phenyl groups is reduced.

That is, a preferable anthracene derivative is represented by General Formula (5).

(5)

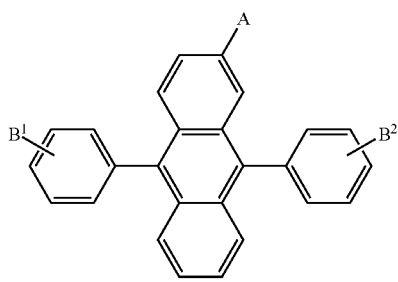

-continued (5-1)

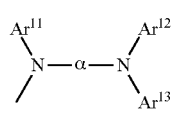

(5-2)

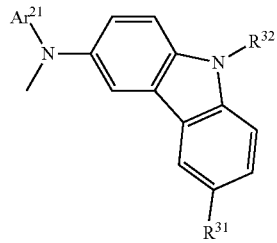

(5-3)

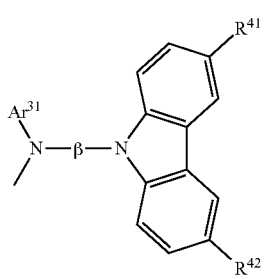

(In the formula, each of $B^1$ and $B^2$ represents any one of halogen, a haloalkyl group, a cyano group, an acyl group, a carboxyl group, an acyloxy group, an alkoxy group, a pyridyl group, a quinolyl group, an isoquinolyl group, and an oxazolyl group, while A represents a substituent given by any one of General Formulae (5-1) to (5-3). In General Formulae (5-1) to (5-3), each of $Ar^{11}$ to $Ar^{13}$ represents an aryl group having 6 to 25 carbon atoms; a represents an arylene group having 6 to 25 carbon atoms; $Ar^{21}$ represents an aryl group having 6 to 25 carbon atoms; $R^{31}$ represents any one of a hydrogen atom, an alkyl group having 1 to 4 carbon atoms, and an aryl group having 6 to 25 carbon atoms; $R^{32}$ represents an alkyl group having 1 to 4 carbon atoms or an aryl group having 6 to 25 carbon atoms; $Ar^{31}$ represents an aryl group having 6 to 25 carbon atoms; represents an arylene group having 6 to 25 carbon atoms; and each of $R^{41}$ and $R^{42}$ represents any one of a hydrogen atom, an alkyl group having 1 to 4 carbon atoms, and an aryl group having 6 to 25 carbon atoms.)

Also, a preferable anthracene derivative is represented by General Formula (6).

(6)

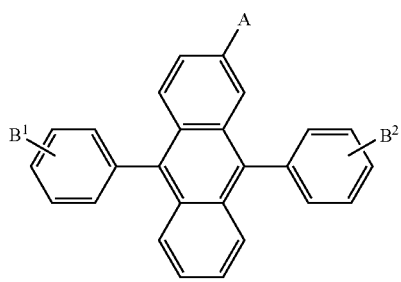

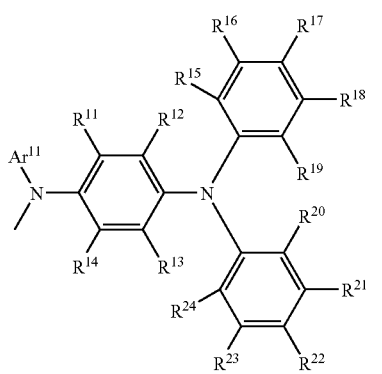

(6-1)

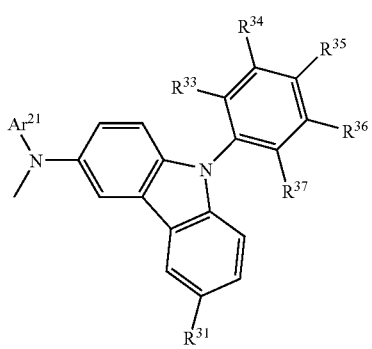

(6-2)

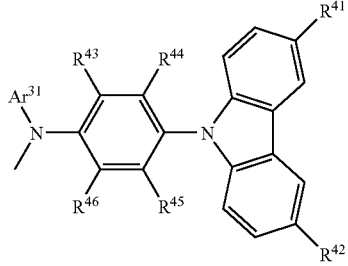

(6-3)

(In the formula, each of $B^1$ and $B^2$ represents any one of halogen, a haloalkyl group, a cyano group, an acyl group, a carboxyl group, an acyloxy group, an alkoxy group, a pyridyl group, a quinolyl group, an isoquinolyl group, and an oxazolyl group, while A represents a substituent given by any one of General Formulae (6-1) to (6-3). In General Formulae (6-1) to (6-3), $Ar^{11}$ represents an aryl group having 6 to 25 carbon atoms; each of $R^{11}$ to $R^{24}$ represents any one of a hydrogen atom, an alkyl group having 1 to 4 carbon atoms, and an aryl group having 6 to 15 carbon atoms; $Ar^{21}$ represents an aryl group having 6 to 25 carbon atoms; $R^{31}$ represents any one of a hydrogen atom, an alkyl group having 1 to 4 carbon atoms, and an aryl group having 6 to 25 carbon atoms; each of $R^{33}$ to $R^{37}$ represents any one of a hydrogen atom, an alkyl group having 1 to 4 carbon atoms, and an aryl group having 6 to 15 carbon atoms; $Ar^{31}$ represents an aryl group having 6 to 25 carbon atoms; each of $R^{41}$ and $R^{42}$ represents any one of a hydrogen atom, an alkyl group having 1 to 4 carbon atoms, and an aryl group having 6 to 25 carbon atoms; and each of $R^{43}$ to $R^{46}$ represents any one of a hydrogen atom, an alkyl group having 1 to 4 carbon atoms, and an aryl group having 6 to 15 carbon atoms.)

Further, the anthracene derivative represented by General Formula (7) is preferable.

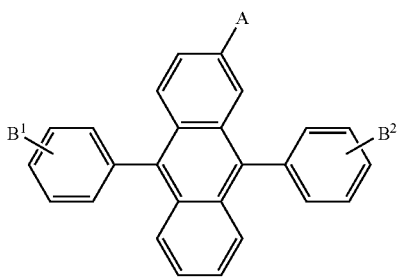

(7)

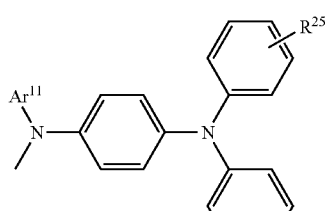

(7-1)

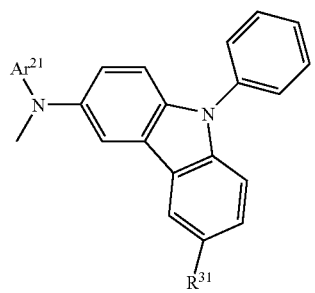

(7-2)

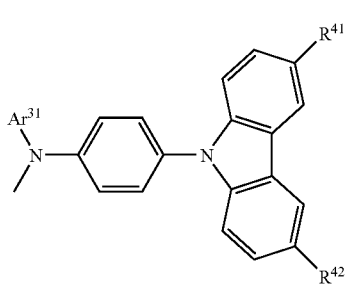

(7-3)

(In the formula, each of $B^1$ and $B^2$ represents any one of halogen, a haloalkyl group, a cyano group, an acyl group, a carboxyl group, an acyloxy group, an alkoxy group, a pyridyl group, a quinolyl group, an isoquinolyl group, and an oxazolyl group, while A represents a substituent given by any one of General Formulae (7-1) to (7-3). In General Formulae (7-1) to (7-3), $Ar^{11}$ represents an aryl group having 6 to 25 carbon atoms; each of $R^2$ and $R^{26}$ represents any one of a hydrogen atom, an alkyl group having 1 to 4 carbon atoms, and an aryl group having 6 to 15 carbon atoms; $Ar^{21}$ represents an aryl group having 6 to 25 carbon atoms; $R^{31}$ represents any one of a hydrogen atom, an alkyl group having 1 to 4 carbon atoms, and an aryl group having 6 to 25 carbon atoms; $Ar^{31}$ represents an aryl group having 6 to 25 carbon atoms; and each of $R^{41}$ and $R^{42}$ represents any one of a hydrogen atom, an alkyl group having 1 to 4 carbon atoms, and an aryl group having 6 to 25 carbon atoms.)

Furthermore, the anthracene derivative represented by General Formula (8) is preferable.

(8)

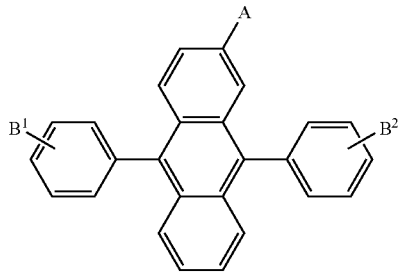

(8-1)

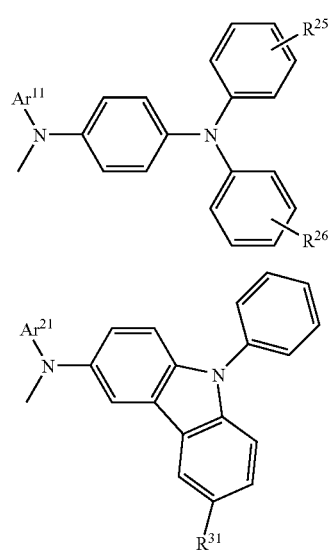

(8-2)

(8-3)

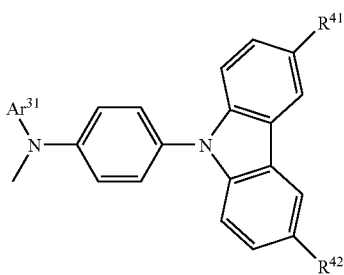

(In the formula, each of $B^1$ and $B^2$ represents any one of halogen, a haloalkyl group, a cyano group, an acyl group, a carboxyl group, an acyloxy group, an alkoxy group, a pyridyl group, a quinolyl group, an isoquinolyl group, and an oxazolyl group, while A represents a substituent given by any one of General Formulae (8-1) to (8-3). In General Formulae (8-1) to (8-3), $Ar^{11}$ represents any one of a phenyl group, a 1-naphthyl group, and a 2-naphthyl group; each of $R^{25}$ and $R^{26}$ represents any one of a hydrogen atom, an alkyl group having 1 to 4 carbon atoms, and an aryl group having 6 to 15 carbon atoms; $A^{21}$ represents any one of a phenyl group, a 1-naphthyl group, and a 2-naphthyl group; $R^{31}$ represents any one of a hydrogen atom, an alkyl group having 1 to 4 carbon atoms, and an aryl group having 6 to 25 carbon atoms; $Ar^{31}$ represents any one of a phenyl group, a 1-naphthyl group, and a 2-naphthyl group; and each of $R^{41}$ and $R^{42}$ represents any one of a hydrogen atom, an alkyl group having 1 to 4 carbon atoms, and an aryl group having 6 to 25 carbon atoms.)

In foregoing General Formulae (5) to (8), $B^1$ and $B^2$ are preferably substituents having the same structure. Using the substituents having the same structure can facilitate synthesis thereof.

As specific examples of the anthracene derivative represented by General Formula (1), the anthracene derivatives represented by Structural Formulae (101) to (160), Structural Formulae (201) to (260), and Structural Formulae (301) to (360) can be given. However, the present invention is not limited thereto.

(101)

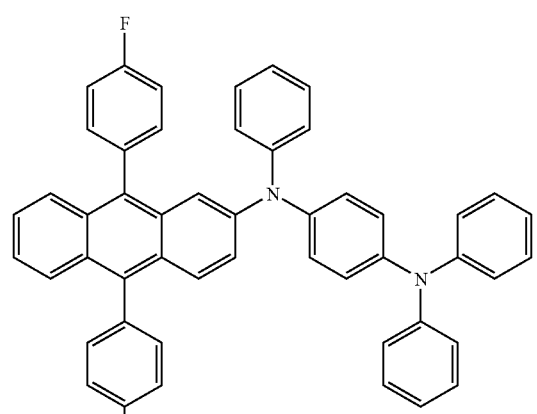

(102)

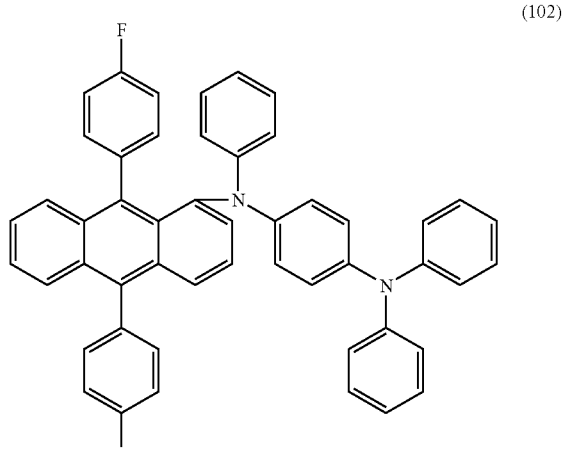

(103)

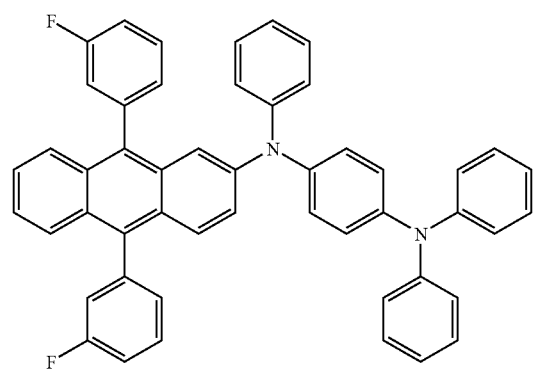

(104)
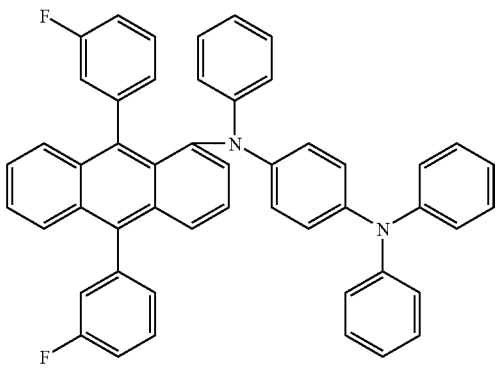
(105)
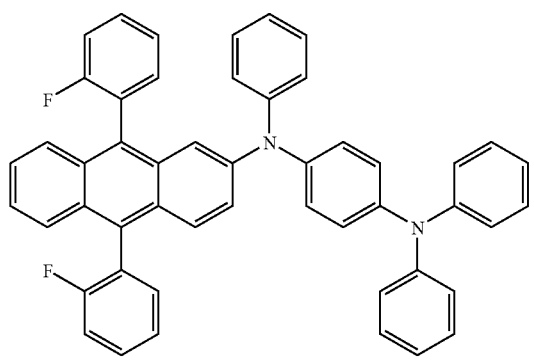
(106)
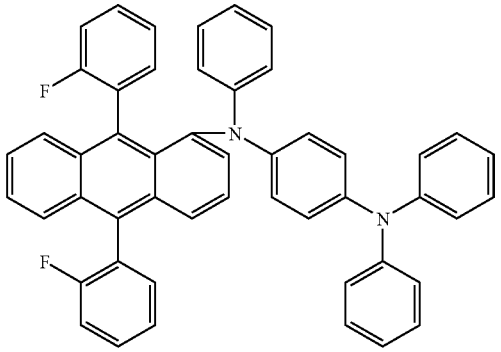
(107)
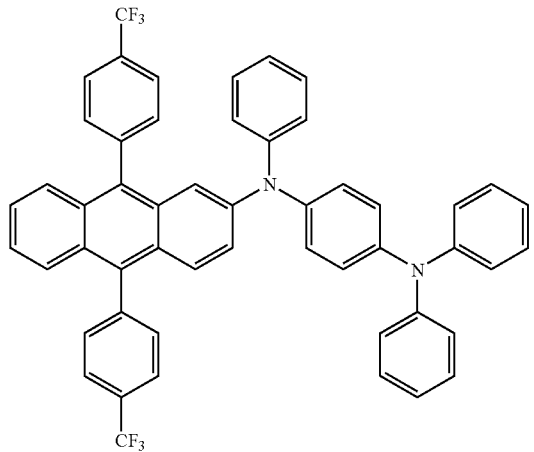
(108)
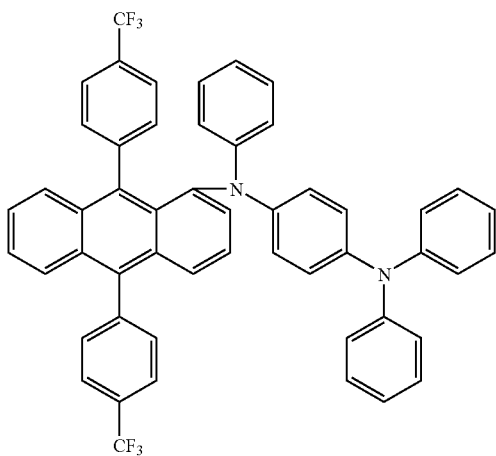
(109)
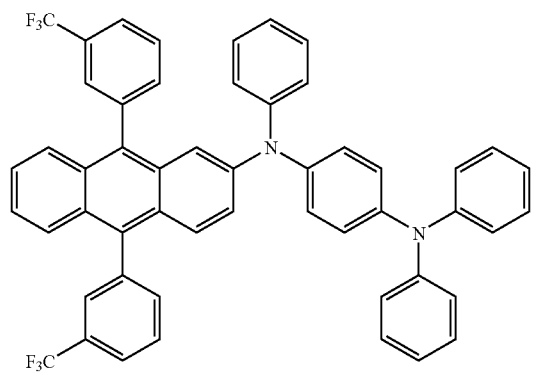
(110)
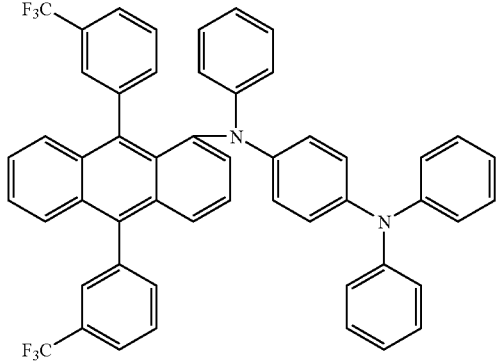
(111)
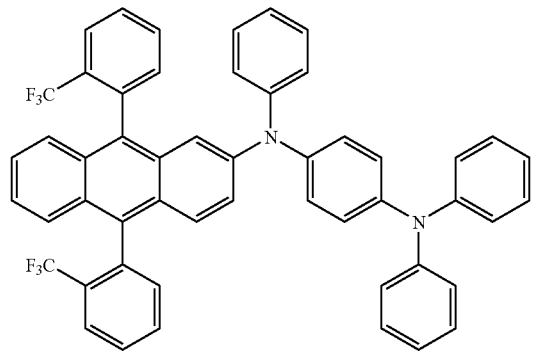

(112)
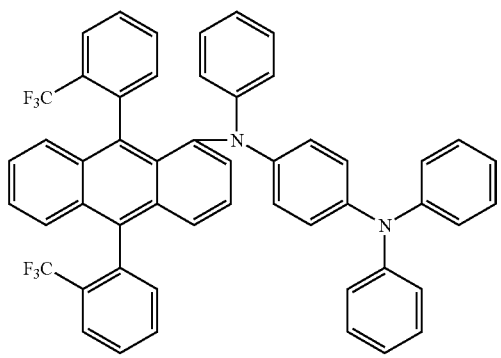
(113)
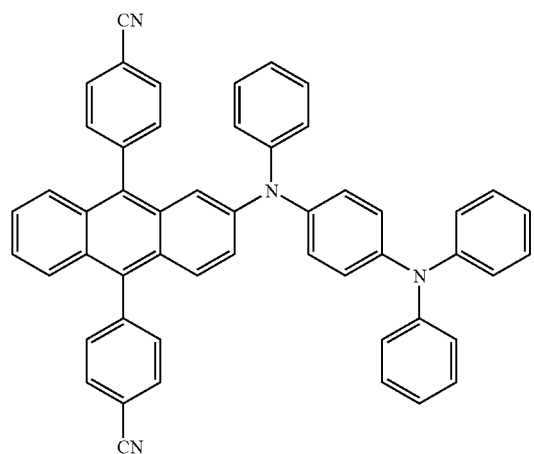
(114)
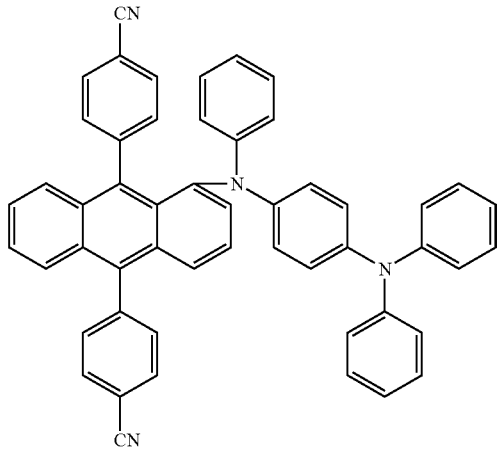
(115)
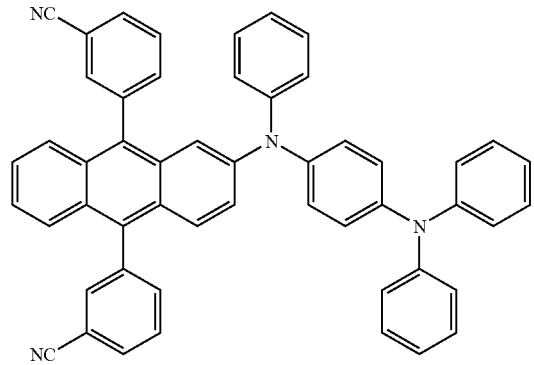
(116)
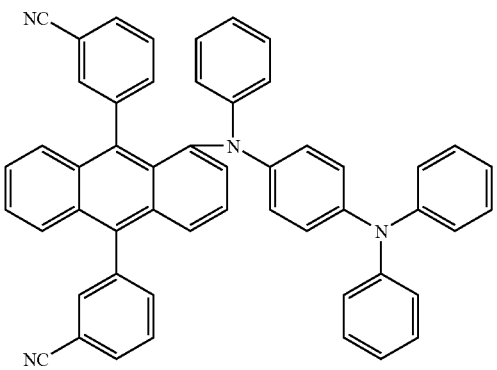
(117)
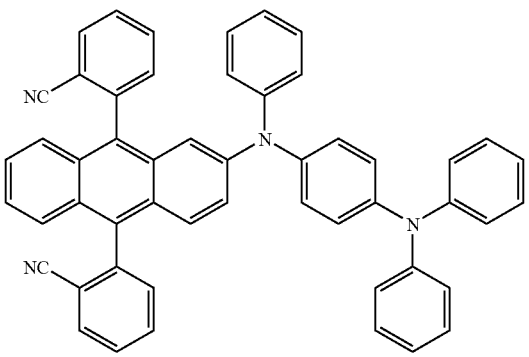
(118)
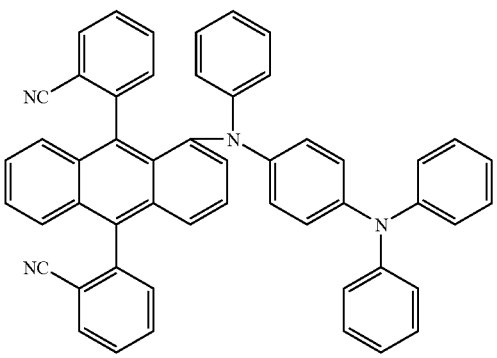
(119)
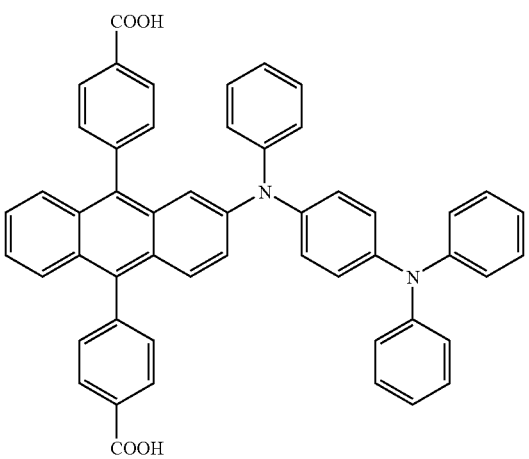

(120)
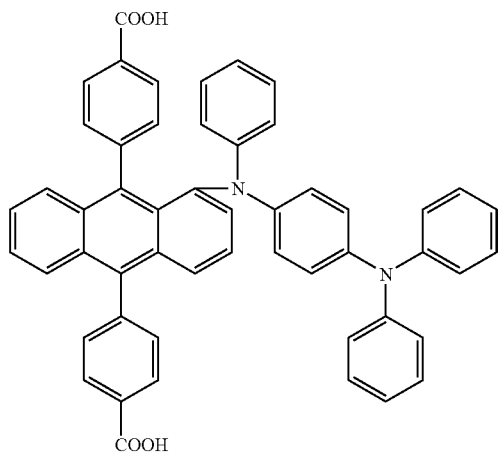
(121)
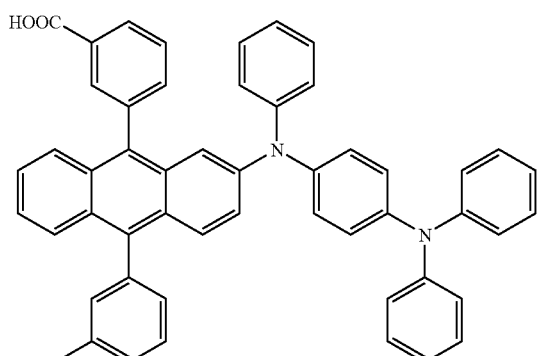
(122)
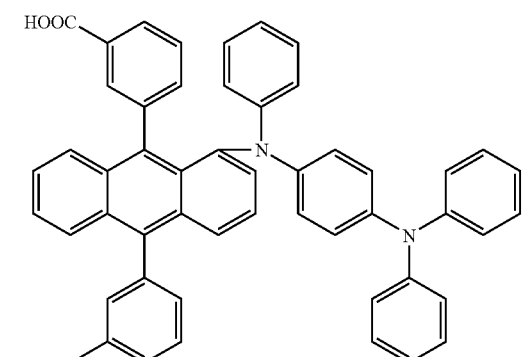
(123)
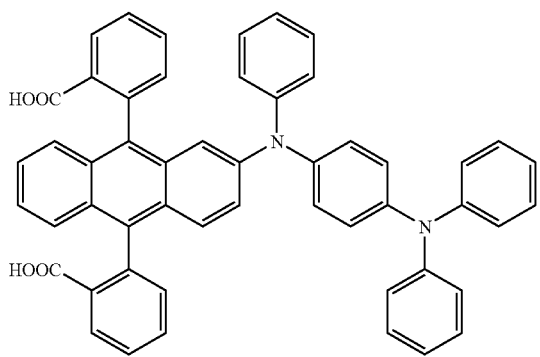
(124)
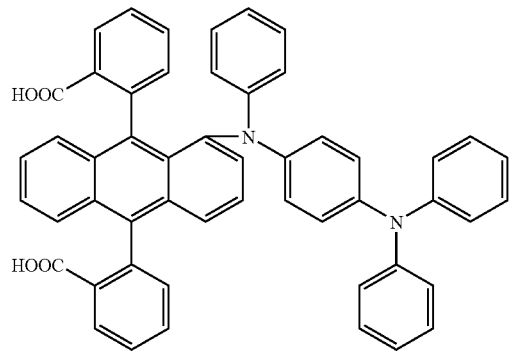
(125)
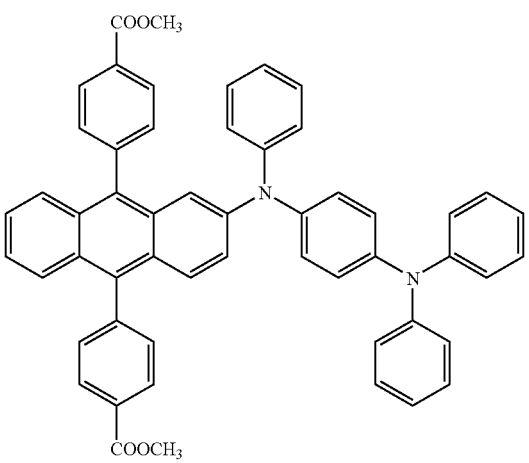
(126)
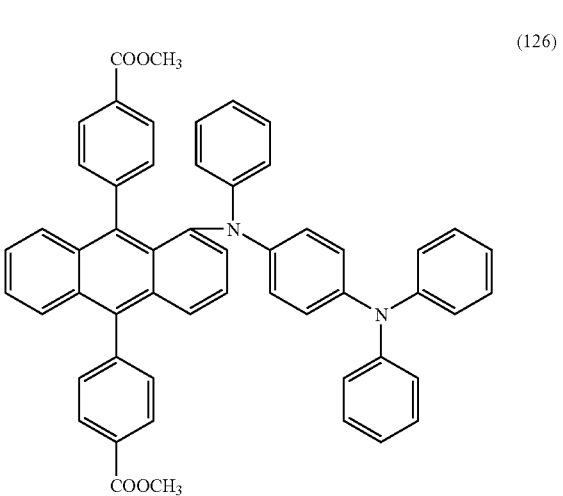

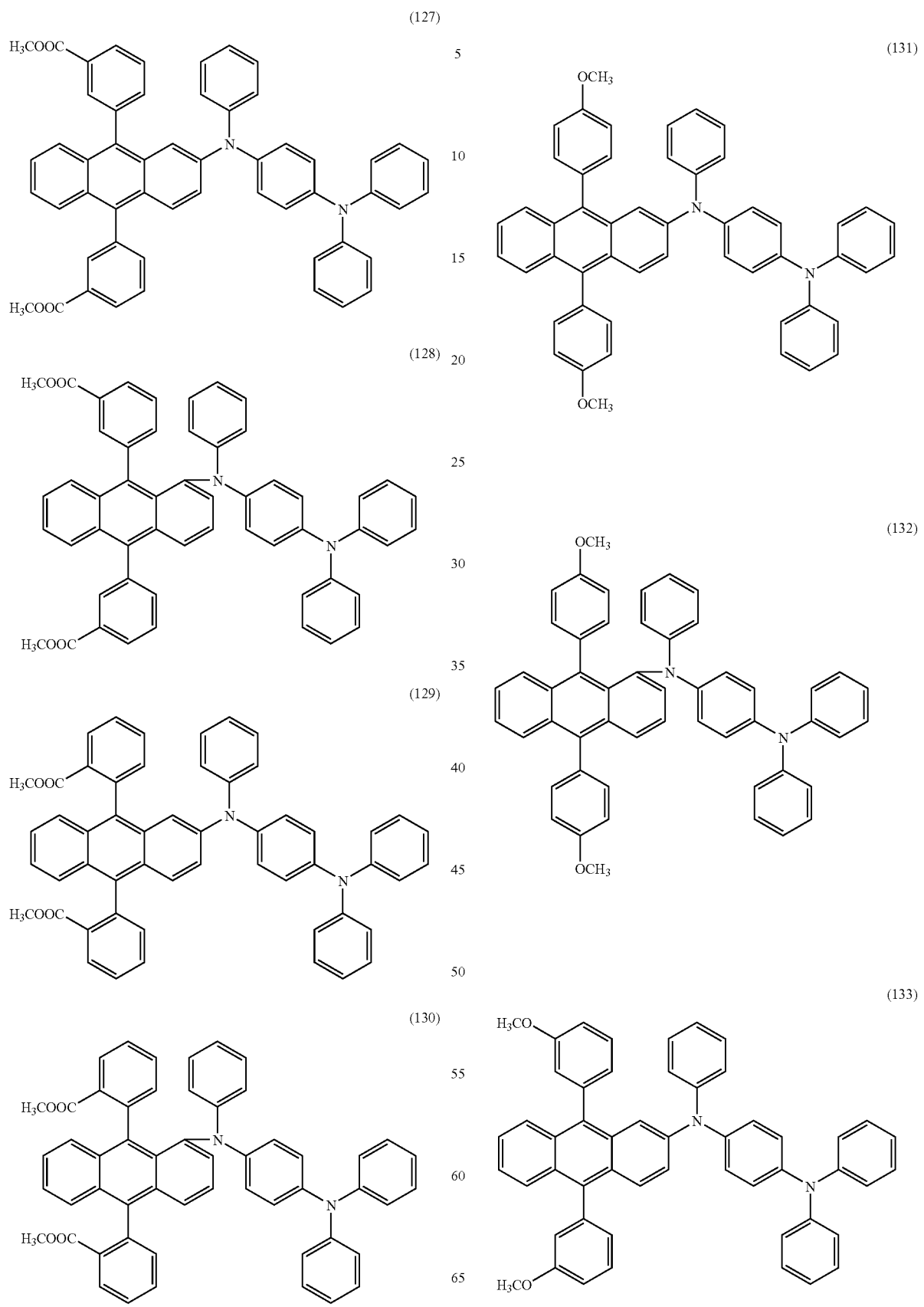

(134)
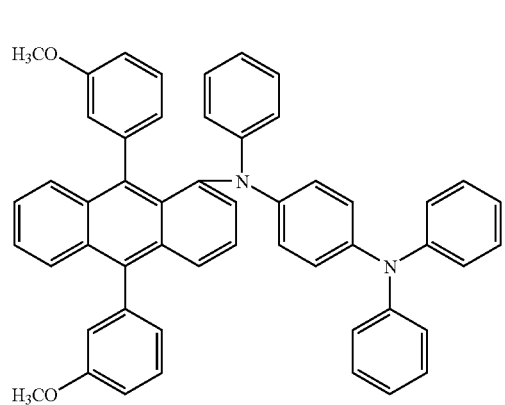
(135)
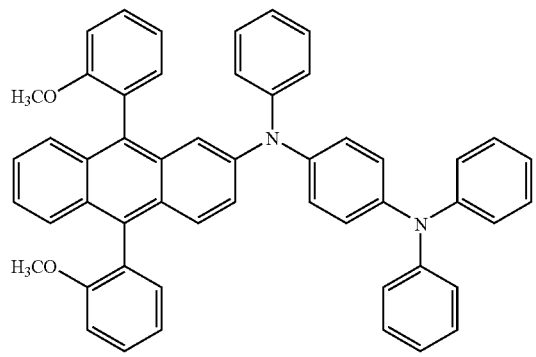
(136)
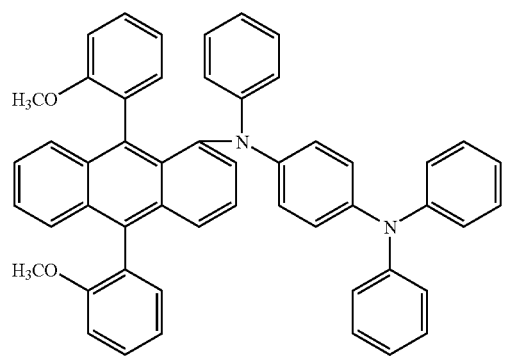
(137)
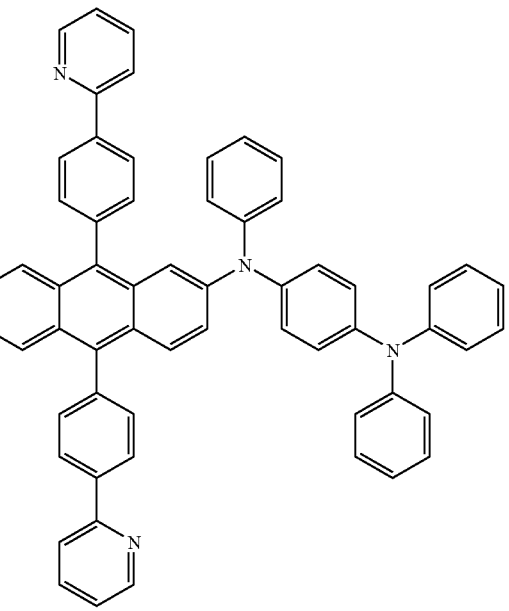
(138)
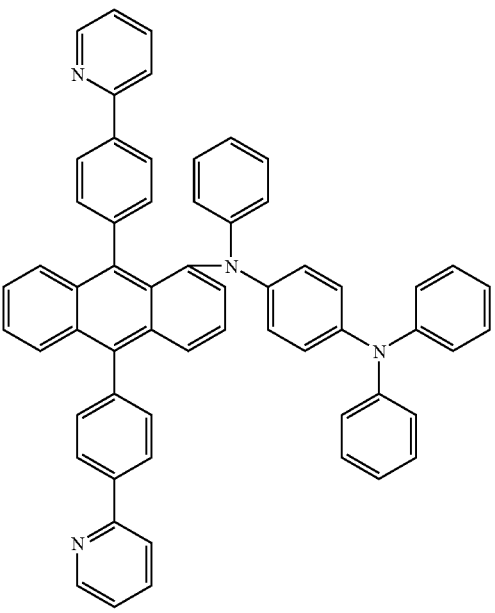

(139)
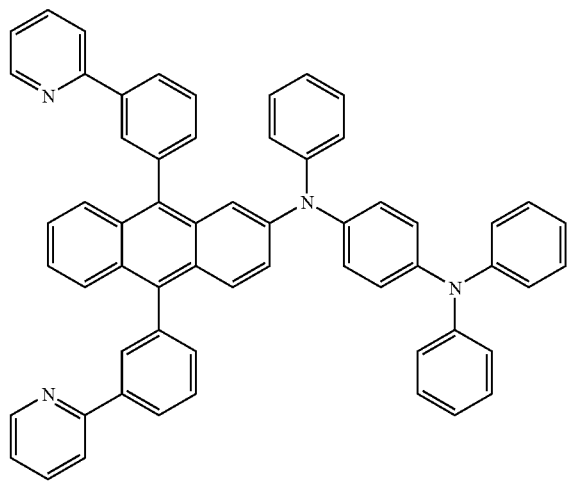
(140)
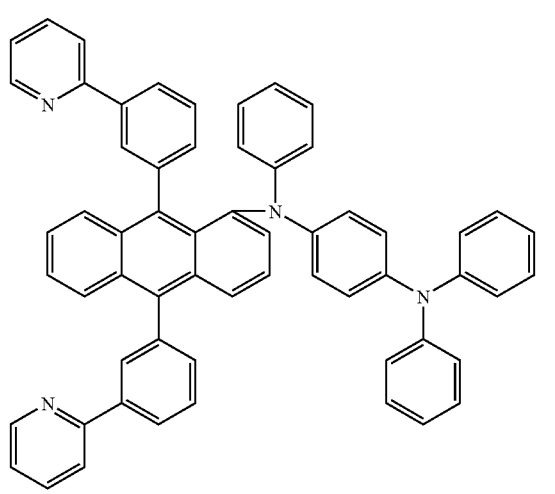
(141)
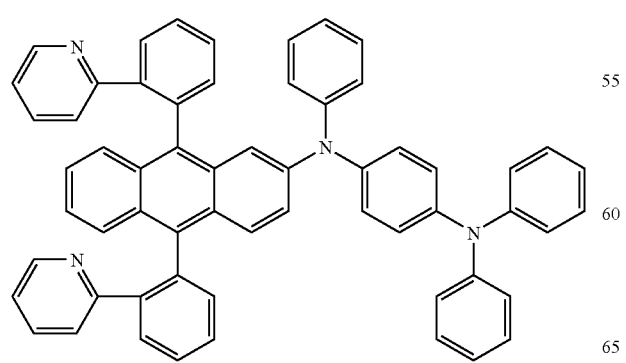
(142)
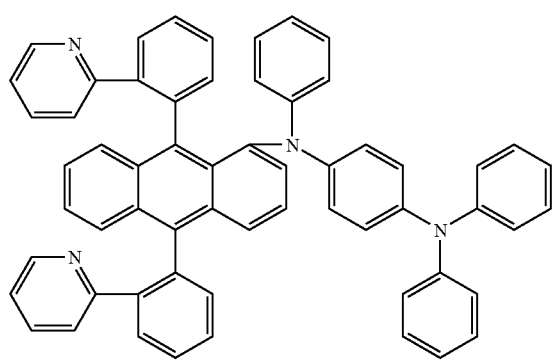
(143)
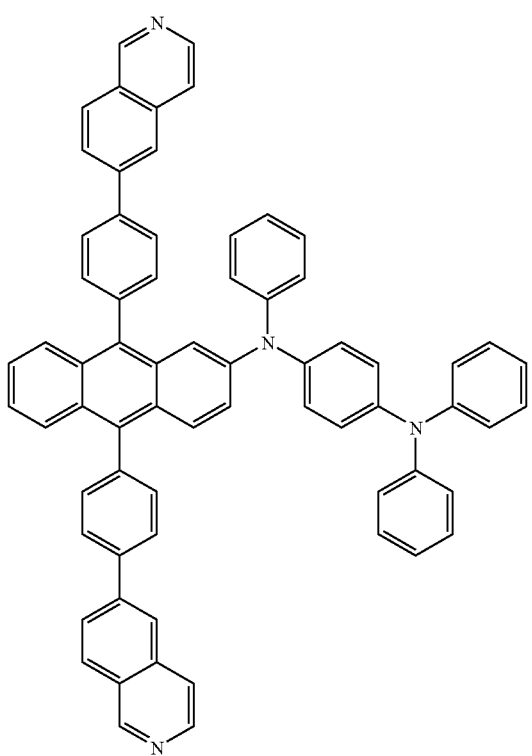

(144)
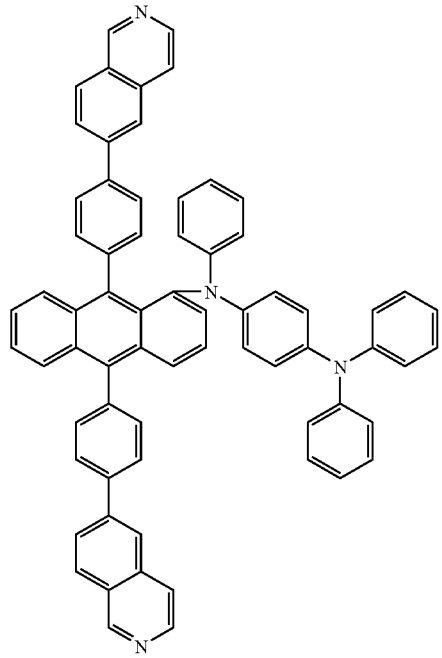
(146)
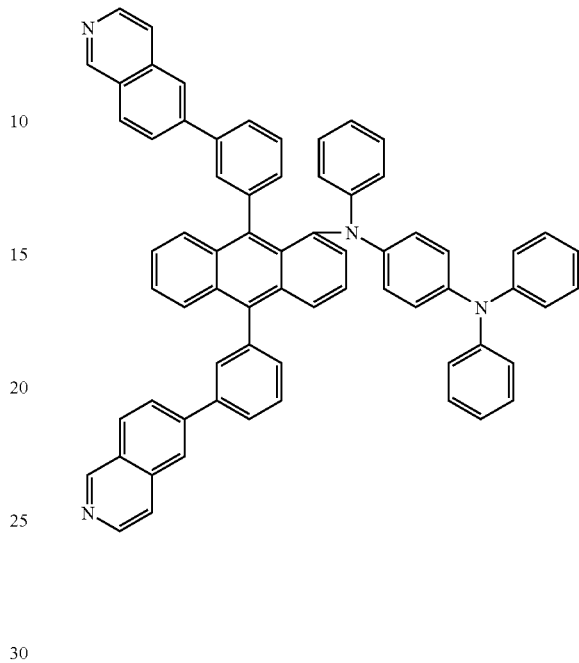
(147)
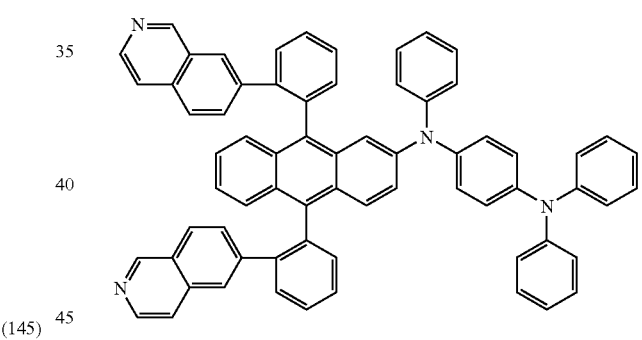
(145)
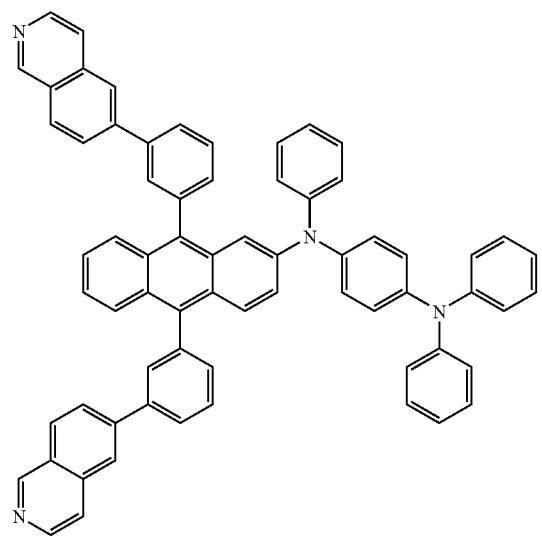
(148)
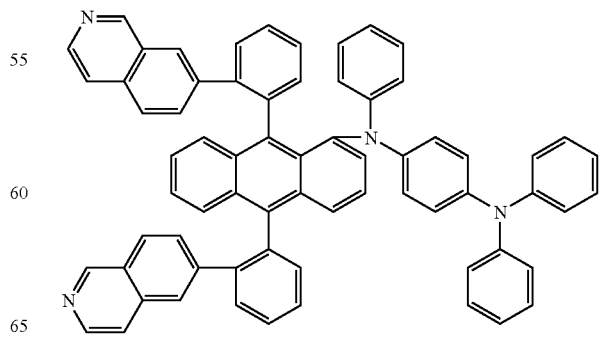

(149)
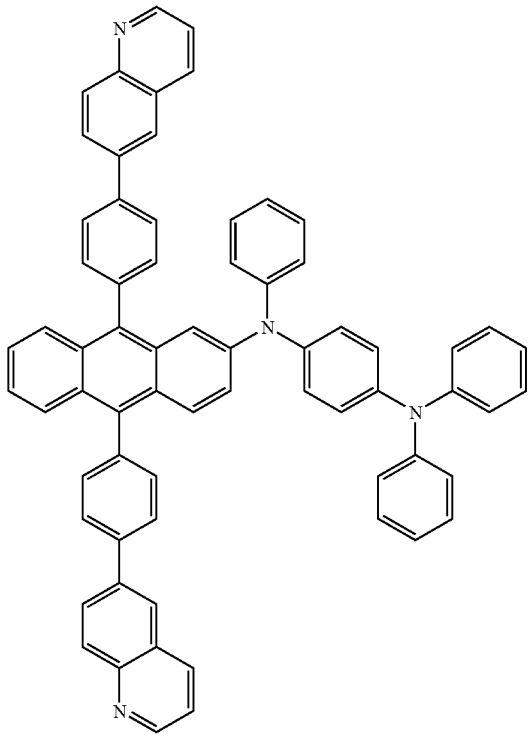
(150)
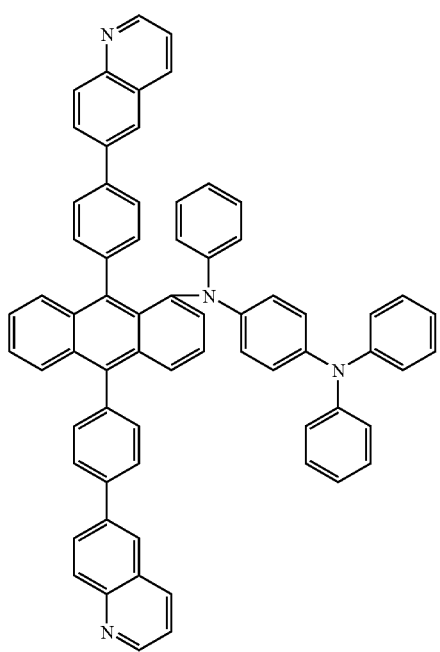
(151)
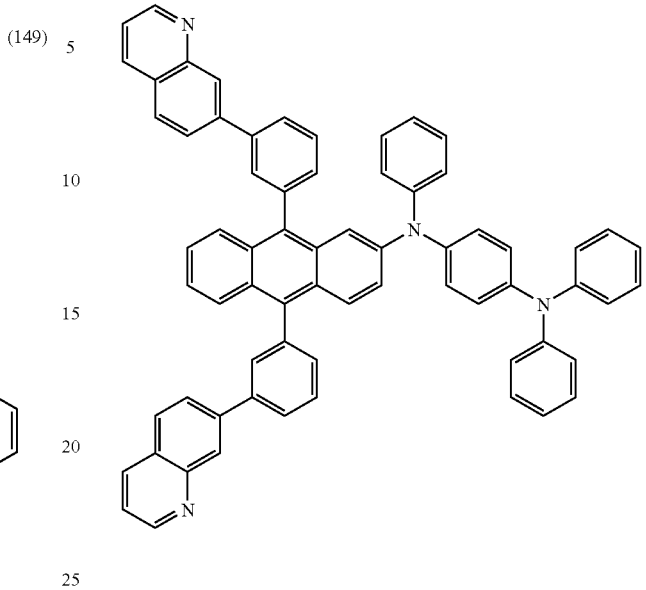
(152)
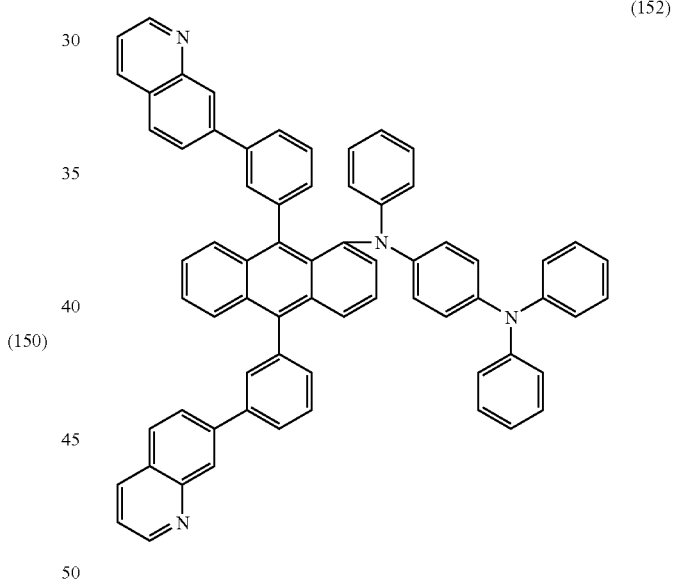
(153)
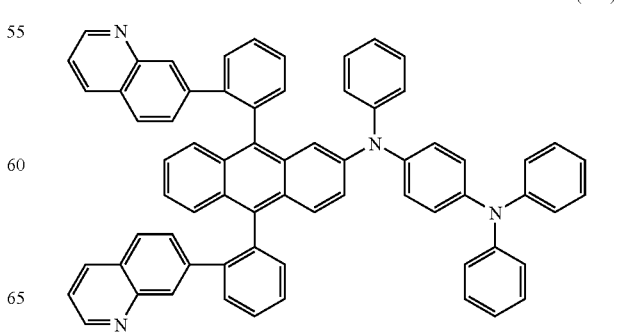

(154)
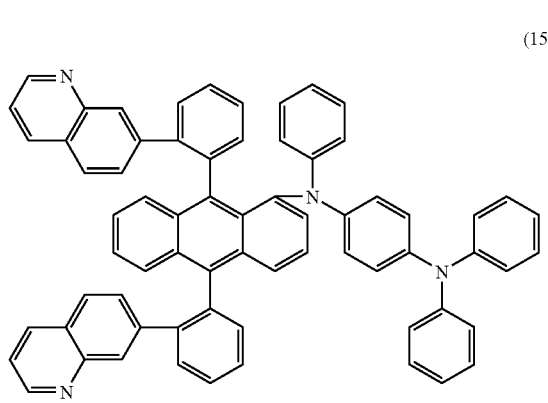
(156)
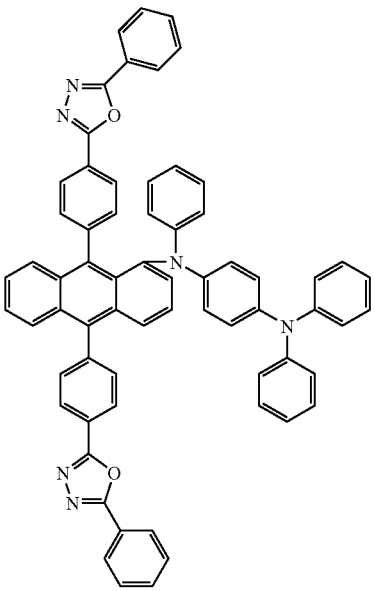
(155)
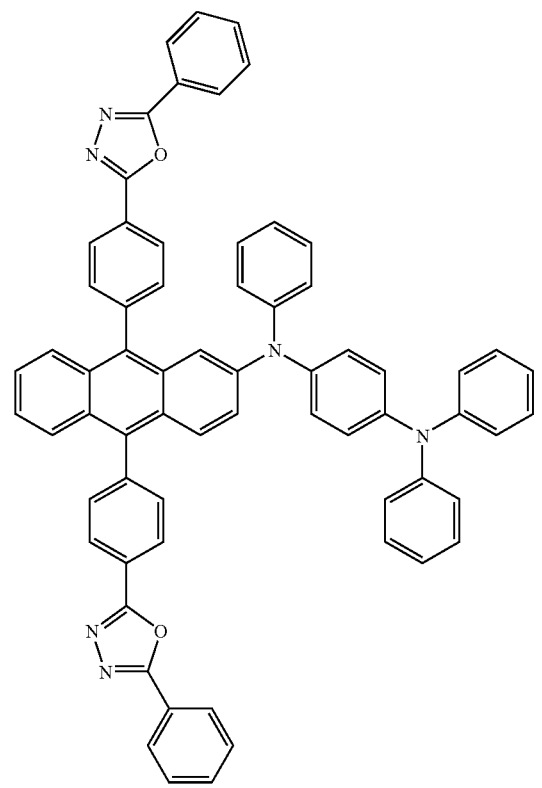
(157)
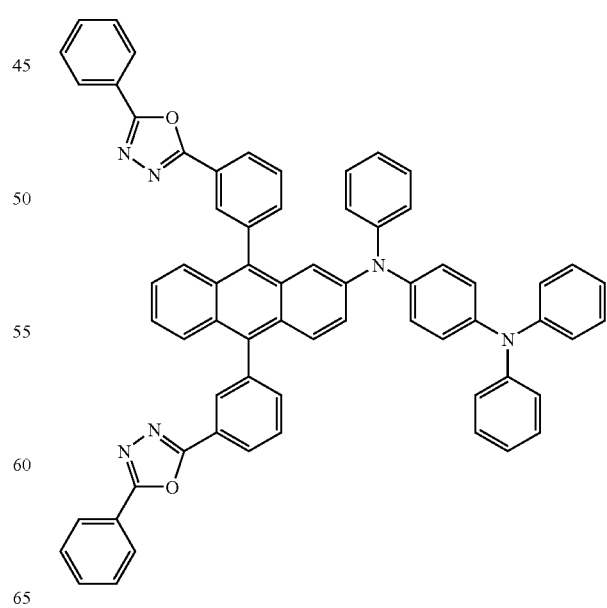

(158)
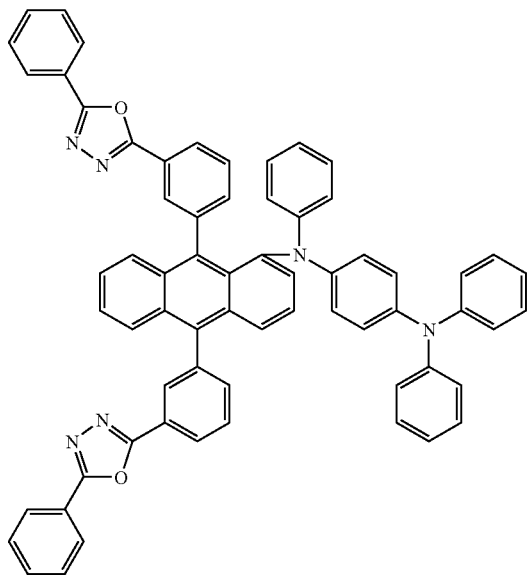
(159)
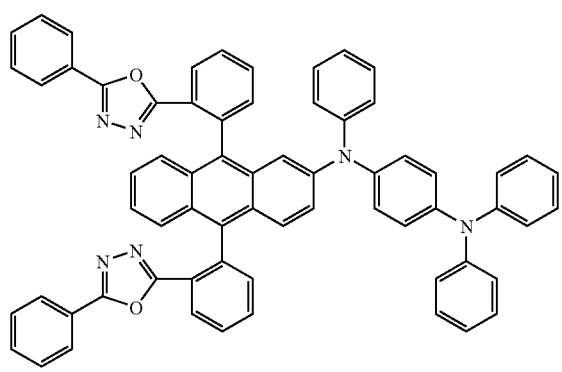
(160)
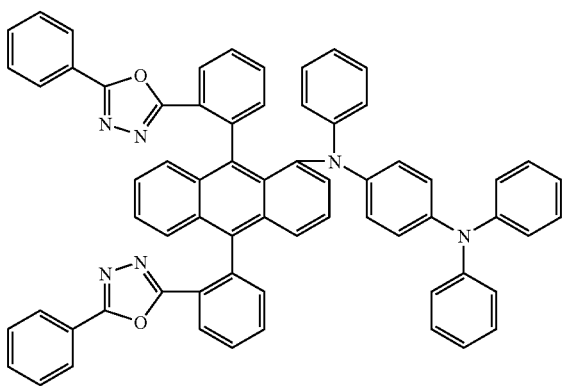
(201)
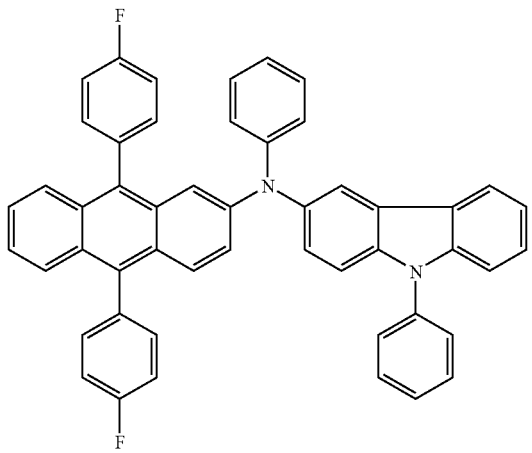
(202)
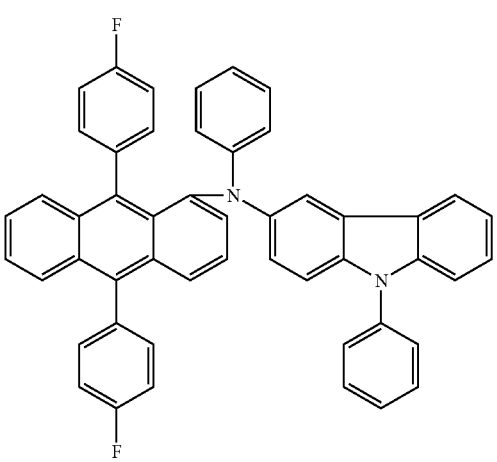
(203)
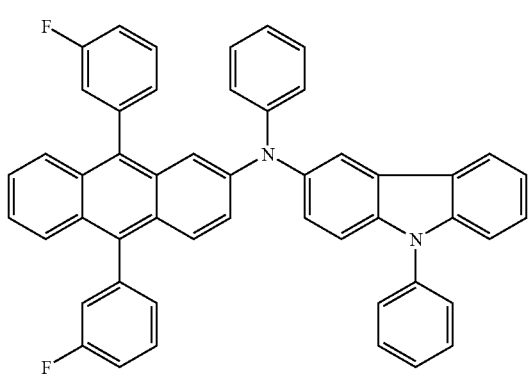

(204)
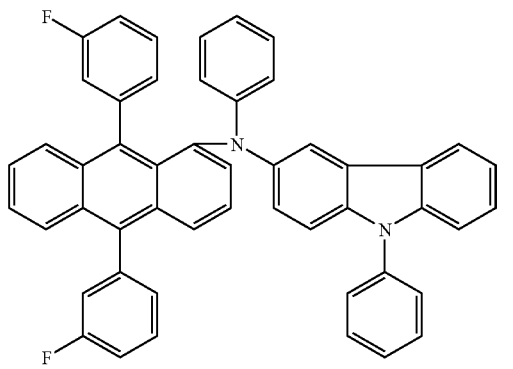
(205)
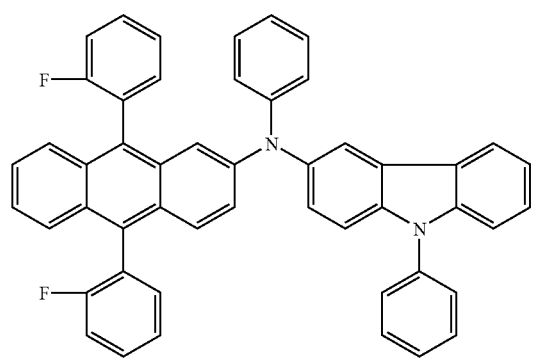
(206)
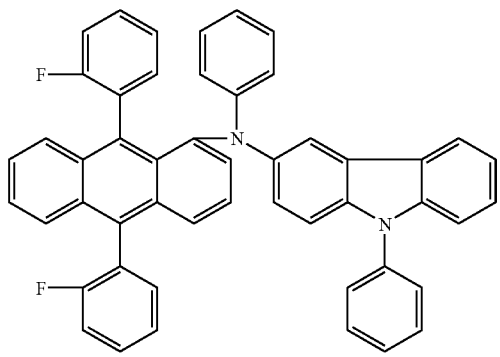
(207)
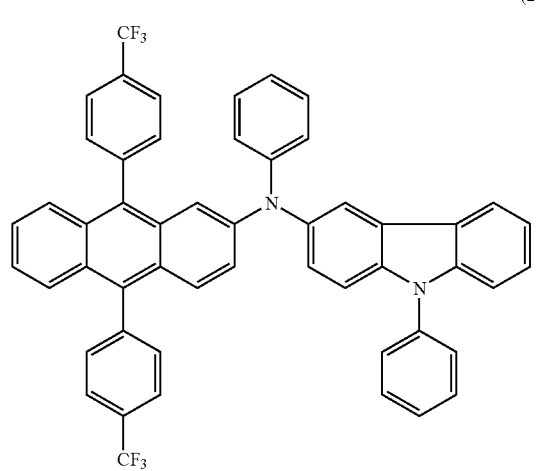
(208)
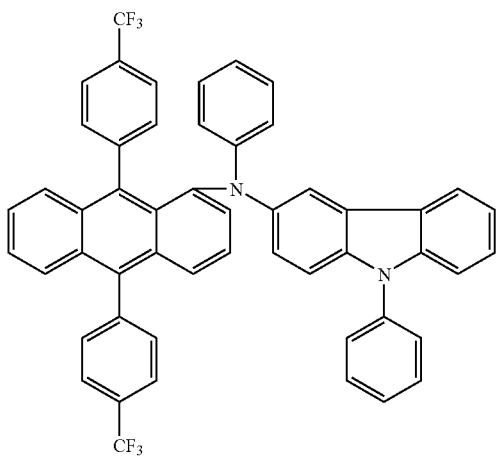
(209)
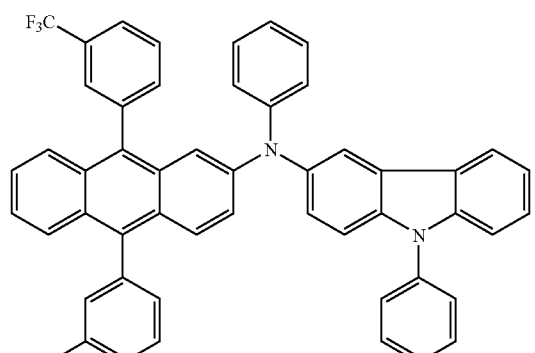
(210)
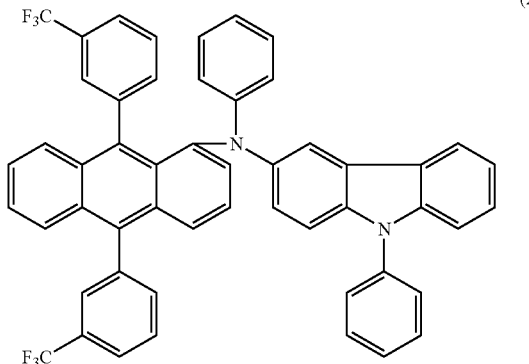
(211)
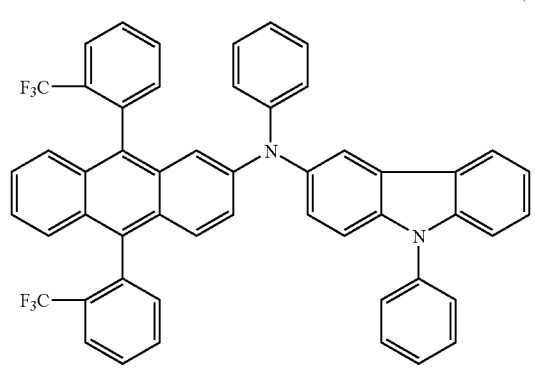

-continued
(212)
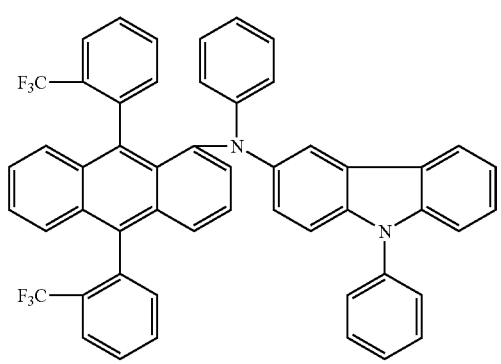
(213)
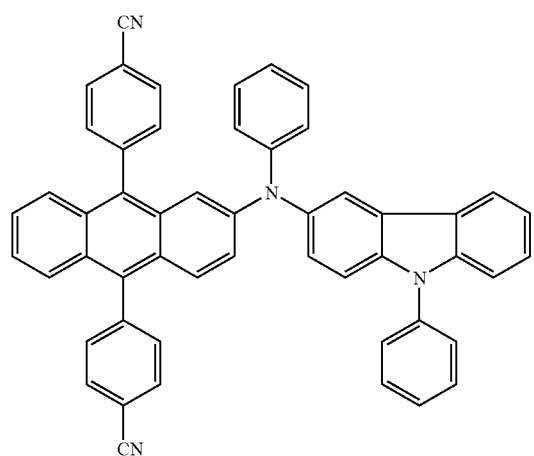
(214)
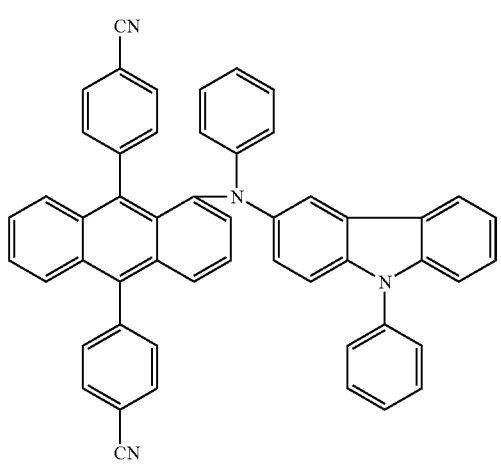
(215)
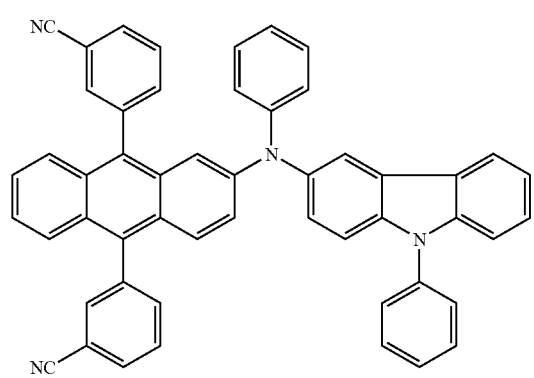
-continued
(216)
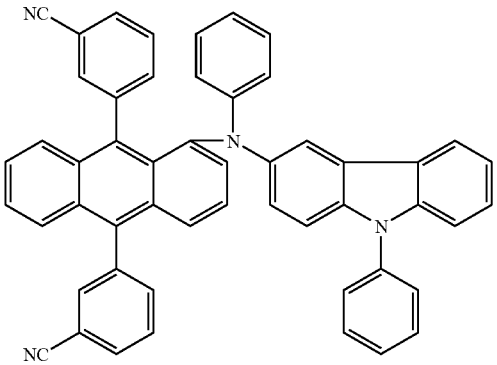
(217)
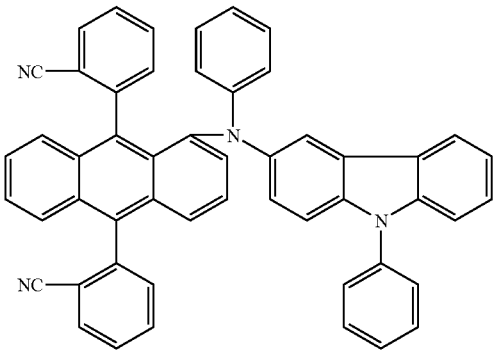
(218)
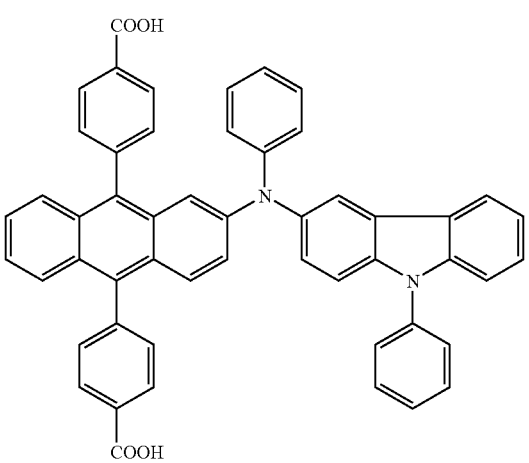
(219)

(220)
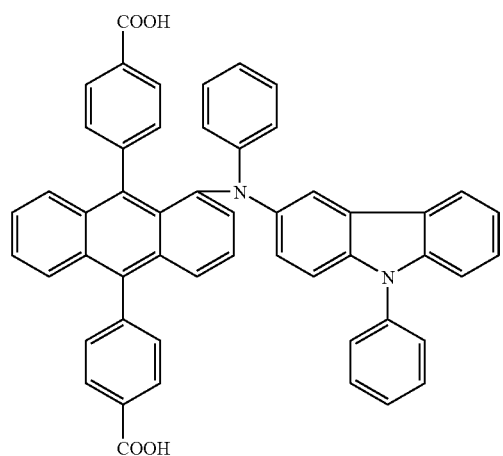
(221)
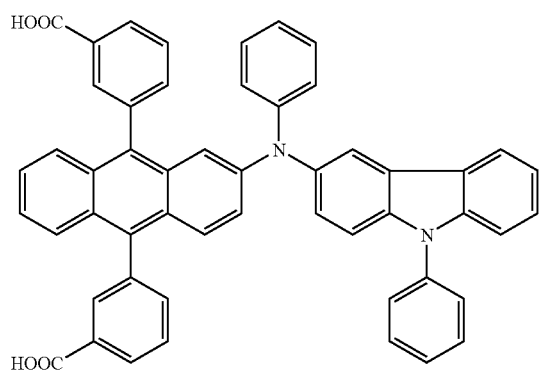
(222)
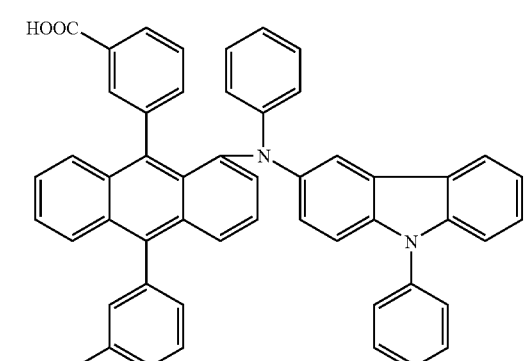
(223)
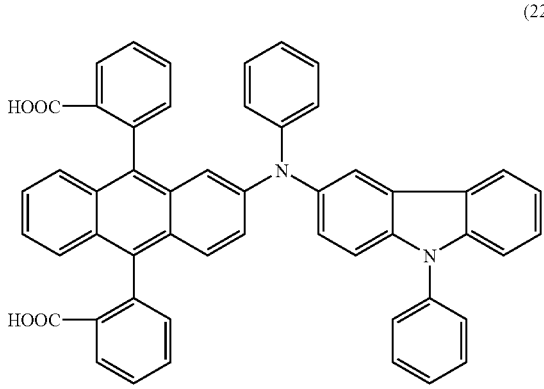
(224)
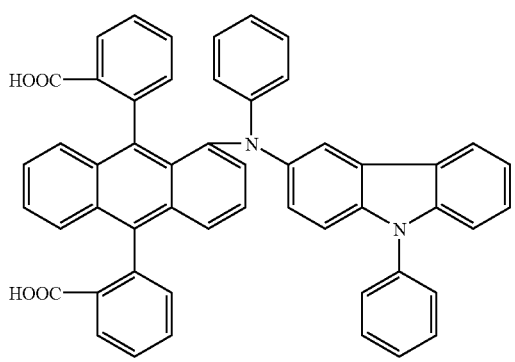
(225)
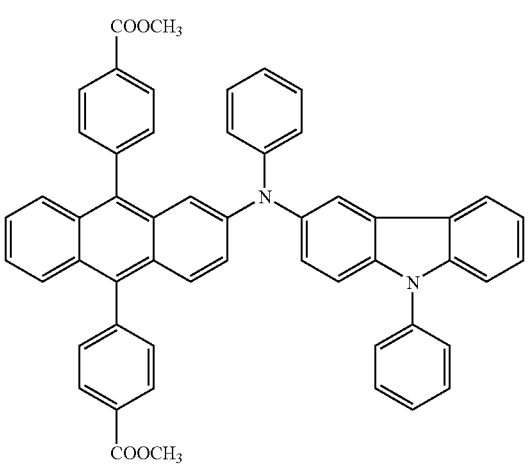
(226)
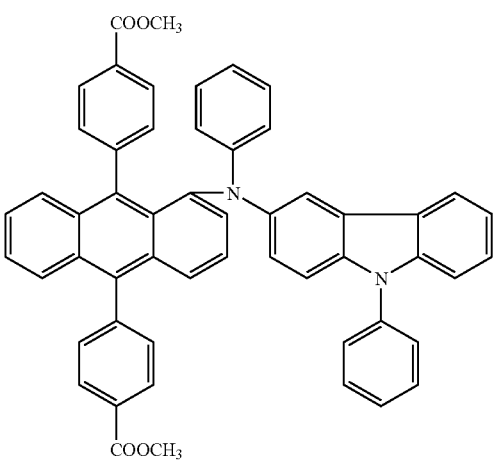

(227)
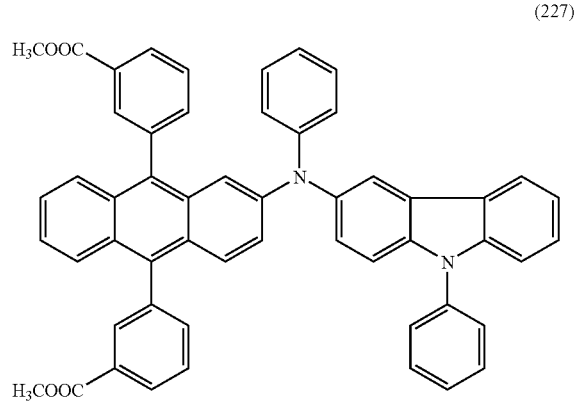
(228)
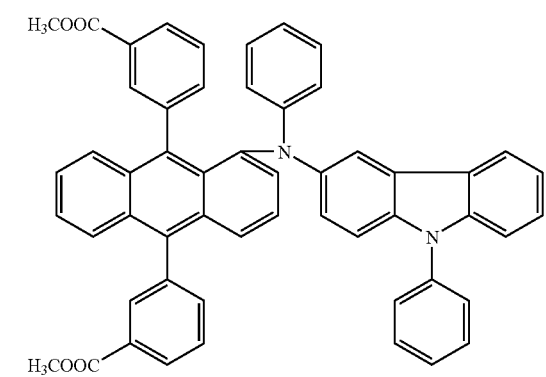
(229)
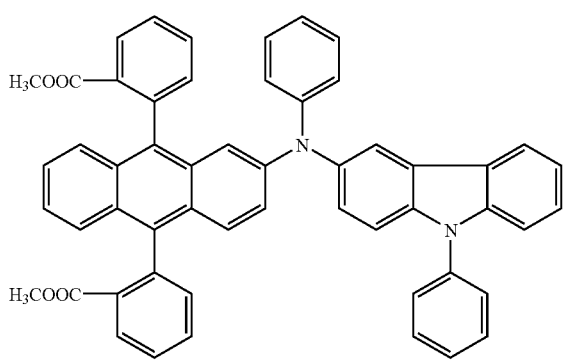
(230)
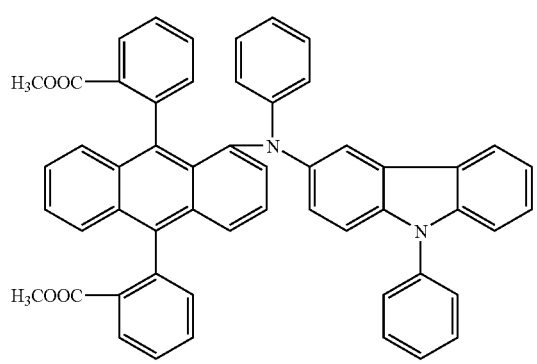
(231)
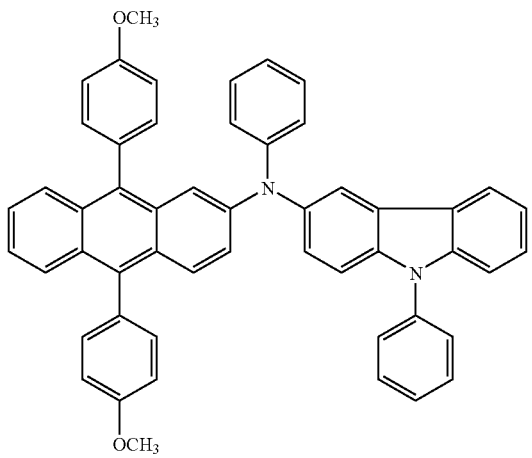
(232)
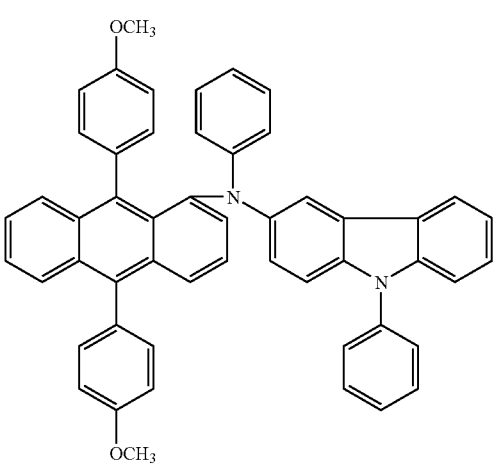
(233)
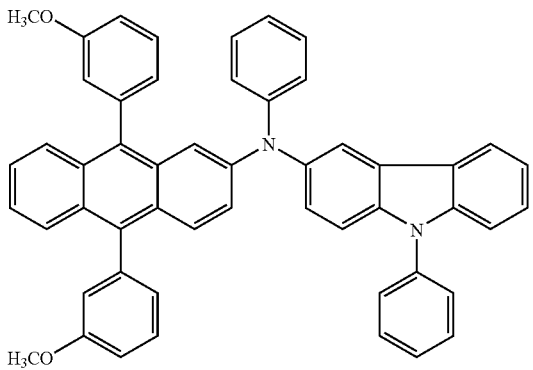

(234)
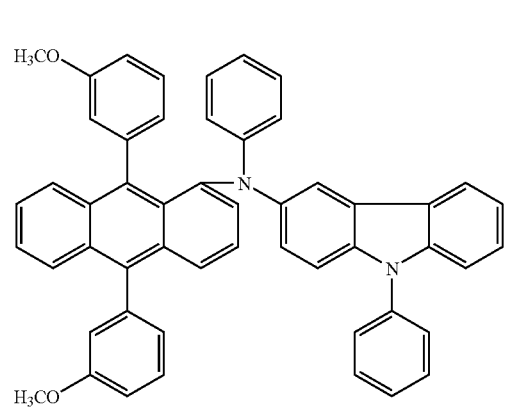
(235)
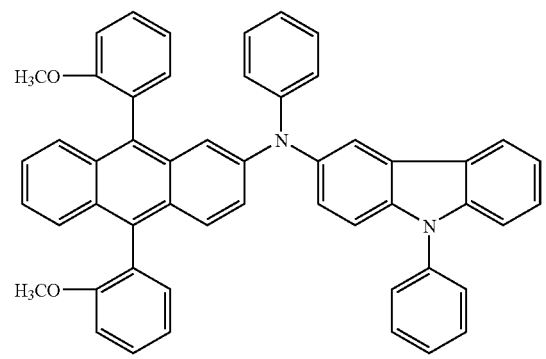
(236)
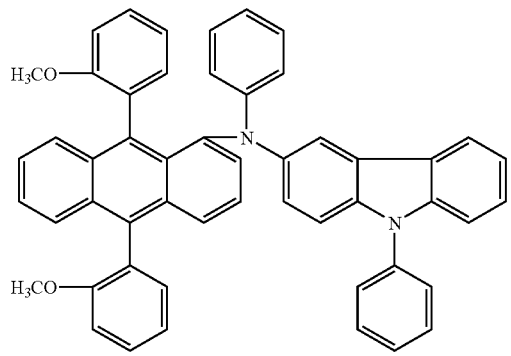
(237)
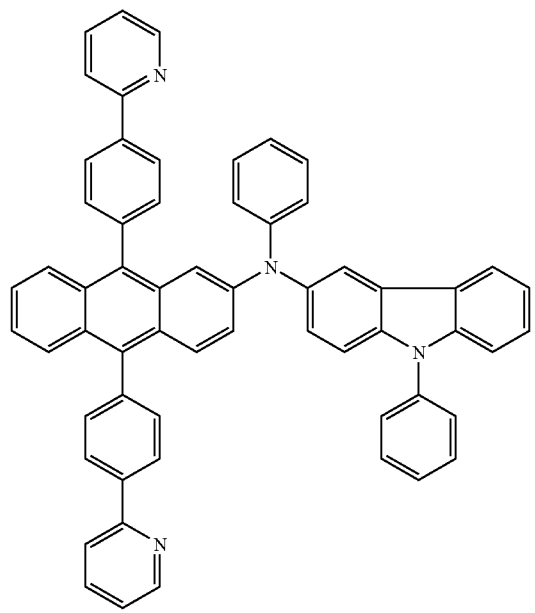
(238)
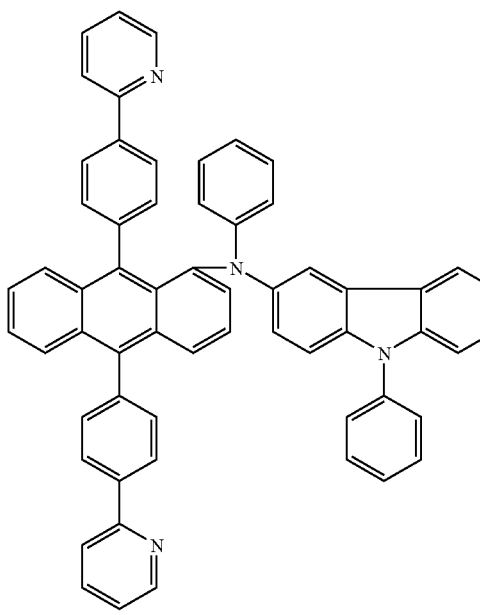

(239)
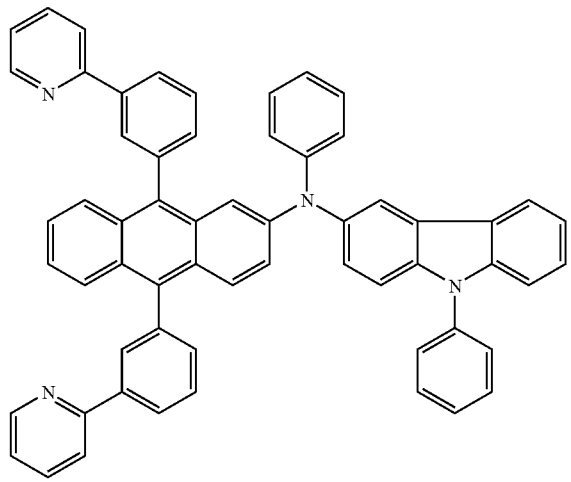
(240)
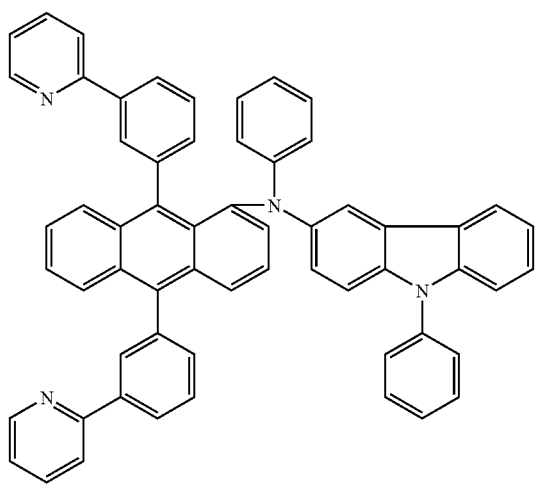
(241)
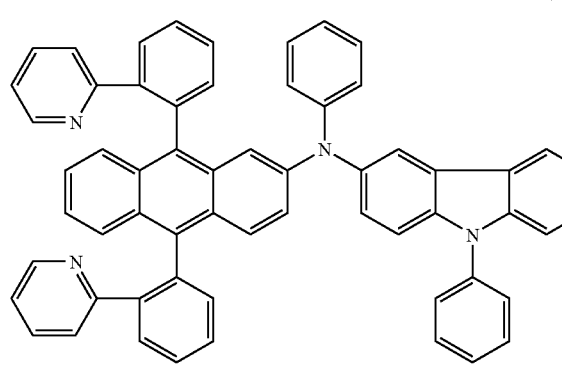
(242)
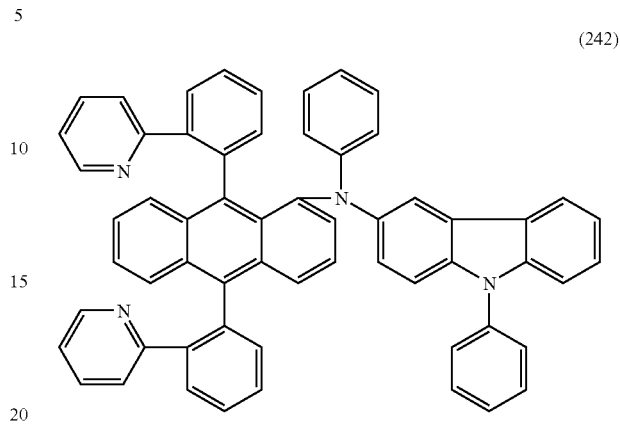
(243)
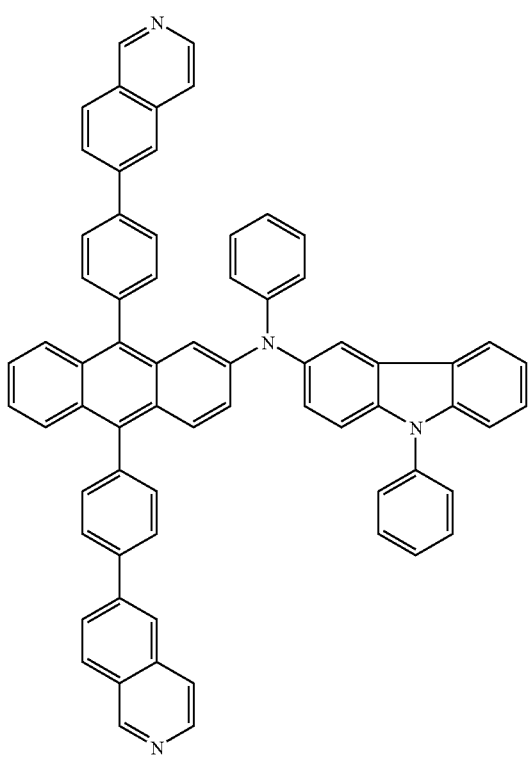

(244)
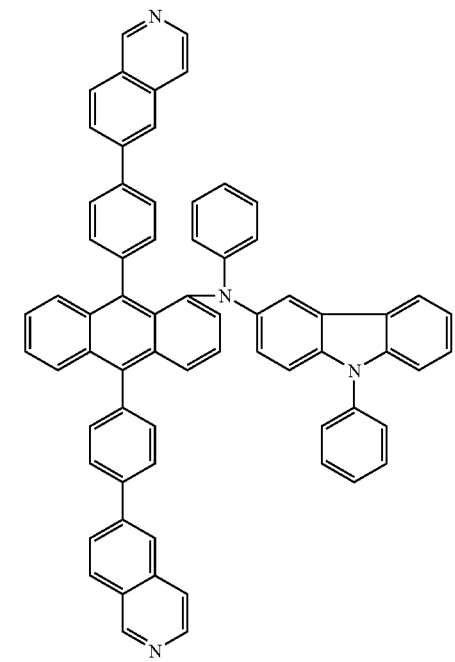
(245)
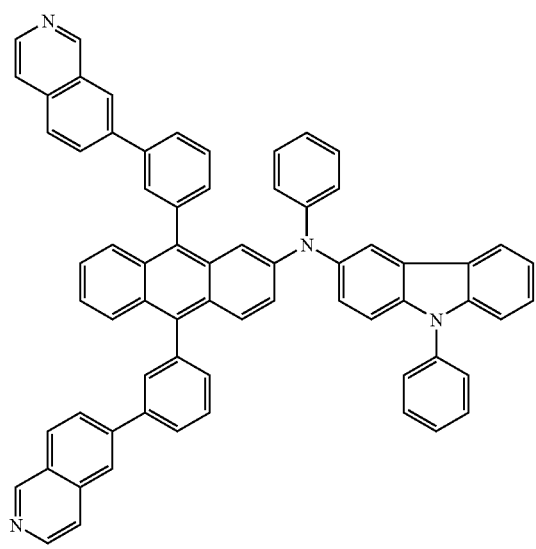
(246)
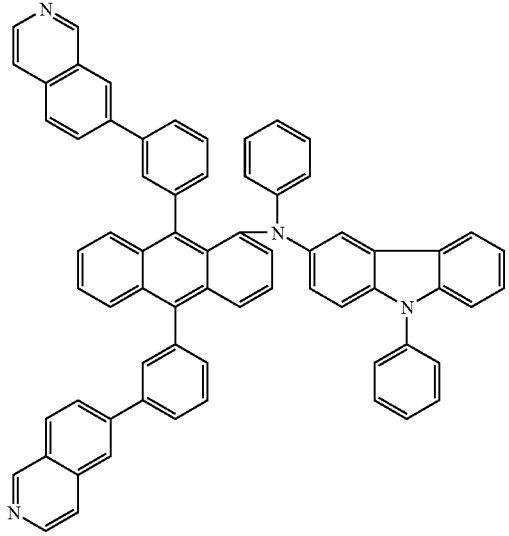
(247)
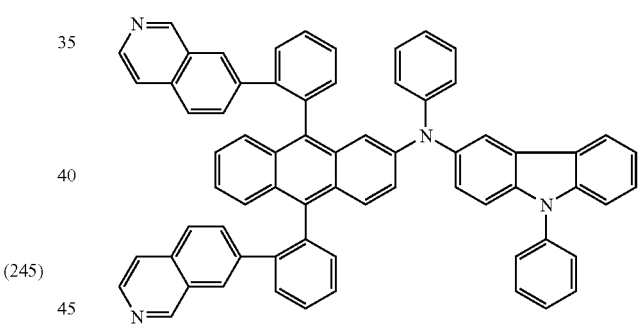
(248)
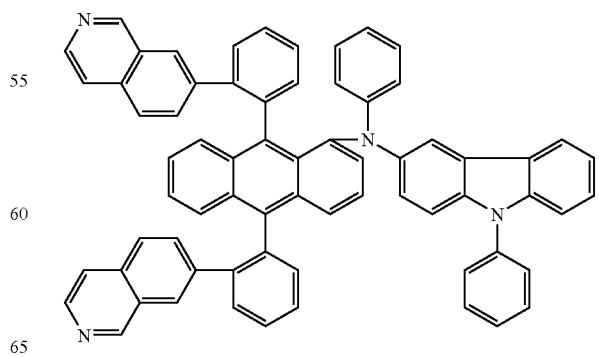

(249)
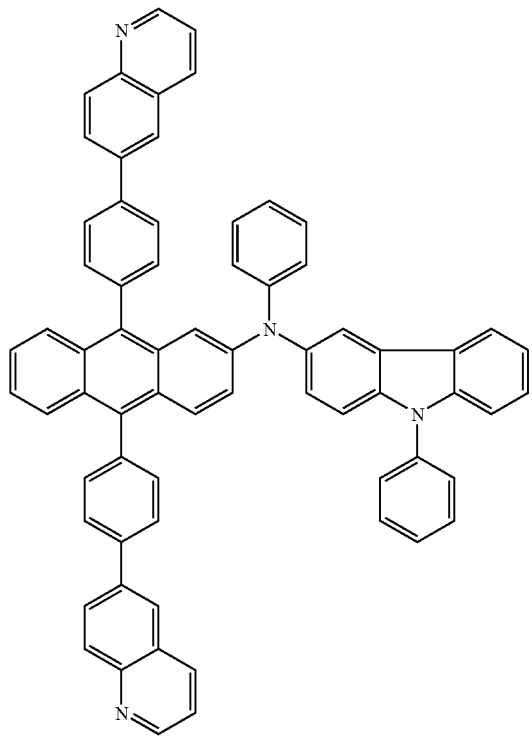
(250)
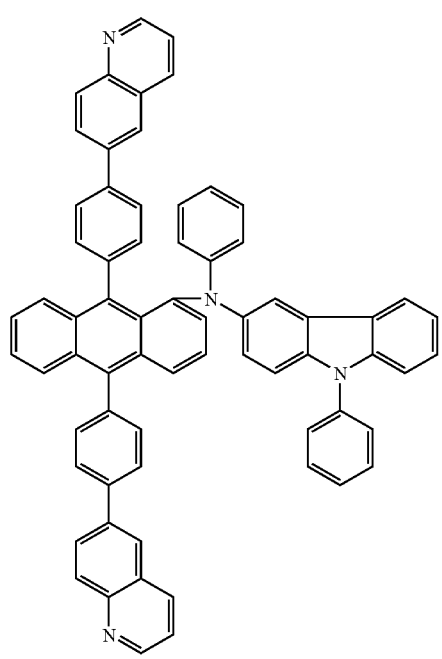
(251)
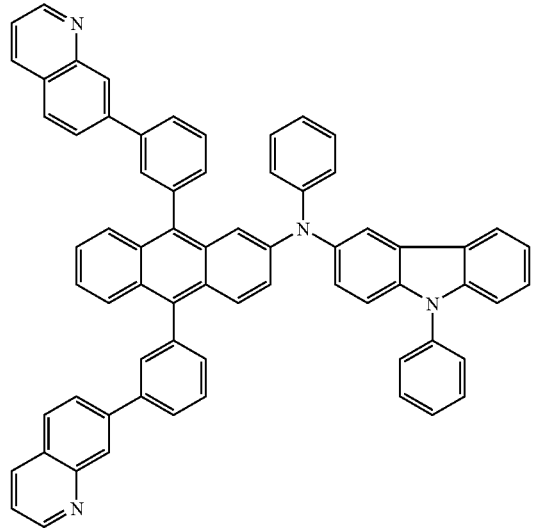
(252)
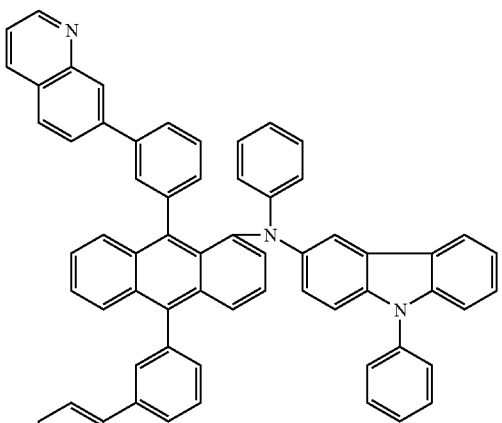
(253)
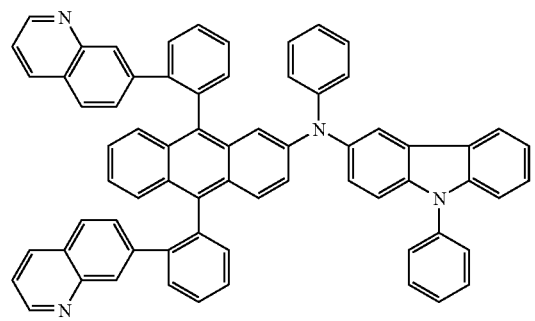

(254)
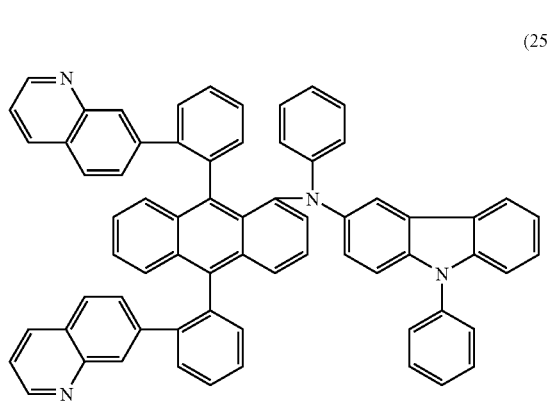
(256)
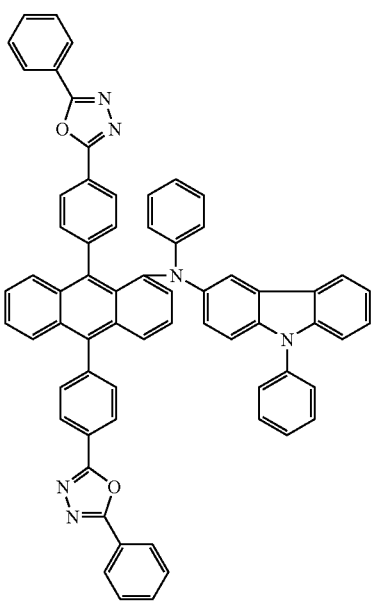
(255)
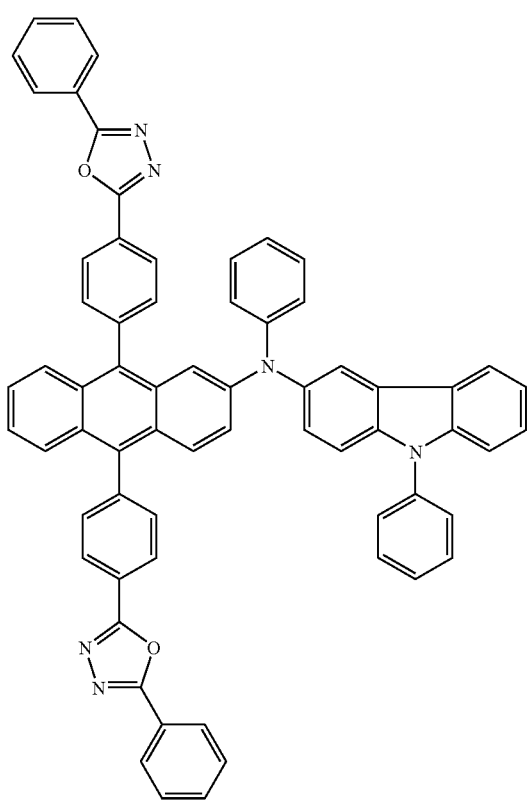
(257)
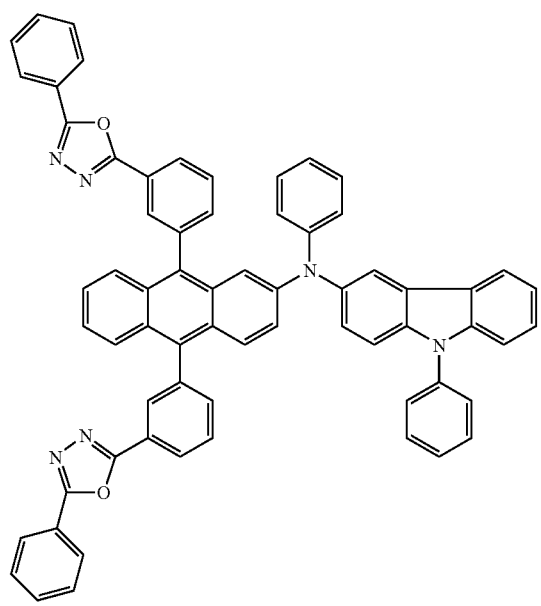

(258)
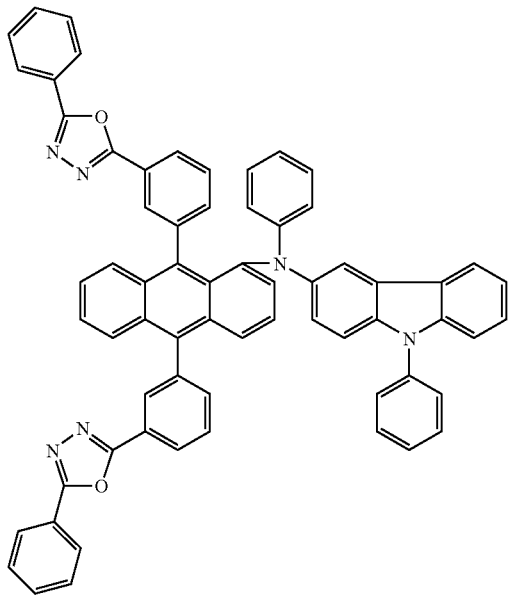
(301)
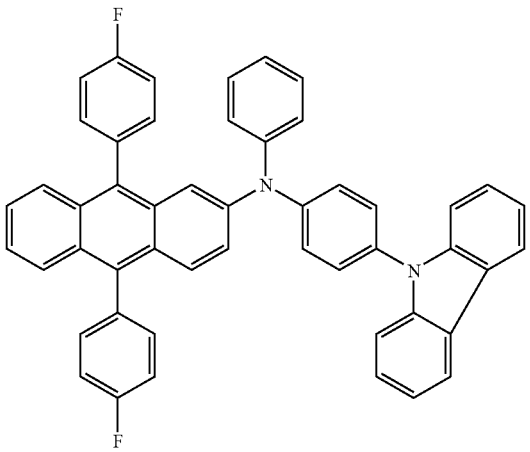
(259)
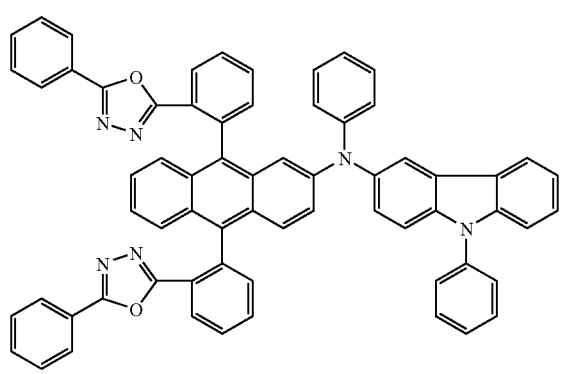
(302)
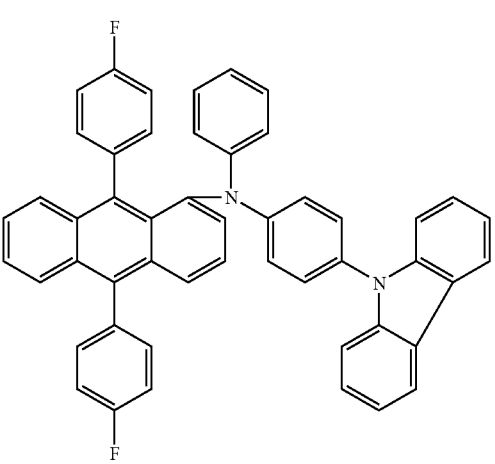
(260)
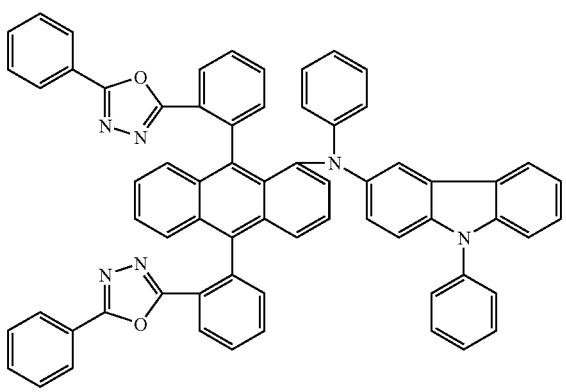
(303)
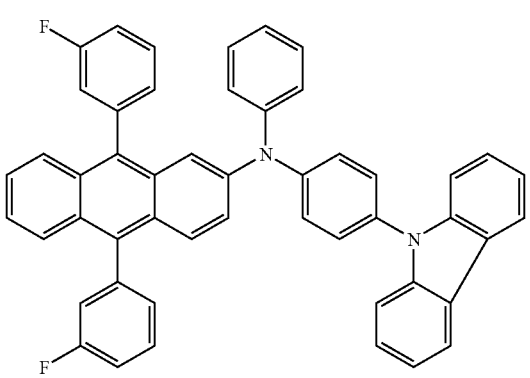

(304)
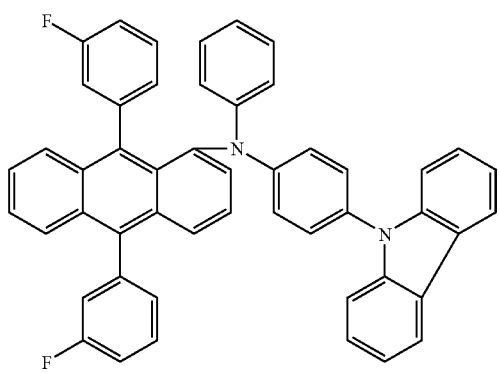
(305)
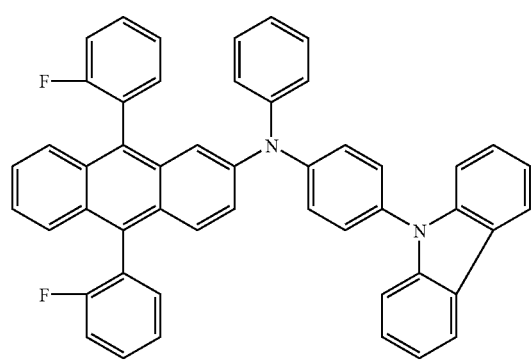
(306)
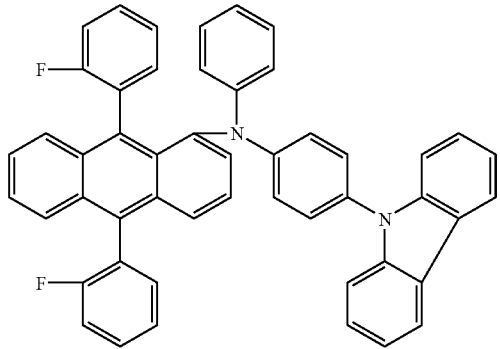
(307)
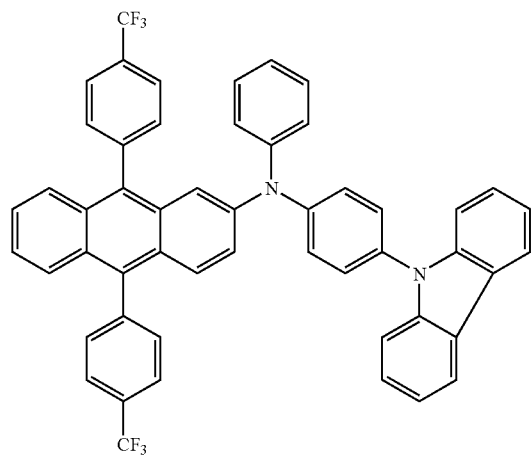
(308)
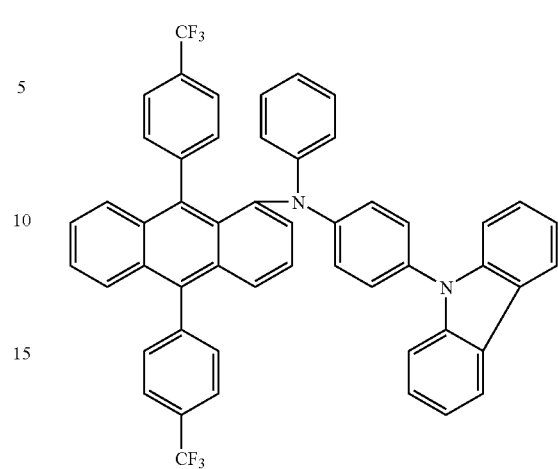
(309)
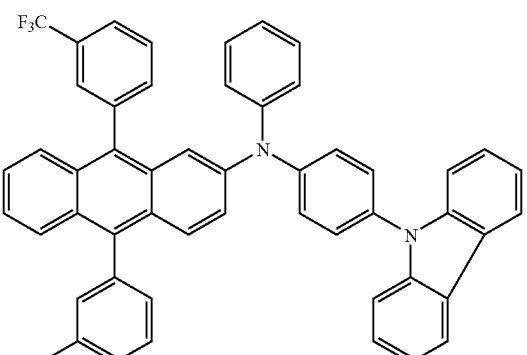
(310)
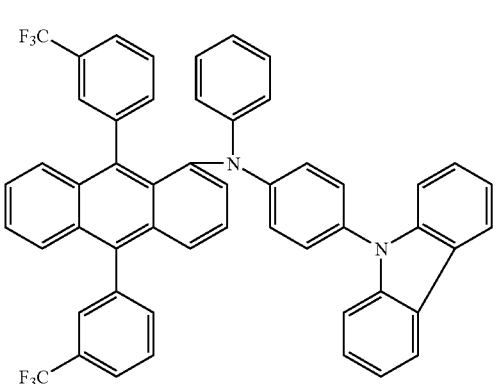
(311)
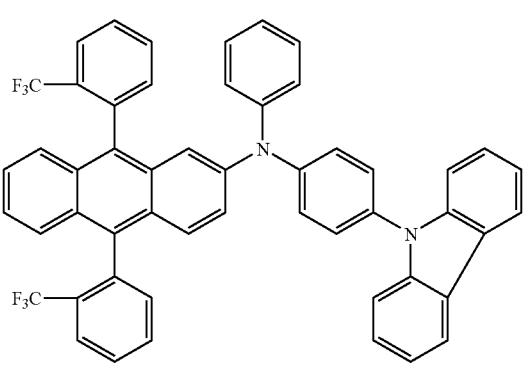

(312)
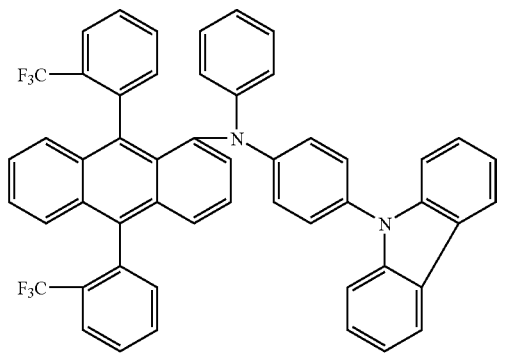
(313)
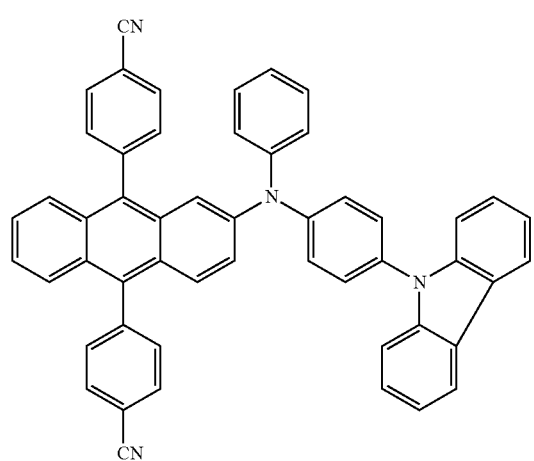
(314)
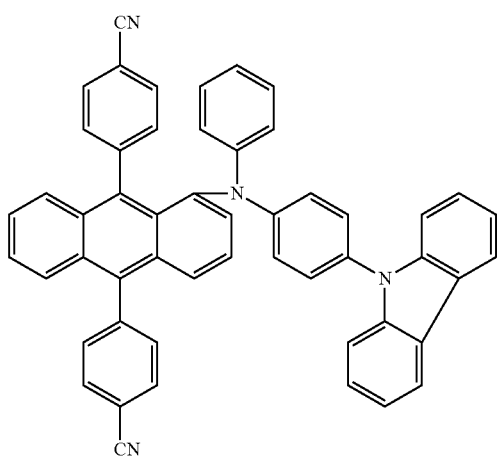
(315)
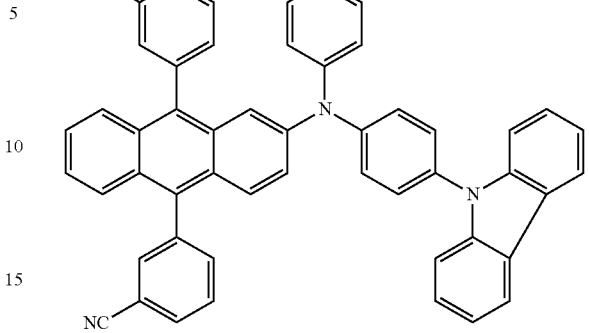
(316)
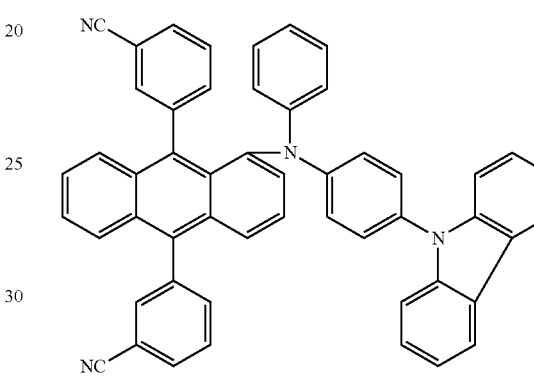
(317)
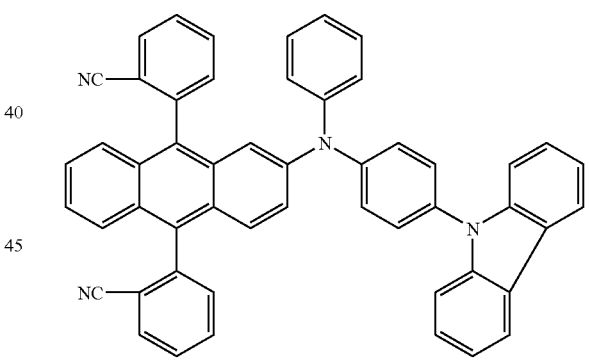
(318)
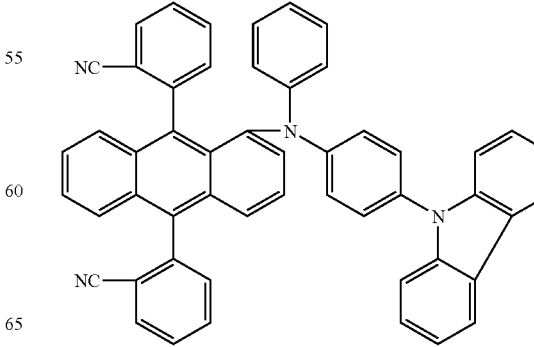

(319) 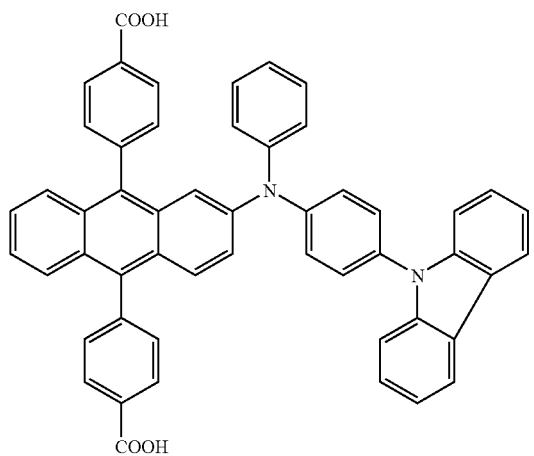
(320) 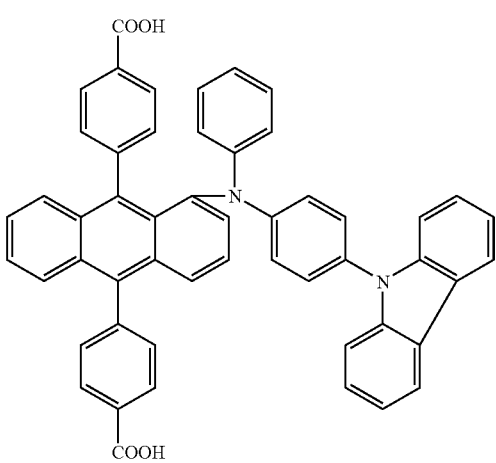
(321) 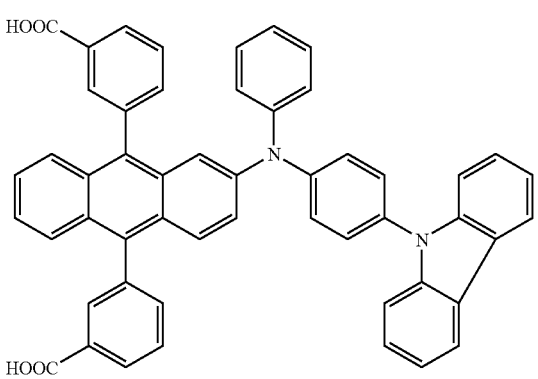
(322) 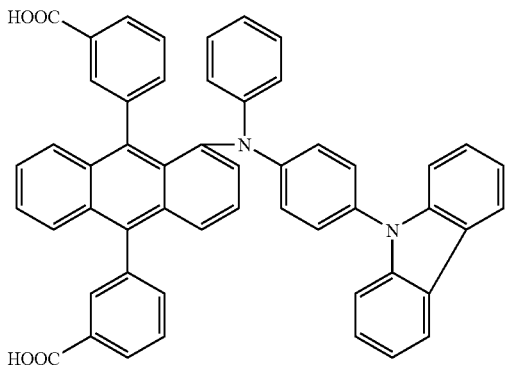
(323) 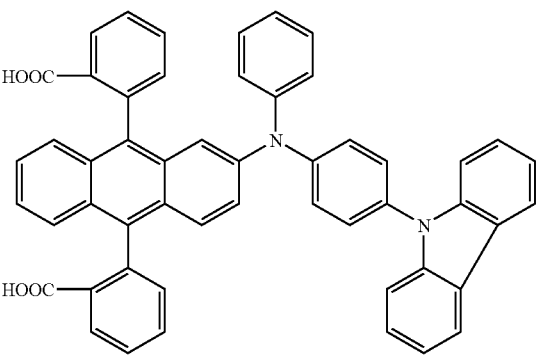
(324) 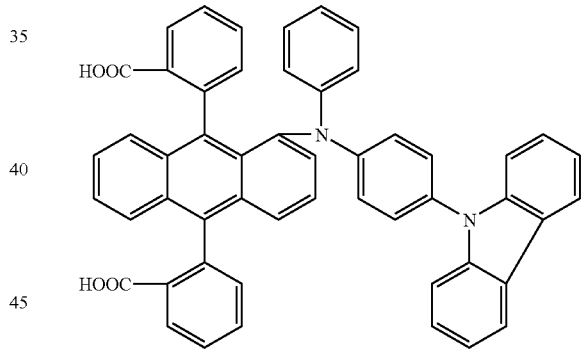
(325) 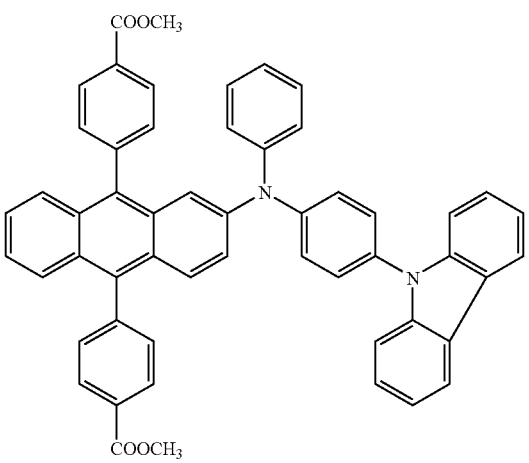

-continued
(326)
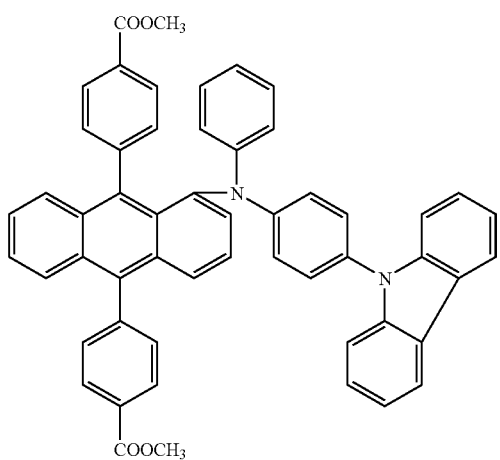
(327)
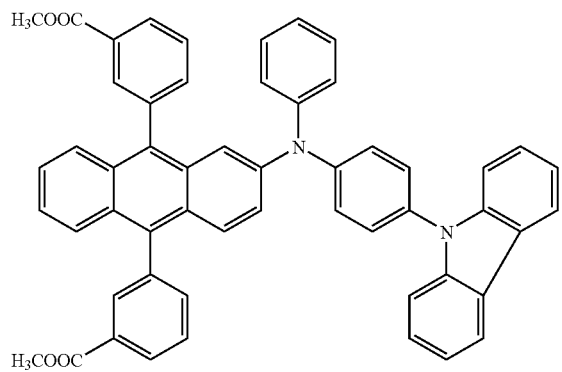
(328)
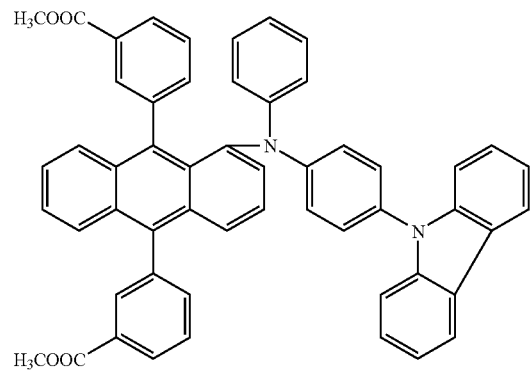
(329)
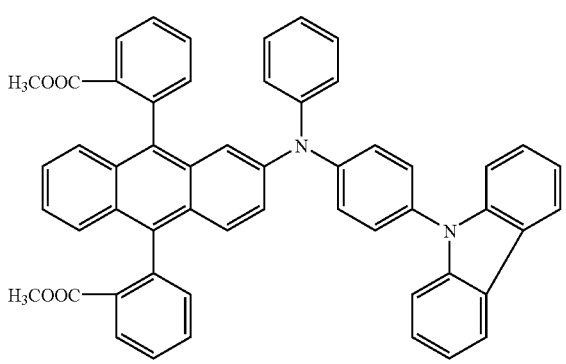
-continued
(330)
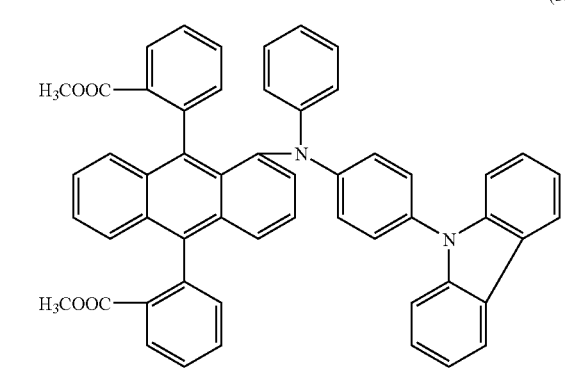
(331)
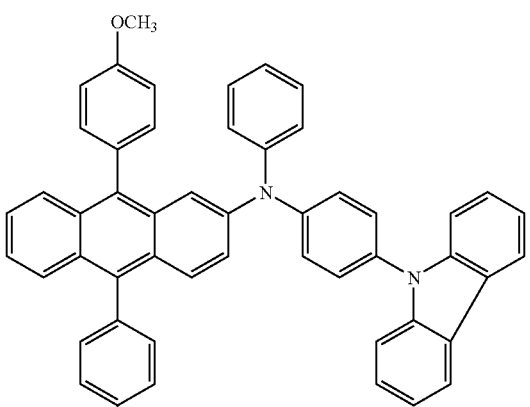
(332)
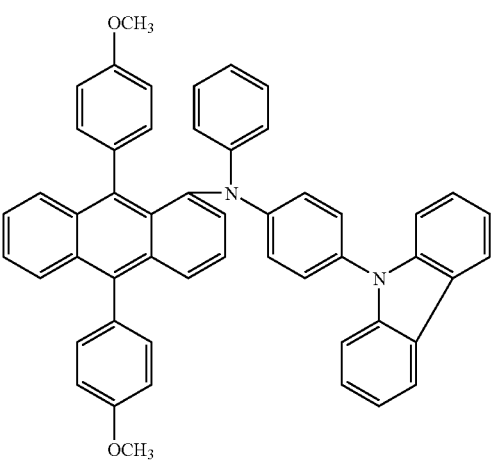

(333)
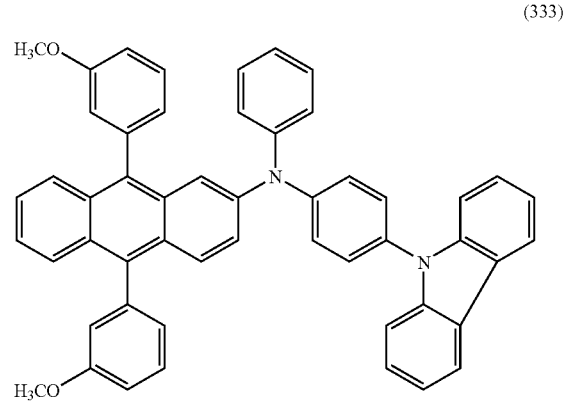
(334)
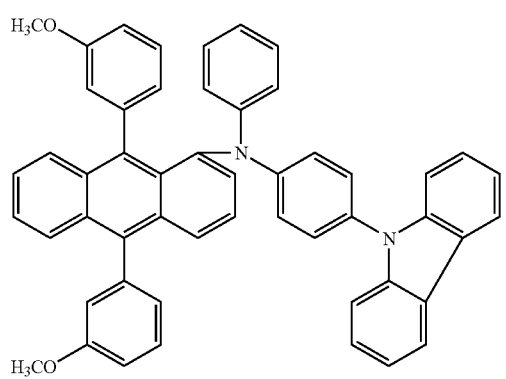
(335)
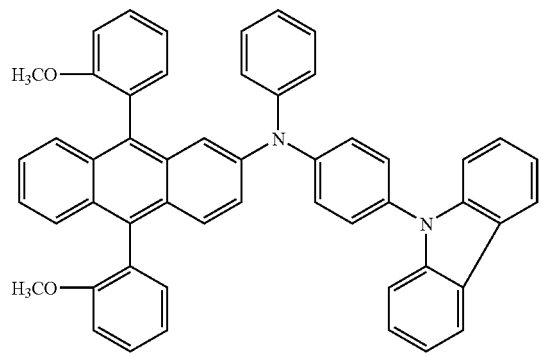
(336)
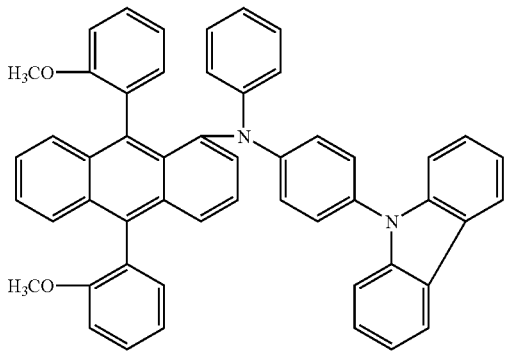
(337)
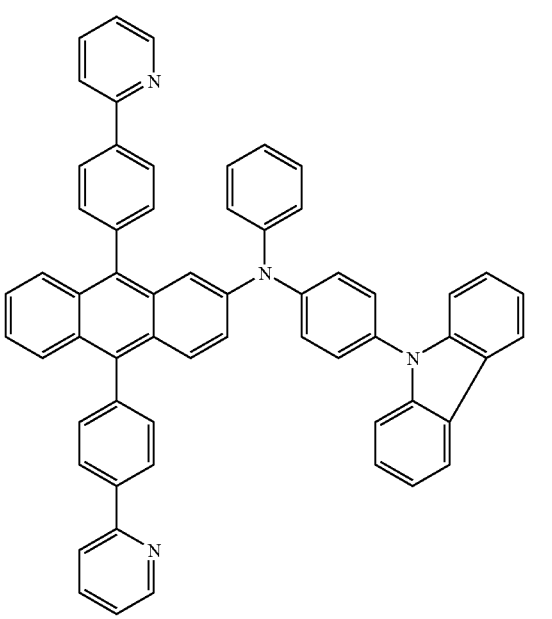
(338)
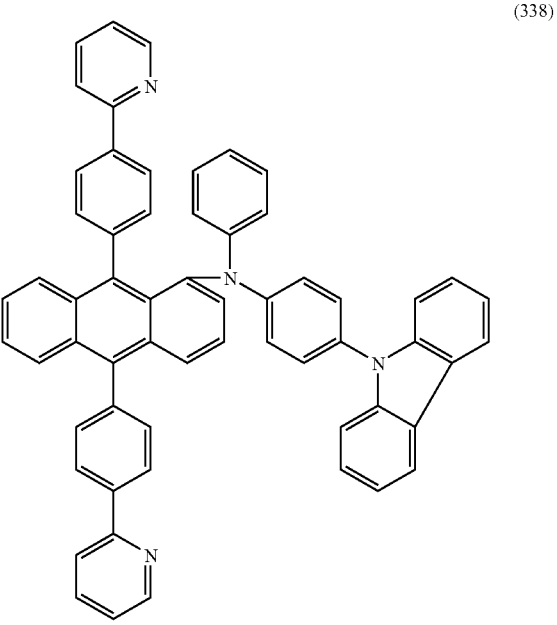

-continued
(339)
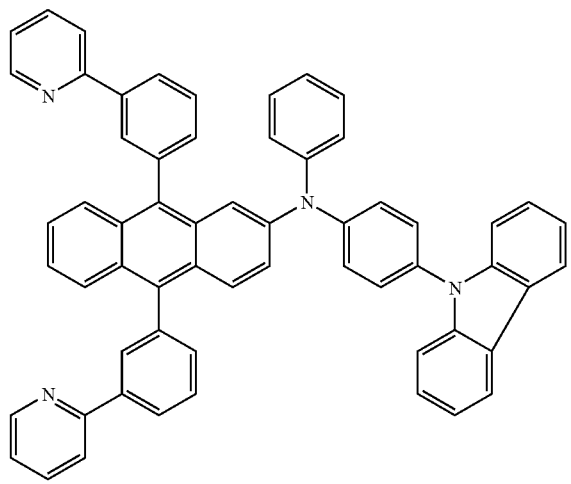
(340)
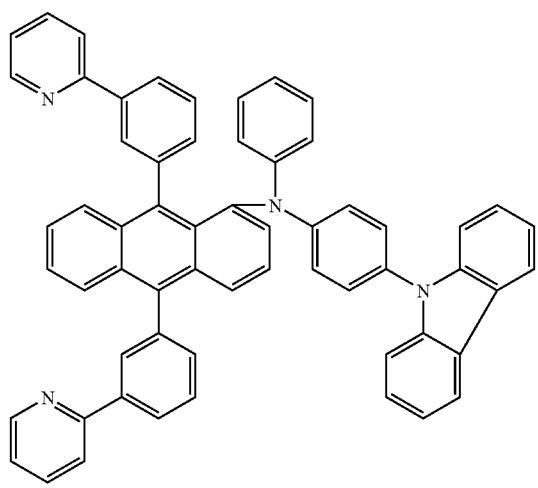
(341)
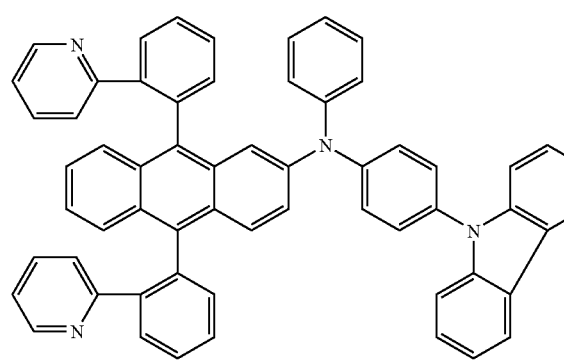
-continued
(342)
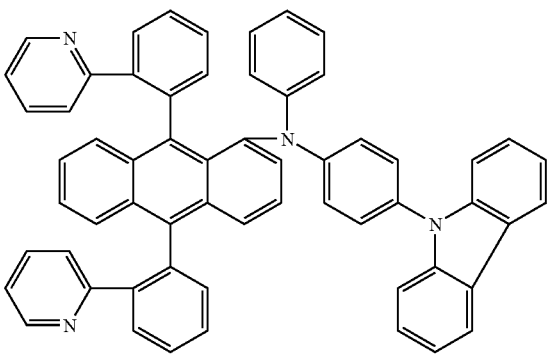
(343)
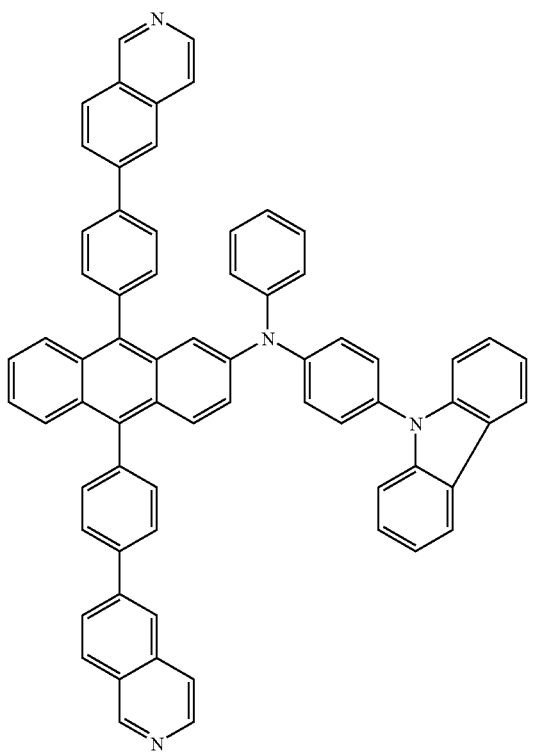

(344)
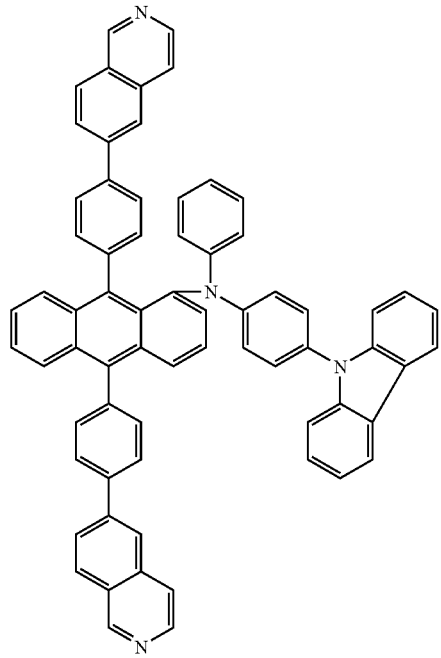
(346)
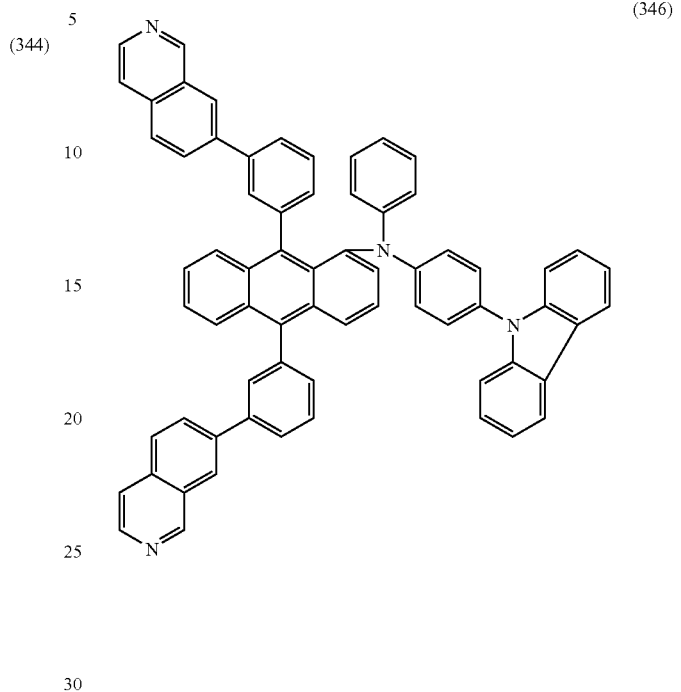
(347)
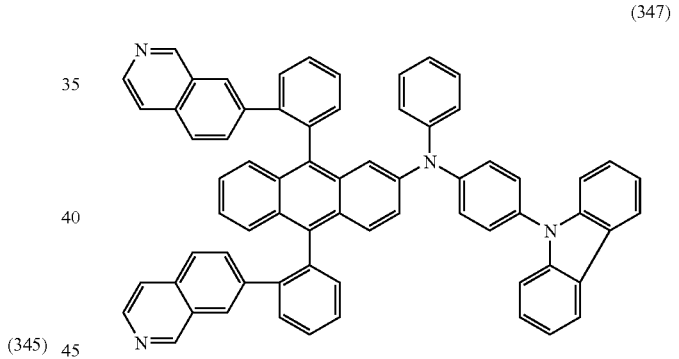
(345)
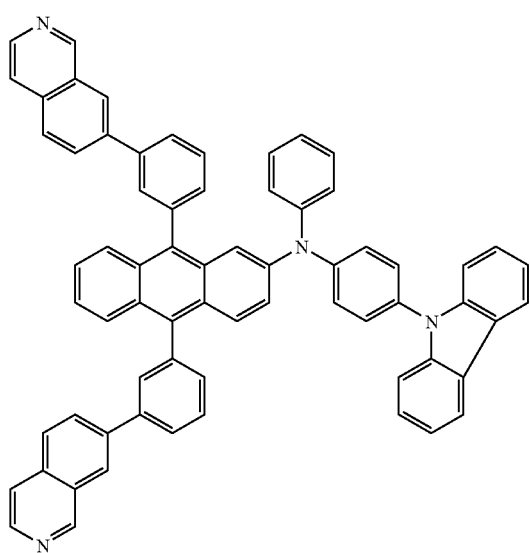
(348)
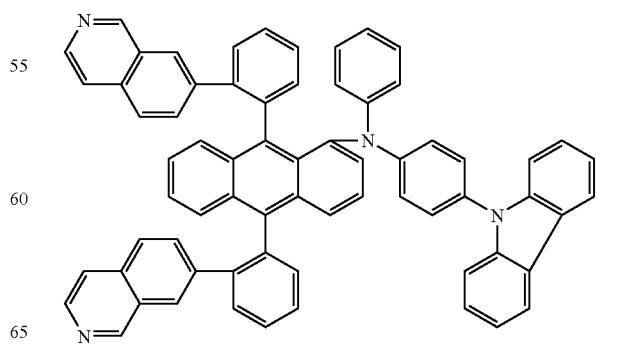

-continued
(349)
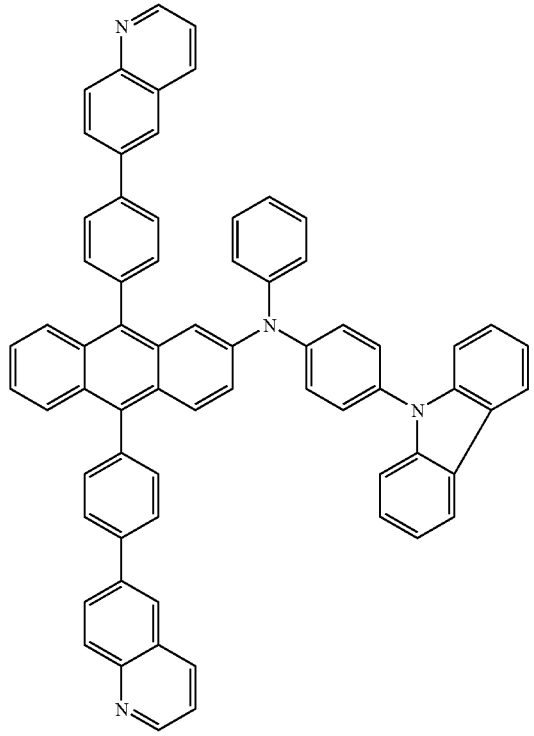
(350)
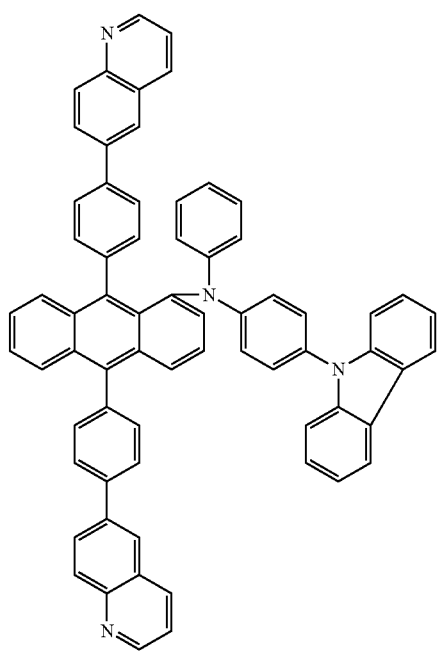
(351)
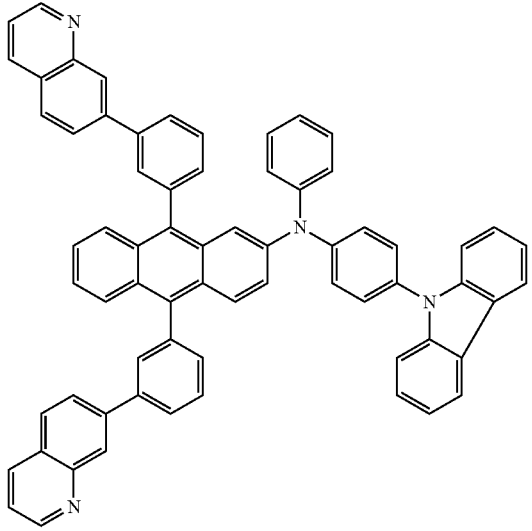
(352)
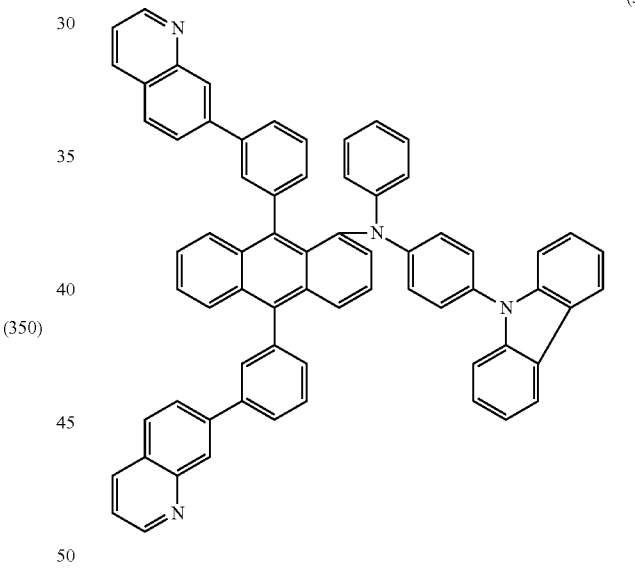
(353)

-continued
(354)
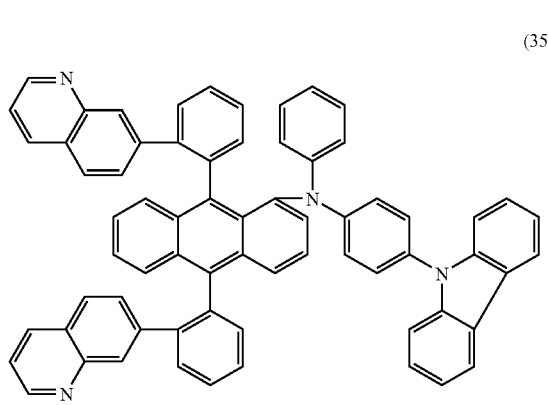
(355)
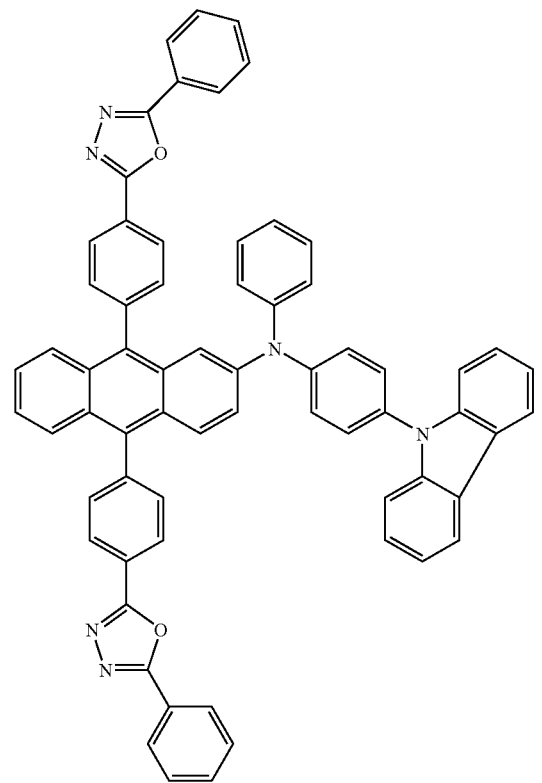
(356)
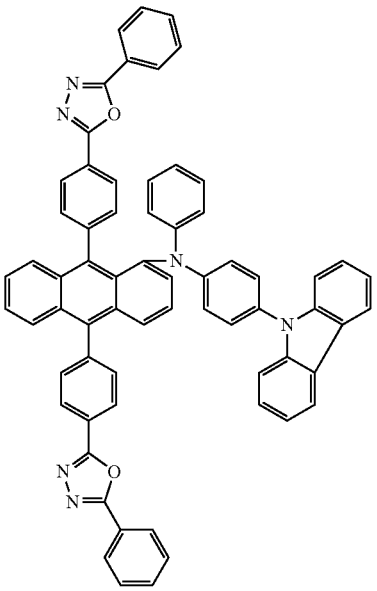
(357)
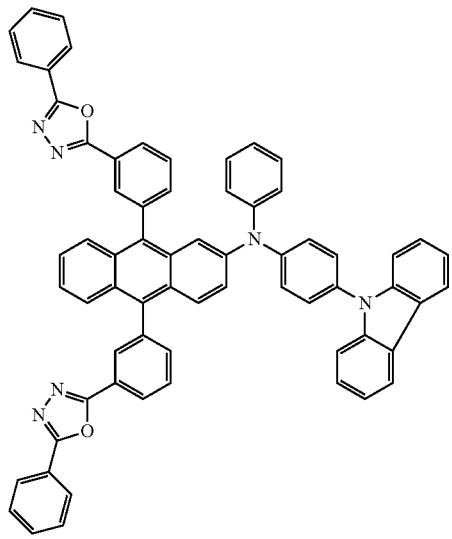

(358)

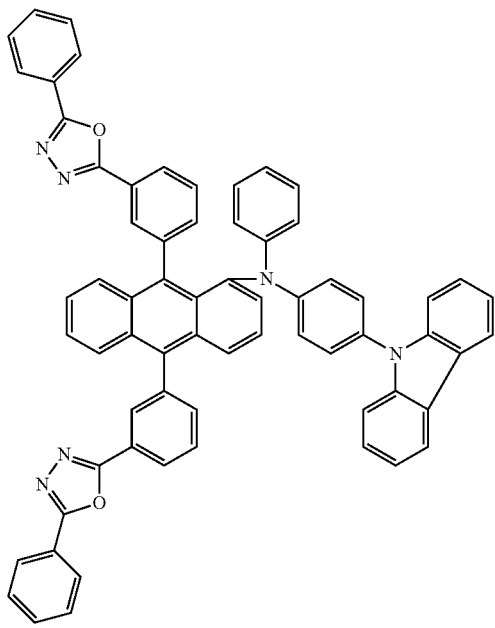

(359)

(360)

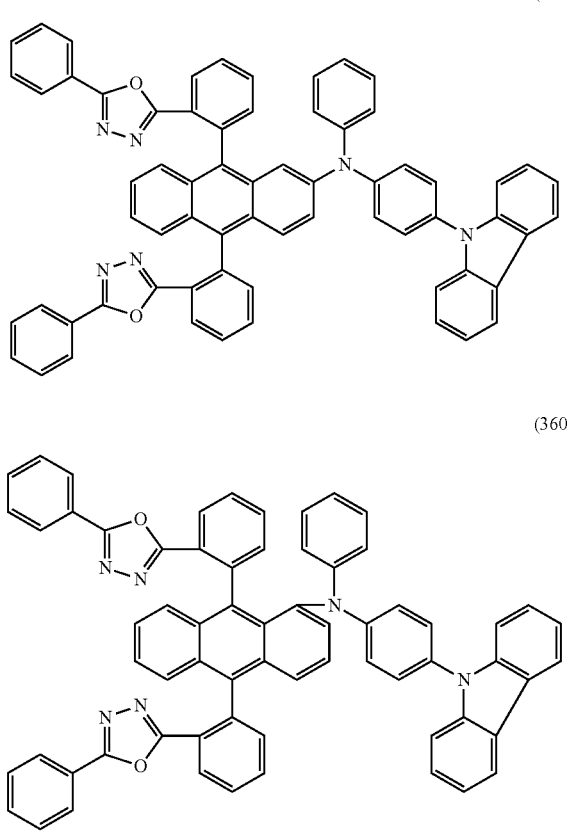

The anthracene derivatives represented by Structural Formulae (101) to (160) are specific examples of General Formula (1) in the case where A is General Formula (1-1), and the anthracene derivatives represented by Structural Formulae (201) to (260) are specific examples of General Formula (1) in the case where A is General Formula (1-2). Also, the anthracene derivatives represented by Structural Formulae (301) to (360) are specific examples of General Formula (1) in the case where A is General Formula (1-3).

A variety of reactions can be applied as a synthetic method of an anthracene derivative of the present invention. For example, the anthracene derivative of the present invention can be synthesized by conducting the synthesis reactions shown in following Reaction Schemes (A-1) to (A-5) and (B-1) to (B-3).

(A-1)

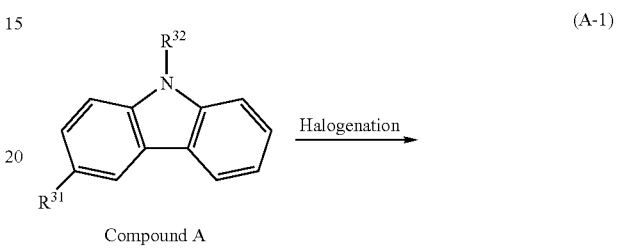

Compound A

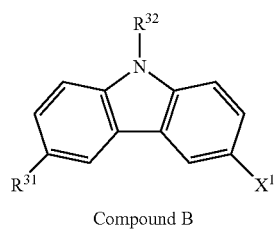

Compound B

Compound C

A compound including carbazole in a skeleton (Compound A) is reacted with a halogen or halogen source such as N-bromosuccinimide (NBS), N-iodosuccinimide (NIS), bromine ($Br_2$), potassium iodide (KI), or iodine ($I_2$) to synthesize a compound including 3-halogenated carbazole in a skeleton (Compound B), and then Compound B is subjected to a coupling reaction with arylamine using a metal catalyst such as a palladium catalyst (Pd catalyst), a metal such as copper, or a metal compound such as Cu(I), thereby obtaining a compound C. In the synthetic scheme (A-1), a halogen element ($X^1$) is preferably iodine or bromine. $R^{31}$ represents any one of a hydrogen atom, an alkyl group having 1 to 4 carbon atoms, and an aryl group having 6 to 25 carbon atoms. $R^{32}$ represents an alkyl group having 1 to 4 carbon atoms or an aryl group having 6 to 25 carbon atoms. Further, $Ar^{11}$ represents an aryl group having 6 to 25 carbon atoms.

(A-2)

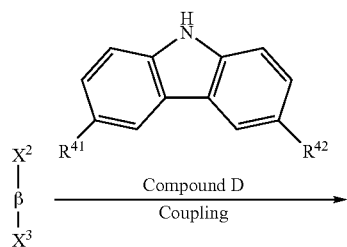

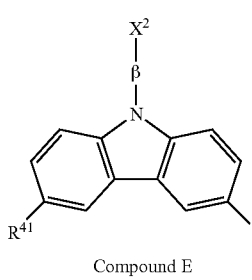

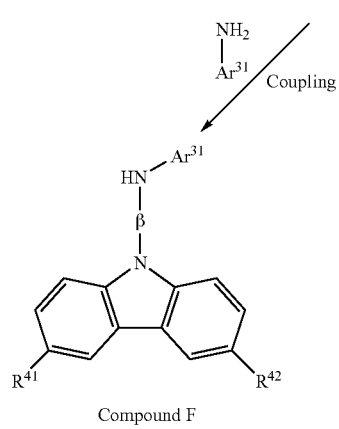

A compound including carbazole in a skeleton (Compound D) is reacted with a dihalide of an aromatic compound to synthesize a compound including N-(aryl halide)carbazole in a skeleton (Compound E), and then Compound E is subjected to a coupling reaction with arylamine using a metal catalyst such as a palladium (Pd) catalyst, a metal such as copper, or a metal compound such as Cu(I), thereby obtaining Compound F. In Synthetic Scheme (A-2), a halogen element ($X_2$ and $X_3$) of the dihalide of an aromatic compound is preferably iodine or bromine. $X_2$ and $X_3$ may be the same or different from each other. Each of $R^{41}$ and $R^{42}$ represents any one of a hydrogen atom, an alkyl group having 1 to 4 carbon atoms, and an aryl group having 6 to 25 carbon atoms. β represents an arylene group having 6 to 25 carbon atoms. $Ar^{31}$ represents an aryl group having 6 to 25 carbon atoms.

(A-3)

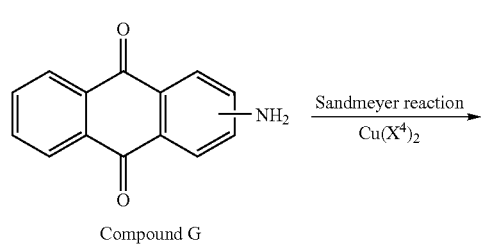

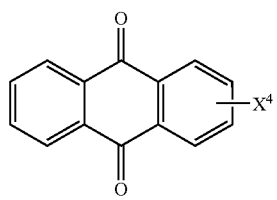

Compound H (A-4)

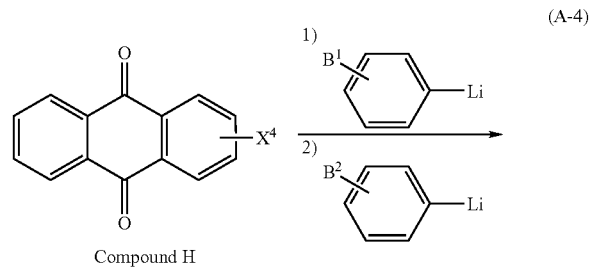

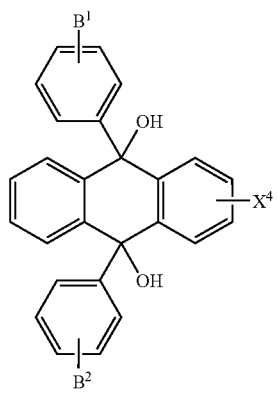

Compound I (A-5)

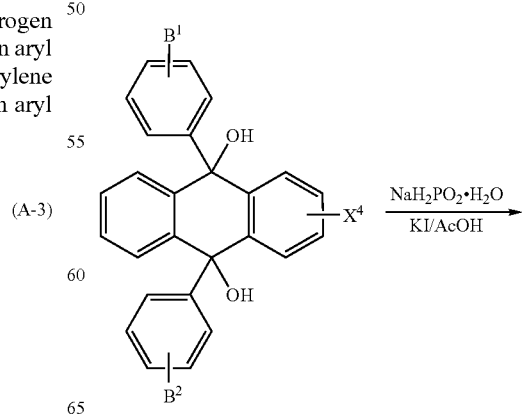

Compound I

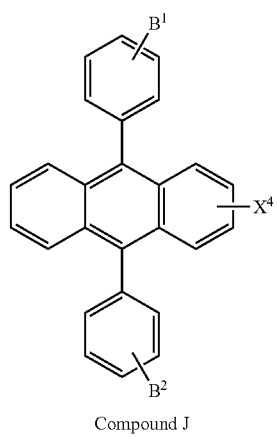

Compound J

A halide of anthraquinone (Compound H) is synthesized by the Sandmeyer reaction of 1-aminoanthraquinone or 2-aminoanthraquinone (Compound G). The halide of anthraquinone (Compound H) is reacted with aryllithium to synthesize a diol of a 9,10-dihydroanthracene derivative (Compound I). Then, the diol of the 9,10-dihydroanthracene derivative (Compound I) is subjected to dehydroxylation using sodium phosphinate monohydrate and potassium iodide in acetic acid, which allows the formation of 9,10-diarylanthracene halide (Compound J).

It is to be noted that in each of Synthetic Schemes (A-3) to (A-5), $X^4$ represents a halogen element. Also, each of $B^1$ and $B^2$ represents any one of halogen, a haloalkyl group, a cyano group, an acyl group, a carboxyl group, an acyloxy group, an alkoxy group, a pyridyl group, a quinolyl group, an isoquinolyl group, and an oxazolyl group.

(B-1)

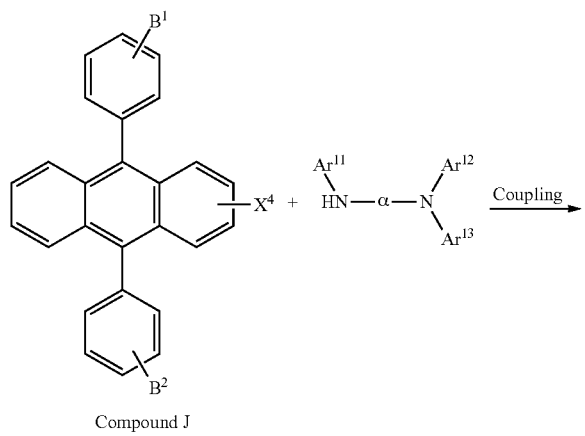

Compound J

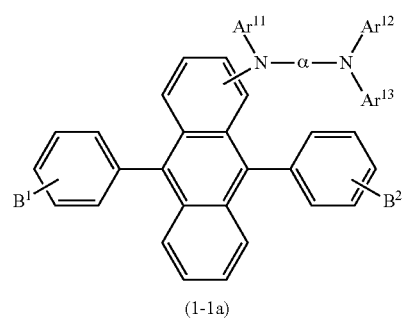

(1-1a)

An anthracene derivative of the present invention can be synthesized by the reaction shown in Synthetic Scheme (B-1) using Compound J prepared in Synthetic Scheme (A-5). By the coupling reaction of Compound J with arylamine using a metal catalyst such as a palladium (Pd) catalyst, a metal such as copper, or a metal compound such as Cu(I), the anthracene derivative of the present invention represented by General Formula (1-1a) can be synthesized. In Synthetic Scheme (B-1), each of $B^1$ and $B^2$ represents any one of halogen, a haloalkyl group, a cyano group, an acyl group, a carboxyl group, an acyloxy group, an alkoxy group, a pyridyl group, a quinolyl group, an isoquinolyl group, and an oxazolyl group; each of $Ar^{11}$ to $Ar^{13}$ represents an aryl group having 6 to 25 carbon atoms; and a represents an arylene group having 6 to 25 carbon atoms. It is to be noted that the compound represented by General Formula (1-1a) corresponds to the case where A in General Formula (1) is General Formula (1-1).

(B-2)

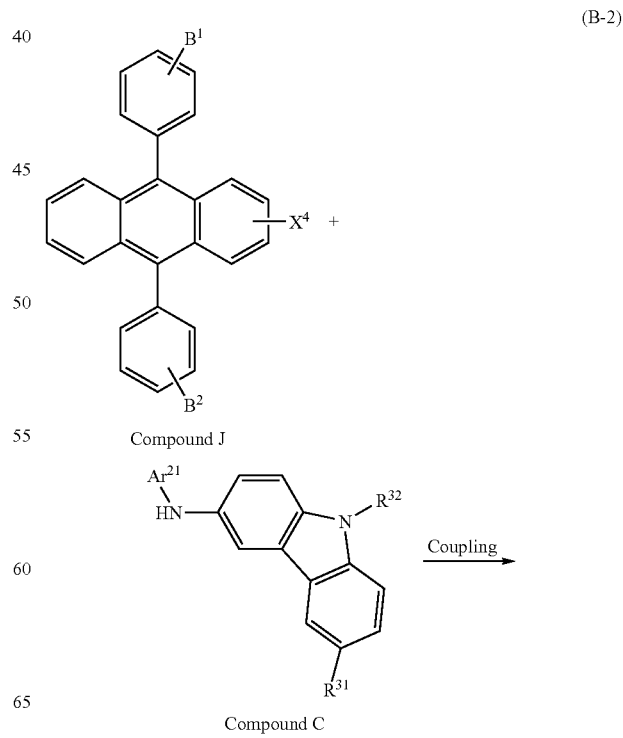

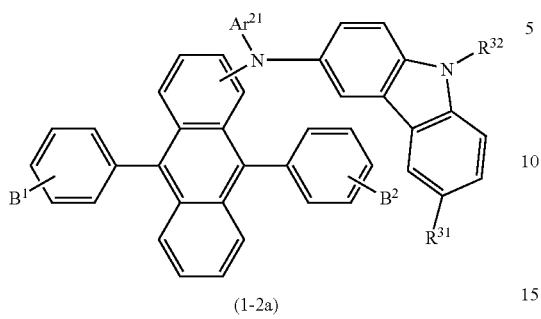

(1-2a)

An anthracene derivative of the present invention can be synthesized by a reaction shown in Synthetic Scheme (B-2), using Compound C prepared according to Synthetic Scheme (A-1) and Compound J prepared according to Synthetic Scheme (A-5). The coupling reaction between Compound C and Compound J using a metal catalyst such as a palladium (Pd) catalyst, a metal such as copper, or a metal compound such as Cu(I) can provide the anthracene derivative of the present invention represented by General Formula (1-2a). In Synthetic Scheme (B-2), each of $B^1$ and $B^2$ represents any one of halogen, a haloalkyl group, a cyano group, an acyl group, a carboxyl group, an acyloxy group, an alkoxy group, a pyridyl group, a quinolyl group, an isoquinolyl group, and an oxazolyl group; $Ar^{21}$ represents an aryl group having 6 to 25 carbon atoms; $R^{31}$ represents any one of a hydrogen atom, an alkyl group having 1 to 4 carbon atoms, and an aryl group having 6 to 25 carbon atoms; and $R^{32}$ represents either of an alkyl group having 1 to 4 carbon atoms and an aryl group having 6 to 25 carbon atoms. It is to be noted that the compound represented by General Formula (1-2a) corresponds to the case where A in foregoing General Formula (1) is General Formula (1-2).

(B-3)

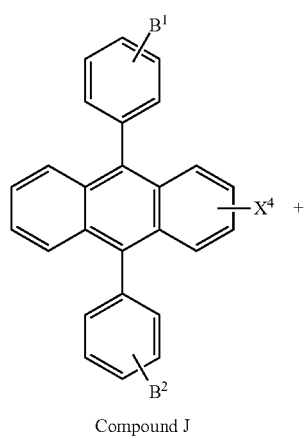

Compound J

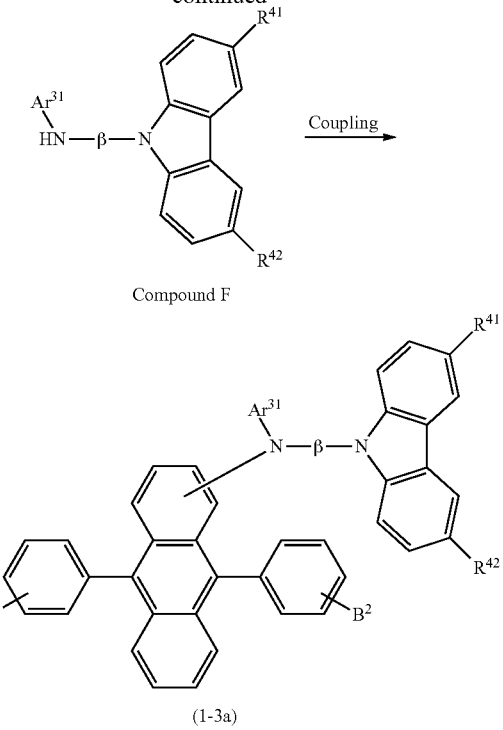

Compound F (1-3a)

An anthracene derivative of the present invention can be synthesized by a reaction shown in Synthetic Scheme (B-3), using Compound F prepared according to Synthetic Scheme (A-2) and Compound J prepared according to Synthetic Scheme (A-5). The coupling reaction between Compound F and Compound J using a metal catalyst such as a palladium (Pd) catalyst, a metal such as copper, or a metal compound such as Cu(I) can provide the anthracene derivative of the present invention represented by General Formula (1-3a). In Synthetic Scheme (B-3), each of $B^1$ and $B^2$ represents any one of halogen, a haloalkyl group, a cyano group, an acyl group, a carboxyl group, an acyloxy group, an alkoxy group, a pyridyl group, a quinolyl group, an isoquinolyl group, and an oxazolyl group; $Ar^{31}$ represents an aryl group having 6 to 25 carbon atoms; β represents an arylene group having 6 to 25 carbon atoms; and each of $R^{41}$ and $R^{42}$ represents any one of a hydrogen atom, an alkyl group having 1 to 4 carbon atoms, and an aryl group having 6 to 25 carbon atoms. It is to be noted that the compound represented by General Formula (1-3a) corresponds to the case where A in foregoing General Formula (1) is General Formula (1-3).

Having a phenyl group with an electron withdrawing group or a heteroaromatic group, the anthracene derivative of the present invention has high luminous efficiency. That is, by the introduction of an electron withdrawing group, a light-emitting material with quite high luminous efficiency can be obtained. Further, the electron withdrawing group is preferably fluorine because it has high electronegativity.

The anthracene derivative of the present invention has high luminous efficiency, and emits visible light, specifically, blue green to yellow green light. Therefore, the anthracene derivative of the present invention can be favorably used for a light-emitting element.

As mentioned above, most light-emitting elements using an organic compound readily exist in the hole-excessive state during operation. However, the anthracene derivative of the present invention has a low lowest unoccupied molecular orbital (LUMO) level, and exhibits an electron trapping property, which prevents the light-emitting layer from existing in the hole-excessive state. Therefore, by using the anthracene derivative of the present invention as a light-emitting substance, recombination probability of electrons and holes in the light-emitting layer can be increased, whereby a light-emitting element with high luminous efficiency can be obtained. In the anthracene derivative of the present invention, each of $B^1$ and $B^2$ is preferably fluorine which provides a high electron trapping property to the anthracene derivative.

Also, since the anthracene derivative of the present invention is capable of green light emission with high efficiency, it can be favorably used for a full-color display. Further, since the use of the anthracene derivative of the present invention allows the fabrication of a light-emitting element with a long lifetime, the anthracene derivative of the present invention can be favorably used for a full-color display.

Furthermore, since the anthracene derivative of the present invention is capable of green light emission with high efficiency, white light emission can be obtained by combining with other light-emitting materials. For example, in order to obtain white light emission using red (R), green (G), and blue (B) emissions positioned at the NTSC chromaticity coordinates, light emissions of these colors should be mixed with a proportion of approximately red (R):green (G):blue (B)=1:6:3. That is, the proportion of green light emission needs to be highest and, therefore, the anthracene derivative of the present invention which is capable of green light emission with high efficiency is favorable for a white emissive light-emitting device.

Also, in the anthracene derivative of the present invention, only one substituent A is bonded to an anthracene skeleton as represented by General Formula (1). Consequently, compared with a disubstituted compound in which two A units are bonded to the anthrace skeleton, the anthracene derivative of the present invention is capable of exhibiting light emission with a short wavelength. Further, since the molecular weight of the disubstituted compound is very high, film formation by an evapolariton method is difficult; however, film formation by an evaporation method is possible with the anthracene derivative of the present invention. In addition, synthesis of a disubstituted compound requires higher cost than that of the anthracene derivative of the present invention which is monosubstituted.

Further, the inventors found that, the monosubstituted anthracene derivative can, when applied to a light-emitting element, provide a longer lifetime than the disubstituted anthracene derivative. Consequently, by applying the anthracene derivative of the present invention to a light-emitting element, a light-emitting element with a long lifetime can be obtained.

Furthermore, the anthracene derivative of the present invention is stable even if it is subjected to oxidation-reduction cycles repeatedly. Consequently, by using the anthracene derivative of the present invention in a light-emitting element, a light-emitting element with a long lifetime can be obtained.

Embodiment Mode 2

One aspect of a light-emitting element using the anthracene derivative of the present invention will be described below with reference to FIG. 1A.

A light-emitting element of the present invention has a plurality of layers between a pair of electrodes. The plurality of layers are formed by stacking the layers of a substance having a high carrier injecting property and a substance having a high carrier transporting property so that a light-emitting region is formed in a region away from the electrodes, that is, recombination of carriers is performed in an area away from the electrodes.

In this embodiment mode, a light-emitting element includes a first electrode 102, a second electrode 104, and an EL layer 103 provided therebetween. It is to be noted that description will be made below in this embodiment mode with an assumption that the first electrode 102 functions as an anode and the second electrode 104 functions as a cathode. That is, light emission is obtained when a voltage is applied between the first electrode 102 and the second electrode 104 such that the first electrode 102 has a higher potential than the second electrode 104.

A substrate 101 is used as a support of the light-emitting element. For the substrate 101, glass, plastic, or the like can be used, for example. It is to be noted that another material may be used as long as it functions as a support in a fabrication process of the light-emitting element.

As the first electrode 102, a metal, an alloy, an electrically conductive compound, a mixture thereof, or the like having a high work function (specifically, 4.0 eV or more) is preferably used. Specifically, indium tin oxide (ITO), ITO including silicon or silicon oxide, indium zinc oxide (IZO), indium oxide including tungsten oxide and zinc oxide (IWZO), or the like can be used. Although these conductive metal oxide films are generally formed by sputtering, they may be formed by applying a sol-gel method or the like. For example, a film of indium zinc oxide (IZO) can be formed by a sputtering method using a target in which 1 to 20 wt % of zinc oxide is added to indium oxide. A film of indium oxide including tungsten oxide and zinc oxide (IWZO) can be formed by a sputtering method using a target in which 0.5 to 5 wt % of tungsten oxide and 0.1 to 1 wt % of zinc oxide are included in indium oxide. In addition, gold (Au), platinum (Pt), nickel (Ni), tungsten (W), chromium (Cr), molybdenum (Mo), iron (Fe), cobalt (Co), copper (Cu), palladium (Pd), a nitride of a metal (such as titanium nitride), or the like can be used.

There is no particular limitation on the stacked structure of the EL layer 103, and layers formed of a substance with a high electron transporting property, a substance with a high hole transporting property, a substance with a high electron injecting property, a substance with a high hole injecting property, a bipolar substance (substance having a high electron transporting property and a high hole transporting property) and/or the like may be combined as appropriate with a light-emitting layer shown in this embodiment mode. For example, the EL layer 103 can be formed by combining as appropriate a hole injecting layer, a hole transporting layer, a hole blocking layer, a light-emitting layer, an electron transporting layer, an electron injecting layer, and the like. This embodiment mode will describe the EL layer 103 having a structure in which a hole injecting layer 111, a hole transporting layer 112, a light-emitting layer 113, and an electron transporting layer 114 are sequentially stacked over the first electrode 102. Materials for the respective layers will be specifically shown below.

The hole injecting layer 111 is a layer including a substance having a high hole injecting property. Molybdenum oxide, vanadium oxide, ruthenium oxide, tungsten oxide, manganese oxide, or the like can be used. Alternatively, the hole injecting layer 111 can be formed using phthalocyanine (abbreviation: H$_2$Pc); phthalocyanine-based compounds such as copper phthalocyanine (CuPc); aromatic amine compounds such as 4,4'-bis[N-(4-diphenylaminophenyl)-N-phenylamino]biphenyl (abbreviation: DPAB) and 4,4'-bis(N-{4-[N-(3-methylphenyl)-N-phenylamino]phenyl}-N-phenylamino)biphenyl (abbreviation: DNTPD); high-molecular compounds such as poly(3,4-ethylenedioxythiophene)/poly(styrenesulfonate) (PEDOT/PSS); or the like.

As a further alternative, a composite material formed by mixing an acceptor substance into a substance with a high hole transporting property can also be used for the hole injecting layer 111. In particular, when a material formed by mixing an acceptor substance into a substance with a high hole transporting property is used, materials for forming the electrode can be selected regardless of the magnitude of work function. That is, not only a material with a high work function, but also a material with a low work function can be used for the first electrode 102. As an acceptor substance, 7,7,8,8-tetracyano-2,3,5,6-tetrafluoroquinodimethane (abbreviation: $F_4$-TCNQ), chloranil, or the like can be used. In addition, an oxide of a transition metal can also be used. Also, oxides of metals belonging to Groups 4 to 8 in the periodic table can also be used. Specifically, it is preferable to use vanadium oxide, niobium oxide, tantalum oxide, chromium oxide, molybdenum oxide, tungsten oxide, manganese oxide, and rhenium oxide because of their high electron accepting properties. Among them, molybdenum oxide is particularly preferable because it is stable under air, has a low moisture absorption property, and is easily handled.

As the organic compound used for the composite material, various compounds such as aromatic amine compounds, carbazole derivatives, aromatic hydrocarbons, oligomer, dendrimer, and high-molecular compounds can be used. The organic compound used for the composite material is preferably an organic compound having a high hole transporting property. Specifically, a substance having a hole mobility of greater than or equal to $10^{-6}$ cm$^2$/Vs is preferably used. However, other materials than these materials may also be used as long as the hole transporting properties thereof are higher than the electron transporting properties thereof. The organic compounds which can be used for the composite material will be specifically shown below. For example, the following aromatic amine compounds can be used: N,N'-di(p-tolyl)-N,N-diphenyl-p-phenylenediamine (abbreviation: DTDPPA); 4,4'-bis[N-(4-diphenylaminophenyl)-N-phenylamino]biphenyl (abbreviation: DPAB); 4,4'-bis(N-{4-[N'-(3-methylphenyl)-N'-phenylamino]phenyl}-N-phenylamino)biphenyl (abbreviation: DNTPD); 1,3,5-tris[N-(4-diphenylaminophenyl)-N-phenylamino]benzene (abbreviation: DPA3B); and the like.

As the carbazole derivatives which can be used for the composite material, the following can be given specifically: 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation: PCzPCA2); 3-[N-(1-naphtyl)-N-(9-phenylcarbazol-3-yl)amino]-9-phenylcarbazole (abbreviation: PCzPCN1); and the like.

Moreover, as the carbazole derivatives which can be used for the composite material, the following can be given: 4,4'-di(N-carbazolyl)biphenyl (abbreviation: CBP); 1,3,5-tris[4-(N-carbazolyl)phenyl]benzene (abbreviation: TCPB); 9-[4-(N-carbazolyl)]phenyl-10-phenylanthracene (abbreviation: CzPA); 1,4-bis[4-(N-carbazolyl)phenyl]-2,3,5,6-tetraphenylbenzene; and the like.

As the aromatic hydrocarbons which can be used for the composite material, the following can be given for example: 2-tert-butyl-9,10-di(2-naphthyl)anthracene (abbreviation: t-BuDNA); 2-tert-butyl-9,10-di(1-naphthyl)anthracene; 9,10-bis(3,5-diphenylphenyl)anthracene (abbreviation: DPPA); 2-tent-butyl-9,10-bis(4-phenylphenyl)anthracene (abbreviation: t-BuDBA); 9,10-di(2-naphthyl)anthracene (abbreviation: DNA); 9,10-diphenylanthracene (abbreviation: DPAnth); 2-tert-butylanthracene (abbreviation: t-BuAnth); 9,10-bis(4-methyl-1-naphthyl)anthracene (abbreviation: DMNA); 2-tert-butyl-9,10-bis[2-(1-naphthyl)phenyl]anthracene; 9,10-bis[2-(1-naphthyl)phenyl]anthracene; 2,3,6,7-tetramethyl-9,10-di(1-naphthyl)anthracene; 2,3,6,7-tetramethyl-9,10-di(2-naphthyl)anthracene; 9,9'-bianthryl; 10,10'-diphenyl-9,9'-bianthryl; 10,10'-bis(2-phenylphenyl)-9,9'-bianthryl; 10,10'-bis[(2,3,4,5,6-pentaphenyl)phenyl]-9,9'-bianthryl; anthracene; tetracene; rubrene; perylene; 2,5,8,11-tetra(tert-butyl)perylene; and the like. Besides these compounds, pentacene, coronene, or the like can also be used. In particular, an aromatic hydrocarbon which has a hole mobility of greater than or equal to $1 \times 10^{-6}$ cm$^2$/Vs and which has 14 to 42 carbon atoms is more preferable.

The aromatic hydrocarbons which can be used for the composite material may have a vinyl moiety. As the aromatic hydrocarbons having a vinyl group, the following are given for example: 4,4'-bis(2,2-diphenylvinyl)biphenyl (abbreviation: DPVBi); 9,10-bis[4-(2,2-diphenylvinyl)phenyl]anthracene (abbreviation: DPVPA); and the like.

Moreover, high-molecular compounds such as poly(N-vinylcarbazole) (abbreviation: PVK) and poly(4-vinyltriphenylamine) (abbreviation: PVTPA) ca$_{n\ a}l_{so}$ be used.

The hole transporting layer 112 is a layer including a substance with a high hole transporting property. As a substance with a high hole transporting property, the following aromatic amine compounds can be used for example:

4,4'-bis[N-(1-napthyl)-N-phenylamino]biphenyl (abbreviation: NPB); N,N'-bis(3-methylphenyl)-N,N'-diphenyl-[1,1'-biphenyl]-4,4'-diamine (abbreviation TPD); 4,4',4"-tris(N,N-diphenylamino)triphenylamine (abbreviation TDATA); 4,4',4"-tris[N-(3-methylphenyl)-N-phenylamino]triphenylamine (abbreviation MTDATA); and 4,4'-bis[N-(spiro-9,9'-bifluoren-2-yl)-N-phenylamino]biphenyl (abbreviation: BSPB). The materials described here mainly are substances each having a hole mobility of greater than or equal to $10^{-6}$ cm$^2$/Vs. However, other materials than these compounds may also be used as long as the hole transporting properties thereof are higher than the electron transporting properties thereof. The hole transporting layer 112 is not limited to a single layer, and two or more layers in which each layer is made of the aforementioned material may be stacked.

The light-emitting layer 113 is a layer including a substance with a high light-emitting property. In the light-emitting element shown in this embodiment mode, the light-emitting layer 113 includes the anthracene derivative of the present invention described in Embodiment Mode 1. The anthracene derivative of the present invention can favorably be applied to a light-emitting element as a substance with a high light-emitting property since the anthracene derivative of the present invention exhibits light emission of blue green to yellow green with high luminance efficiency.

As the electron transporting layer 114, a substance having a high electron transporting property can be used. For example, a layer including a metal complex or the like having a quinoline or benzoquinoline moiety, such as tris(8-quinolinolato)aluminum (abbreviation: Alq), tris(4-methyl-8-quinolinolato)aluminum (abbreviation: Almq$_3$), bis(10-hydroxybenzo[h]quinolinato)beryllium (abbreviation: BeBq$_2$), or bis(2-methyl-8-quinolinolato)(4-phenylphenolato)aluminum (abbreviation: BAlq) can be used. Alternatively, a metal complex or the like having an oxazole-based or thiazole-based ligand, such as bis[2-(2-hydroxyphenyl)benzoxazolato]zinc (abbreviation: Zn(BOX)$_2$) or bis[2-(2-hydroxyphenyl)-benzothiazolato]zinc (abbreviation: Zn(BTZ)$_2$) can be used. Besides the metal complexes, 2-(4-biphenylyl)-5-(4-tert-butylphenyl)-1,3,4-oxadiazole (abbreviation: PBD), 1,3-bis[5-(p-tert-butylphenyl)-1,3,4-oxadiazole-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like can also be used. The substances described here mainly are substances each having an electron mobility of greater than or equal to $10^{-6}$ cm$^2$/Vs. The electron transporting layer may be formed using other materials than those described above as long as the materials have higher electron transporting properties than hole transporting properties. Furthermore, the electron transporting layer is not limited to a single layer, and two or more layers in which each layer is made of the aforementioned material may be stacked.

As a substance forming the second electrode 104, a metal, an alloy, an electrically conductive compound, a mixture thereof, or the like having a low work function (specifically, 3.8 eV or less) can be used. As a specific example of such a cathode material, an element belonging to Group 1 or Group 2 in the periodic table, that is, an alkali metal such as lithium (Li) or cesium (Cs), an alkaline earth metal such as magnesium (Mg), calcium (Ca), or strontium (Sr), an alloy including these metals (MgAg, AlLi) can be employed. A rare earth metal such as europium (Eu) or ytterbium (Yb), an alloy including these rare earth metals, or the like is also suitable. However, by providing a layer having a function of promoting electron injection between the second electrode 104 and the electron transporting layer, various conductive materials such as Al, Ag, ITO, or ITO including silicon or silicon oxide can be used for the second electrode 104 regardless of the magnitude of work function.

As the layer having a function of promoting electron injection, an alkali metal, an alkaline earth metal, or a compound thereof such as lithium fluoride (LiF), cesium fluoride (CsF), or calcium fluoride (CaF$_2$) can be used. Alternatively, a layer which contains a substance having an electron transporting property and an alkali metal, an alkaline earth metal, or a compound thereof (Alq including magnesium (Mg) for example) can be used. The use of such a layer is advantageous because electron injection from the second electrode 107 proceeds efficiently.

Various methods can be used for forming the EL layer 103 regardless of a dry method or a wet method. For example, a vacuum evaporation method, an ink-jet method, a spin coating method, or the like may be used. Furthermore, each electrode or each layer may be formed by a different film formation method.

By applying a voltage between the first electrode 102 and the second electrode 104 of the light-emitting element of the present invention with the abovementioned structure, holes and electrons are recombined in the light-emitting layer 113 that is a layer including a substance with a high light-emitting property, whereby light emission is obtained. That is, the light-emitting element of the present invention has a structure in which a light-emitting region is formed in the light-emitting layer 113.

Light emission is extracted outside through one or both of the first electrode 102 and the second electrode 104. Therefore, one or both of the first electrode 102 and the second electrode 104 is/are formed using an electrode having a light transmitting property. In a case where only the first electrode 102 has a light transmitting property, light emission is extracted from a substrate side through the first electrode 102 as shown in FIG. 1A. Alternatively, in a case where only the second electrode 104 has a light transmitting property, light emission is extracted from the side opposite to the substrate through the second electrode 104 as shown in FIG. 1B. In a case where each of the first electrode 102 and the second electrode 104 has a light transmitting property, light emission is extracted from both of the substrate side and the side opposite to the substrate through the first electrode 102 and the second electrode 104, as shown in FIG. 1C.

The structure of layers provided between the first electrode 102 and the second electrode 104 is not limited to the abovementioned structure. A structure other than the abovementioned structure may be used as long as the light-emitting region, in which holes and electrons are recombined, is located away from the first electrode 102 and the second electrode 104, so that a quenching phenomenon that would otherwise be caused by the proximity of the light-emitting region to metal can be prevented In other words, a stacked structure of the layers is not specifically limited to the abovementioned structure, and a layer formed using a substance having a high electron transporting property, a substance having a high hole transporting property, a substance having a high electron injecting property, a substance having a high hole injecting property, a bipolar substance (substance having a high electron transporting property and a high hole transporting property), a hole blocking material, or the like may be freely combined with the anthracene derivative of the present invention.

Figure 2:
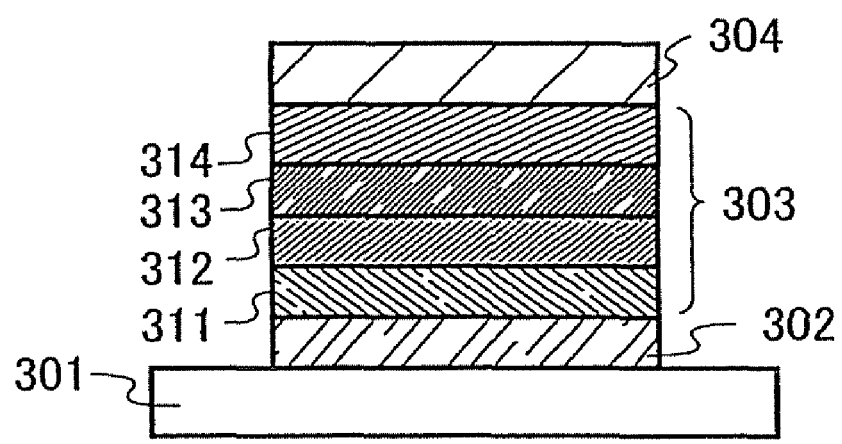
FIG. 2 illustrates a light-emitting element of the present invention.

A light-emitting element shown in FIG. 2 has a structure in which a first electrode 302 serving as a cathode, an electron transporting layer 311, a light-emitting layer 312, a hole transporting layer 313, a hole injecting layer 314, and a second electrode 304 serving as an anode are sequentially stacked over a substrate 301.

In this embodiment mode, a light-emitting element is fabricated over a substrate made of glass, plastic, or the like. By fabricating a plurality of the light-emitting elements described above over one substrate, a passive matrix light-emitting device can be manufactured. Alternatively, for example, by fabricating thin film transistors (TFTs) over a substrate made of glass, plastic, or the like, and then fabricating the light-emitting elements over electrodes electrically connected to the respective TFTs, an active matrix light-emitting device can be manufactured, in which driving of the light-emitting elements is controlled by the TFTs. The structure of the TFT is not specifically limited, and the TFT may be a staggered TFT or an inverted staggered TFT. Crystallinity of a semiconductor used for the TFT is also not limited, and an amorphous semiconductor or a crystalline semiconductor may be used. In addition, a driver circuit formed over a TFT substrate may be constructed from N-channel TFTs and P-channel TFTs, or may be constructed from one of N-channel TFTs or P-channel As shown in this embodiment mode, the anthracene derivative of the present invention can be used for a light-emitting layer without adding any other light-emissive substance, since the anthracene derivative of the present invention exhibits light emission of blue green to yellow green with high luminance efficiency.

Since the anthracene derivative of the present invention has high luminous efficiency, a light-emitting element with high luminous efficiency can be obtained by using the anthracene derivative of the present invention as a light-emitting substance. Further, by using the anthracene derivative of the present invention as a light-emitting substance, a light-emitting element with low power consumption can be obtained. Also, by using the anthracene derivative of the present invention as a light-emitting substance, a light-emitting element with a long lifetime can be obtained.

As mentioned above, most light-emitting elements using an organic compound readily have the hole-excessive state during operation. However, the anthracene derivative of the present invention has a low lowest unoccupied molecular orbital (LUMO) level, and exhibits an electron trapping property, which prevents the light-emitting from existing in the hole-excessive state. Therefore, by using the anthracene derivative of the present invention as a light-emitting substance, recombination probability of electrons and holes in the light-emitting substance can be increased, whereby a light-emitting element with high luminous efficiency can be obtained.

Also, since the anthracene derivative of the present invention is capable of green light emission with high efficiency, it can be favorably used for a full-color display. Further, since the anthracene derivative of the present invention capable of green light emission has a long lifetime, it can be favorably used for a full-color display.

Furthermore, since the anthracene derivative of the present invention is capable of green light emission with high efficiency, white light emission can be obtained by combining with other light-emitting materials. For example, in order to obtain white light emission using red (R), green (G), and blue (B) emissions positioned at the NTSC chromaticity coordinates, light emissions of these colors should be mixed with a proportion of approximately red (R):green (G):blue (B)=1:6:3. That is, the proportion of green light emission needs to be highest and, therefore, the anthracene derivative of the present invention which is capable of green light emission with high efficiency is favorable for a light-emitting device.

Embodiment Mode 3

In this embodiment mode, a light-emitting element having a different structure from that described in Embodiment Mode 2 will be described.

Figure 1B:
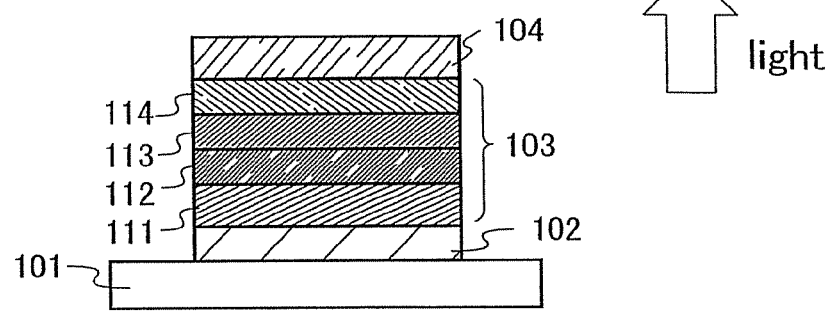
Figure 1C:
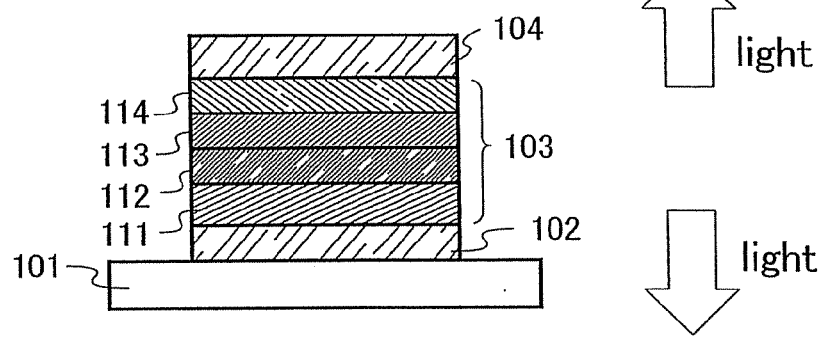

In this embodiment mode, the light-emitting layer 113 shown in FIGS. 1A to 1C is formed by dispersing the anthracene derivative of the present invention into another substance, whereby light emission can be obtained from the anthracene derivative of the present invention. Since the anthracene derivative of the present invention exhibits light emission of blue green to yellow green, a light-emitting element exhibiting light emission of blue green to yellow green can be obtained.

Various materials can be used as a substance in which the anthracene derivative of the present invention is dispersed. In addition to the substance having a high hole transporting property and the substance having a high electron transporting property, which are described in Embodiment Mode 2, the following materials can be used: 4,4'-bis(N-carbazolyl)-biphenyl (abbreviation: CBP); 2,2',2''-(1,3,5-benzenetri-yl)-tris[1-phenyl-1H-benzimidazole] (abbreviation: TPBI); 9,10-di(2-naphthyl)anthracene (abbreviation: DNA); 2-tert-butyl-9,10-di(2-naphthyl)anthracene (abbreviation: t-BuDNA); 9-[4-(N-carbazolyl)]phenyl-10-phenylanthracene (abbreviation: CzPA); bis(2-methyl-8-quinolinolato)(4-phenylphenolato)aluminum(III) (abbreviation: BAlq); 4,4'-bis[N-(1-napthyl)-N-phenylamino]biphenyl (abbreviation: NPB); and the like.

Since the anthracene derivative of the present invention has high luminous efficiency, a light-emitting element with high luminous efficiency can be obtained by using the anthracene derivative of the present invention as a light-emitting substance of a light-emitting element. Further, by using the anthracene derivative of the present invention as a light-emitting substance, a light-emitting element with low power consumption can be obtained. Also, by using the anthracene derivative of the present invention as a light-emitting substance, a light-emitting element with a long lifetime can be obtained.

As mentioned above, most light-emitting elements using an organic compound readily exist in the hole-excessive state during driving. However, the anthracene derivative of the present invention has a low lowest unoccupied molecular orbital (LUMO) level, and exhibits an electron trapping property, which prevents the light-emitting from existing in the hole-excessive state. Therefore, by using the anthracene derivative of the present invention as a light-emitting substance, recombination probability of electrons and holes in the light-emitting substance can be increased, whereby a light-emitting element with high luminous efficiency can be obtained.

Also, since the anthracene derivative of the present invention is capable of green light emission with high efficiency, it can be favorably used for a full-color display. Further, since the anthracene derivative of the present invention capable of green light emission has a long lifetime, it can be favorably used for a full-color display.

Furthermore, since the anthracene derivative of the present invention is capable of green light emission with high efficiency, white light emission can be obtained by combining with other light-emitting materials. For example, in order to obtain white light emission using red (R), green (G), and blue (B) emissions positioned at the NTSC chromaticity coordinates, light emissions of these colors should be mixed with a proportion of approximately red (R):green (G):blue (B)=1:6:3. That is, the proportion of green light emission needs to be highest and, therefore, the anthracene derivative of the present invention which is capable of green light emission with high efficiency is favorable for a light-emitting device.

Note that, regarding the layers other than the light-emitting layer 113, the structure shown in Embodiment Mode 2 can be used as appropriate.

Embodiment Mode 4

In this embodiment mode, a light-emitting element with a structure different from the structures described in Embodiment Modes 2 and 3 will be described.

In this embodiment mode, the light-emitting layer 113 shown in FIGS. 1A to 1C is formed by dispersing a light-emissive substance in the anthracene derivative of the present invention, whereby light emission from the light-emissive substance can be obtained.

In a case where the anthracene derivative of the present invention is used as a material in which another light-emissive substance is dispersed, a light-emission color derived from the light-emissive substance can be obtained. Further, light emission having a mixed color derived from the anthracene derivative of the present invention and the light-emissive substance dispersed in the anthracene derivative can also be obtained.

Various materials can be used as a light-emissive substance dispersed in the anthracene derivative of the present invention. Specifically, the following materials can be used: a fluorescence-emissive substance that emits fluorescence such as 4-(dicyanomethylene)-2-methyl-6-(p-dimethylaminostyryl)-4H-pyran (abbreviation: DCM1); 4-(dicyanomethylene)-2-methyl-6-(julolidine-4-yl-vinyl)-4H-pyran (abbreviation: DCM2); N,N-dimethylquinacridone (abbreviation: DMQd); or rubrene. Further, a phosphorescence-emissive substance that emits phosphorescence such as (acetylacetonato)bis[2,3-bis(4-fluorophenyl)quinoxalinato]iridium(III) (abbreviation: Ir(Fdpq)$_2$(acac)); 2,3,7,8,12,13,17,18-octaethyl-21H,23H-porphyrinplatinum(II) (abbreviation: PtOEP), or the like can also be used.

Note that, regarding the layers other than the light-emitting layer 113, the structure shown in Embodiment Mode 2 can be used as appropriate.

Embodiment Mode 5

In this embodiment mode, a light-emitting element with a structure different from the structures described in Embodiment Modes 2 and 3 will be described.

An anthracene derivative of the present invention has a hole transporting property. Therefore, a layer including the anthracene derivative of the present invention can be provided between the anode and the light-emitting layer. Specifically, the anthracene derivative of the present invention can be used in the hole injecting layer 111 and the hole transporting layer 112 described in Embodiment Mode 2.

Also, in a case of applying the anthracene derivative of the present invention as the hole injecting layer 111, it is preferable to compose the anthracene derivative of the present invention and an inorganic compound having an electron accepting property with respect to the anthracene derivative of the present invention. By using such a composite layer, carrier density of the hole injecting layer 111 increases, which contributes to improvement of the hole injecting property and hole transporting property. Also, in a case of using the composite layer as the hole injecting layer 111, the hole injecting layer 111 can achieve an ohmic contact with the first electrode 102; therefore, a material of the first electrode can be selected regardless of the magnitude of work function.

As the inorganic compound used for the composite material, an oxide of a transition metal is preferably used. Moreover, oxides of metals belonging to Groups 4 to 8 in the periodic table can be used. Specifically, it is preferable to use vanadium oxide, niobium oxide, tantalum oxide, chromium oxide, molybdenum oxide, tungsten oxide, manganese oxide, and rhenium oxide, because of their high electron accepting properties. Among them, molybdenum oxide is particularly preferable because it is stable under air, has a low hygroscopicity, and is easily handled.

This embodiment mode can be combined as appropriate with another embodiment mode.

Embodiment Mode 6

Figure 25:
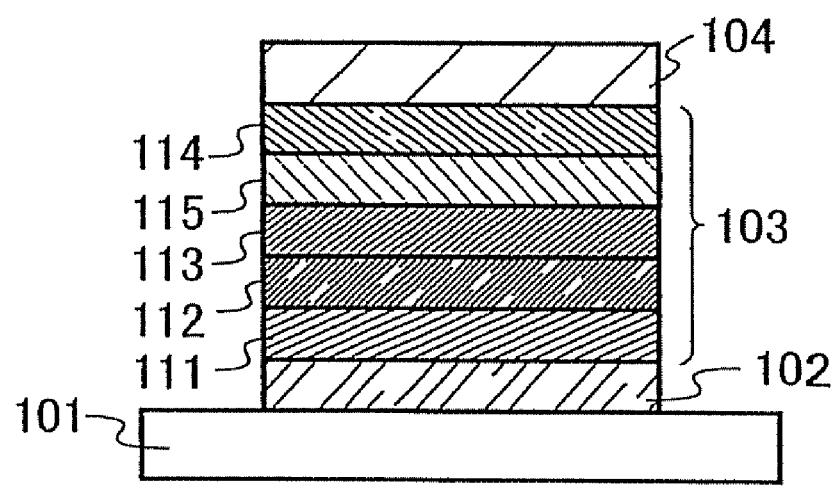
FIG. 25 illustrates a light-emitting element of the present invention.

In this embodiment mode, a light-emitting element with a structure different from the structures described in Embodiment Modes 2 to 4 will be described with reference to FIG. 25.

A light-emitting element shown in this embodiment mode is provided with a functional layer 115 between the light-emitting layer 113 and the electron transporting layer 114 of the light-emitting element shown in Embodiment Mode 2.

In this embodiment mode, the light-emitting layer 113 preferably includes a first organic compound and a second organic compound. That is, the light-emitting layer 113 preferably has a structure in which the first organic compound with a light-emitting property is dispersed in the second organic compound. Since the anthracene derivative of the present invention has high luminous efficiency, it can be favorably used for the first organic compound with a light-emitting property.

As the second organic compound in which the anthracene derivative of the present invention is dispersed, various materials can be used as shown in Embodiment Mode 3. In this embodiment mode, a functional layer which controls the rate of carrier transport is provided between the light-emitting layer and the second electrode serving as the cathode. Therefore, the light-emitting layer 113 preferably has an electron transporting property. That is, the light-emitting layer 113 preferably has a higher electron transporting property than a hole transporting property. Therefore, the second organic compound included in the light-emitting layer 113 is preferably an organic compound with an electron transporting property. Specifically, the following materials can be used: metal complexes such as tris(8-quinolinolato)aluminum(III) (abbreviation: Alq), tris(4-methyl-8-quinolinolato)aluminum (III) (abbreviation: Almq$_3$), bis(10-hydroxybenzo[h]-quinolinato)beryllium(II) (abbreviation: BeBq$_2$), bis(2-methyl-8-quinolinolato)(4-phenylphenolato)aluminum(III) (BAlq), bis(8-quinolinolato)zinc(II) (abbreviation: Znq), bis[2-(2-benzoxazolyl)phenolato]zinc(II) (Abbreviation: ZnPBO), and bis[2-(2-benzothiazolyl)phenolato]zinc(II) (abbreviation: Zn(BTZ)$_2$); heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2''-(1,3,5-benzenetriyl)-tris(1-phenyl-1H-benzimidazole) (abbreviation: TPBI), bathophenanthroline (abbreviation: BPhen), and bathocuproin (abbreviation: BCP); and condensed aromatic compounds such as 9-[4-(10-phenyl-9-anthracenyl)phenyl]-9H-carbazole (abbreviation: CzPA), 3,6-diphenyl-9-[4-(10-phenyl-9-anthracenyl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilben-3,3'-diyl)diphenanthrene (abbreviation: DPNS), 9,9'-(stilben-4,4'-diyl)diphenanthrene (abbreviation: DPNS2), and 3,3',3''-(benzene-1,3,5-triyl)tripyrene (abbreviation: TPB3). Alternatively, the following materials can also be used: 4,4'-(quinoxaline-2,3-diyl)bis(N,N-diphenylaniline) (abbreviation: TPAQn), 9,10-diphenylanthracene (abbreviation: DPAnth), 2,3-bis{4-[N-(4-biphenylyl)-N-phenylamino]phenyl}quinoxaline (abbreviation: BPAPQ), and 4,4'-(quinoxaline-2,3-diyl)bis{N-[4-(9H-carbazol-9-yl)phenyl]-N-phenylaniline} (abbreviation: YGAPQ).

The functional layer 115 includes a third organic compound and a fourth organic compound. The functional layer 115 functions to control the rate of transport of electrons injected from the second electrode 104.

Generally, when a light-emitting layer has an electron transporting property, an electron blocking layer is often provided between the light-emitting layer and an anode in order to prevent electrons from penetrating the light-emitting layer. However, when the electron blocking layer is deteriorated over time, a recombination region expands to the inside of the electron blocking layer (or inside of the hole transporting layer), which results in a significant decrease in current efficiency (i.e., luminance decay). On the other hand, in the light-emitting element shown in this embodiment mode, the rate of transport of electrons is controlled by the functional layer 115 to prevent electrons from penetrating the light-emitting layer. Therefore, the recombination region is kept in the light-emitting layer and does not expand to the other layers such as hole transporting layer. Consequently, even when the light-emitting element is operated for a long time, the initially well-tuned carrier balance can be maintained, which contributes to suppression of the luminance decay upon driving.

The functional layer 115 can have various structures. The first structure is a structure in which the third organic compound having a function of trapping electrons is added into the fourth organic compound having an electron transporting property. In this structure, electrons injected from the second electrode 104 serving as the cathode are injected into the functional layer 115 through the electron transporting layer and the like. The electrons injected into the functional layer 115 are temporarily trapped by the third organic compound, whereby the transport of the electrons is retarded and, thus, electron injection can be controlled in such a way that the recombination is accomplished only in the light-emitting layer 113.

In this structure, the third organic compound included in the functional layer 115 is an organic compound having a function of trapping electrons. Therefore, the lowest unoccupied molecular orbital (LUMO) level of the third organic compound is preferably lower than the lowest unoccupied molecular orbital (LUMO) level of the fourth organic compound included in the functional layer 115 by 0.3 eV or more. When the functional layer 115 includes the third organic compound, the electron transporting rate of this layer is lower as compared with the case where this layer is made of only the fourth organic compound. That is, the transporting rate of carriers can be decreased by adding the third organic compound. Furthermore, the transporting rate of electrons can be tuned by adjusting the concentration of the third organic compound. The third organic compound may emit light. In that case, the light-emission colors of the first organic compound and the third organic compound are preferably similar in order to keep the color purity of the light-emitting element.

As the third organic compound included in the functional layer 115, for example, the following substances exhibiting light emission of blue green to yellow green can be used: N,N'-dimethylquinacridone (abbreviation: DMQd), N,N'-diphenylquinacridone (abbreviation: DPQd), 9,18-dihydro-benzo[h]benzo[7,8]quino[2,3-b]acridine-7,16-dione (abbreviation: DMNQd-1), 9,18-dihydro-9,18-dimethyl-benzo[h]benzo[7,8]quino[2,3-b]acridine-7,16-dione (abbreviation: DMNQd-2), Coumarin 30, Coumarin 6, Coumarin 545T, and Coumarin 153.

The fourth organic compound included in the functional layer 115 is an organic compound having an electron transporting property. That is, the fourth organic compound is a substance having a higher electron transporting property than a hole transporting property. Specifically, the following materials can be used: metal complexes such as tris(8-quinolinolato)aluminum(III) (abbreviation: Alq), $Almq_3$, $BeBq_2$, BAlq, Znq, BAlq, ZnPBO, and ZnBTz; heterocyclic compounds such as PBD, OXD-7, TAZ, TPBI, BPhen, and BCP; and condensed aromatic compounds such as CzPA, DPCzPA, DPPA, DNA, t-BuDNA, BANT, DPNS, DPNS2, and TPB3. Among them, metal complexes that are stable against electrons are preferably used. In addition, as has been mentioned earlier, the LUMO level of the third organic compound is preferably lower than that of the fourth organic compound by 0.3 eV or more. Therefore, a material of the fourth organic compound may be selected as appropriate so as to satisfy such condition, according to the kind of a material used for the third organic compound.

In the light-emitting element of the present invention having the above structure, a current flows by a potential difference applied between the first electrode 102 and the second electrode 104, whereby holes and electrons are recombined in the EL layer 103, providing light emission. Specifically, a light-emitting region is formed in a region from the light-emitting layer 113 to the interface between the light-emitting layer 113 and the functional layer 115. The mechanism for this phenomenon is explained below.

Holes injected from the first electrode 102 are injected into the light-emitting layer 113 through the hole injecting layer 111 and the hole transporting layer 112. Meanwhile, electrons injected from the second electrode 104 are injected into the functional layer 115 which is the layer for controlling the transporting rate of electrons, through the electron transporting layer 114. The transport of the electrons injected into the functional layer 115 is retarded by the third organic compound having an electron trapping property. The electrons whose transporting rate is retarded are injected into the light-emitting layer 113 and recombined with holes, providing light emission.

When the light-emitting layer 113 has an electron transporting property, the transport of holes injected form the hole transporting layer 112 to the light-emitting layer 113 is retarded. In addition, the functional layer 115 controls the transport rate of electrons to prevent electrons from penetrating the light-emitting layer 113. Therefore, recombination probability is increased and luminous efficiency is improved.

The second structure of the functional layer 115 is a structure including the third organic compound and the fourth organic compound. The weight percent of the fourth organic compound is higher than the weight percent of the third organic compound. In addition, the fourth organic compound and the third organic compound transport different carriers. This embodiment mode will describe a case where the functional layer for controlling the transporting rate of carriers is provided on the side of the second electrode serving as the cathode than the light-emitting layer. That is, the functional layer is provided between the light-emitting layer 113 and the second electrode 104.

When the functional layer is provided on the side of the second electrode serving as the cathode than the light-emitting layer, the fourth organic compound is preferably an organic compound with an electron transporting property, while the third organic compound is preferably an organic compound with a hole transporting property. That is, the fourth organic compound is preferably a substance having a higher electron transporting property than a hole transporting property, while the third organic compound is preferably a substance having a higher hole transporting property than an electron transporting property. In addition, a difference between the lowest unoccupied molecular orbital (LUMO) levels of the fourth organic compound and the third organic compound is preferably less than 0.3 eV, or more preferably less than 0.2 eV. That is, it is preferable that, in thermodynamic terms, electron can be easily transported between the fourth organic compound and the third organic compound.

In this structure, as described above, the fourth organic compound is preferably an organic compound with an electron transporting property. Specifically, metal complexes such as Alq, $Almq_3$, $BeBq_2$, BAlq, Znq, ZnPBO, and ZnBTz; heterocyclic compounds such as PBD, OXD-7, TAZ, TPBI, BPhen, and BCP; and condensed aromatic compounds such as CzPA, DPCzPA, DPPA, DNA, t-BuDNA, BANT, DPNS, DPNS2, and TPB3 can be used.

In addition, the third organic compound is preferably an organic compound with a hole transporting property. Specifically, the following materials can be used: condensed aromatic hydrocarbons such as 9,10-diphenylanthracene (abbreviation: DPAnth) and 6,12-dimethoxy-5,11-diphenylchrysene; aromatic amine compounds such as N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), N,9-diphenyl-N-[4-

(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N-(9,10-diphenyl-2-anthryl)-N,9-diphenyl-9H-carbazol-3-amine (abbreviation: 2PCAPA), NPB (or α-NPD), TPD, DFLDPBi, and BSPB; and compounds having an amino group such as Coumarin 7 and Coumarin 30.

With the abovementioned combinations, the transport of electrons from the fourth organic compound to the third organic compound or from the third organic compound to the fourth organic compound can be retarded, whereby the transport rate of electrons through the functional layer 115 can be decreased. Further, since the functional layer 115 has a structure in which the third organic compound is dispersed in the fourth organic compound, crystallization or agglutination of the fourth organic compound over time does not readily occur. Therefore, the abovementioned effect of retarding the electron transport rate does not easily change over time. As a result, carrier balance can be maintained over time. This leads to improvement of the lifetime of the light-emitting element, that is, improvement of reliability.

It is to be noted that among the abovementioned combinations, it is preferable to combine a metal complex and an aromatic amine compound as the fourth organic compound and the third organic compound, respectively. A metal complex has a high electron transporting property and has large dipole moment, whereas an aromatic amine compound has a high hole transporting property and has comparatively small dipole moment. Thus, by combination of substances whose dipole moments differ greatly from each other, the abovementioned effect of electron trasnport can be further increased. Specifically, it is preferable to combine substances which satisfy $P_1/P_2 \geqq 3$ or $P_1/P_2 \leqq 0.33$, where the dipole moment of the fourth organic compound is $P_1$ and the dipole moment of the third organic compound is $P_2$.

In the light-emitting element of the present invention having the above structure, a current flows by a potential difference applied between the first electrode 102 and the second electrode 104, whereby holes and electrons are recombined in the EL layer 103, providing light emission. Specifically, a light-emitting region is formed in a region from the light-emitting layer 113 of the EL layer 103 to the interface between the light-emitting layer 113 and the functional layer 115.

Since the fourth organic compound has an electron transporting property, electrons are easily injected to the functional layer 115 and easily transported toward the neighboring fourth organic compound. That is, the rate at which electrons are injected into the fourth organic compound and the rate (v) at which electrons are released form the fourth organic compound are high.

Meanwhile, in thermodynamic terms, there is a possibility that electrons are injected into the third organic compound which is the organic compound having a hole transporting property because the third organic compound has a close LUMO level to that of the fourth organic compound. However, the rate ($v_1$) at which electrons are injected from the fourth organic compound which is the organic compound having an electron transporting property into the third organic compound which is the organic compound having a hole transporting property, or the rate ($v_2$) at which electrons are injected from the third organic compound into the fourth organic compound is lower than the rate (v) at which electrons are transported between the fourth organic compounds.

Therefore, when the functional layer 115 includes the third organic compound, the electron transporting rate of this layer is lower as compared with the case where the layer is made of only the fourth organic compound. That is, the transport of carriers can be retarded by adding the third organic compound. Also, the transport rate of carriers can be tuned by adjusting the concentration of the third organic compound.

In the case of a conventional light-emitting element without the functional layer 115 having the abovementioned structures, the transport of electrons is not retarded and the electrons are directly injected to the light-emitting layer 113, reaching the vicinity of the interface between the light-emitting layer 113 and the hole transporting layer 112. Therefore, a light-emitting region is formed around the interface between the hole transporting layer 112 and the light-emitting layer 113. In that case, there is a possibility that the electrons may reach and deteriorate the hole transporting layer 112. Further, when the amount of electrons that is transported into the hole transporting layer 112 is increased over time, the recombination probability in the light-emitting layer decreases over time, which leads to a shorter lifetime of the light-emitting element (luminance decay over time).

The light-emitting element shown in this embodiment mode is characterized by having the functional layer 115. Electrons injected from the second electrode 104 are injected into the functional layer 115 through the electron transporting layer 114. The transport of the electrons injected into the functional layer 115 is retarded and, thus, the quantity of carriers in the light-emitting layer 113 is well-balanced. As a result, a light-emitting region, which has conventionally been localized in the vicinity of the interface between the hole transporting layer 112 and the light-emitting layer 113, is formed in a region from the light-emitting layer 113 to the vicinity of the interface between the light-emitting layer 113 and the functional layer 115. Therefore, there is a low possibility that electrons may reach and deteriorate the hole transporting layer 112. Similarly, as for holes, there is also a low possibility that holes may reach and deteriorate the electron transporting layer 114 because the second organic compound included in the light-emitting layer 113 has an electron transporting property.

Further, it is an important point of this embodiment mode that not merely a substance with low electron mobility is applied to the functional layer 115, but an organic compound having an electron trapping function or an organic compound having a hole transporting property is added to an organic compound having an electron transporting property. With such a structure, it becomes possible not only to control the electron injection to the light-emitting layer 113 but also to suppress changes in the controlled amount of injected electron over time. Further, since the second organic compound included in the light-emitting layer 113 has an electron transporting property and the first organic compound which is the light-emissive substance is added into the light-emitting layer 113, the amount of holes in the light-emitting layer 113 also does not readily change over time. Therefore, the light-emitting element of the present invention can prevent a phenomenon that carrier balance is lost over time, which could otherwise lower the recombination probability. Thus, the lifetime of the element can be improved (luminance decay over time can be suppressed).

In the light-emitting element shown in this embodiment mode, the light-emitting region is not localized at the interface between the light-emitting layer and the hole transporting layer or the interface between the light-emitting layer and the electron transporting layer, but formed around the center of the light-emitting layer. Therefore, there is no adverse effect of deterioration which would otherwise be caused if the light-emitting region is positioned close to the hole transporting layer or the electron transporting layer. Further, changes in carrier balance over time (in particular, changes in amount of injected electron over time) can be suppressed. Therefore, a long-lifetime light-emitting element which does not easily deteriorate can be obtained.

It is preferable that the light-emission colors of the third organic compound included in the functional layer 115 and the first organic compound included in the light-emitting layer 113 be similar colors. Specifically, it is preferable that a difference between a peak value of the emission spectrum of the first organic compound and a peak value of the emission spectrum of the third organic compound be within the range of 30 nm. When the difference in peak values is within 30 nm, the light-emission colors of the third organic compound and the first organic compound can be similar colors. Therefore, even when the third organic compound emits light due to changes in driving voltage or the like, changes in light-emission color can be suppressed. It is to be noted that the third organic compound does not necessarily emit light.

The thickness of the functional layer 115 is preferably in the range of 5 to 20 nm. When the functional layer 115 is too thick, the transport of carriers becomes too slow, which could result in high driving voltage. When the functional layer 115 is too thin, on the other hand, it is impossible to implement the function of controlling the transporting rate of carriers. Therefore, the thickness of the functional layer 115 is preferably in the range of 5 to 20 nm.

In the light-emitting element shown in this embodiment mode, the first organic compound and the third organic compound have similar light-emission colors. Therefore, almost no change in emission color is observed even if not only the first organic compound but also the third organic compound emits light. Further, since the anthracene derivative of the present invention exhibits light emission of blue green to yellow green, the element structure shown in this embodiment mode is particularly effective for a light-emitting element with a green color. A green color requires the highest luminance in fabrication of a full-color display; therefore, the deterioration of the light-emitting element with a green color could be faster than other light-emitting elements. However, such problem can be solved by applying the present invention.

Embodiment Mode 7

This embodiment mode will describe a structure in which the anthracene derivative of the present invention is applied to the functional layer 115 of the light-emitting element with the structure shown in Embodiment Mode 6.

The light-emitting element shown in Embodiment Mode 6 includes the functional layer 115 between the light-emitting layer 113 and the electron transporting layer 114. The anthracene derivative of the present invention can be favorably used for the functional layer 115.

The functional layer 115 can have a structure in which the anthracene derivative of the present invention is added, as the third organic compound having an electron trapping function, into the fourth organic compound having an electron transporting property. In this structure, electrons injected from the second electrode 104 serving as the cathode are injected into the functional layer 115 through the electron transporting layer. The electrons injected into the functional layer 115 are temporarily trapped by the third organic compound, whereby the transport of the electrons is retarded and, thus, electron injection into the light-emitting layer 113 is controlled.

The anthracene derivative of the present invention has an electron withdrawing group; therefore, it has a low lowest unoccupied molecular orbital (LUMO) level. Therefore, the anthracene derivative of the present invention can be favorably used for the third organic compound.

The anthracene derivative of the present invention has high luminous efficiency. Therefore, even when the third organic compound emits light due to changes in driving voltage or the like, high luminous efficiency can be maintained. Therefore, the anthracene derivative of the present invention can be favorably used for the third organic compound.

In the case where the anthracene derivative of the present invention is used as the third organic compound of the functional layer 115, the first organic compound of the light-emitting layer may be either the anthracene derivative of the present invention or a different substance. In particular, it is preferable that the anthracene derivative of the present invention is used for both the first organic compound and the third organic compound, since light-emission colors do not change due to changes in driving voltage or the like.

In the case where a substance other than the anthracene derivative of the present invention is used as the first organic compound of the light-emitting layer, various materials can be used. It is to be noted that the light-emission colors of the third organic compound included in the functional layer 115 and the first organic compound included in the light-emitting layer 113 are preferably similar colors. Therefore, a light-emitting material with a green color (blue green to yellow green) emission is preferably used for the first organic compound.

Specifically, the following materials can be used: N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N[9,10-bis(1,1'-biphenyl-2-yl)]-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), and the like.

In the light-emitting element shown in this embodiment mode, the light-emitting region is not localized at the interface between the light-emitting layer and the hole transporting layer or the interface between the light-emitting layer and the electron transporting layer, but formed around the center of the light-emitting layer. Therefore, there is no adverse effect of deterioration which would otherwise be caused if the light-emitting region is positioned close to the hole transporting layer or the electron transporting layer. Further, changes in carrier balance over time (in particular, changes in amount of injected electron over time) can be suppressed. Therefore, a long-lifetime light-emitting element which does not easily deteriorate can be obtained.

Further, since the anthracene derivative of the present invention exhibits light emission of blue green to yellow green, the element structure shown in this embodiment mode is particularly effective for a light-emitting element with a green color. A green color requires the highest luminance in fabrication of a full-color display; therefore, the deterioration of the light-emitting element with a green color could be faster than other light-emitting elements. However, such problem can be solved by applying the present invention.

In the light-emitting element shown in this embodiment mode, the first organic compound and the third organic compound have similar light-emission colors. Therefore, almost no change in emission color is observed even if not only the first organic compound but also the third organic compound exhibits light emission. Further, by using the anthracene derivative shown in Embodiment Mode 1 for the third organic compound, a light-emitting element with high luminous efficiency can be obtained even when the third organic compound emits light.

This embodiment mode can be combined as appropriate with another embodiment mode.

Embodiment Mode 8

In this embodiment mode, a light-emitting element it which a plurality of light-emitting units according to the present invention is stacked (hereinafter, referred to as a stacked type element) will be described with reference to FIG. 3. This light-emitting element is a stacked type light-emitting element that has a plurality of light-emitting units between a first electrode and a second electrode.

Figure 3:
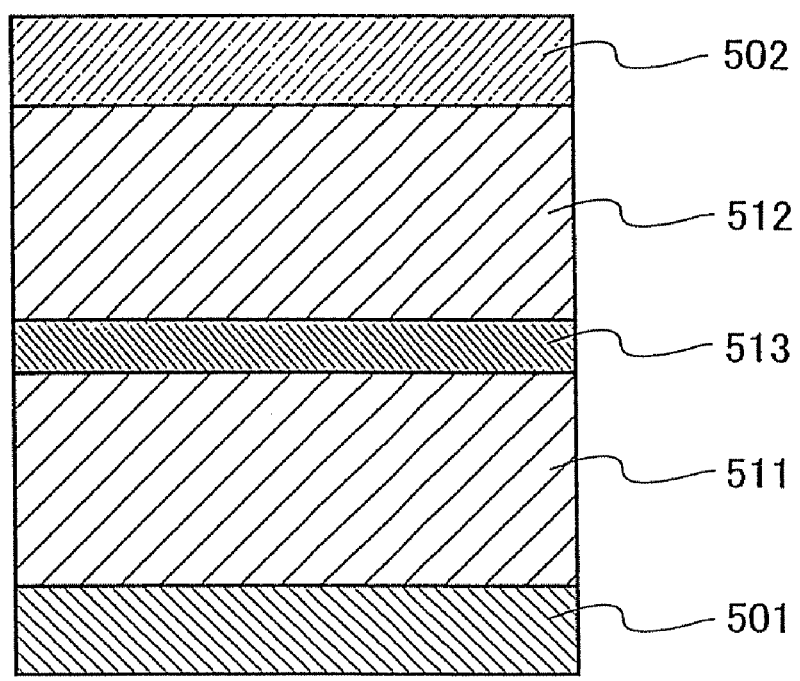
FIG. 3 illustrates a light-emitting element of the present invention.

In FIG. 3, a first light-emitting unit 511 and a second light-emitting unit 512 are stacked between a first electrode 501 and a second electrode 502. An electrode similar to that described in Embodiment Mode 2 can be applied to the first electrode 501 and the second electrode 502. The first light-emitting unit 511 and the second light-emitting unit 512 may have the same structure or different structures, and a structure similar to those described in Embodiment Modes 2 to 7 can be applied.

A charge generation layer 513 includes a composite material of an organic compound and metal oxide. The composite material of an organic compound and metal oxide is described in Embodiment Mode 2 or 5, and includes an organic compound and metal oxide such as vanadium oxide, molybdenum oxide or tungsten oxide. As the organic compound, various compounds such as aromatic amine compounds, carbazole derivatives, aromatic hydrocarbons, oligomer, dendrimer, and high molecular compounds can be used. An organic compound having a hole mobility of greater than or equal to $1 \times 10^{-6}$ cm$^2$/Vs is preferably applied as the organic compound. However, other substances than these compounds may also be used as long as the hole transporting properties thereof are higher than the electron transporting properties thereof. The composite material of an organic compound and metal oxide is superior in carrier injecting property and carrier transporting property, and accordingly, low-voltage driving and low-current driving can be realized.

It is to be noted that the charge generation layer 513 may be formed with a combination of a composite material of an organic compound and metal oxide and other materials. For example, the charge generation layer 513 may be formed with a combination of a layer including the composite material of an organic compound and metal oxide and a layer including one compound selected from electron donating substances and a compound having a high electron transporting property. Further, the charge generation layer 513 may be formed with a combination of a layer including the composite material of an organic compound and metal oxide and a transparent conductive film.

In any case, the charge generation layer 513, which is interposed between the first light-emitting unit 511 and the second light-emitting unit 512, is acceptable as long as electrons are injected to one light-emitting unit and holes are injected to the other light-emitting unit when a voltage is applied between the first electrode 501 and the second electrode 502.

In this embodiment mode, the light-emitting element having two light-emitting units is described; however, the present invention can also be applied to a light-emitting element in which three or more light-emitting units are stacked. By arranging a plurality of light-emitting units between a pair of electrodes in such a manner that the plurality of light-emitting units is partitioned with a charge generation layer, high luminance emission can be realized at a low current density, whereby a long-lifetime light-emitting element can be realized.

This embodiment mode can be combined as appropriate with another embodiment mode.

Embodiment Mode 9

In this embodiment mode, a light-emitting device manufactured using the anthracene derivative of the present invention will be described.

In this embodiment mode, a light-emitting device manufactured using the anthracene derivative of the present invention will be described with reference to FIGS. 4A and 4B. FIG. 4A is a top view showing a light-emitting device, and FIG. 4B is a cross-sectional view of FIG. 4A taken along lines A-A' and B-B'. A driver circuit portion (source driver circuit), a pixel portion, and a driver circuit portion (gate driver circuit) are denoted by reference numerals 601, 602, and 603, respectively, and are indicated by dotted lines. Also, a sealing substrate and a sealing material are denoted by reference numerals 604 and 605, respectively, and a portion surrounded by the sealing material 605 corresponds to a space 607.

A leading wiring 608 is a wiring for transmitting a signal to be inputted to the source driver circuit 601 and the gate driver circuit 603, and this wiring 608 receives a video signal, a clock signal, a start signal, a reset signal, and the like from an FPC (flexible printed circuit) 609 that is an external input terminal. It is to be noted that only the FPC is shown here; however, the FPC may be provided with a printed wiring board (PWB). The light-emitting device in this specification includes not only a light-emitting device itself but also a light-emitting device attached with an FPC or a PWB.

Subsequently, a cross-sectional structure will be described with reference to FIG. 4B. The driver circuit portion and the pixel portion are formed over an element substrate 610. Here, the source driver circuit 601, which is the driver circuit portion, and one pixel in the pixel portion 602 are shown.

A CMOS circuit, which is a combination of an n-channel TFT 623 and a p-channel TFT 624, is formed as the source driver circuit 601. The driver circuit may be formed using various CMOS circuits, PMOS circuits, or NMOS circuits. Although a driver-integration type device, in which a driver circuit is formed over the same substrate as the pixel portion, is described in this embodiment mode, a driver circuit is not necessarily formed over the substrate and can be formed outside the substrate.

The pixel portion 602 has a plurality of pixels, each of which includes a switching TFT 611 a current control TFT 612, and a first electrode 613 which is electrically connected to a drain of the current control TFT 612. It is to be noted that an insulator 614 is formed so as to cover an edge portion of the first electrode 613. Here, a positive photosensitive acrylic resin film is used for the insulator 614.

The insulator 614 is formed so as to have a curved surface having curvature at an upper end portion or a lower end portion thereof in order to obtain favorable coverage. For example, in a case of using positive photosensitive acrylic resin as a material for the insulator 614, the insulator 614 is preferably formed so as to have a curved surface with a curvature radius (0.2 μm to 3 μm) only at the upper end portion thereof. Either a negative type resin which becomes insoluble in an etchant by photo-irradiation or a positive type resin which becomes soluble in an etchant by photo-irradiation can be used for the insulator 614.

An EL layer 616 and a second electrode 617 are formed over the first electrode 613. Here, a material having a high work function is preferably used as a material for the first electrode 613 serving as an anode. For example, the first electrode 613 can be formed by using stacked layers of a titanium nitride film and a film including aluminum as its main component; a three-layer structure of a titanium nitride film, a film including aluminum as its main component, and a titanium nitride film; or the like as well as a single-layer film such as an ITO film, an ITO film including silicon, an indium oxide film including 2 to 20 wt % of zinc oxide, a titanium nitride film, a chromium film, a tungsten film, a Zn film, or a Pt film. When the first electrode 613 has a stacked structure, the first electrode 613 shows low resistance enough to serve as a wiring, giving a good ohmic contact. Further, the first electrode 613 can serve as an anode.

In addition, the EL layer 616 is formed by various methods such as an evaporation method using an evaporation mask, an ink-jet method, and a spin coating method. The EL layer 616 has the anthracene derivative of the present invention described in Embodiment Mode 1. Further, the EL layer 616 may be formed using another material including a low molecular compound, oligomer, dendrimer, or a high molecular compound.

As a material used for the second electrode 617, which is formed over the EL layer 616 and serves as a cathode, a material having a low work function (Al, Mg, Li, Ca, or an alloy or a compound thereof such as MgAg, Men, AlLi, LiF, or $CaF_2$) is preferably used. In a case where light generated in the EL layer 616 is transmitted through the second electrode 617, the second electrode 617 preferably has stacked layers of a metal thin film and a transparent conductive film (ITO, indium oxide including 2 to 20 wt % of zinc oxide, ITO including silicon or silicon oxide, zinc oxide, or the like).

By attachment of the sealing substrate 604 to the element substrate 610 with the sealing material 605, a light-emitting element 618 is provided in the space 607 surrounded by the element substrate 610, the sealing substrate 604, and the sealing material 605. It is to be noted that the space 607 is filled with an inert gas (nitrogen, argon, or the like). There is also a case where the space 607 is filled with the sealing material 605.

It is to be noted that an epoxy-based resin is preferably used as the sealing material 605. It is desired that the material allows as little moisture and oxygen as possible to penetrate. As the sealing substrate 604, a plastic substrate formed using FRP (Fiberglass-Reinforced Plastics), PVF (polyvinyl fluoride), polyester, acrylic resin, or the like can be used as well as a glass substrate or a quartz substrate.

By the abovementioned process, a light-emitting device having the anthracene derivative of the present invention can be obtained.

Since the anthracene derivative described in Embodiment Mode 1 is used for the light-emitting device of the present invention, a light-emitting device having high perfoimance can be obtained. Specifically, a light-emitting device having a long lifetime can be obtained.

Also, since the anthracene derivative of the present invention has high luminous efficiency, a light-emitting device with low power consumption can be obtained.

Also, since the anthracene derivative of the present invention is capable of green light emission with high efficiency, it can be favorably used for a full-color display. Further, since the anthracene derivative of the present invention capable of green light emission has low power consumption and a long lifetime, it can be favorably used for a full-color display.

Furthermore, since the anthracene derivative of the present invention is capable of green light emission with high efficiency, white light emission can be obtained by combining with other light-emitting materials. For example, in order to obtain white light emission using red (R), green (G), and blue (B) emissions positioned at the NTSC chromaticity coordinates, light emissions of these colors should be mixed with a proportion of approximately red (R):green (G):blue (B)=1:6:3. That is, the proportion of green light emission needs to be highest and, therefore, the anthracene derivative of the present invention which is capable of green light emission with high efficiency is favorable for a light-emitting device.

The light-emitting elements shown in Embodiment Modes 6 and 7 hardly deteriorate and have a long lifetime. Therefore, by applying such light-emitting elements to a light-emitting device, a light-emitting device with a longer lifetime can be obtained.

Figure 5A:
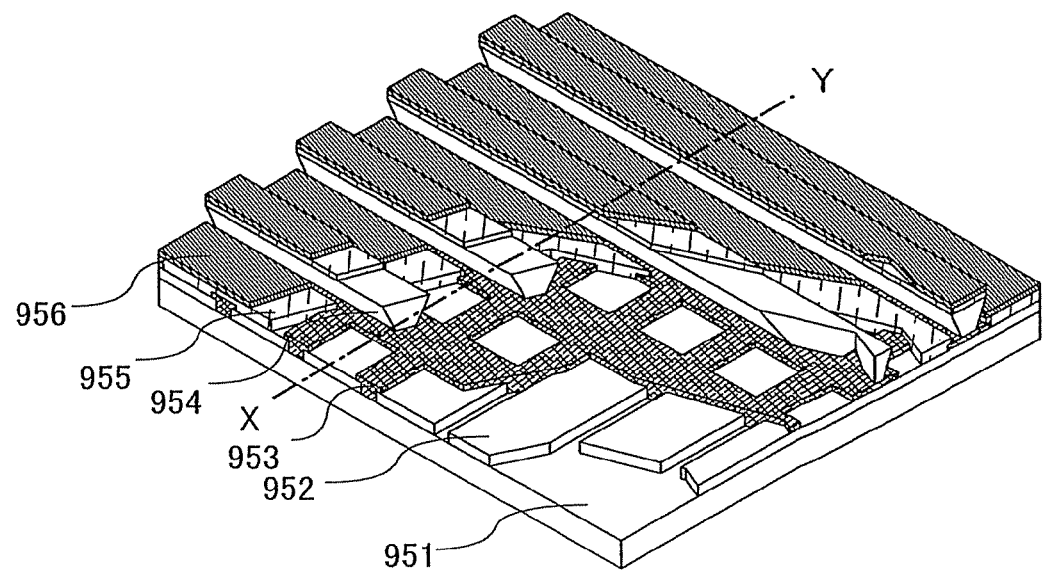
FIGS. 5A and 5B illustrate a light-emitting device of the present invention.
Figure 5B:
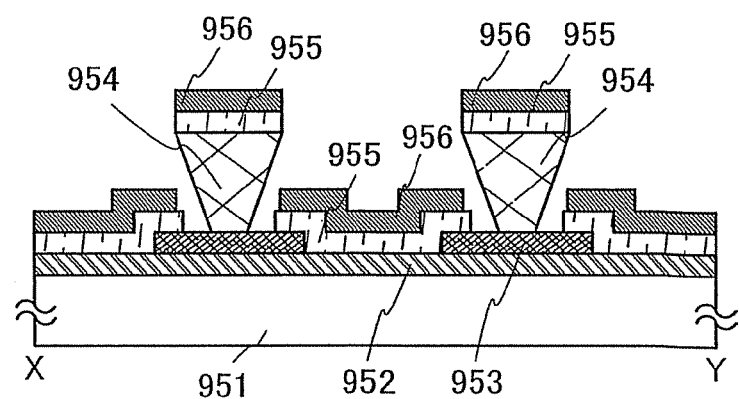

As described above, in this embodiment mode, an active matrix light-emitting device in which driving of a light-emitting element is controlled by a transistor is described. However, the present invention can also be applied to a passive matrix light-emitting device. FIGS. 5A and 5B are a perspective view and a cross-sectional view, respectively, of a passive matrix light-emitting device which is manufactured by applying the present invention. In FIGS. 5A and 5B, a layer 955 including a light-emitting substance is provided between an electrode 952 and an electrode 956 over a substrate 951. An edge of the electrode 952 is covered with an insulating layer 953. Then, a partition layer 954 is provided over the insulating layer 953. A side wall of the partition layer 954 slopes so that a distance between one side wall and the other side wall becomes narrow toward a substrate surface. In other words, a cross section of the partition layer 954 in the direction of a short side is trapezoidal, and a base (a side expanding in the same direction as a plane direction of the insulating layer 953 and in contact with the insulating layer 953) is shorter than an upper side (a side expanding in the same direction as the plane direction of the insulating layer 953 and not in contact with the insulating layer 953). The partition layer 954 provided in this manner can prevent defects of a light-emitting element resulting from static electricity and the like. Thus, even when the light-emitting element of the present invention is applied to a passive matrix light-emitting device, a light-emitting device with a long lifetime can be obtained. Further, a light-emitting device with low power consumption can be obtained.

Embodiment Mode 10

In this embodiment mode, an electronic device of the present invention including the light-emitting device described in Embodiment Mode 9 will be described. The electronic device of the present invention includes the anthracene derivative described in Embodiment Mode 1, and has a display portion with a long lifetime. Also, the electronic device of the present invention possesses a display portion with reduced power consumption.

As an electronic device including a light-emitting element fabricated using the anthracene derivative of the present invention, a camera such as a video camera or a digital camera, a goggle type display, a navigation system, an audio reproducing device (car audio component stereo, audio component stereo, or the like), a computer, a game machine, a portable information terminal (mobile computer, mobile phone, portable game machine, electronic book, or the like), and an image reproducing device provided with a recording medium (specifically, a device capable of reproducing a recording medium such as a digital versatile disc (DVD) and provided with a display device that can display the image), and the like are given. Specific examples of these electronic devices are shown in FIGS. 6A to 6D.

Figure 6A:
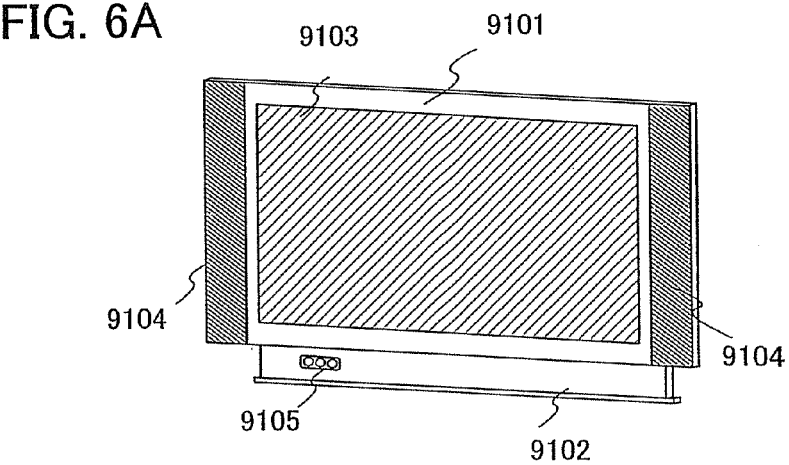
FIGS. 6A to 6D each illustrate an electronic device of the present invention.

FIG. 6A shows a television device according to the present invention, which includes a housing 9101, a supporting base 9102, a display portion 9103, speaker portions 9104, video input terminals 9105, and the like. In the television device, the display portion 9103 has light-emitting elements similar to those described in Embodiment Modes 2 to 8, and the light-emitting elements are arranged in matrix. The features of the light-emitting elements are exemplified by high luminous efficiency and long lifetime. The display portion 9103 which includes the light-emitting elements has similar features. Therefore, in the television device, image quality is hardly deteriorated and low power consumption is achieved. Therefore, deterioration compensation function circuits and power supply circuits can be significantly reduced or downsized in the television device, which enables reduction of the size and weight of the housing 9101 and supporting base 9102. In the television device according to the present invention, low power consumption, high image quality, and small size and lightweight are achieved; therefore, a product which is suitable for living environment can be provided. Also, since the anthracene derivative described in Embodiment Mode 1 is capable of green light emission, full-color display is possible, and a television device having a display portion with a long life can be obtained.

Figure 6B:
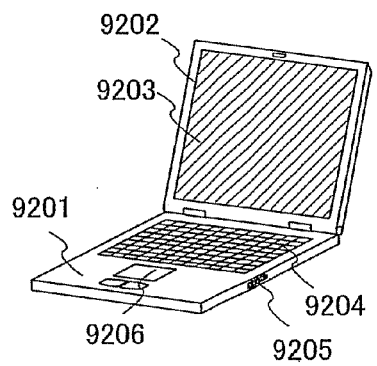

FIG. 6B shows a computer according to the present invention, which includes a main body 9201, a housing 9202, a display portion 9203, a keyboard 9204, an external connection port 9205, a pointing device 9206, and the like. In the computer, the display portion 9203 has light-emitting elements similar to those described in Embodiment Modes 2 to 8, and the light-emitting elements are arranged in matrix. The features of the light-emitting elements are given by high luminous efficiency and long lifetime. The display portion 9203 which includes the light-emitting elements has similar features. Therefore, in the computer, image quality is hardly deteriorated and lower power consumption is achieved. Due to such features, deterioration compensation function circuits and power supply circuits can be significantly reduced or downsized in the computer; therefore, small sized and lightweight main body 9201 and housing 9202 can be achieved. In the computer according to the present invention, low power consumption, high image quality, and small size and lightweight are achieved; therefore, a product which is suitable for living environment can be provided. Further, since the anthracene derivative described in Embodiment Mode 1 is capable of green light emission, full-color display is possible, and a computer having a display portion with a long lifetime can be obtained.

Figure 6C:
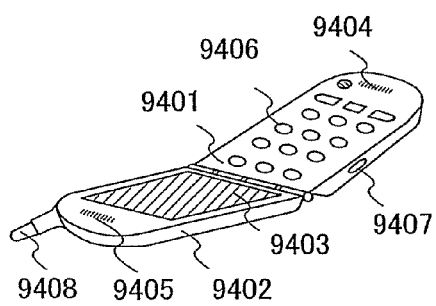

FIG. 6C shows a mobile phone according to the present invention, which includes a main body 9401, a housing 9402, a display portion 9403, an audio input portion 9404, an audio output portion 9405, operation keys 9406, an external connection port 9407, an antenna 9408, and the like. In the mobile phone, the display portion 9403 has light-emitting elements similar to those described in Embodiment Modes 2 to 8, and the light-emitting elements are arranged in matrix. The features of the light-emitting elements are exemplified by high luminous efficiency and long lifetime. The display portion 9403 which includes the light-emitting elements has similar features. Therefore, in the mobile phone, image quality is hardly deteriorated and lower power consumption is achieved. Owing to such features, deterioration compensation function circuits and power supply circuits can be significantly reduced or downsized in the mobile phone; therefore, small sized and lightweight main body 9401 and housing 9402 can be achieved. In the mobile phone according to the present invention, low power consumption, high image quality, and a small size and lightweight are achieved; therefore, a product which is suitable for carrying can be provided. Further, since the anthracene derivative described in Embodiment Mode 1 is capable of green light emission, full-color display is possible, and a mobile phone having a display portion with a long lifetime can be obtained.

Figure 6D:
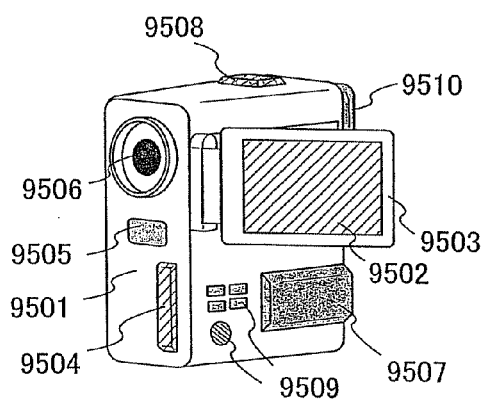

FIG. 6D shows a camera according to the present invention, which includes a main body 9501, a display portion 9502, a housing 9503, an external connection port 9504, a remote control receiving portion 9505, an image receiving portion 9506, a battery 9507, an audio input portion 9508, operation keys 9509, an eye piece portion 9510, and the like. In the camera, the display portion 9502 has light-emitting elements similar to those described in Embodiment Modes 2 to 8, and the light-emitting elements are arranged in matrix. The features of the light-emitting elements are exemplified by high luminous efficiency and long lifetime. The display portion 9502 which includes the light-emitting elements has similar features. Therefore, in the camera, image quality is hardly deteriorated and lower power consumption can be achieved. Such features contribute to significant reduction and downsizing of the deterioration compensation function circuits and power supply circuits in the camera; therefore, a small sized and lightweight main body 9501 can be achieved. In the camera according to the present invention, low power consumption, high image quality, and small size and lightweight are achieved; therefore, a product which is suitable for carrying can be provided. Further, since the anthracene derivative described in Embodiment Mode 1 is capable of green light emission, full-color display is possible, and a camera having a display portion with a long lifetime can be obtained.

As described above, the applicable range of the light-emitting device of the present invention is so wide that the light-emitting device can be applied to electronic devices in various fields. By using the anthracene derivative of the present invention, electronic devices having display portions with a long lifetime can be provided.

The light-emitting device of the present invention can also be used as a lighting device. An example in which the light-emitting element of the present invention is used for a lighting device will be described with reference to FIG. 7.

Figure 7:
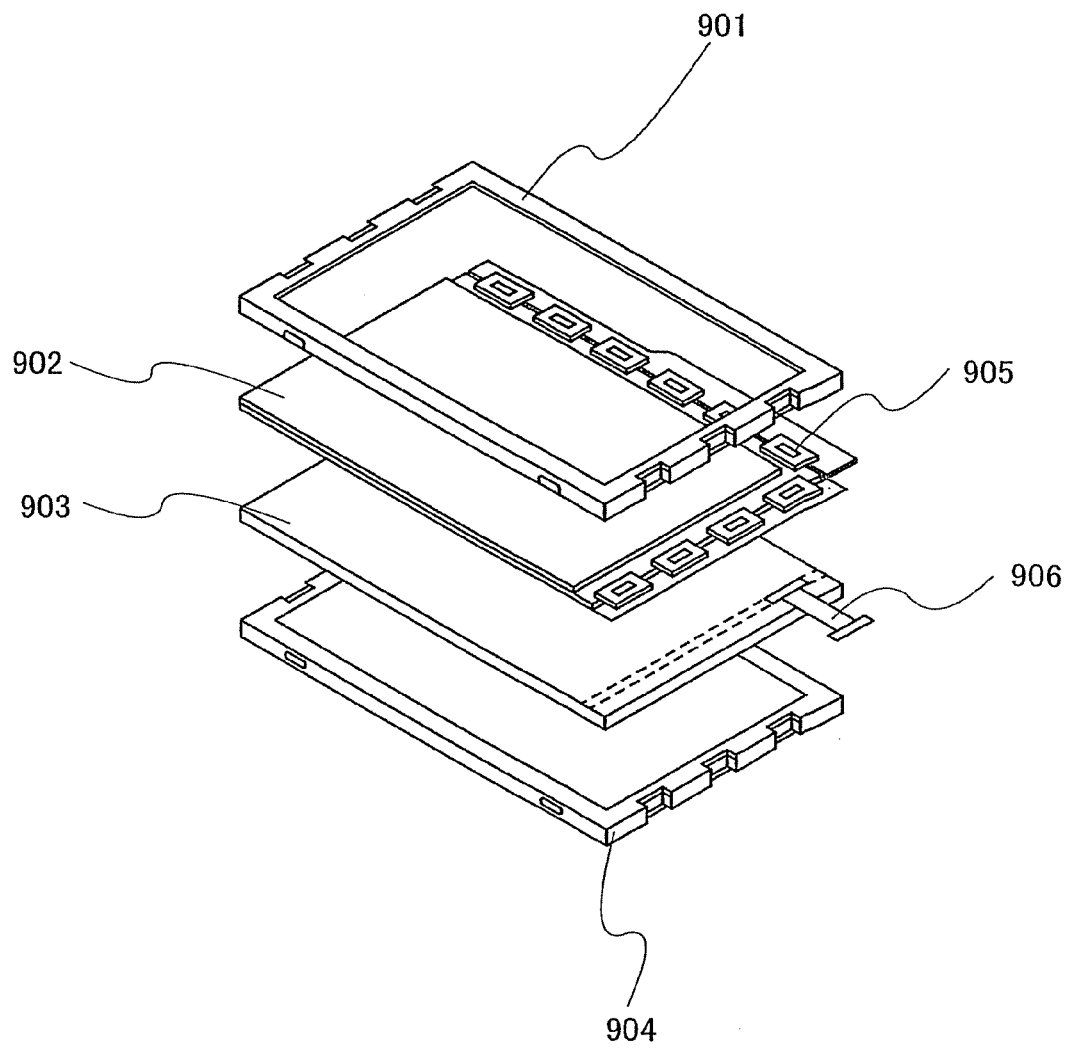
FIG. 7 illustrates an electronic device of the present invention.

FIG. 7 shows an example of a liquid crystal display device using the light-emitting device of the present invention as a backlight. The liquid crystal display device shown in FIG. 7 includes a housing 901, a liquid crystal layer 902, a backlight 903, and a housing 904, and the liquid crystal layer 902 is connected to a driver IC 905. The light-emitting device of the present invention is used for the backlight 903, and current is supplied through a terminal 906.

By using the light-emitting device of the present invention as the backlight of the liquid crystal display device, a backlight with reduced power consumption and high luminous efficiency can be obtained. The light-emitting device of the present invention is a lighting device with a plane light emission area, and can have a large area. Therefore, the backlight can have a large area, and a liquid crystal display device having a large area can be obtained. Furthermore, the light-emitting device of the present invention has a thin shape and has low power consumption; therefore, a thin shape and low power consumption of a display device can also be achieved.

Since the light-emitting device of the present invention has a long lifetime, a liquid crystal display device using the light-emitting device of the present invention also has a long lifetime.

Figure 8:
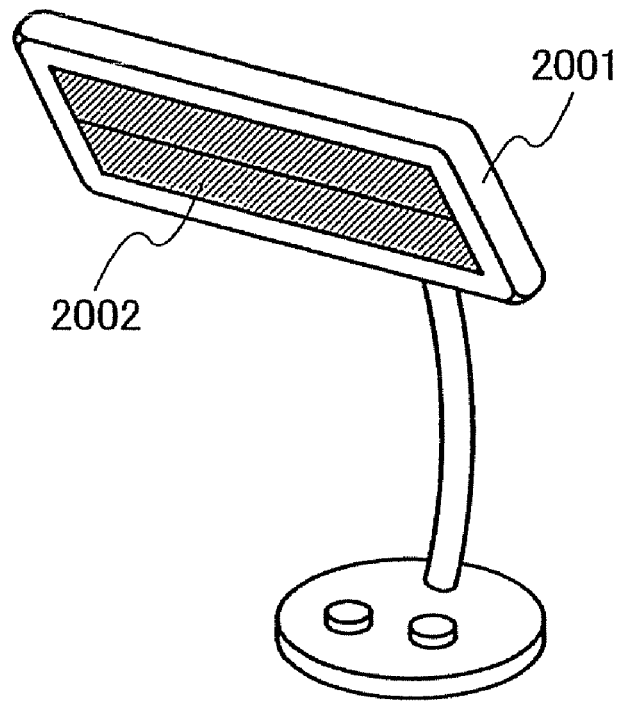
FIG. 8 illustrates a lighting device of the present invention.

FIG. 8 shows an example of a light-emitting device to which the present invention is applied. FIG. 8 illustrates an example in which the light-emitting device of the present invention is applied to a table lamp as a lighting device. A table lamp shown in FIG. 8 has a housing 2001 and a light source 2002, and the light-emitting device of the present invention is used as the light source 2002. The light-emitting device of the present invention has high luminous efficiency and has a long lifetime; therefore, a table lamp also has high luminous efficiency and a long lifetime.

Figure 9:
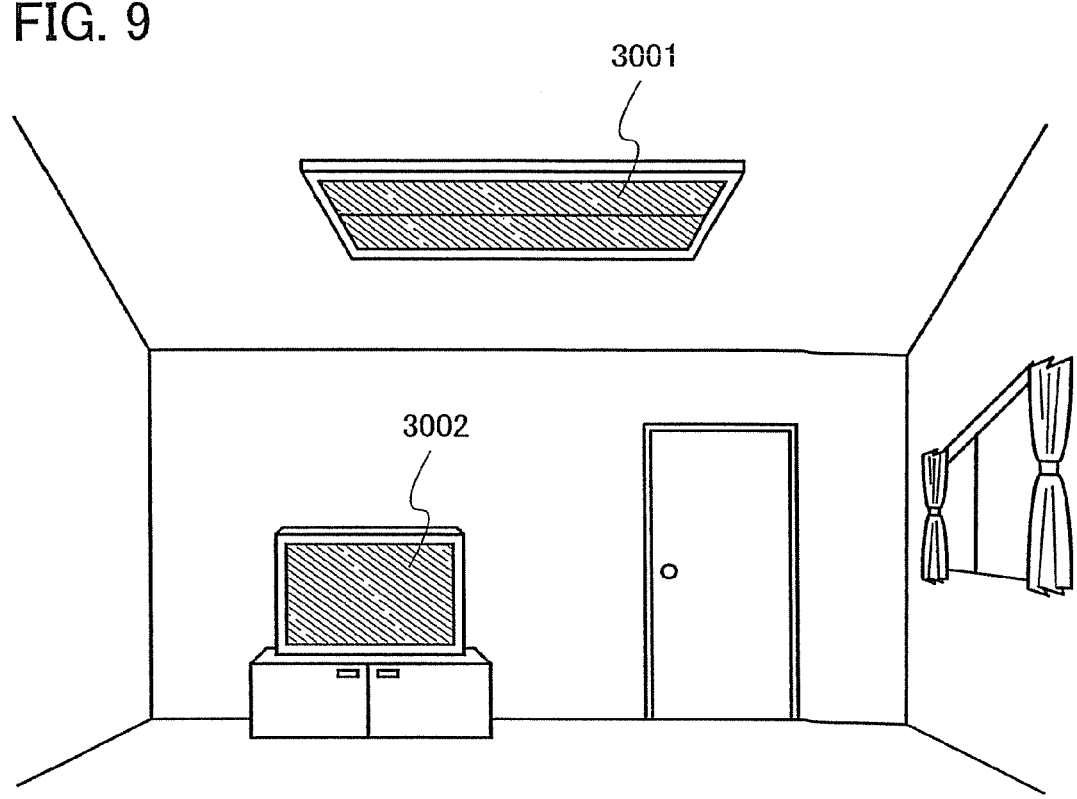
FIG. 9 illustrates a lighting device of the present invention.

FIG. 9 shows an example of a light-emitting device to which the present invention is applied. FIG. 9 illustrates an example in which the light-emitting device of the present invention is applied to an indoor lighting device 3001. Since the light-emitting device of the present invention can also have a large area, the light-emitting device of the present invention can be used as a lighting device having a large emission area. Further, the light-emitting device of the present invention has a thin shape and consumes low power; therefore, the light-emitting device of the present invention can be used as a lighting device having a thin shape and low power consumption. A television device 3002 according to the present invention as illustrated in FIG. 6A is placed in a room in which the light-emitting device fabricated according to the present invention is used as the indoor lighting device 3001, and public broadcasting and movies can be watched. In such a case, since both of the devices consume low power, a powerful image can be watched in a bright room without concern about electricity charges.

EXAMPLE 1

In this example, a synthetic method of 9,10-bis(4-fluorophenyl)-2-[N-phenyl-N-(9-phenyl-9H-carbazol-3-yl)amino]anthracene (abbreviation: 2PCAFPA), which is the anthracene derivative of the present invention represented by Structural Formula (201), will be specifically described.

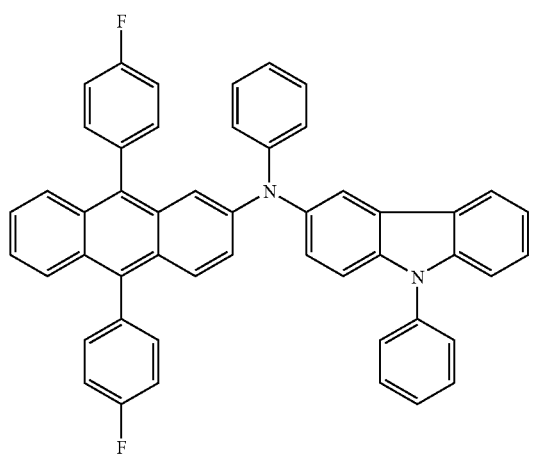

(201)

[Step 1] Synthesis of 2-bromo-9,10-bis(4-fluorophenyl)anthracene (i) Synthesis of 2-bromo-9,10-anthraquinone A Synthetic Scheme of 2-bromo-9,10-anthraquinone is shown in (C-1).

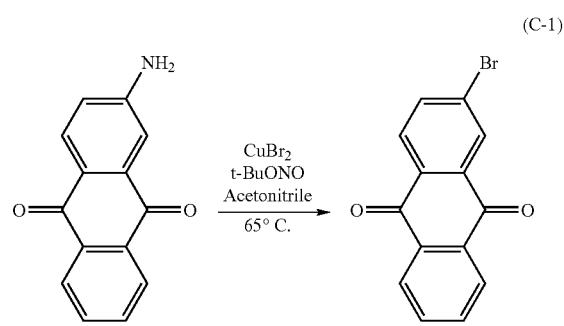

(C-1)

46 g (206 mmol) of copper bromide(II) and 500 mL of acetonitrile were put into a 1 L three-neck flask, and 17.3 g (168 mmol) of tert-butyl nitrite was added into the suspension, which was followed by heating at 65° C. Thereafter, 25 g (111.0 mmol) of 2-amino-9,10-anthraquinone was added into the mixture, and then the mixture was stirred for 6 hours at the same temperature. After the reaction, the reaction mixture was poured into a 3M hydrochloric acid and stirred for 3 hours. Then the precipitate was filtered and washed with water and then with ethanol. The precipitate was dissolved in toluene, and the resulting solution was filtered through Florisil, celite, and then alumina. The filtrate was concentrated, and the residue was recrystallized with chloroform and hexane, giving 18.6 g of 2-bromo-9,10-anthraquinone as a cream-colored solid in 58% yield.

(ii) Synthesis of 2-bromo-9,10-bis(4-fluorophenyl)-9,10-dihydro-9,10-anthracenediol A Synthetic Scheme of 2-bromo-9,10-bis(4-fluorophenyl)-9,10-dihydro-9,10-anthracenediol is shown in (C-2) and (C-3).

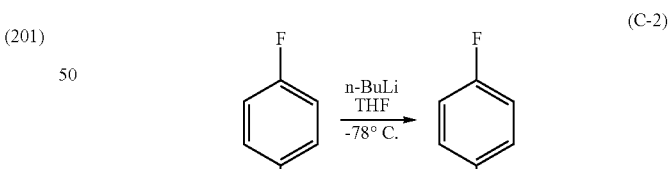

(C-2)

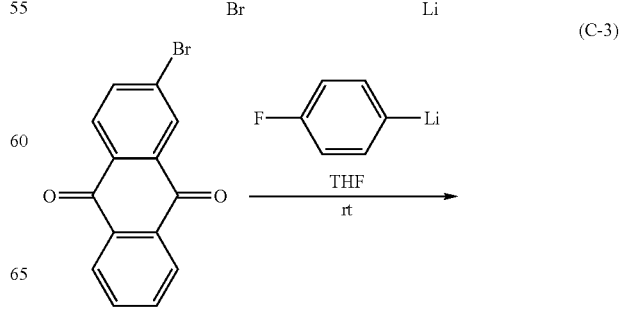

(C-3)

-continued

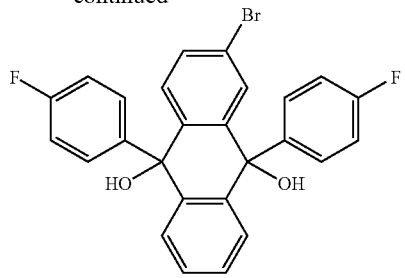

6.66 g (38.1 mmol) of 4-bromofluorobenzene was put into a 200 mL three-neck flask, and the atmosphere of the flask was substituted with nitrogen. Then, 50 mL of tetrahydrofuran (THF) was put into the flask. After setting this solution at −78° C., 23.8 mL (38.1 mmol) of n-butyllithium (1.6 mol/L hexane solution) was dropped into the solution. Then, the solution was stirred for 2 hours at the same temperature. This reaction solution was dropped into a solution in which 5.00 g (17.3 mmol) of 2-bromo-9,10-anthraquinone is dissolved in 100 mL of THF at room temperature, and after the dropping, the reaction solution was stirred for 24 hours at room temperature. After the reaction, the reaction solution was washed with water, and the aqueous layer was extracted with ethyl acetate. This extracted solution was combined with the organic layer and washed with brine, and then the organic layer was dried with magnesium sulfate. After drying, the mixture was subjected to suction filtration, and the filtrate was concentrated, resulting in a brown, oily compound of 2-bromo-9,10-bis(4-fluorophenyl)-9,10-dihydro-9,10-anthracenediol.

(ii) Synthesis of 2-bromo-9,10-bis(4-fluorophenyl)anthracene

A synthetic scheme of 2-bromo-9,10-bis(4-fluorophenyl)anthracene is shown in (C-4).

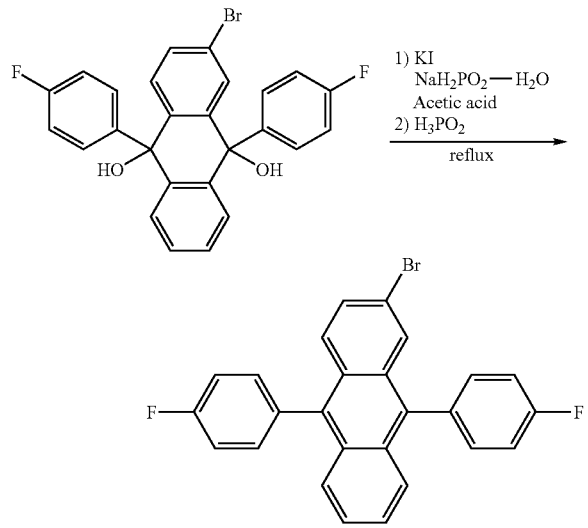

(C-4)

8.32 (17.3 mmol) of 2-bromo-9,10-bis(4-fluorophenyl)-9,10-dihydro-9,10-anthracenediol, 5.17 g (31.1 mmol) of potassium iodide, 9.90 g (93.4 mmol) of sodium phosphinate monohydrate, and 50 mL of glacial acetic acid were put into a 200 mL three-neck flask, and the mixture was refluxed at 120° C. for 4 hours. Then, 20 mL of a 50% phosphinic acid was added into the reaction mixture, and the mixture was stirred for 1 hour at 120° C. After the reaction, the reaction mixture was washed with water, and the aqueous layer was extracted with ethyl acetate. This extracted solution was combined with the organic layer, and then dried with magnesium sulfate. After drying, the mixture was subjected to suction filtration, and the filtrate was concentrated. The obtained residue was dissolved in toluene, and filtered through Florisil, celite, and then alumina, and the filtrate was concentrated. The obtained residue was recrystallized with chloroform and hexane, giving 7.2 g of 2-bromo-9,10-bis(4-fluorophenyl)anthracene as light yellow powder in 74% yield.

[Step 2] Synthesis of N,9-diphenyl-9H-carbazol-3-amine (abbreviation: PCA)

(i) Synthesis of 3-bromo-9-phenylcarbazole

A synthetic scheme of 3-bromo-9-phenylcarbazole is shown in (C-5).

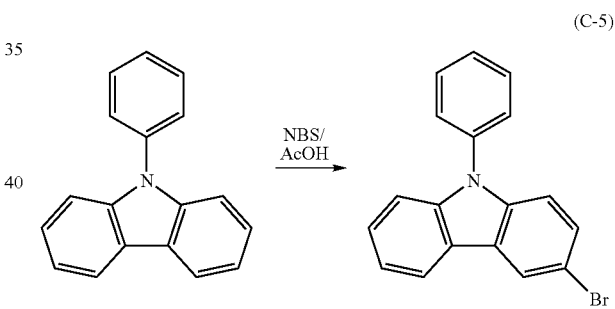

(C-5)

24.3 g (100 mmol) of 9-phenylcarbazole was put into a 2L Meyer flask, and dissolved in 600 mL of glacial acetic acid. Then, 17.8 g (100 mmol) of N-bromosuccinimide was slowly added, and the solution was stirred for about 12 hours at room temperature. This solution was dropped into 1 L of ice water while stirring. A white solid precipitated was collected by suction filtration, and then washed with water three times. This solid was dissolved in 150 mL of diethyl ether, and the solution was washed with a saturated aqueous solution of sodium bicarbonate and then with water. The organic layer was dried over magnesium sulfate, filtered, and concentrated, and then the residue was dissolved in ca. 50 mL of ethanol. The precipitate formed as a white solid was collected by suction filtration and dried, giving 28.4 g (88% yield) of 3-bromo-9-phenylcarbazole as white powder.

159

(ii) Synthesis of N,9-diphenyl-9H-carbazol-3-amine (abbreviation: PCA)

A synthetic scheme of N,9-diphenyl-9H-carbazol-3-amine (abbreviation: PCA) is shown in (C-6).

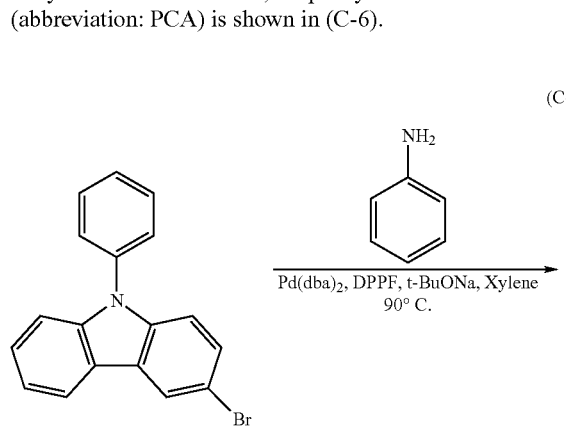

(C-6)

160

[Step 2] Synthetic Method of 2PCAFPA

A synthetic scheme of 2PCAFPA is shown in (C-7).

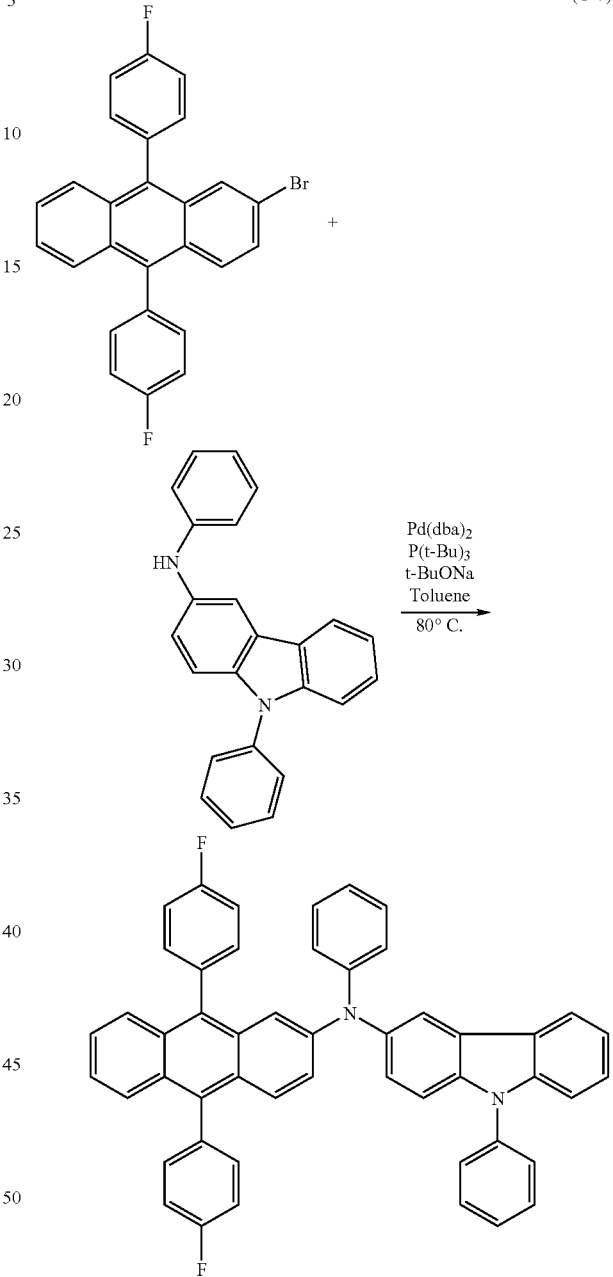

(C-7)

Into a 500 mL three-neck flask were put 19 g (60 mmol) of 3-bromo-9-phenylcarbazole, 340 mg (0.6 mmol) bis(dibenzylideneacetone)palladium(0), 1.6 g (3.0 mmol) of 1,1-bis(diphenylphosphino)ferrocene, and 13 g (180 mmol) of sodium tert-butoxide, and then the atmosphere in the flask was substituted with nitrogen. Thereafter, 110 mL of dehydrated xylene and 7.0 g (75 mmol) of aniline were added to the mixture. This mixture was heated and stirred for 7.5 hours at 90° C. After the reaction was completed, about 500 mL of hot toluene was added to the reaction solution, and this solution was filtered through Florisil, alumina, and celite. The obtained filtrate was concentrated, and hexane and ethyl acetate were added to the residue, which was followed by irradiation with ultrasound. A solid precipitated was collected by suction filtration and dried to give 15 g (75% yield) of N,9-diphenyl-9H-carbazol-3-amine (abbreviation: PCA) as light brown powder. By a nuclear magnetic resonance measurement (NMR), this compound was determined to be N,9-diphenyl-9H-carbazol-3-amine (abbreviation: PCA).

Figure 10A:
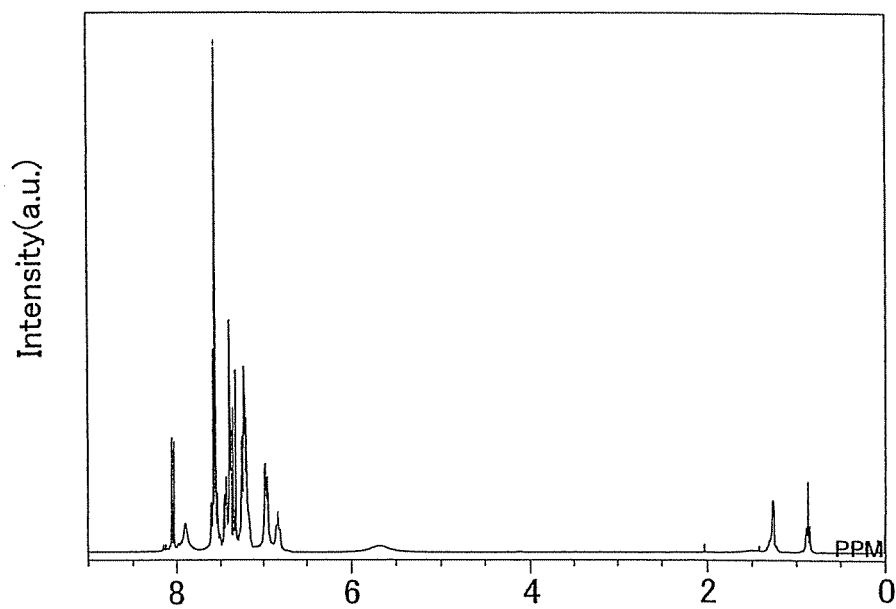
FIGS. 10A and 10B each show the $^1$H NMR chart of N-phenyl-(9-phenyl-9H-carbozol-3-yl)amine (abbreviation: PCA)
Figure 10B:
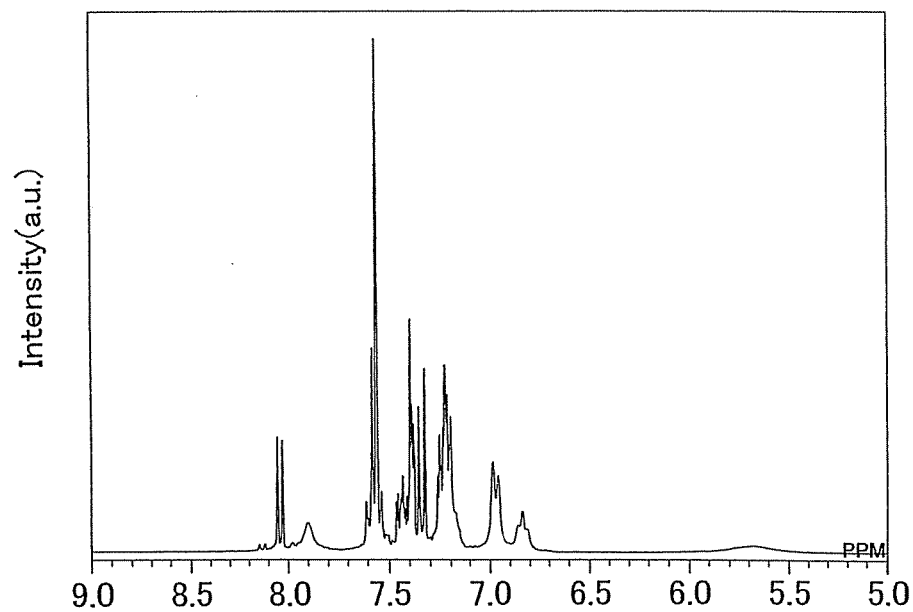

$^1$H NMR data of this compound is shown below. $^1$H NMR (300 MHz, CDCl$_3$): δ=6.84 (t, J=6.9 Hz, 1H), 6.97 (d, J=7.8 Hz, 2H), 7.20-7.61 (m, 13H), 7.90 (s, 1H), 8.04 (d, J=7.8 Hz, 1H). The $^1$H NMR chart is shown in FIGS. 10A and 10B. It is to be noted that the range of 5.0 ppm to 9.0 ppm in FIG. 10A is expanded and shown in FIG. 10B.

2.0 g (4.5 mmol) of 2-bromo-9,10-bis(4-fluorophenyl)anthracene, 1.7 g (4.9 mmol) of N,9-diphenyl-9H-carbazol-3-amine (PCA), 0.13 g (0.23 mmol) of bis(dibenzylideneacetone)palladium(0), and 1.1 g (11 mmol) of sodium tert-butoxide were put into a 100 mL three-neck flask, and the atmosphere of the flask was substituted with nitrogen. Thereafter, 30 mL of toluene and 0.45 g (0.23 mmol) of tri(tert-butyl)phosphine (10% hexane solution) were added to the mixture, and this reaction mixture was stirred for 6 hours at 80° C. After the reaction was completed, the reaction solution was washed with water, and the aqueous layer was extracted with ethyl acetate. The extracted solution was combined with the organic layer, and then dried with magnesium sulfate. After drying, this mixture was subjected to suction filtration, and the filtrate was concentrated. The obtained residue was purified by silica gel column chromatography (eluent: toluene), and then concentrated. The obtained solid was recrystallized with a mixed solvent of chloroform and hexane, giving 2.0 g of 9,10-bis(4-fluorophenyl)-2-[N-phenyl-N-(9-phenyl-9H-carbazol-3-yl)amino]anthracene (abbreviation: 2PCAFPA) as yellow powder in 62% yield. By nuclear magnetic resonance measurement (NMR), this compound was determined to be 9,10-bis(4-fluorophenyl)-2-[N-phenyl-N-(9-phenyl-9H-carbazol-3-yl)amino]anthracene (abbreviation: 2PCAFPA).

Figure 11A:
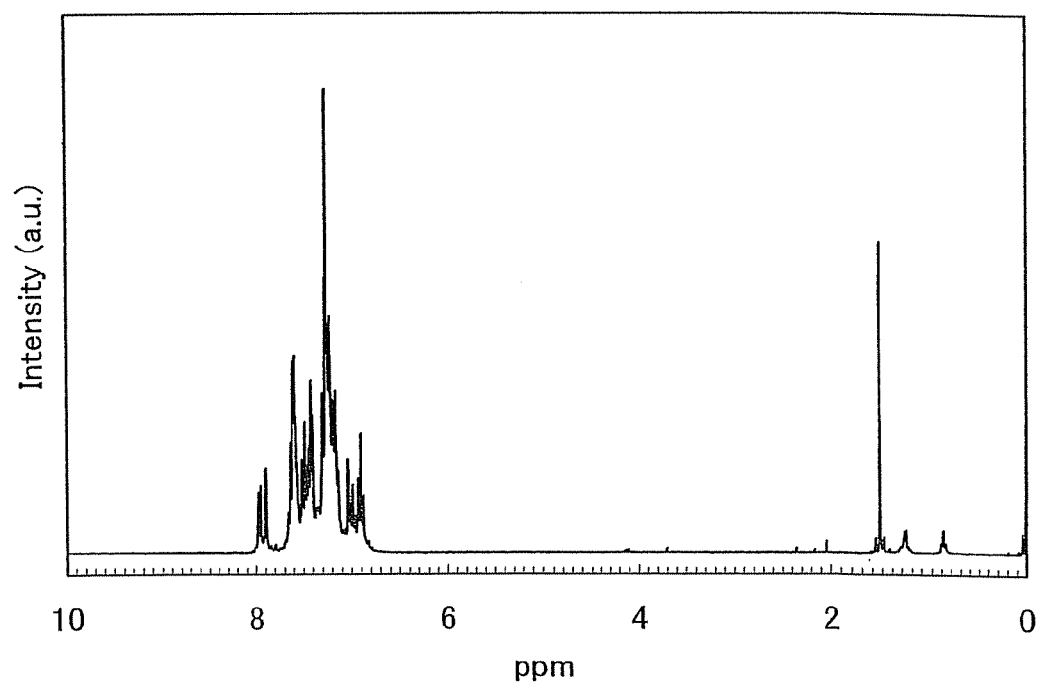
FIGS. 11A and 11B each show the $^1$H NMR chart of 9,10-bis(4-fluorophenyl)-2-[N-phenyl-N-(9-phenyl-9H-carbazol-3-yl)amino]anthracene (abbreviation: 2PCAFPA)
Figure 11B:
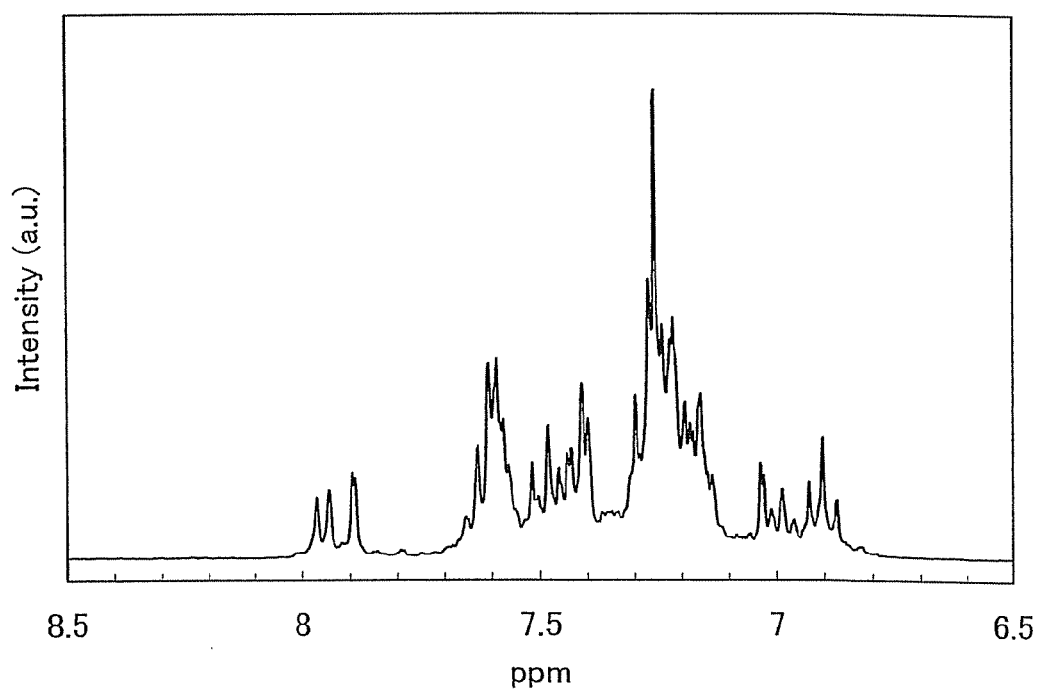

$^1$H NMR data of this compound is shown below. $^1$H NMR (CDCl$_3$, 300 MHz): δ=6.87-7.03 (m, 4H), 7.13-7.30 (m, 14H), 7.40-7.51 (m, 6H), 7.57-7.63 (m, 6H), 7.89-7.97 (m, 2H). The $^1$H NMR chart is shown in each of FIGS. 11A and 11B. It is to be noted that the range of 6.5 ppm to 8.5 ppm in FIG. 11A was expanded and shown in FIG. 11B.

Thermogravimetric/differential thermal analysis (TG-DTA) of 2PCAFPA was carried out. In measuring, a high vacuum differential type differential thermal balance (type DTA2410SA, manufactured by Bruker AXS K.K.) was used. When measuring was carried out under reduced pressure of 10 Pa, it was found that the 5% weight-loss temperature was 255.5° C., which is indicative of high thermal stability of 2PCAFPA.

Figure 12:
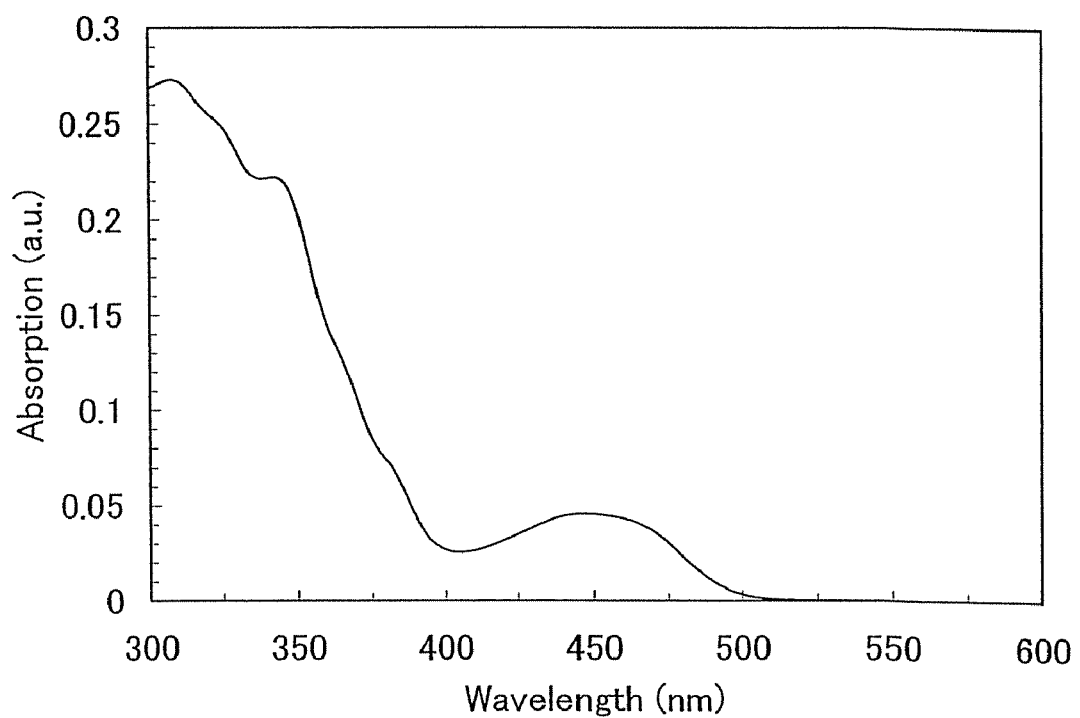
FIG. 12 shows the absorption spectrum of a toluene solution of 9,10-bis(4-fluorophenyl)-2-[N-phenyl-N-(9-phenyl-9H-carbazol-3-yl)amino]anthracene (abbreviation: 2PCAFPA)
Figure 13:
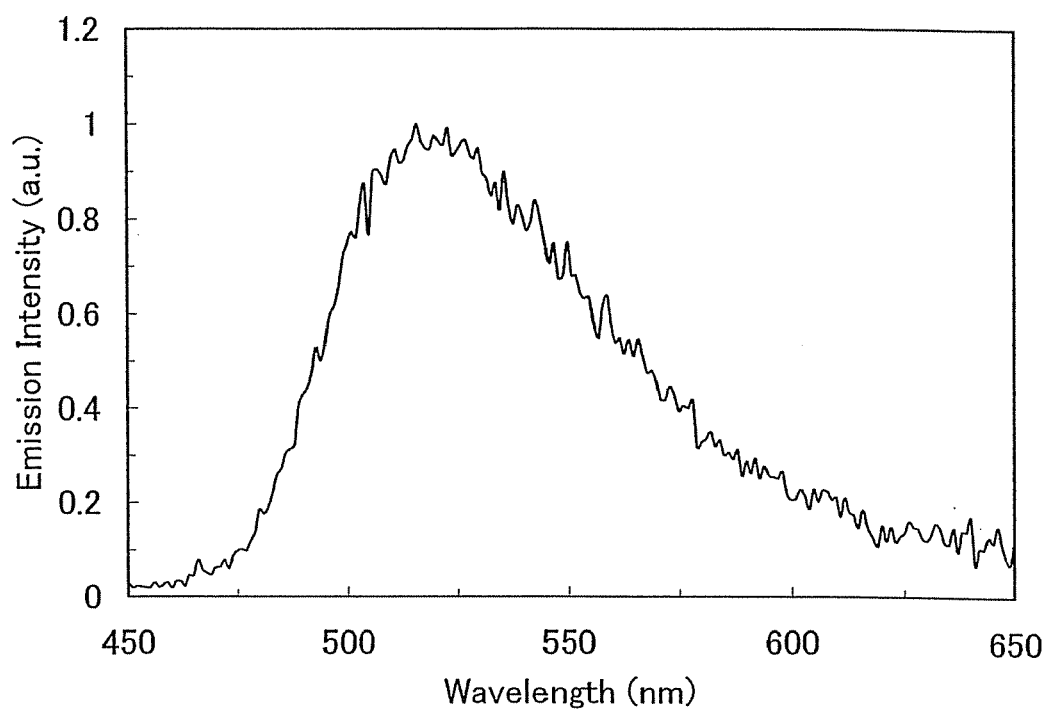
FIG. 13 shows the emission spectrum of a toluene solution of 9,10-bis(4-fluorophenyl)-2-[N-phenyl-N-(9-phenyl-9H-carbazol-3-yl)amino]anthracene (abbreviation: 2PCAFPA)

The absorption spectrum of a toluene solution of 2PCAFPA is shown in FIG. 12. An ultraviolet-visible spectrophotometer (type V550, manufactured by Japan Spectroscopy Corporation) was used for measurement. The spectrum of the solution was measured in a quartz cell. The absorption spectrum of the solution is shown in FIG. 12, which is obtained by subtracting the absorption spectrum of the quartz substrate from the raw spectrum of the sample solution located in a quartz cell. In FIG. 12, a horizontal axis shows wavelength (nm) and a vertical axis shows absorption intensity (an arbitrary unit). In the case of the toluene solution, absorption was observed at around 448 nm. Further, an emission spectrum of the toluene solution (excitation wavelength of 452 nm) of 2PCAFPA is shown in FIG. 13. In FIG. 13, a horizontal axis shows wavelength (nm) and a vertical axis shows emission intensity (an arbitrary unit). In the case of the toluene solution, the maximum light emission wavelength was 520 nm (excitation wavelength of 452 nm).

An oxidation-reduction characteristic of 2PCAFPA was determined by cyclic voltammetry (CV) measurement. For the measurement, an electrochemical analyzer (ALS model 600A, manufactured by BAS Inc.) was used.

As for a solution used in the CV measurement, dehydrated N,N-dimethylformamide (DMF) (manufactured by Aldrich, 99.8%, catalog number: 22705-6) was used as a solvent. Tetra-n-butylammonium perchlorate (n-Bu$_4$NClO$_4$) (manufactured by Tokyo Chemical Industry Co., Ltd., catalog number: T0836) was dissolved, as a supporting electrolyte, in DMF at a concentration of 100 mmol/L to prepare the electrolysis solution. The sample solution was prepared by dissolving the sample in the electrolysis solution at a concentration of 1 mmol/L. A platinum electrode (a PTE platinum electrode, manufactured by BAS Inc.) was used as a working electrode. A platinum electrode (a VC-3 Pt counter electrode (5 cm), manufactured by BAS Inc.) was used as a counter electrode. An Ag/Ag$^+$ electrode (an RE5 non-aqueous solvent type reference electrode, manufactured by BAS Inc.) was used as a reference electrode. The measurement was conducted at room temperature.

An oxidation characteristic of 2PCAFPA was evaluated in the following manner. The potential of the working electrode with respect to a reference electrode was changed from −0.34 V to 0.60 V, and then changed from 0.60 V to −0.34 V. This cycle was set as one cycle, and 100 cycles were performed. Also, a reduction characteristic of 2PCAFPA was evaluated in the following manner. The potential of the working electrode with respect to the reference electrode was changed from −0.33 V to −2.40 V, and then changed from −2.40 V to −0.33 V. This cycle was set as one cycle, and 100 cycles were performed. The scan rate of the CV measurement was set to be 0.1 V/s.

Figure 23:
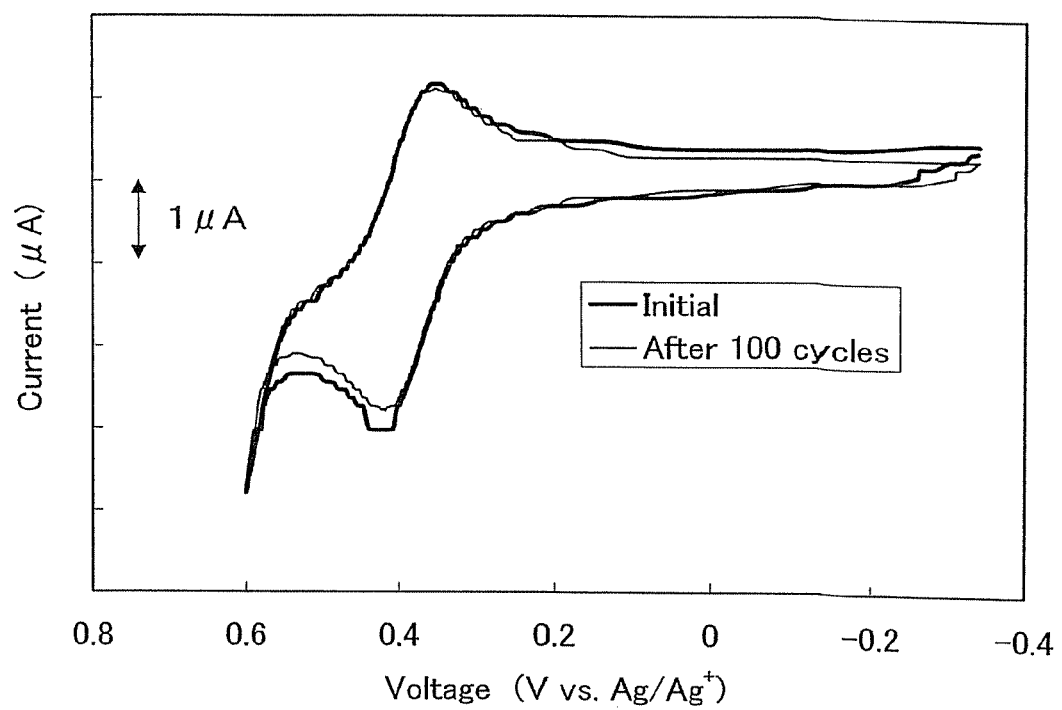
FIG. 23 shows the CV measurement result of the oxidation side of 9,10-bis(4-fluorophenyl)-2-[N-phenyl-N-(9-phenyl-9H-carbazol-3-yl)amino]anthracene (abbreviation: 2PCAFPA)
Figure 24:
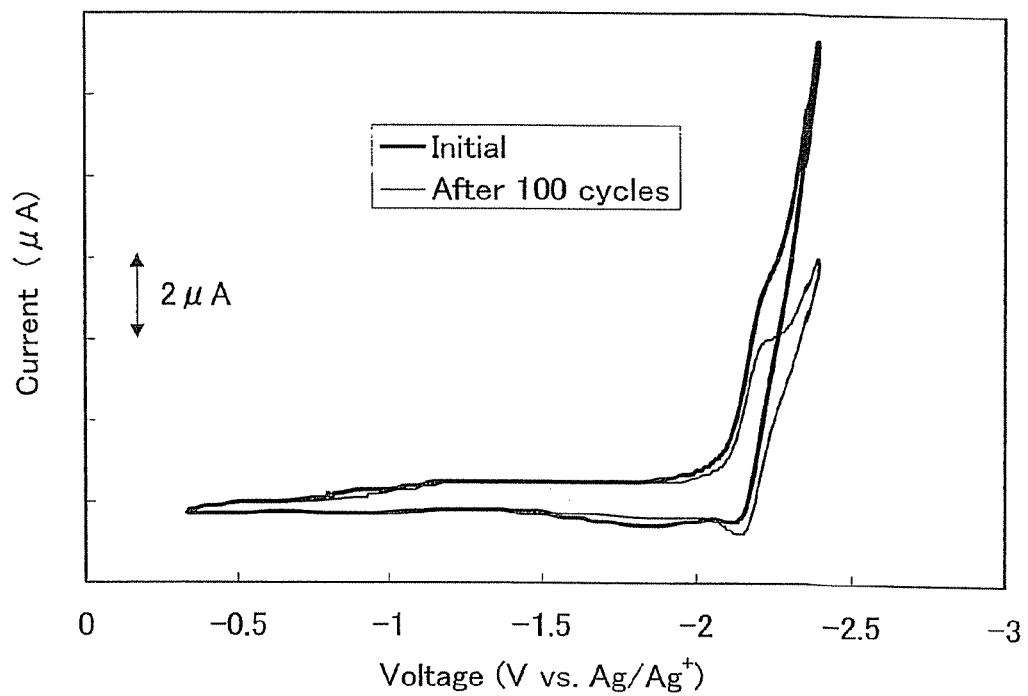
FIG. 24 shows the CV measurement result of the reduction side of 9,10-bis(4-fluorophenyl)-2-[N-phenyl-N-(9-phenyl-9H-carbazol-3-yl)amino]anthracene (abbreviation: 2PCAFPA)

The CV measurement result of an oxidation side of 2PCAFPA and the CV measurement result of a reduction side of 2PCAFPA are shown in FIGS. 23 and 24, respectively. In each of FIGS. 23 and 24, a horizontal axis shows a potential (V) of the working electrode with respect to the reference electrode, and a vertical axis shows a current value (μA) that flowed between the working electrode and the counter electrode. From FIG. 23, a current exhibiting oxidation was observed at around 0.35 V (vs. Ag/Ag$^+$). From FIG. 24, a current exhibiting reduction was observed at around −2.14 V (vs. Ag/Ag$^+$).

In spite of the fact that 100 cycles of measurement were repeated, a peak position and a peak intensity at the CV curve hardly changed in the oxidation and reduction, which reveals that the anthracene derivative of the present invention is extremely stable against repetition of the oxidation and reduction.

EXAMPLE 2

Figure 14:
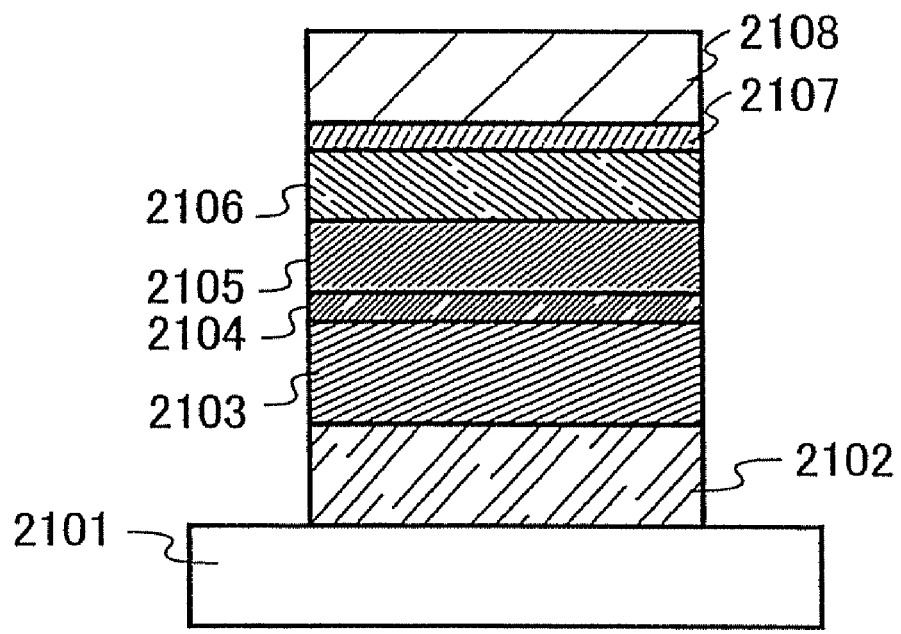
FIG. 14 illustrates a light-emitting element of an example.

In this example, a light-emitting element of the present invention will be described with reference to FIG. 14. A structural formula used in Examples 2 and 3 is shown below.

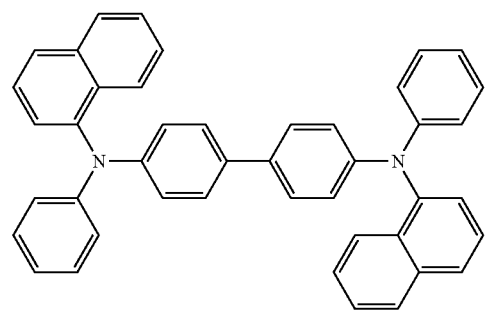

NPB

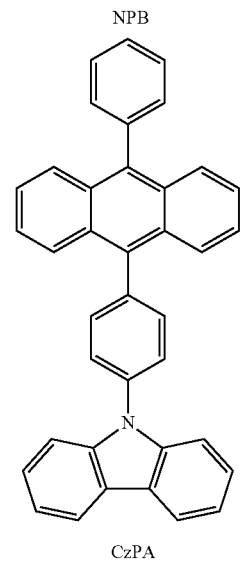

CzPA

-continued

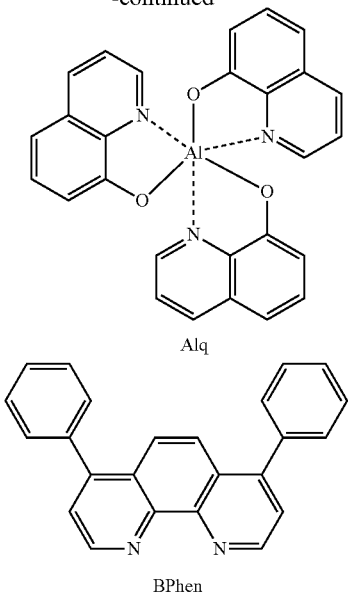

Alq

BPhen

A fabrication method of the light-emitting element of this example is described below.
(Light-Emitting Element 1)

First, a film of ITO including silicon oxide (ITSO) was formed by sputtering over a glass substrate 2101 to form a first electrode 2102. It is to be noted that the film thickness of the first electrode was 110 nm, and an area of the electrode was 2 mm×2 mm.

Next, the substrate over which the first electrode was formed was fixed to a substrate holder provided in a vacuum evaporation apparatus, so that a surface over which the first electrode was formed faced down. Then, after reducing the pressure of the vacuum evaporation apparatus to about $10^{-4}$ Pa, a layer 2103 containing a composite material of an organic compound and an inorganic compound was formed over the first electrode 2102 by co-evaporating 4,4'-bis[N-(1-napthyl)-N-phenylamino]biphenyl (abbreviation: NPB) and molybdenum oxide(VI). The film thickness of the layer 2103 was to be 50 nm, and the weight ratio of NPB and molybdenum oxide(VI) was adjusted to be 4:1 (=NPB:molybdenum oxide). It is to be noted that a co-evaporation method is an evaporation method in which evaporation is carried out from a plurality of evaporation sources at the same time in one treatment chamber.

Subsequently, a film of 4,4'-bis[N-(1-napthyl)-N-phenylamino]biphenyl (abbreviation: NPB) was formed at a thickness of 10 nm over the layer 2103 containing the composite material by an evaporation method using a resistance heating system, whereby a hole transporting layer 2104 was formed.

Further, by co-evaporating 9-[4-(N-carbazolyl)]phenyl-10-phenylanthracene (abbreviation: CzPA) and 9,10-bis(4-fluorophenyl)-2-[N-phenyl-N-(9-phenyl-9H-carbazol-3-yl)amino]anthracene (abbreviation: 2PCAFPA), which is the anthracene derivative of the present invention represented by Structural Formula (201), a light-emitting layer 2105 with a thickness of 40 nm was formed over the hole transporting layer 2104. The weight ratio of CzPA and 2PCAFPA was adjusted to be 1:0.1 (=CzPA:2PCAFPA).

Thereafter, tris(8-quinolinolato)aluminum (abbreviation: Alq) was formed at a film thickness of 30 nm over the light-emitting layer 2105 by means of an evaporation method using a resistance heating system, whereby an electron transporting layer 2106 was formed.

Furthermore, a film of lithium fluoride (LiF) was formed at a thickness of 1 nm over the electron transporting layer 2106, whereby an electron injecting layer 2107 was formed.

Finally, by forming a film of aluminum with a film thickness of 200 nm over the electron injecting layer 2107 by means of an evaporation method using a resistance heating system, a second electrode 2108 was faulted. Accordingly, a light-emitting element 1 was fabricated.

Figure 15:
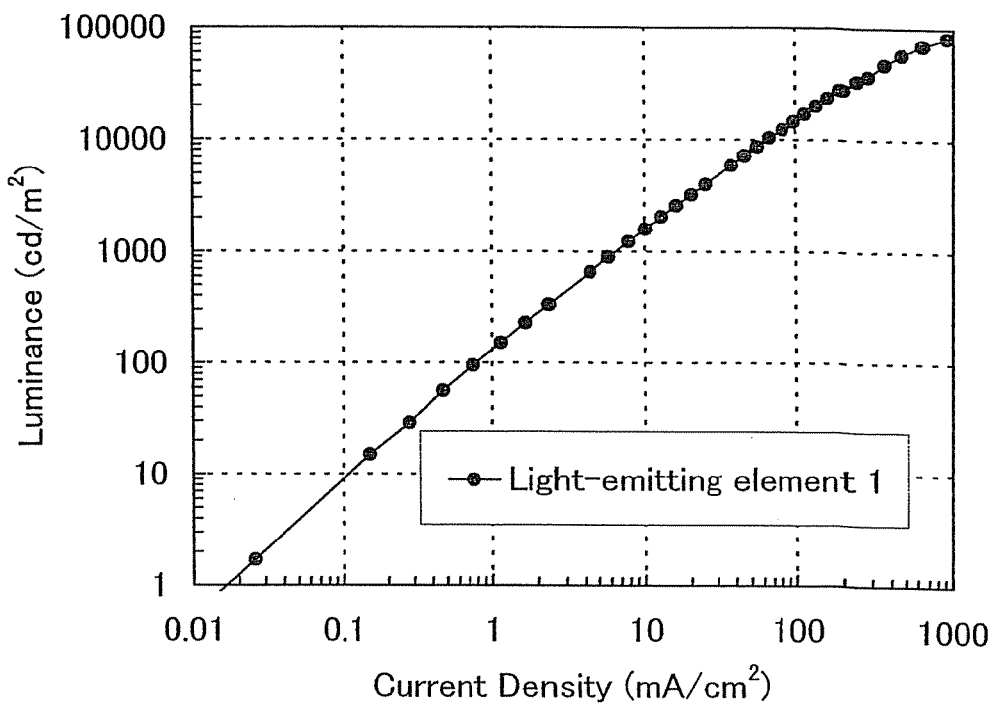
FIG. 15 shows the current density vs. luminance characteristics of a light-emitting element 1.
Figure 16:
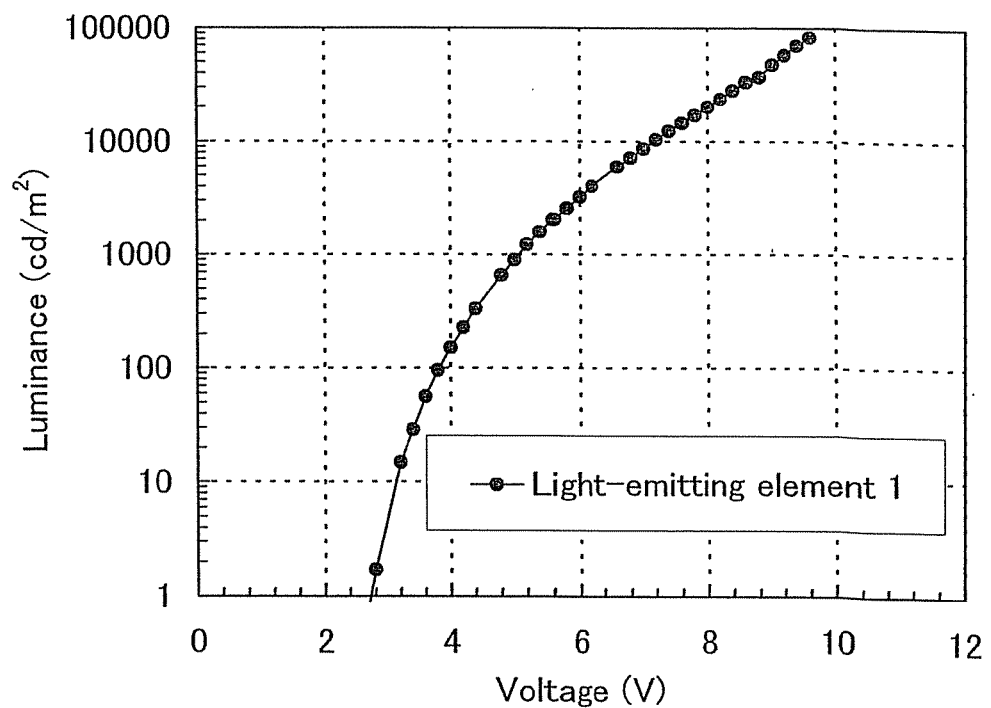
FIG. 16 shows the voltage vs. luminance characteristics of the light-emitting element 1.
Figure 17:
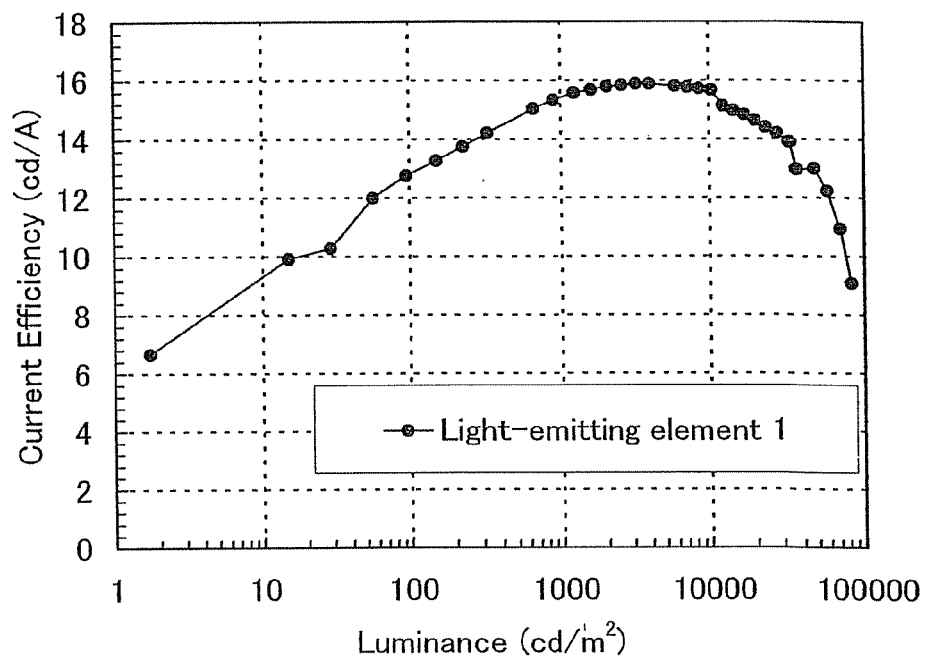
FIG. 17 shows the luminance vs. current efficiency characteristics of the light-emitting element 1.
Figure 18:
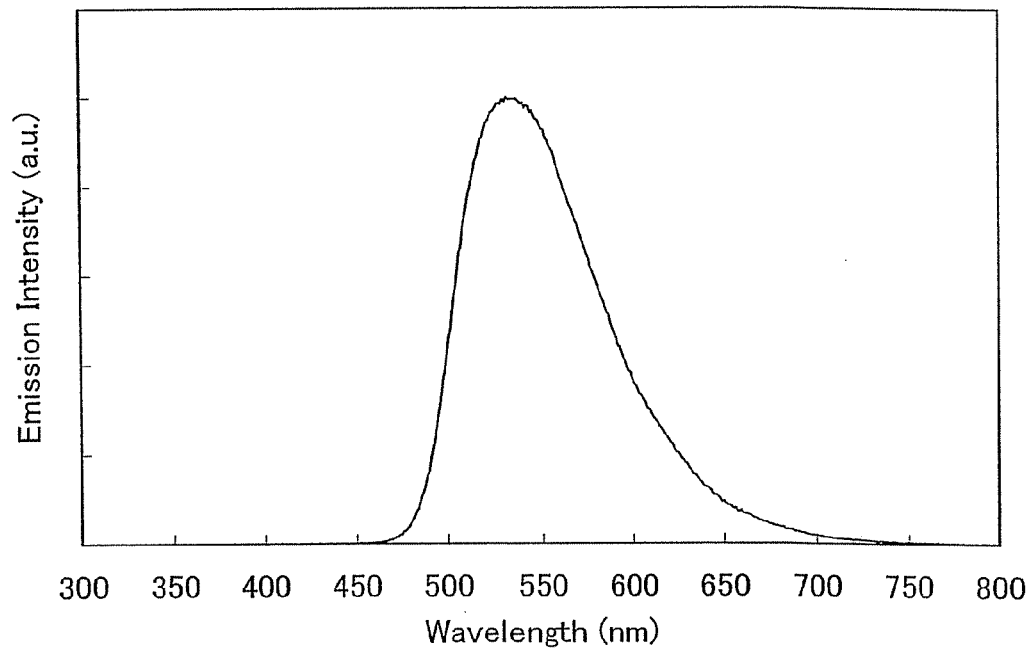
FIG. 18 shows the emission spectrum of the light-emitting element 1.

Current density vs. luminance characteristics, voltage vs. luminance characteristics, and luminance vs. current efficiency characteristics of the light-emitting element 1 are shown in FIGS. 15, 16, and 17, respectively. Also, the emission spectrum which was obtained at a current of 1 mA is shown in FIG. 18. A CIE chromaticity coordinate of the light-emitting element 1 at a luminance of 894 cd/$_m^2$ was (x=0.35, y=0.60), and light emission was green. Current efficiency at a luminance of 894 cd/m$^2$ was 15.3 cd/A, which means high current efficiency. Voltage, current density, and power efficiency at a luminance of 894 cd/m$^2$ were 5.0 V, 5.83 mA/cm$^2$, and 9.6 (lm/W), respectively. In addition, as shown in FIG. 18, the maximum emission wavelength at a current of 1 mA was 535 nm.

Thus, a light-emitting element with high luminous efficiency and reduced power consumption can be obtained by using the present invention.

EXAMPLE 3

In this example, a light-emitting element of the present invention will be described with reference to FIG. 14. A fabrication method of the light-emitting element of this example is described below.
(Light-Emitting Element 2)

First, a film of ITO including silicon oxide (ITSO) was formed by sputtering over a glass substrate 2101 to form a first electrode 2102. It is to be noted that the film thickness of the first electrode was 110 nm, and an area of the electrode was 2 mm×2 mm.

Next, the substrate over which the first electrode was formed was fixed to a substrate holder provided in a vacuum evaporation apparatus, so that a surface over which the first electrode was formed faced down. Then, after reducing the pressure of the vacuum evaporation apparatus to about $10^{-4}$ Pa, a layer 2103 containing a composite material of an organic compound and an inorganic compound was formed over the first electrode 2102 by co-evaporating 4,4'-bis[N-(1-napthyl)-N-phenylamino]biphenyl (abbreviation: NPB) and molybdenum oxide(VI). The film thickness of the layer 2103 was to be 50 nm, and the weight ratio of NPB and molybdenum oxide(VI) was adjusted to be 4:1 (=NPB:molybdenum oxide).

Subsequently, a film of 4,4'-bis[N-(1-napthyl)-N-phenylamino]biphenyl (abbreviation: NPB) was formed at a thickness of 10 nm over the layer 2103 containing the composite material by an evaporation method using a resistance heating system, whereby a hole transporting layer 2104 was formed.

Further, by co-evaporating 9-[4-(N-carbazolyl)]phenyl-10-phenylanthracene (abbreviation: CzPA) and 9,10-bis(4-fluorophenyl)-2-[N-phenyl-N-(9-phenyl-9H-carbazol-3-yl)amino]anthracene (abbreviation: 2PCAFPA), which is the anthracene derivative of the present invention represented by Structural Formula (201), a light-emitting layer 2105 with a thickness of 40 nm was formed over the hole transporting layer 2104. The weight ratio of CzPA and 2PCAFPA was adjusted to be 1:0.1 (CzPA:2PCAFPA).

Thereafter, a film of bathophenanthroline (abbreviation: BPhen) was formed at a thickness of 30 nm over the light-emitting layer 2105 by means of an evaporation method using a resistance heating system, whereby an electron transporting layer 2106 was formed.

Furthermore, a film of lithium fluoride (LiF) was formed at a thickness of 1 nm over the electron transporting layer 2106, whereby an electron injecting layer 2107 was formed.

Finally, by forming a film of aluminum with a film thickness of 200 nm over the electron injecting layer 2107 by means of an evaporation method using a resistance heating system, a second electrode 2108 was formed. Accordingly, light-emitting elements 2 was fabricated.

Figure 19:
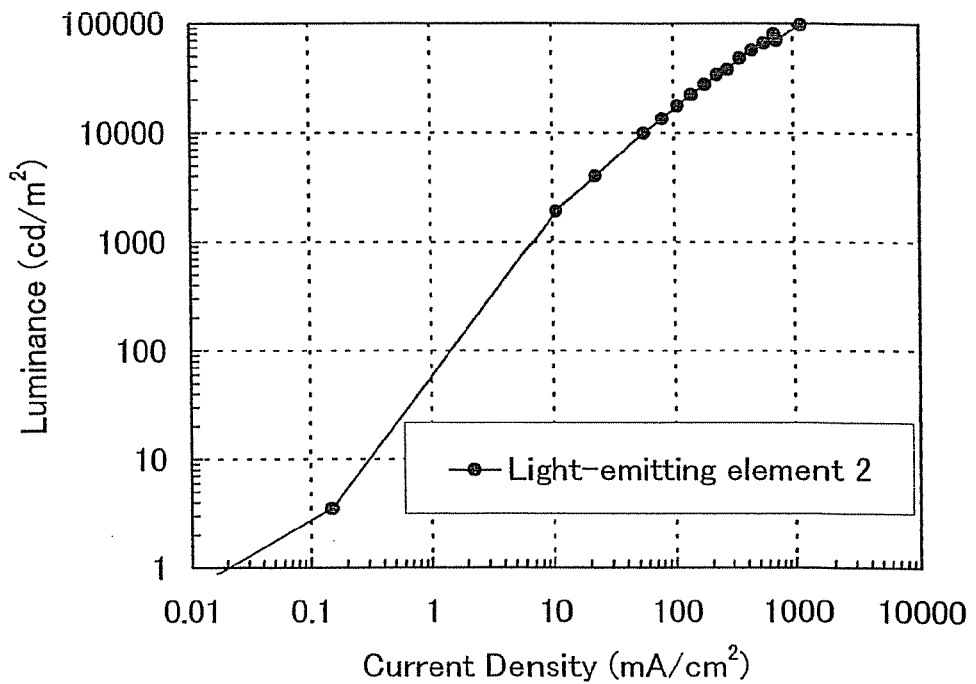
FIG. 19 shows the current density vs. luminance characteristics of a light-emitting element 2.
Figure 20:
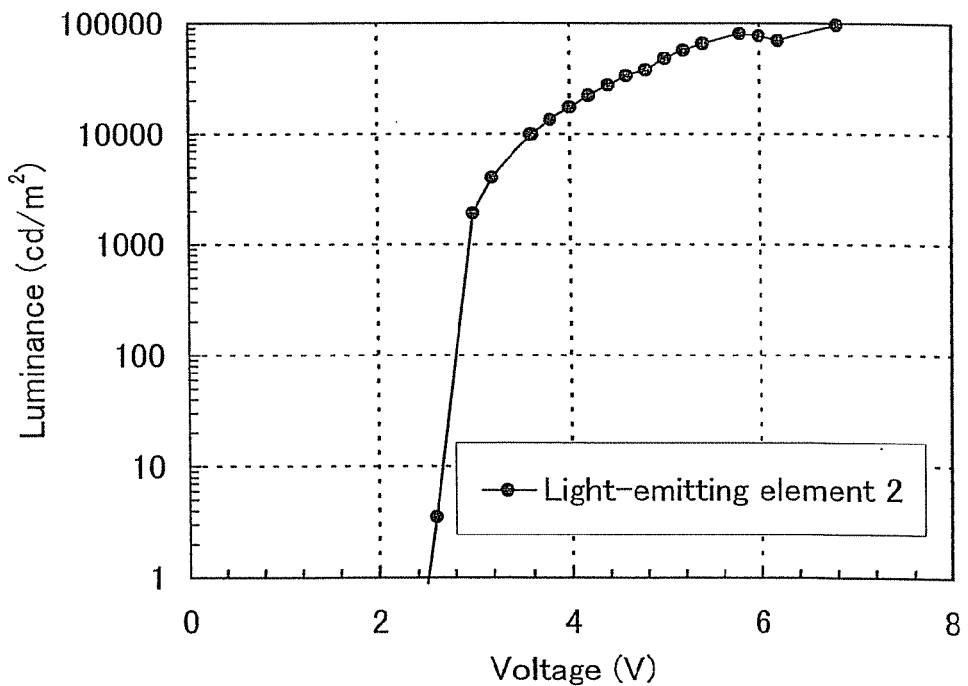
FIG. 20 shows the voltage vs. luminance characteristics of the light-emitting element 2.
Figure 21:
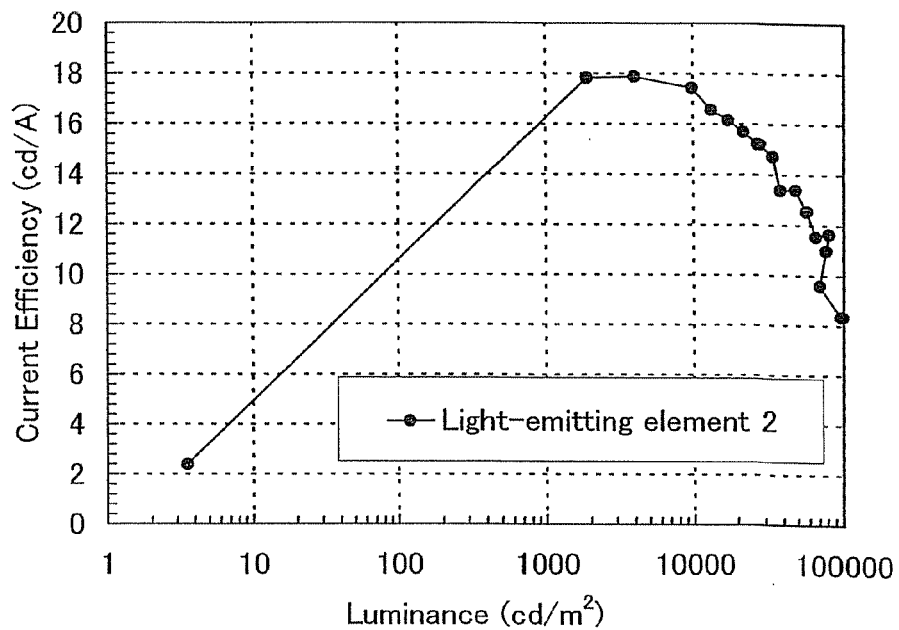
FIG. 21 shows the luminance vs. current efficiency characteristics of the light-emitting element 2.
Figure 22:
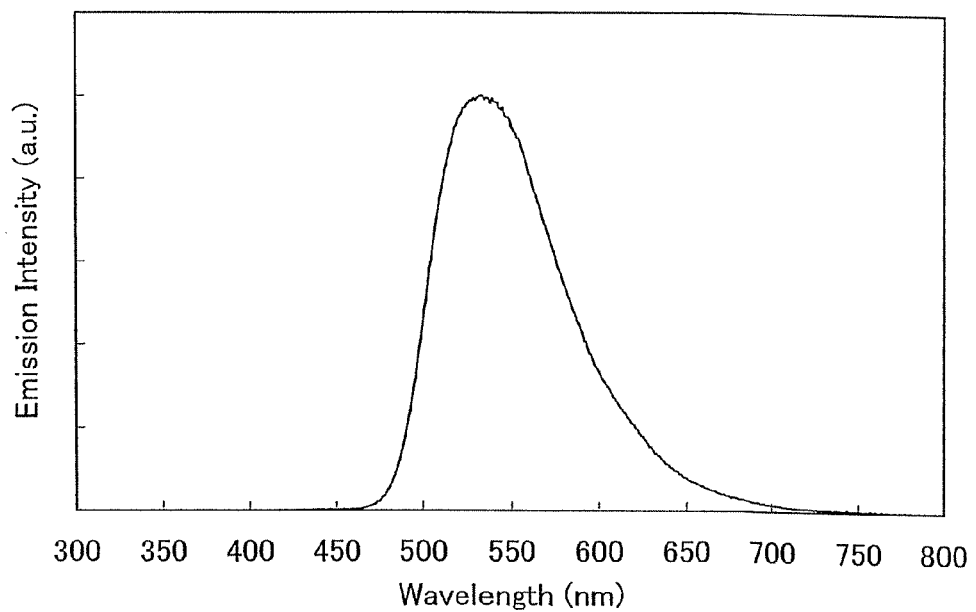
FIG. 22 shows the emission spectrum of the light-emitting element 2.

Current density vs. luminance characteristics, voltage vs. luminance characteristics, and luminance vs. current efficiency characteristics of the light-emitting element 2 are shown in FIGS. 19, 20, and 21, respectively. Also, the emission spectrum which was obtained at a current of 1 mA is shown in FIG. 22. A CIE chromaticity coordinate of the light-emitting element 2 at a luminance of 1920 cd/m$^2$ was (x=0.35, y=0.60), and light emission was green. Current efficiency at a luminance of 1920 cd/m$^2$ was 17.8 cd/A, which means high current efficiency. Voltage, current density, and power efficiency at a luminance of 1920 cd/m$^2$ were 3.0 V, 10.8 mA/cm$^2$, and 19 (lm/W), respectively. In addition, as shown in FIG. 22, the maximum emission wavelength at a current of 1 mA was 534 nm.

Thus, a light-emitting element with high luminous efficiency and reduced power consumption can be obtained by using the present invention.

EXAMPLE 4

Figure 26:
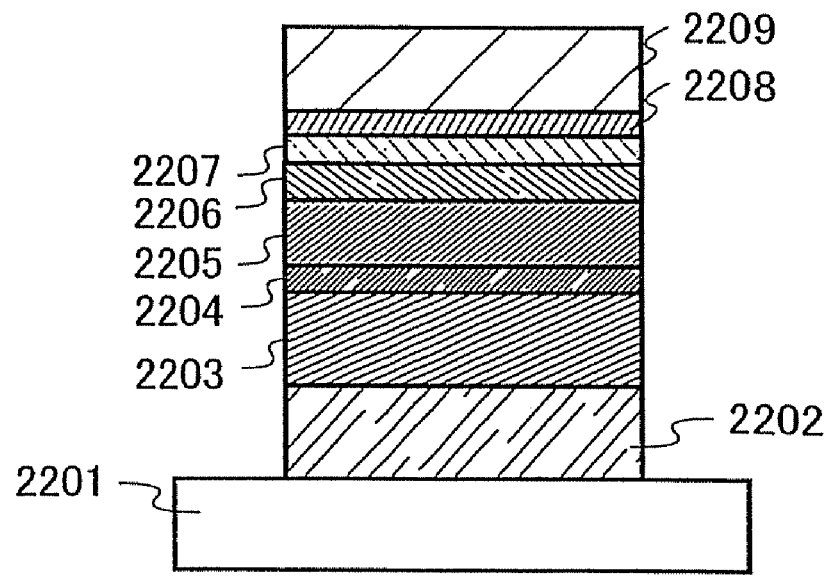
FIG. 26 illustrates a light-emitting element of an example.

In this example, a light-emitting element of the present invention will be described with reference to FIG. 26. A fabrication method of the light-emitting element of this example is described below.

(Light-emitting Element 3)

First, a film of ITO including silicon oxide (ITSO) was formed by sputtering over a glass substrate 2201 to form a first electrode 2202. It is to be noted that the film thickness of the first electrode was 110 nm, and an area of the electrode was 2 mm×2 mm.

Next, the substrate over which the first electrode was formed was fixed to a substrate holder provided in a vacuum evaporation apparatus, so that a surface over which the first electrode was formed faced down. Then, after reducing the pressure of the vacuum evaporation apparatus to about 10$^{-4}$ Pa, a layer 2203 containing a composite material of an organic compound and an inorganic compound was formed over the first electrode 2202 by co-evaporating 4,4'-bis[N-(1-napthyl)-N-phenylamino]biphenyl (abbreviation: NPB) and molybdenum oxide(VI). The film thickness of the layer 2203 was to be 50 nm, and the weight ratio of NPB and molybdenum oxide(VI) was adjusted to be 4:1 (=NPB:molybdenum oxide).

Subsequently, a film of 4,4'-bis[N-(1-napthyl)-N-phenylamino]biphenyl (abbreviation: NPB) was formed at a thickness of 10 nm over the layer 2203 containing the composite material by an evaporation method using a resistance heating system, whereby a hole transporting layer 2204 was formed.

Further, by co-evaporating 9-[4-(N-carbazolyl)]phenyl-10-phenylanthracene (abbreviation: CzPA) and N-(9,10-diphenyl-2-anthryl)-N,9-diphenyl-9H-carbazol-3-amine (abbreviation: 2PCAPA), a light-emitting layer 2205 with a thickness of 30 nm was formed over the hole transporting layer 2204. The weight ratio of CzPA and 2PCAPA was adjusted to be 1:0.05 (=CzPA:2PCAPA).

Thereafter, by co-evaporating tris(8-quinolinolato)aluminum (abbreviation: Alq) and 9,10-bis(4-fluorophenyl)-2-[N-phenyl-N-(9-phenyl-9H-carbazol-3-yl)amino]anthracene (abbreviation: 2PCAFPA), which is the anthracene derivative of the present invention represented by Structural Formula (201), a functional layer 2206 with a film thickness of 10 nm was formed over the light-emitting layer 2205. The weight ratio of Alq and 2PCAFPA was adjusted to be 1:0.1 (=Alq: 2PCAFPA).

Furthermore, a film of bathophenanthroline (abbreviation: BPhen) was formed at a thickness of 30 nm over the functional layer 2206 by means of an evaporation method using a resistance heating system, whereby an electron transporting layer 2207 was formed.

Furthermore, a film of lithium fluoride (LiF) was formed at a thickness of 1 nm over the electron transporting layer 2207, whereby an electron injecting layer 2208 was formed.

Finally, by forming a film of aluminum with a film thickness of 200 nm over the electron injecting layer 2208 by means of an evaporation method using a resistance heating system, a second electrode 2209 was formed. Accordingly, a light-emitting element 3 was fabricated.

(Reference Light-emitting Element 4)

By co-evaporating 9-[4-(N-carbazolyl)]phenyl-10-phenylanthracene (abbreviation: CzPA) and N-(9,10-diphenyl-2-anthryl)-N,9-diphenyl-9H-carbazol-3-amine (abbreviation: 2PCAPA), a light-emitting layer 2205 with a film thickness of 40 nm was formed, so that a light-emitting element without the functional layer 2206 was formed. Structures other than that are similar to those of the light-emitting element 3.

Figure 27:
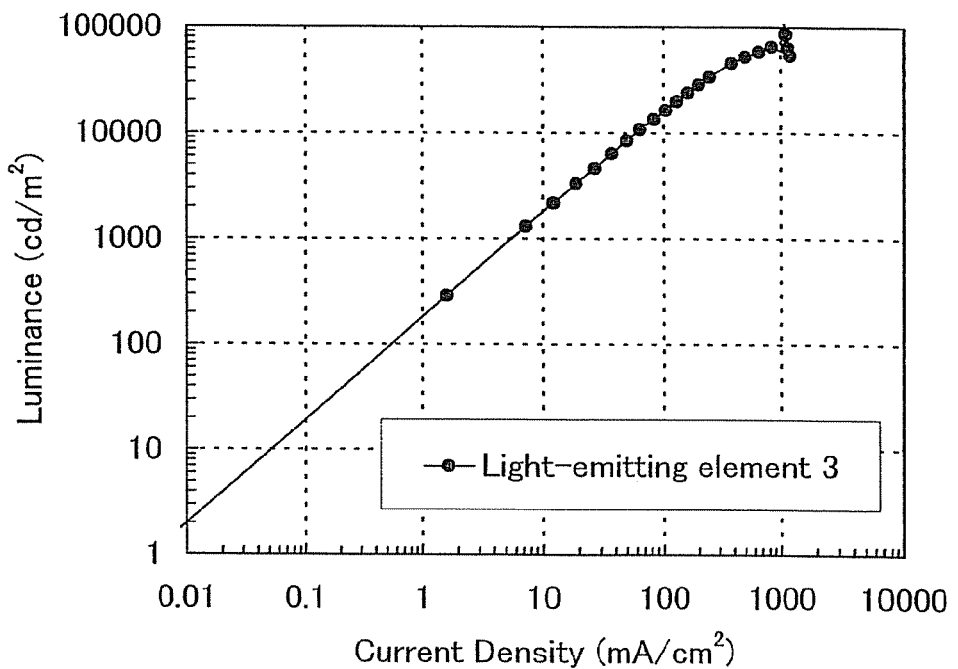
FIG. 27 shows the current density vs. luminance characteristics of a light-emitting element 3.
Figure 28:
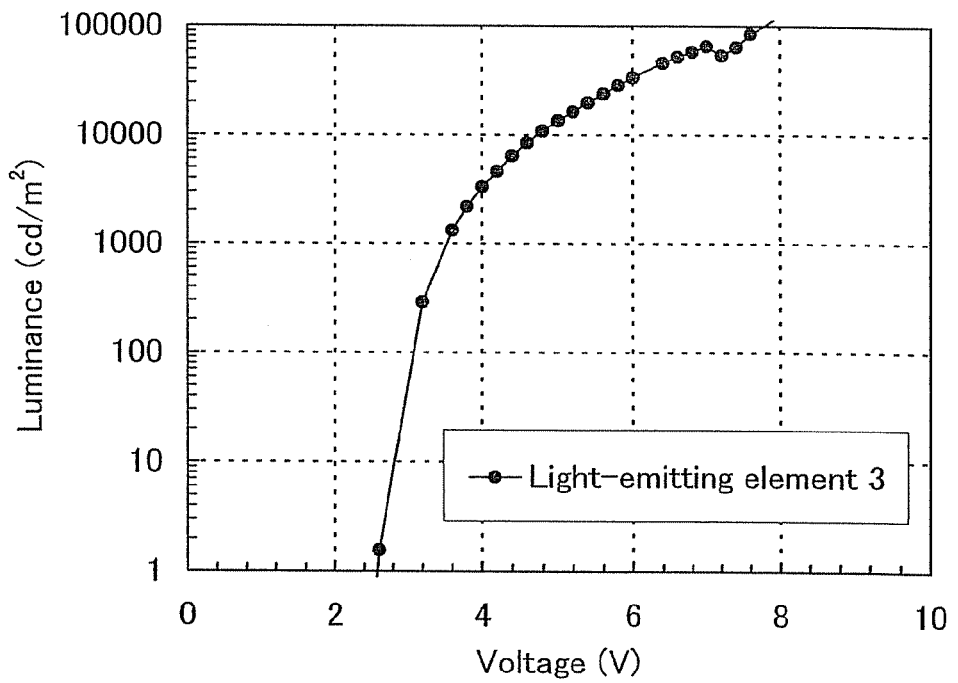
FIG. 28 shows the voltage vs. luminance characteristics of the light-emitting element 3.
Figure 29:
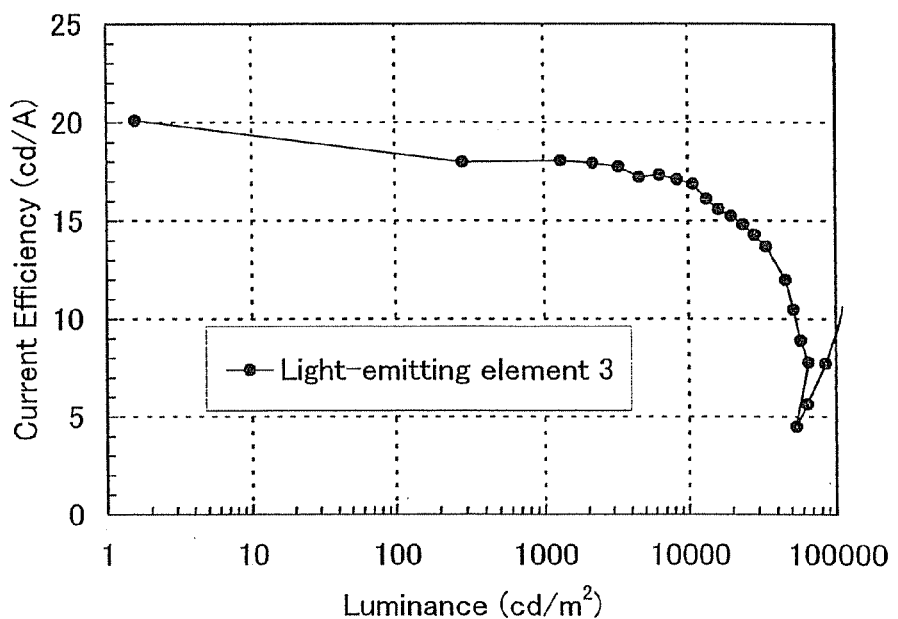
FIG. 29 shows the luminance vs. current efficiency characteristics of the light-emitting element 3.
Figure 30:
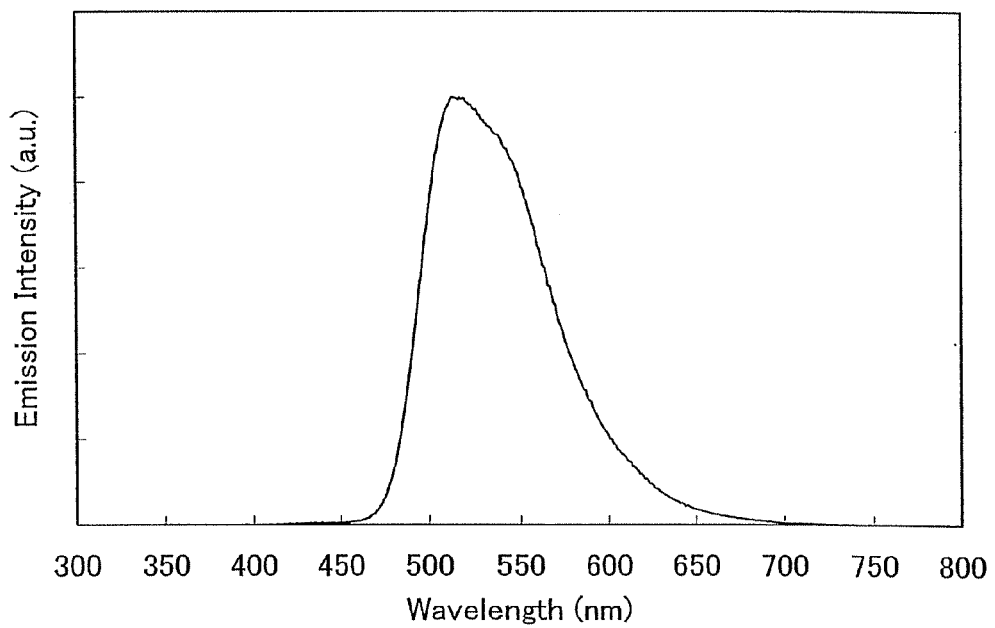
FIG. 30 shows the emission spectrum of the light-emitting element 3.

Current density vs. luminance characteristics, voltage vs. luminance characteristics, and luminance vs. current efficiency characteristics of the light-emitting element 3 are shown in FIGS. 27, 28, and 29, respectively. Also, the emission spectrum which was obtained at a current of 1 mA is shown in FIG. 30. A CIE chromaticity coordinate of the light-emitting element 3 at a luminance of 3320 cd/m$^2$ was (x=0.28, y=0.63), and light emission was green. Current efficiency at a luminance of 3220 cd/m$^2$ was 17.7 cd/A, which means high current efficiency. Voltage, current density, and power efficiency at a luminance of 3320 cd/m$^2$ were 4.0 V, 18.7 mA/cm$^2$, and 14 (lm/W), respectively. In addition, as shown in FIG. 30, the maximum emission wavelength at a current of 1 mA was 514 nm.

Figure 31:
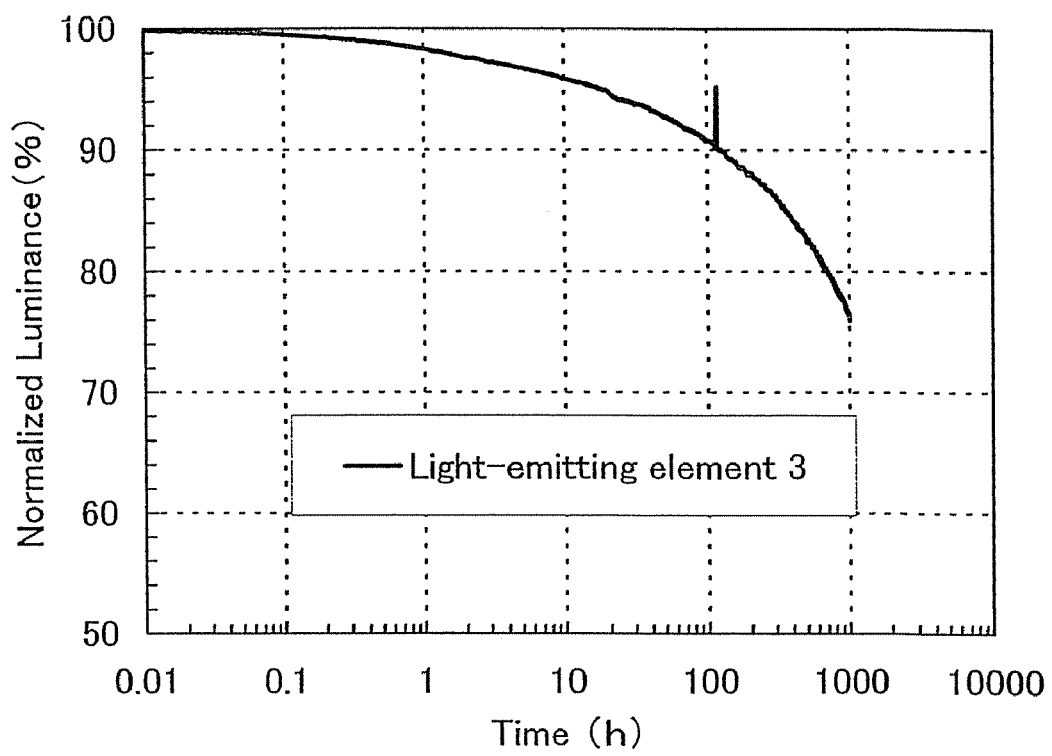
FIG. 31 shows the result of a continuous lighting test of the light-emitting element 3.

FIG. 31 shows the result of a continuous lighting test of the light-emitting element 3 by constant current driving with the initial luminance set at 5000 cd/m$^2$. A vertical axis shows relative luminance (standardized luminance) where the luminance of 5000 cd/m$^2$ is assumed to be 100%. When the continuous lighting test of the light-emitting element 3 by constant current driving was conducted with the initial luminance set at 5000 cd/m$^2$, 76% of the initial luminance was maintained even after 1000 hours, whereby the light-emitting element 3 was determined to have a long lifetime.

Figure 32:
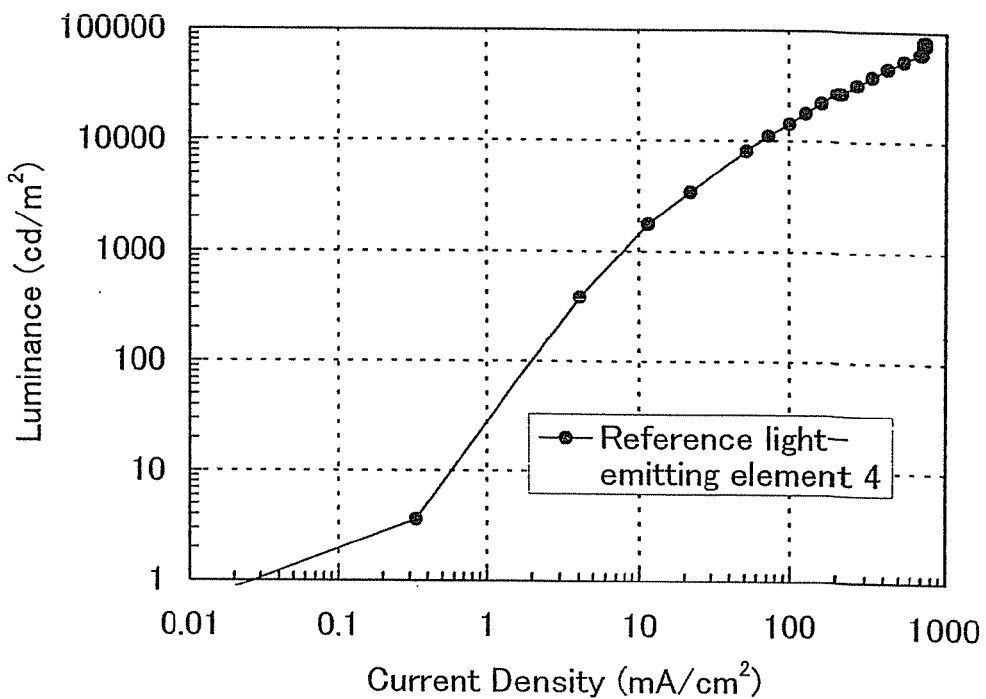
FIG. 32 shows the current density vs. luminance characteristics of a reference light-emitting element 4.
Figure 33:
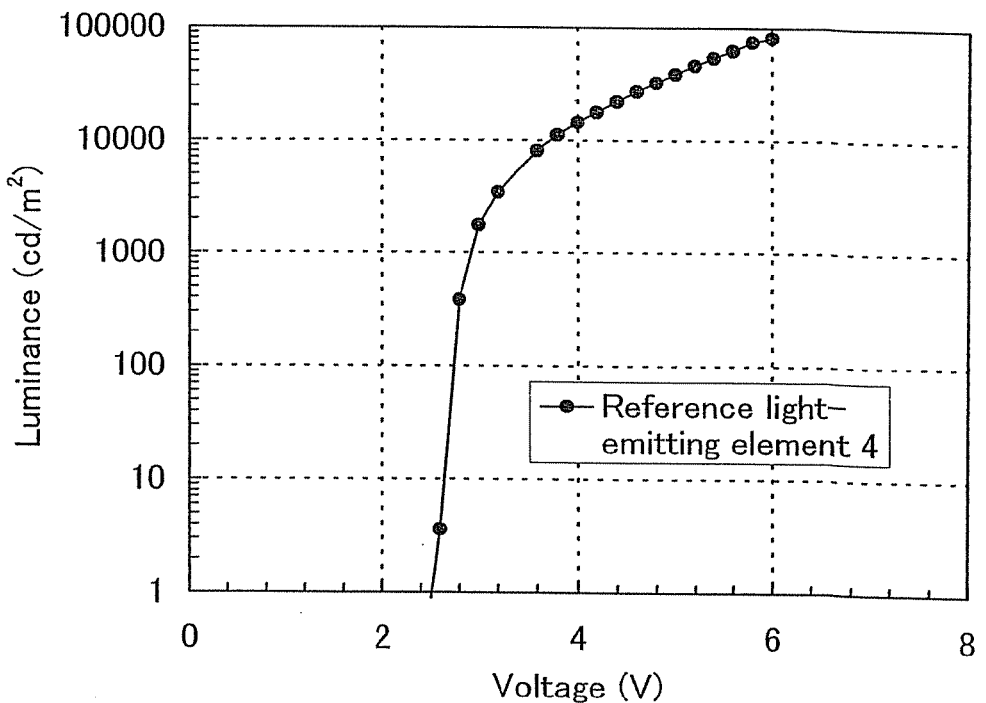
FIG. 33 shows the voltage vs. luminance characteristics of the reference light-emitting element 4.
Figure 34:
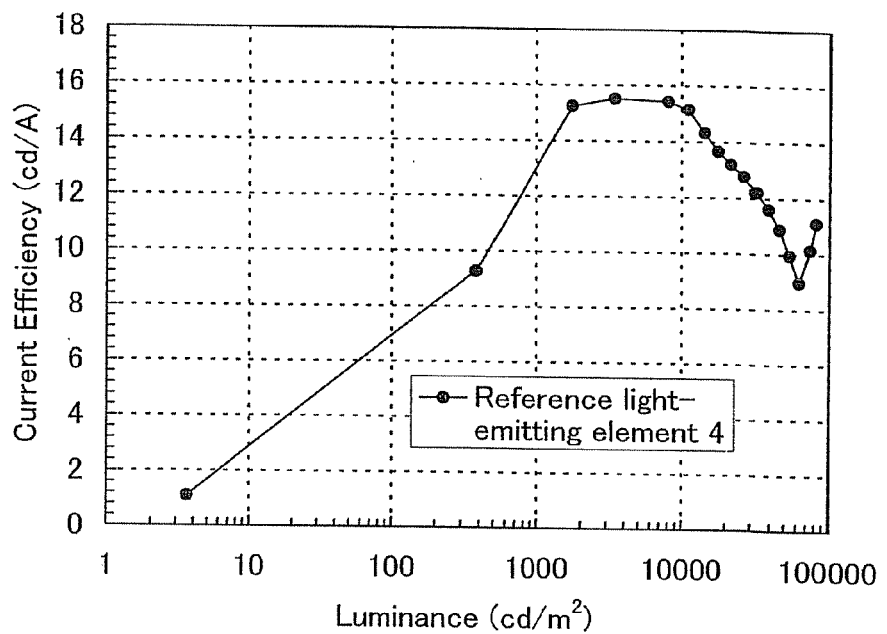
FIG. 34 shows the luminance vs. current efficiency characteristics of the reference light-emitting element 4.
Figure 35:
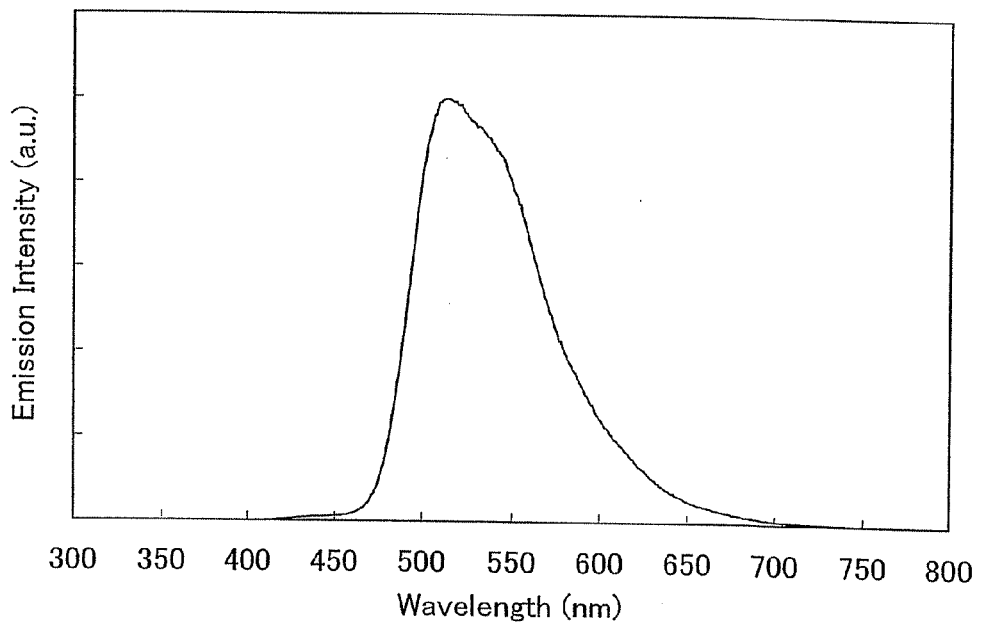
FIG. 35 shows the emission spectrum of the reference light-emitting element 4.

Current density vs. luminance characteristics, voltage vs. luminance characteristics, and luminance vs. current efficiency characteristics of the reference light-emitting element 4 are shown in FIGS. 32, 33, and 34, respectively. Also, the emission spectrum which was obtained at a current of 1 mA is shown in FIG. 35. A CIE chromaticity coordinate of the reference light-emitting element 4 at a luminance of 3340 cd/m$^2$ was (x=0.29, y=0.62), and light emission was green. Current efficiency at a luminance of 3440 cd/m$^2$ was 15.5 cd/A. Voltage, current density, and power efficiency at a luminance of 3440 cd/m$^2$ were 3.2 V, 22.2 mA/cm$^2$, and 16 (lm/W), respectively. In addition, as shown in FIG. 35, the maximum emission wavelength at a current of 1 mA was 514 nm.

Figure 36:
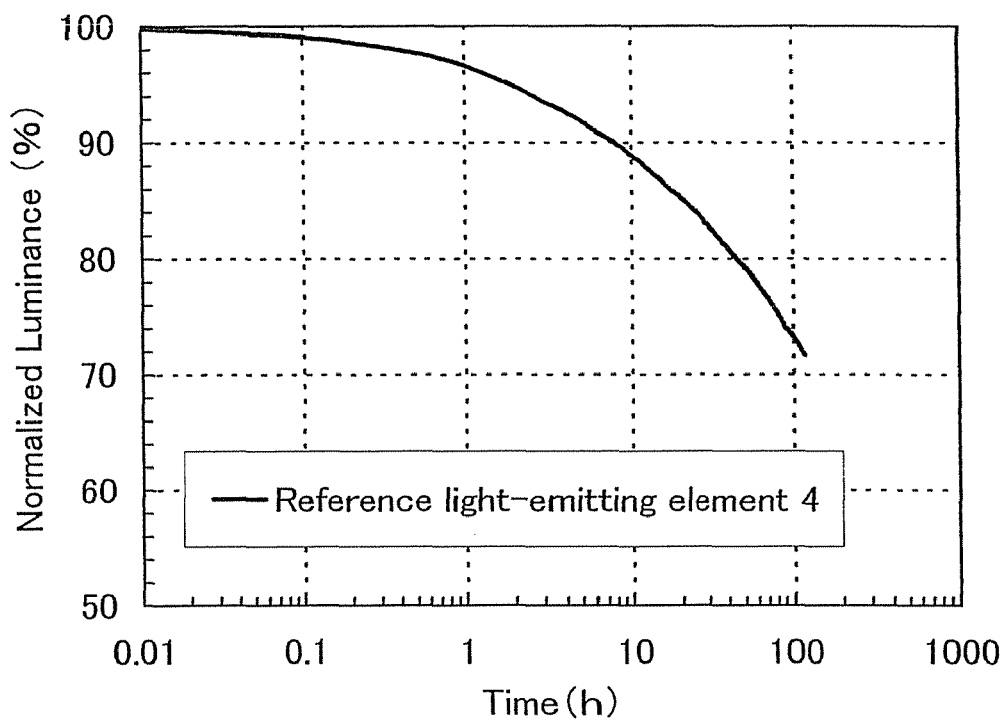
FIG. 36 shows the result of a continuous lighting test of the reference light-emitting element 4.

FIG. 36 shows the result of a continuous lighting test of the reference light-emitting element 4 by constant current driving with the initial luminance set at 5000 cd/m$^2$. A vertical axis shows relative luminance (standardized luminance) where the luminance of 5000 cd/m$^2$ is assumed to be 100%. When the continuous lighting test of the reference light-emitting element 4 by constant current driving was conducted with the initial luminance set at 5000 cd/m$^2$, 72% of the initial luminance was maintained after 120 hours.

Thus, a light-emitting element with high luminous efficiency and reduced power consumption could be obtained by using the present invention. In addition, comparison of the result of the continuous lighting test of the light-emitting element 3 with that of the reference light-emitting element 4 clearly demonstrated that a light-emitting element with a long lifetime can be readily obtained by applying the present invention.

The present application is based on Japanese Priority application No. 2006-288924 filed on Oct. 24, 2006 with the Japanese Patent Office, the entire contents of which are hereby incorporated by reference.

What is claimed is:

1. A light-emitting device comprising a light-emitting element which comprises an anthracene derivative between a pair of electrodes,
wherein the anthracene derivative is represented by the General Formula (1),

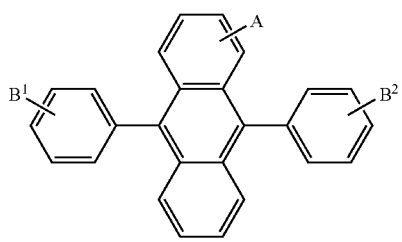

(1)

wherein each of B$^1$ and B$^2$ represents one selected from the group consisting of halogen, a cyano group, an acyl group, a carboxyl group, an acyloxy group, an alkoxy group, a pyridyl group, a quinolyl group, an isoquinolyl group, and an oxazolyl group, and
wherein A represents a substituent given by one of General Formulae (1-1) to (1-3):

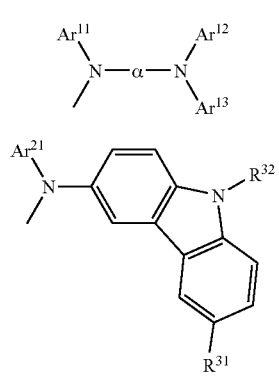

(1-1)

(1-2)

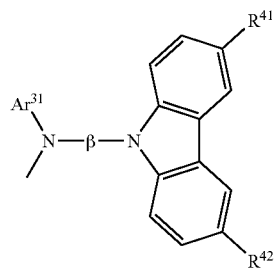

(1-3)

wherein:
each of Ar$^{11}$ to Ar$^{13}$ represents an aryl group having 6 to 25 carbon atoms;
α represents an arylene group having 6 to 25 carbon atoms;
Ar$^{21}$ represents an aryl group having 6 to 25 carbon atoms;
R$^{31}$ represents one selected from the group consisting of a hydrogen atom, an alkyl group having 1 to 4 carbon atoms, and an aryl group having 6 to 25 carbon atoms;
R$^{32}$ represents an alkyl group having 1 to 4 carbon atoms or an aryl group having 6 to 25 carbon atoms;
Ar$^{31}$ represents an aryl group having 6 to 25 carbon atoms;
β represents an arylene group having 6 to 25 carbon atoms; and
each of R$^{41}$ and R$^{42}$ represents one selected from the group consisting of a hydrogen atom, an alkyl group having 1 to 4 carbon atoms, and an aryl group having 6 to 25 carbon atoms.

2. The light-emitting device according to claim 1, wherein A is bonded at the 2-position of the anthracene skeleton of the General Formula (1).

3. A light-emitting device comprising a light-emitting element which comprises:
an anode;
a hole transporting layer over the anode;
a first layer over the hole transporting layer;
a second layer over the first layer;
an electron transporting layer over the second layer; and
a cathode over the electron transporting layer,
wherein:
the first layer includes a first organic compound; and
the second layer includes a second organic compound and a third organic compound,
wherein the first organic compound and the second organic compound have an electron transporting property,
wherein the third organic compound is an anthracene derivative represented by General Formula (1):

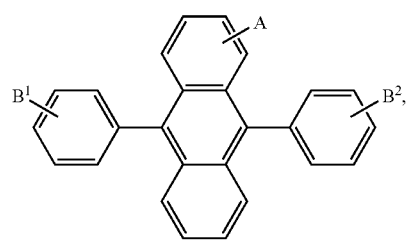

(1)

wherein each of B$^1$ and B$^2$ represents one selected from the group consisting of halogen, a cyano group, an acyl group, a carboxyl group, an acyloxy group, an alkoxy group, a pyridyl group, a quinolyl group, an isoquinolyl group, and an oxazolyl group,
wherein A represents a substituent given by one of General Formulae (1-1) to (1-3):

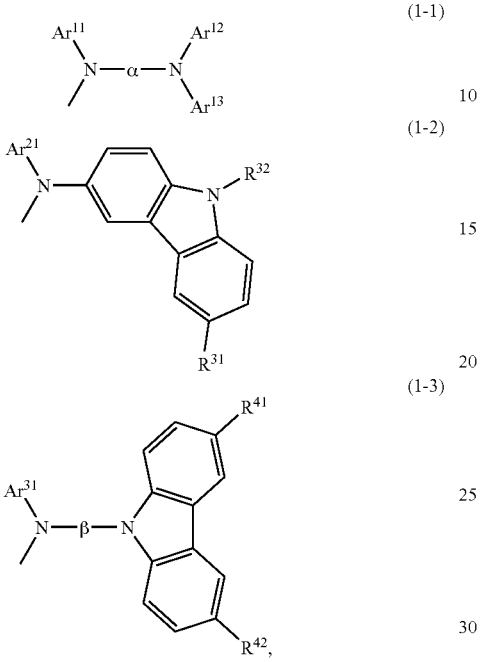

and
wherein:
each of $Ar^{11}$ to $Ar^{13}$ represents an aryl group having 6 to 25 carbon atoms;
α represents an arylene group having 6 to 25 carbon atoms;
$Ar^{21}$ represents an aryl group having 6 to 25 carbon atoms;
$R^{31}$ represents one selected from the group consisting of a hydrogen atom, an alkyl group having 1 to 4 carbon atoms, and an aryl group having 6 to 25 carbon atoms;
$R^{32}$ represents an alkyl group having 1 to 4 carbon atoms or an aryl group having 6 to 25 carbon atoms;
$Ar^{31}$ represents an aryl group having 6 to 25 carbon atoms;
β represents an arylene group having 6 to 25 carbon atoms; and
each of $R^{41}$ and $R^{42}$ represents one selected from the group consisting of a hydrogen atom, an alkyl group having 1 to 4 carbon atoms, and an aryl group having 6 to 25 carbon atoms.

4. The light-emitting device according to claim 3, wherein A is bonded at the 2-position of the anthracene skeleton of the General Formula (1).

5. The light-emitting device according to claim 3, further comprising a fourth organic compound in the first layer,
wherein a difference in wavelength between an emission peak of the third organic compound and an emission peak of the fourth organic compound is less than or equal to 30 nm.

6. A light-emitting device comprising a light-emitting element which comprises:
an anode;
a hole transporting layer over the anode;
a first layer over the hole transporting layer;
a second layer over the first layer;
an electron transporting layer over the second layer; and
a cathode over the electron transporting layer,
wherein:
the first layer includes a first organic compound and a second organic compound; and
the second layer includes a third organic compound,
wherein the first organic compound and the third organic compound have an electron transporting property,
wherein the second organic compound is an anthracene derivative represented by General Formula (1):

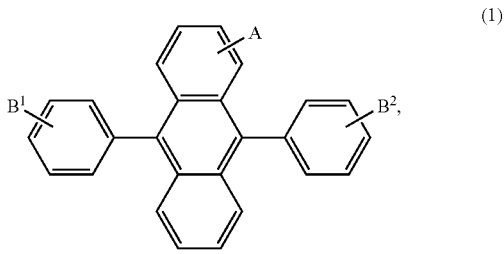

wherein each of $B^1$ and $B^2$ represents one selected from the group consisting of halogen, a cyano group, an acyl group, a carboxyl group, an acyloxy group, an alkoxy group, a pyridyl group, a quinolyl group, an isoquinolyl group, and an oxazolyl group,
wherein A represents a substituent given by one of General Formulae (1-1) to (1-3):

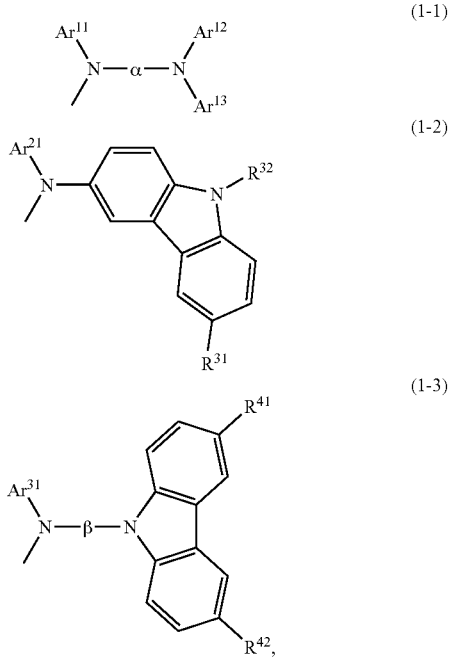

and
wherein:
each of $Ar^{11}$ to $Ar^{13}$ represents an aryl group having 6 to 25 carbon atoms;
α represents an arylene group having 6 to 25 carbon atoms;
$Ar^{21}$ represents an aryl group having 6 to 25 carbon atoms;

$R^{31}$ represents one selected from the group consisting of a hydrogen atom, an alkyl group having 1 to 4 carbon atoms, and an aryl group having 6 to 25 carbon atoms;

$R^{32}$ represents an alkyl group having 1 to 4 carbon atoms or an aryl group having 6 to 25 carbon atoms;

$Ar^{31}$ represents an aryl group having 6 to 25 carbon atoms;

β represents an arylene group having 6 to 25 carbon atoms; and each of $R^{41}$ and $R^{42}$ represents one selected from the group consisting of a hydrogen atom, an alkyl group having 1 to 4 carbon atoms, and an aryl group having 6 to 25 carbon atoms.

7. The light-emitting device according to claim 6, wherein A is bonded at the 2-position of the anthracene skeleton of the General Formula (1).

8. The light-emitting device according to claim 6, further comprising a fourth organic compound in the second layer, wherein the lowest unoccupied molecular orbital level of the fourth organic compound is lower than the lowest unoccupied molecular orbital level of the third organic compound by 0.3 eV or more.

9. The light-emitting device according to claim 6, further comprising a fourth organic compound in the second layer, wherein the lowest unoccupied molecular orbital level of the fourth organic compound is lower than the lowest unoccupied molecular orbital level of the third organic compound by 0.3 eV or more, and wherein a difference in wavelength between an emission peak of the second organic compound and an emission peak of the fourth organic compound is less than or equal to 30 nm.

10. The light-emitting device according to claim 6, further comprising a fourth organic compound in the second layer, wherein the fourth organic compound has a hole transporting property.

11. The light-emitting device according to claim 6, further comprising a fourth organic compound in the second layer, wherein the fourth organic compound has a hole transporting property, and wherein a difference between the lowest unoccupied molecular orbital levels of the third organic compound and the fourth organic compound is preferably less than 0.3 eV.

12. The light-emitting device according to claim 6, further comprising a fourth organic compound in the second layer, wherein the fourth organic compound has a hole transporting property, and wherein a difference between the lowest unoccupied molecular orbital levels of the third organic compound and the fourth organic compound is preferably less than 0.3 eV, and wherein a difference in wavelength between an emission peak of the second organic compound and an emission peak of the fourth organic compound is less than or equal to 30 nm.

13. The light-emitting device according to claim 6, further comprising a fourth organic compound in the second layer, wherein the fourth organic compound is an anthracene derivative represented by General Formula (1):

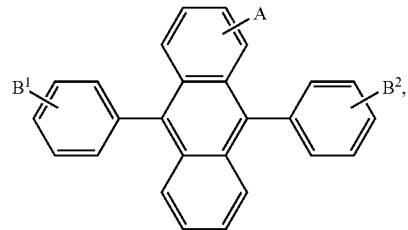

(1)

wherein each of $B^1$ and $B^2$ represents one selected from the group consisting of halogen, a cyano group, an acyl group, a carboxyl group, an acyloxy group, an alkoxy group, a pyridyl group, a quinolyl group, an isoquinolyl group, and an oxazolyl group, wherein A represents a substituent given by one of General Formulae (1-1) to (1-3):

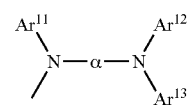

(1-1)

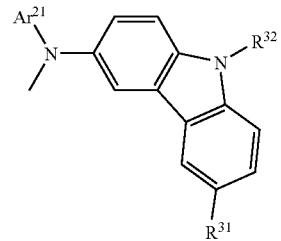

(1-2)

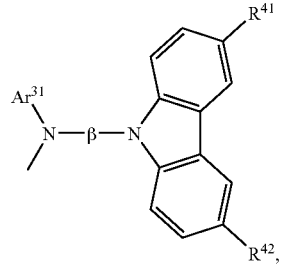

(1-3)

and
wherein:
each of $Ar^{11}$ to $Ar^{13}$ represents an aryl group having 6 to 25 carbon atoms;

α represents an arylene group having 6 to 25 carbon atoms;

$Ar^{21}$ represents an aryl group having 6 to 25 carbon atoms;

$R^{31}$ represents one selected from the group consisting of a hydrogen atom, an alkyl group having 1 to 4 carbon atoms, and an aryl group having 6 to 25 carbon atoms;

$R^{32}$ represents an alkyl group having 1 to 4 carbon atoms or an aryl group having 6 to 25 carbon atoms;

$Ar^{31}$ represents an aryl group having 6 to 25 carbon atoms;

β represents an arylene group having 6 to 25 carbon atoms; and each of $R^{41}$ and $R^{42}$ represents one selected from the group consisting of a hydrogen atom, an alkyl group having 1 to 4 carbon atoms, and an aryl group having 6 to 25 carbon atoms.

14. The light-emitting device according to claim 6, further comprising a fourth organic compound in the second layer,
wherein the second compound is the same as the fourth organic compound.

15. A lighting device comprising a light-emitting element which comprises an anthracene derivative between a pair of electrodes,
wherein the anthracene derivative is represented by the General Formula (1),

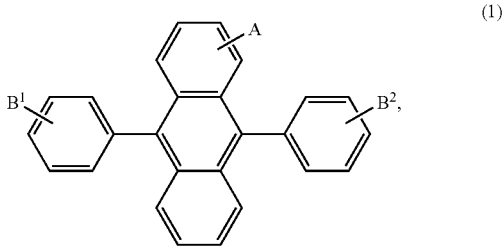

wherein each of $B^1$ and $B^2$ represents one selected from the group consisting of halogen, a cyano group, an acyl group, a carboxyl group, an acyloxy group, an alkoxy group, a pyridyl group, a quinolyl group, an isoquinolyl group, and an oxazolyl group, and
wherein A represents a substituent given by one of General Formulae (1-1) to (1-3):

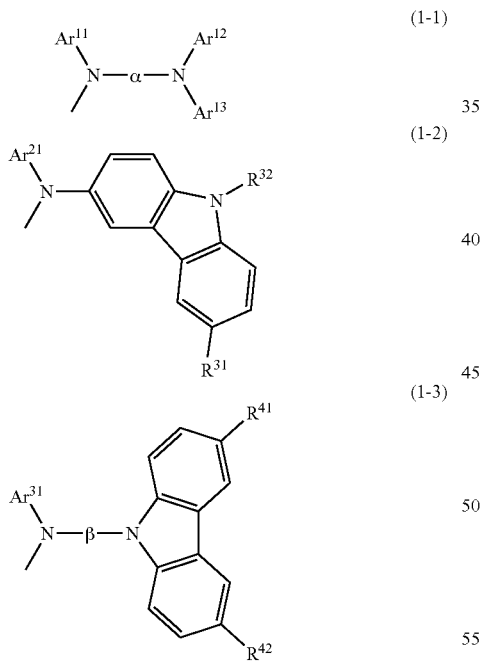

wherein:
each of $Ar^{11}$ to $Ar^{13}$ represents an aryl group having 6 to 25 carbon atoms;
α represents an arylene group having 6 to 25 carbon atoms;
$Ar^{21}$ represents an aryl group having 6 to 25 carbon atoms;
$R^{31}$ represents one selected from the group consisting of a hydrogen atom, an alkyl group having 1 to 4 carbon atoms, and an aryl group having 6 to 25 carbon atoms;
$R^{32}$ represents an alkyl group having 1 to 4 carbon atoms or an aryl group having 6 to 25 carbon atoms;
$Ar^{31}$ represents an aryl group having 6 to 25 carbon atoms;
β represents an arylene group having 6 to 25 carbon atoms; and
each of $R^{41}$ and $R^{42}$ represents one selected from the group consisting of a hydrogen atom, an alkyl group having 1 to 4 carbon atoms, and an aryl group having 6 to 25 carbon atoms.

16. The lighting device according to claim 15,
wherein A is bonded at the 2-position of the anthracene skeleton of the General Formula (1).

17. A lighting device comprising a light-emitting element which comprises:
an anode;
a hole transporting layer over the anode;
a first layer over the hole transporting layer;
a second layer over the first layer;
an electron transporting layer over the second layer; and
a cathode over the electron transporting layer,
wherein:
the first layer includes a first organic compound; and
the second layer includes a second organic compound and a third organic compound,
wherein the first organic compound and the second organic compound have an electron transporting property,
wherein the third organic compound is an anthracene derivative represented by General Formula (1):

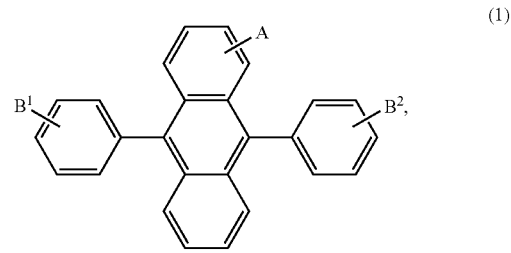

wherein each of $B^1$ and $B^2$ represents one selected from the group consisting of halogen, a cyano group, an acyl group, a carboxyl group, an acyloxy group, an alkoxy group, a pyridyl group, a quinolyl group, an isoquinolyl group, and an oxazolyl group,
wherein A represents a substituent given by one of General Formulae (1-1) to (1-3):

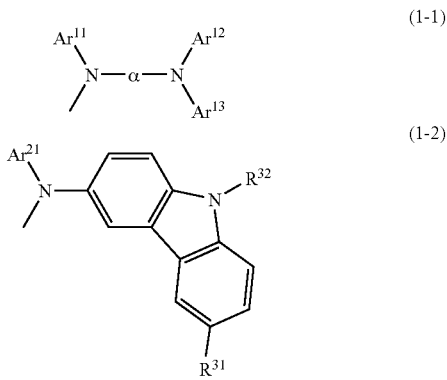

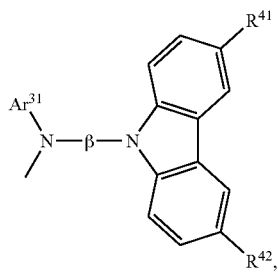

and
wherein:
each of $Ar^{11}$ to $Ar^{ja}$ represents an aryl group having 6 to 25 carbon atoms;
α represents an arylene group having 6 to 25 carbon atoms;
$Ar^{21}$ represents an aryl group having 6 to 25 carbon atoms;
$R^{31}$ represents one selected from the group consisting of a hydrogen atom, an alkyl group having 1 to 4 carbon atoms, and an aryl group having 6 to 25 carbon atoms;
$R^{32}$ represents an alkyl group having 1 to 4 carbon atoms or an aryl group having 6 to 25 carbon atoms;
$Ar^{31}$ represents an aryl group having 6 to 25 carbon atoms;
β represents an arylene group having 6 to 25 carbon atoms; and
each of $R^{41}$ and $R^{42}$ represents one selected from the group consisting of a hydrogen atom, an alkyl group having 1 to 4 carbon atoms, and an aryl group having 6 to 25 carbon atoms.

18. The lighting device according to claim 17, wherein A is bonded at the 2-position of the anthracene skeleton of the General Formula (1).

19. The lighting device according to claim 17, further comprising a fourth organic compound in the first layer, wherein a difference in wavelength between an emission peak of the third organic compound and an emission peak of the fourth organic compound is less than or equal to 30 nm.

20. A lighting device comprising a light-emitting element which comprises:
an anode;
a hole transporting layer over the anode;
a first layer over the hole transporting layer;
a second layer over the first layer;
an electron transporting layer over the second layer; and
a cathode over the electron transporting layer,
wherein:
the first layer includes a first organic compound and a second organic compound; and
the second layer includes a third organic compound,
wherein the first organic compound and the third organic compound have an electron transporting property,
wherein the second organic compound is an anthracene derivative represented by General Formula (1):

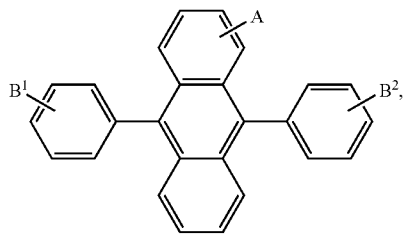

wherein each of $B^1$ and $B^2$ represents one selected from the group consisting of halogen, a cyano group, an acyl group, a carboxyl group, an acyloxy group, an alkoxy group, a pyridyl group, a quinolyl group, an isoquinolyl group, and an oxazolyl group,
wherein A represents a substituent given by one of General Formulae (1-1) to (1-3):

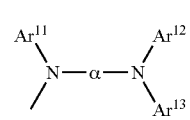

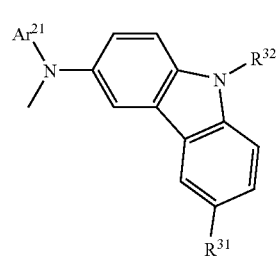

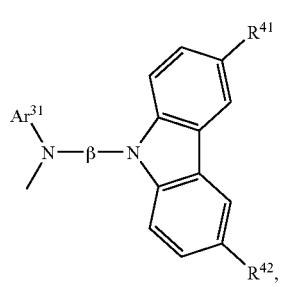

and
wherein:
each of $Ar^{11}$ to $Ar^{13}$ represents an aryl group having 6 to 25 carbon atoms;
α represents an arylene group having 6 to 25 carbon atoms;
$Ar^{21}$ represents an aryl group having 6 to 25 carbon atoms;
$R^{31}$ represents one selected from the group consisting of a hydrogen atom, an alkyl group having 1 to 4 carbon atoms, and an aryl group having 6 to 25 carbon atoms;
$R^{32}$ represents an alkyl group having 1 to 4 carbon atoms or an aryl group having 6 to 25 carbon atoms;
$Ar^{31}$ represents an aryl group having 6 to 25 carbon atoms;
β represents an arylene group having 6 to 25 carbon atoms; and
each of $R^{41}$ and $R^{42}$ represents one selected from the group consisting of a hydrogen atom, an alkyl group having 1 to 4 carbon atoms, and an aryl group having 6 to 25 carbon atoms.

21. The lighting device according to claim 20,
wherein A is bonded at the 2-position of the anthracene skeleton of the General Formula (1).

22. The lighting device according to claim 20, further comprising a fourth organic compound in the second layer,
wherein the lowest unoccupied molecular orbital level of the fourth organic compound is lower than the lowest unoccupied molecular orbital level of the third organic compound by 0.3 eV or more.

23. The lighting device according to claim 20, further comprising a fourth organic compound in the second layer,
wherein the lowest unoccupied molecular orbital level of the fourth organic compound is lower than the lowest unoccupied molecular orbital level of the third organic compound by 0.3 eV or more, and
wherein a difference in wavelength between an emission peak of the second organic compound and an emission peak of the fourth organic compound is less than or equal to 30 nm.

24. The lighting device according to claim 20, further comprising a fourth organic compound in the second layer,
wherein the fourth organic compound has a hole transporting property.

25. The lighting device according to claim 20, further comprising a fourth organic compound in the second layer,
wherein the fourth organic compound has a hole transporting property, and
wherein a difference between the lowest unoccupied molecular orbital levels of the third organic compound and the fourth organic compound is preferably less than 0.3 eV.

26. The lighting device according to claim 20, further comprising a fourth organic compound in the second layer,
wherein the fourth organic compound has a hole transporting property, and
wherein a difference between the lowest unoccupied molecular orbital levels of the third organic compound and the fourth organic compound is preferably less than 0.3 eV, and
wherein a difference in wavelength between an emission peak of the second organic compound and an emission peak of the fourth organic compound is less than or equal to 30 nm.

27. The lighting device according to claim 20, further comprising a fourth organic compound in the second layer,
wherein the fourth organic compound is an anthracene derivative represented by General Formula (1):

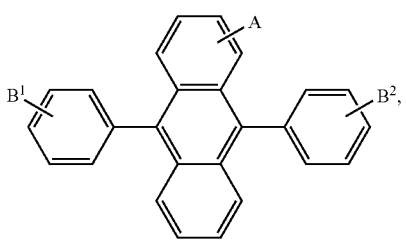

(1)

wherein each of $B^1$ and $B^2$ represents one selected from the group consisting of halogen, a cyano group, an acyl group, a carboxyl group, an acyloxy group, an alkoxy group, a pyridyl group, a quinolyl group, an isoquinolyl group, and an oxazolyl group,
wherein A represents a substituent given by one of General Formulae (1-1) to (1-3):

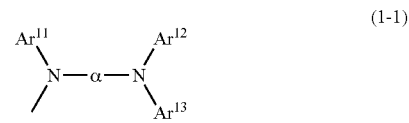

(1-1)

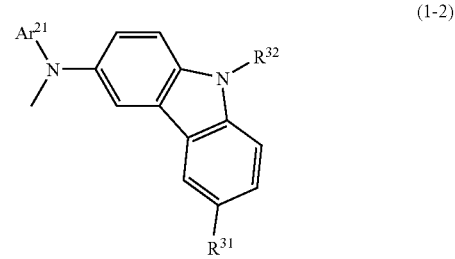

(1-2)

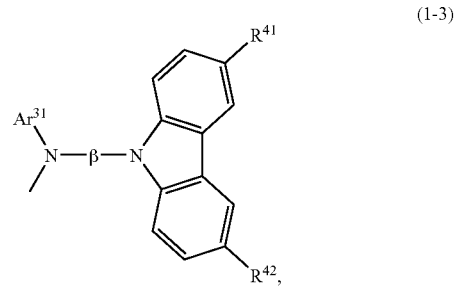

(1-3)

and
wherein:
each of $Ar^{11}$ to $Ar^{13}$ represents an aryl group having 6 to 25 carbon atoms;
α represents an arylene group having 6 to 25 carbon atoms;
$Ar^{21}$ represents an aryl group having 6 to 25 carbon atoms;
$R^{31}$ represents one selected from the group consisting of a hydrogen atom, an alkyl group having 1 to 4 carbon atoms, and an aryl group having 6 to 25 carbon atoms;
$R^{32}$ represents an alkyl group having 1 to 4 carbon atoms or an aryl group having 6 to 25 carbon atoms;
$Ar^{31}$ represents an aryl group having 6 to 25 carbon atoms;
β represents an arylene group having 6 to 25 carbon atoms; and
each of $R^{41}$ and $R^{42}$ represents one selected from the group consisting of a hydrogen atom, an alkyl group having 1 to 4 carbon atoms, and an aryl group having 6 to 25 carbon atoms.

28. The lighting device according to claim 20, further comprising a fourth organic compound in the second layer,
wherein the second compound is the same as the fourth organic compound.

* * * * *

UNITED STATES PATENT AND TRADEMARK OFFICE
CERTIFICATE OF CORRECTION

| | |
|---|---|
| PATENT NO. | : 8,110,980 B2 |
| APPLICATION NO. | : 12/717218 |
| DATED | : February 7, 2012 |
| INVENTOR(S) | : Masakazu Egawa et al. |

It is certified that error appears in the above-identified patent and that said Letters Patent is hereby corrected as shown below:

In the Specification:

Column 7, Line 58; Change "General Formulae (64) to (6-3)." to
--General Formulae (6-1) to (6-3).--.

Column 7, Line 62; Change "$A^{21}$ represents" to --$Ar^{21}$ represents--.

Column 64, Line 58; Change "$R^2$ and $R^{26}$" to --$R^{25}$ and $R^{26}$--.

Column 65, Line 60; Change "$A^{21}$ represents" to --$Ar^{21}$ represents--.

Column 135, Line 65; Change "2-tent-butyl-9,10-bis(4-phenylphenyl)anthracene" to
--2-tert-butyl-9,10-bis(4-phenylphenyl)anthracene--.

Column 138, Line 49; Change "P-channel" to --P-channel TFTs.--.

Column 143, Line 49; Change "BAIq, Znq, BAIq," to --BAlq, Znq, BAlq,--.

Column 151, Line 31; Change "MgAg, Men," to --MgAg, MgIn,--.

Column 151, Line 58; Change "perfoimance" to --performance--.

Column 157, Line 65; Change "8.32 (17.3 mmol)" to --8.32 g (17.3 mmol)--.

Column 159, Line 41-42; Change
"340 mg (0.6 mmol) bis(dibenzylideneacetone)palladium(0)," to
--340 mg (0.6 mmol) of bis(dibenzylideneacetone)palladium(0),--.

Column 164, Line 7; Change "faulted" to --formed--.

Signed and Sealed this
Seventeenth Day of April, 2012

David J. Kappos
*Director of the United States Patent and Trademark Office*

CERTIFICATE OF CORRECTION (continued)
U.S. Pat. No. 8,110,980 B2

In the Claims:

Column 168, Line 15, Claim 1; Change "$Ar^{11}$ to $Ar^{13}$" to --$Ar^{11}$ to $Ar^{13}$--.

Column 175, Line 17, Claim 17; Change "$Ar^{11}$ to $Ar^{ia}$" to --$Ar^{11}$ to $Ar^{13}$--.